US012340903B2

(12) United States Patent
Joao

(10) Patent No.: US 12,340,903 B2
(45) Date of Patent: Jun. 24, 2025

(54) APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK

(71) Applicant: Raymond Anthony Joao, Yonkers, NY (US)

(72) Inventor: Raymond Anthony Joao, Yonkers, NY (US)

( * ) Notice: Subject to any disclaimer, the term of this patent is extended or adjusted under 35 U.S.C. 154(b) by 82 days.

(21) Appl. No.: 17/224,838

(22) Filed: Apr. 7, 2021

(65) Prior Publication Data

US 2021/0319895 A1    Oct. 14, 2021

Related U.S. Application Data

(60) Provisional application No. 63/009,986, filed on Apr. 14, 2020, provisional application No. 63/019,410, (Continued)

(51) Int. Cl.
*G16H 40/67* (2018.01)
*G06F 16/182* (2019.01)
(Continued)

(52) U.S. Cl.
CPC .......... *G16H 40/67* (2018.01); *G06F 16/182* (2019.01); *G06K 7/10297* (2013.01);
(Continued)

(58) Field of Classification Search
CPC ........ G16H 40/40; G16H 10/60; G16H 30/20; G16H 40/00; G16H 40/20; G16H 40/63; G16H 40/67; G16H 50/50; G06F 3/0482
(Continued)

(56) References Cited

U.S. PATENT DOCUMENTS 3,978,850 A    9/1976   Moore et al.
4,110,723 A    8/1978   Hetz et al.
(Continued)

OTHER PUBLICATIONS

Aboudi et al., (2018). Big data management for healthcare systems: Architecture, requirements, and implementation. Advances in Bioinformatics, 2018 doi:http://dx.doi.org/10.1155/2018/4059018 (Year: 2018).*

(Continued)

*Primary Examiner* — Joy Chng
(74) *Attorney, Agent, or Firm* — Raymond A. Joao, Esq.

(57) ABSTRACT

An apparatus, including a computer which includes a database which stores a first electronic healthcare record associated with an individual or patient and a master records file. The apparatus facilitates a video call between a user device associated with the individual or patient and a provider device associated with a healthcare provider. Video information is displayed with a portion of the first electronic healthcare record on a display of the provider device. The provider device processes information for updating the first electronic healthcare record. The computer stores the information for updating, and stores an update to, the first electronic healthcare record in the database. The computer utilizes information stored in the master records file and automatically updates a second electronic healthcare record, or automatically updates an electronic medical record, electronic dental record, electronic pharmacy record, electronic behavioral health record, or personal health record, associated with the individual or patient.

31 Claims, 32 Drawing Sheets

Related U.S. Application Data filed on May 3, 2020, provisional application No. 63/038,866, filed on Jun. 14, 2020.

(51) Int. Cl.

| | |
|---|---|
| *G06K 7/10* | (2006.01) |
| *G06K 19/07* | (2006.01) |
| *G06Q 40/08* | (2012.01) |
| *G16H 10/65* | (2018.01) |
| *G16H 40/20* | (2018.01) |
| *G16H 80/00* | (2018.01) |
| *H04L 9/40* | (2022.01) |
| *H04N 7/14* | (2006.01) |

(52) U.S. Cl.
CPC ......... *G06K 19/0723* (2013.01); *G06Q 40/08* (2013.01); *G16H 10/65* (2018.01); *G16H 40/20* (2018.01); *G16H 80/00* (2018.01); *H04L 63/0876* (2013.01); *H04N 7/141* (2013.01)

(58) Field of Classification Search
USPC ..................................................... 705/2–3
See application file for complete search history.

(56) References Cited

U.S. PATENT DOCUMENTS

| | | |
|---|---|---|
| 4,170,987 A | 10/1979 | Anselmo et al. |
| 4,209,022 A | 6/1980 | Dory |
| 4,235,454 A | 11/1980 | Gray et al. |
| 4,242,911 A | 1/1981 | Martin |
| 4,251,850 A | 2/1981 | Kalbitz et al. |
| 4,290,114 A | 9/1981 | Sinay |
| 4,491,725 A | 1/1985 | Pritchard |
| 4,641,659 A | 2/1987 | Sepponen |
| 4,648,036 A | 3/1987 | Gallant |
| 4,674,108 A | 6/1987 | Asahina et al. |
| 4,674,512 A | 6/1987 | Rolf |
| 4,731,725 A | 3/1988 | Suto et al. |
| 4,733,354 A | 3/1988 | Potter et al. |
| 4,803,625 A | 2/1989 | Fu et al. |
| 4,803,652 A | 2/1989 | Maeser et al. |
| 4,835,372 A | 5/1989 | Gombrich et al. |
| 4,858,121 A | 8/1989 | Barber |
| 4,895,518 A | 1/1990 | Arnold et al. |
| 4,987,538 A | 1/1991 | Johnson et al. |
| 5,036,852 A | 8/1991 | Leishman |
| 5,070,452 A | 12/1991 | Doyle, Jr. et al. |
| 5,090,417 A | 2/1992 | Mollan et al. |
| 5,185,857 A | 2/1993 | Rozmanith et al. |
| 5,217,379 A | 6/1993 | Kirschenbaum et al. |
| 5,219,322 A | 6/1993 | Weathers |
| 5,235,510 A | 8/1993 | Yamada et al. |
| 5,255,187 A | 10/1993 | Sorensen |
| 5,262,943 A | 11/1993 | Thibado et al. |
| 5,265,010 A | 11/1993 | Evans-Paganelli et al. |
| 5,279,294 A | 1/1994 | Anderson et al. |
| 5,283,761 A | 2/1994 | Gillingham |
| 5,301,105 A | 4/1994 | Cummings, Jr. |
| 5,305,748 A | 4/1994 | Wilk |
| 5,324,077 A | 6/1994 | Kessler et al. |
| 5,325,293 A | 6/1994 | Dorne |
| 5,331,550 A | 7/1994 | Stafford et al. |
| 5,344,324 A | 9/1994 | O'Donnell et al. |
| 5,360,005 A | 11/1994 | Wilk |
| 5,404,292 A | 4/1995 | Hendrickson |
| 5,415,167 A | 5/1995 | Wilk |
| 5,424,945 A | 6/1995 | Bell |
| 5,435,324 A | 7/1995 | Brill |
| 5,437,278 A | 9/1995 | Wilk |
| 5,465,082 A | 11/1995 | Chaco |
| 5,519,607 A | 5/1996 | Tawil |
| 5,530,438 A | 6/1996 | Bickham et al. |
| 5,544,649 A | 8/1996 | David et al. |
| 5,544,651 A | 8/1996 | Wilk |
| 5,551,436 A | 9/1996 | Yago |
| 5,583,758 A | 12/1996 | Mcilroy et al. |
| 5,594,638 A | 1/1997 | Iliff |
| 5,615,110 A | 3/1997 | Wong |
| 5,644,778 A | 7/1997 | Burks |
| 5,654,750 A | 8/1997 | Weil |
| 5,660,176 A | 8/1997 | Iliff |
| 5,666,953 A | 9/1997 | Wilk |
| 5,696,981 A | 12/1997 | Shovers |
| 5,708,422 A | 1/1998 | Blonder |
| 5,724,968 A | 3/1998 | Iliff |
| 5,730,146 A | 3/1998 | Itil et al. |
| 5,737,539 A | 4/1998 | Edelson et al. |
| 5,748,907 A | 5/1998 | Crane |
| 5,754,111 A | 5/1998 | Garcia |
| 5,761,334 A | 6/1998 | Nakajima et al. |
| 5,772,585 A | 6/1998 | Lavin et al. |
| 5,776,057 A | 7/1998 | Swenson et al. |
| 5,779,634 A | 7/1998 | Ema et al. |
| 5,797,901 A | 8/1998 | Cosmescu |
| 5,801,755 A | 9/1998 | Echerer |
| 5,807,246 A | 9/1998 | Sakaguchi et al. |
| 5,807,256 A | 9/1998 | Taguchi et al. |
| 5,807,336 A | 9/1998 | Russo et al. |
| 5,839,438 A | 11/1998 | Graettinger et al. |
| 5,845,255 A | 12/1998 | Mayaud |
| 5,862,803 A | 1/1999 | Besson et al. |
| 5,867,821 A | 2/1999 | Ballantyne et al. |
| 5,868,669 A | 2/1999 | Iliff |
| 5,876,351 A | 3/1999 | Rohde |
| 5,878,337 A | 3/1999 | Joao et al. |
| 5,878,746 A | 3/1999 | Lemelson et al. |
| 5,890,129 A | 3/1999 | Spurgeon |
| 5,895,354 A | 4/1999 | Simmons |
| 5,899,857 A | 5/1999 | Wilk |
| 5,903,830 A | 5/1999 | Joao et al. |
| 5,910,107 A | 6/1999 | Iliff |
| 5,915,241 A | 6/1999 | Giannini |
| 5,917,405 A | 6/1999 | Joao |
| 5,930,759 A | 7/1999 | Moore et al. |
| 5,935,060 A | 8/1999 | Iliff |
| 5,942,986 A | 8/1999 | Shabot et al. |
| 5,946,659 A | 8/1999 | Lancelot et al. |
| 5,954,641 A | 9/1999 | Kehr et al. |
| 5,957,854 A | 9/1999 | Besson et al. |
| 5,961,332 A | 10/1999 | Joao |
| 5,961,448 A | 10/1999 | Swenson et al. |
| 5,974,124 A | 10/1999 | Schlueter, Jr. et al. |
| 5,974,389 A | 10/1999 | Clark et al. |
| 5,988,851 A | 11/1999 | Gent |
| 5,992,742 A | 11/1999 | Sullivan et al. |
| 6,003,007 A | 12/1999 | Derienzo |
| 6,014,629 A | 1/2000 | Debruin-Ashton |
| 6,018,713 A | 1/2000 | Coli et al. |
| 6,021,202 A | 2/2000 | Anderson et al. |
| 6,044,352 A | 3/2000 | Deavers |
| 6,047,259 A | 4/2000 | Campbell et al. |
| 6,047,270 A | 4/2000 | Joao et al. |
| 6,073,106 A | 6/2000 | Rozen et al. |
| 6,076,066 A | 6/2000 | Dirienzo et al. |
| 6,090,044 A | 7/2000 | Bishop et al. |
| 6,101,478 A | 8/2000 | Brown |
| 6,208,973 B1 | 3/2001 | Boyer et al. |
| 6,216,104 B1 | 4/2001 | Moshfeghi et al. |
| 6,273,856 B1 | 8/2001 | Sun et al. |
| 6,283,761 B1 | 9/2001 | Joao |
| 6,302,844 B1 | 10/2001 | Walker et al. |
| 6,341,265 B1 | 1/2002 | Provost et al. |
| 6,343,271 B1 | 1/2002 | Peterson et al. |
| 6,345,260 B1 | 2/2002 | Cummings et al. |
| 6,364,834 B1 | 4/2002 | Reuss et al. |
| 6,476,833 B1 | 11/2002 | Moshfeghi |
| 6,484,144 B2 | 11/2002 | Martin et al. |
| 6,523,009 B1 | 2/2003 | Wilkins |
| 6,529,725 B1 | 3/2003 | Joao et al. |
| 6,542,076 B1 | 4/2003 | Joao |
| 6,542,077 B2 | 4/2003 | Joao |

(56) References Cited

U.S. PATENT DOCUMENTS

| | | |
|---|---|---|
| 6,549,130 B1 | 4/2003 | Joao |
| 6,587,046 B2 | 7/2003 | Joao |
| 6,662,194 B1 | 12/2003 | Joao |
| 6,757,898 B1 | 6/2004 | Ilsen et al. |
| 6,776,341 B1 | 8/2004 | Sullivan et al. |
| 6,799,725 B1 | 10/2004 | Hess et al. |
| 6,804,558 B2 | 10/2004 | Haller et al. |
| 6,804,656 B1 | 10/2004 | Rosenfeld et al. |
| 6,845,448 B1 | 1/2005 | Chaganti et al. |
| 6,915,265 B1 | 7/2005 | Johnson |
| 6,988,075 B1 | 1/2006 | Hacker |
| 7,028,049 B1 | 4/2006 | Shelton |
| 7,059,526 B1 | 6/2006 | Sullivan et al. |
| 7,096,003 B2 | 8/2006 | Joao et al. |
| 7,110,955 B1 | 9/2006 | Barhnart et al. |
| 7,149,773 B2 | 12/2006 | Haller et al. |
| 7,181,505 B2 | 2/2007 | Haller et al. |
| 7,194,416 B1 | 3/2007 | Provost et al. |
| 7,277,010 B2 | 10/2007 | Joao |
| 7,370,797 B1 | 5/2008 | Sullivan et al. |
| 7,397,363 B2 | 7/2008 | Joao |
| 7,464,040 B2 | 12/2008 | Joao |
| 7,464,043 B1 | 12/2008 | Dussia |
| 7,490,048 B2 | 2/2009 | Joao |
| 7,593,952 B2 | 9/2009 | Soll et al. |
| 7,647,234 B1 | 1/2010 | Ruderman et al. |
| 7,685,005 B2 | 3/2010 | Riff et al. |
| 7,698,154 B2 | 4/2010 | Marchosky |
| 8,131,563 B2 | 3/2012 | Hasan et al. |
| 8,316,237 B1 | 11/2012 | Felsher et al. |
| 8,606,594 B2 | 12/2013 | Stern et al. |
| 8,793,142 B2 | 7/2014 | Fishman et al. |
| 8,852,093 B2 | 10/2014 | Clapp et al. |
| 8,905,927 B2 | 12/2014 | Cheung et al. |
| 9,235,841 B2 | 1/2016 | Joao |
| 9,245,270 B2 | 1/2016 | Joao |
| 9,465,913 B1 | 10/2016 | Chaganti et al. |
| 9,759,570 B2 | 9/2017 | Joao et al. |
| 9,911,124 B2 | 3/2018 | Joao |
| 9,961,249 B2 | 5/2018 | Joao et al. |
| 10,011,247 B2 | 7/2018 | Joao |
| 10,048,078 B2 | 8/2018 | Joao et al. |
| 10,152,876 B2 | 12/2018 | Joao |
| 10,157,385 B2 | 12/2018 | Joao |
| 10,197,406 B2 | 2/2019 | Joao et al. |
| 10,218,888 B2 | 2/2019 | Joao et al. |
| 10,504,123 B2 | 12/2019 | Joao |
| 10,562,492 B2 | 2/2020 | Joao |
| 10,571,284 B2 | 2/2020 | Joao et al. |
| 10,791,256 B2 | 9/2020 | Joao et al. |
| 10,861,020 B2 | 12/2020 | Joao |
| 10,885,170 B1 * | 1/2021 | Maliani .................. H04L 9/0643 |
| 10,942,032 B2 | 3/2021 | Joao et al. |
| 11,587,688 B2 | 2/2023 | Joao |
| 2001/0032099 A1 | 10/2001 | Joao |
| 2001/0037220 A1 | 11/2001 | Merry et al. |
| 2001/0041991 A1 | 11/2001 | Segal et al. |
| 2001/0049610 A1 | 12/2001 | Hazumi |
| 2001/0051787 A1 | 12/2001 | Haller et al. |
| 2001/0051920 A1 | 12/2001 | Joao et al. |
| 2002/0004725 A1 | 1/2002 | Martin et al. |
| 2002/0004727 A1 | 1/2002 | Knaus et al. |
| 2002/0025797 A1 | 2/2002 | Joao et al. |
| 2002/0026332 A1 | 2/2002 | Snowden et al. |
| 2002/0029157 A1 | 3/2002 | Marchosky |
| 2002/0032583 A1 | 3/2002 | Joao |
| 2002/0038424 A1 | 3/2002 | Joao et al. |
| 2002/0052539 A1 | 5/2002 | Haller et al. |
| 2002/0087113 A1 | 7/2002 | Hartlaub |
| 2002/0120471 A1 | 8/2002 | Drazen |
| 2002/0161795 A1 | 10/2002 | O'Rourke |
| 2002/0194027 A1 | 12/2002 | Smith |
| 2003/0028399 A1 | 2/2003 | Davis et al. |
| 2003/0055679 A1 | 3/2003 | Soll et al. |
| 2003/0069752 A1 | 4/2003 | Ledain et al. |
| 2003/0069760 A1 | 4/2003 | Gelber |
| 2003/0074248 A1 | 4/2003 | Braud et al. |
| 2003/0110215 A1 | 6/2003 | Joao |
| 2003/0144711 A1 | 7/2003 | Pless et al. |
| 2003/0158754 A1 | 8/2003 | Elkind |
| 2003/0208391 A1 | 11/2003 | Dvorak et al. |
| 2003/0212579 A1 | 11/2003 | Brown et al. |
| 2004/0044546 A1 | 3/2004 | Moore |
| 2004/0083395 A1 | 4/2004 | Blechman |
| 2004/0107192 A1 | 6/2004 | Joao |
| 2004/0139044 A1 | 7/2004 | Rehwald |
| 2004/0185830 A1 | 9/2004 | Joao et al. |
| 2004/0199765 A1 | 10/2004 | Kohane et al. |
| 2004/0215492 A1 | 10/2004 | Choi |
| 2004/0249665 A1 | 12/2004 | David |
| 2005/0021370 A1 | 1/2005 | Riff et al. |
| 2005/0033604 A1 | 2/2005 | Hogan |
| 2005/0115561 A1 | 6/2005 | Stahmann et al. |
| 2005/0170814 A1 | 8/2005 | Joao et al. |
| 2005/0187789 A1 | 8/2005 | Hatlestad et al. |
| 2005/0192844 A1 | 9/2005 | Esler et al. |
| 2005/0222875 A1 | 10/2005 | Lordeman et al. |
| 2006/0287885 A1 | 12/2006 | Frick |
| 2006/0293570 A1 | 12/2006 | Croghan et al. |
| 2007/0013529 A1 | 1/2007 | Kantrowitz et al. |
| 2007/0122824 A1 | 5/2007 | Tucker |
| 2007/0250352 A1 | 10/2007 | Tawil |
| 2007/0260484 A1 | 11/2007 | Kimmel |
| 2007/0294105 A1 | 12/2007 | Pierce |
| 2007/0299349 A1 | 12/2007 | Alt et al. |
| 2008/0059249 A1 | 3/2008 | Joao |
| 2008/0059250 A1 | 3/2008 | Joao |
| 2008/0097786 A1 | 4/2008 | Sachdeva |
| 2008/0120190 A1 | 5/2008 | Joao et al. |
| 2008/0126131 A1 | 5/2008 | Lou |
| 2008/0176203 A1 | 7/2008 | Kuntz et al. |
| 2008/0188198 A1 | 8/2008 | Patel et al. |
| 2009/0023555 A1 | 1/2009 | Raymond |
| 2009/0025081 A1 | 1/2009 | Quigley et al. |
| 2009/0060148 A1 | 3/2009 | Jacob et al. |
| 2009/0075630 A1 | 3/2009 | McLean |
| 2009/0269329 A1 | 10/2009 | Hyde et al. |
| 2009/0281833 A1 | 11/2009 | Boppana |
| 2009/0298650 A1 | 12/2009 | Kutliroff |
| 2009/0313049 A1 | 12/2009 | Joao et al. |
| 2010/0042440 A1 | 2/2010 | Joao |
| 2010/0063930 A1 | 3/2010 | Kenedy et al. |
| 2010/0114602 A1 | 5/2010 | Joao et al. |
| 2010/0174505 A1 | 7/2010 | Abraham-Fuchs et al. |
| 2010/0292556 A1 | 11/2010 | Golden |
| 2011/0010200 A1 | 1/2011 | Firozvi et al. |
| 2011/0015693 A1 | 1/2011 | Williamson |
| 2011/0029327 A1 | 2/2011 | Dunlop |
| 2011/0166988 A1 | 7/2011 | Coulter |
| 2011/0184249 A1 | 7/2011 | Davis, Jr. |
| 2011/0213625 A1 | 9/2011 | Joao |
| 2011/0276396 A1 | 11/2011 | Rathod |
| 2012/0029303 A1 * | 2/2012 | Shaya ................ A61B 5/02233 |
| | | 348/E7.083 |
| 2012/0253848 A1 | 10/2012 | Gazula |
| 2013/0066653 A1 | 3/2013 | Joao et al. |
| 2013/0090949 A1 | 4/2013 | Tibebu |
| 2013/0218582 A1 * | 8/2013 | LaLonde ................ A61B 7/003 |
| | | 600/324 |
| 2013/0226601 A1 | 8/2013 | Razmi et al. |
| 2014/0067423 A1 | 3/2014 | Joao |
| 2014/0081667 A1 | 3/2014 | Joao |
| 2014/0108055 A1 | 4/2014 | Phillips |
| 2014/0364230 A1 | 12/2014 | Borghese et al. |
| 2015/0004581 A1 | 1/2015 | Selman et al. |
| 2015/0033305 A1 | 1/2015 | Shear et al. |
| 2015/0077502 A1 | 3/2015 | Jordan et al. |
| 2015/0112702 A1 | 4/2015 | Joao et al. |
| 2015/0151199 A1 | 6/2015 | Klein et al. |
| 2015/0161330 A1 | 6/2015 | Joao et al. |
| 2015/0248536 A1 | 9/2015 | Tawil et al. |
| 2015/0278453 A1 | 10/2015 | Joao |
| 2015/0331997 A1 | 11/2015 | Joao |
| 2016/0042651 A1 | 2/2016 | Joao |

(56) References Cited

U.S. PATENT DOCUMENTS

| | | |
|---|---|---|
| 2016/0125549 A1 | 5/2016 | Joao et al. |
| 2016/0125550 A1 | 5/2016 | Joao et al. |
| 2016/0342744 A1 | 11/2016 | Joao |
| 2017/0011190 A1 | 1/2017 | Joao |
| 2017/0091397 A1 | 3/2017 | Shah |
| 2017/0300627 A1* | 10/2017 | Giordano ............ G06F 21/6245 |
| 2018/0060496 A1* | 3/2018 | Bulleit .................. H04L 9/0643 |
| 2018/0082024 A1* | 3/2018 | Curbera .................. G06F 21/00 |
| 2018/0190136 A1 | 7/2018 | Joao |
| 2018/0233237 A1* | 8/2018 | Joao ....................... G16H 15/00 |
| 2019/0096534 A1* | 3/2019 | Joao ....................... G16H 10/60 |
| 2020/0177386 A1* | 6/2020 | Mahmood ............. H04L 63/102 |
| 2020/0184838 A1 | 6/2020 | Joao |
| 2021/0319895 A1 | 10/2021 | Joao |

OTHER PUBLICATIONS

Aboudi et al.: Big data management for healthcare systems: Architecture, requirements, and implementation; Advances in Bioinformatics, 2018 doi:http://dx.doi.org/10.1155/2018/4059018 (Year: 2018).*

U.S. Appl. No. 09/489,657, Joao, et al.

U.S. Appl. No. 60/172,555, Joao.

L. McCullough et al., "The Development of a Microcomputer-Based Mental Health Information System, a Potential Tool for Bridging the Scientist-Practitioner Gap".

McCullough Continued) American Psychologist, Feb. 1986, pp. 207-213.

Watson, the Doctor is In!, Jun. 1995, Accounting Technology, vol. 11, ISS. 5, pp. 24-30.

Edicomm Unveils All-Payer Solution for Healthcare Edi Transactions, Feb. 1999, Business Wire.

U.S. Appl. No. 60/169,065, filed Dec. 6, 1999, Snowden, et al.

U.S. Appl. No. 60/235,977, filed Sep. 28, 2000, Davis, et al.

Grumitt, "Real-Time Record Management in General Practice," 8 Int'l J. Bio-Medical Computing 131 (1977), Apr. 1977.

Wang, et al., "A Real Time Patient Monitoring System on the World Wide Web," Proc. Amia Annual Fall Symp. 729 (1996).

Office Action, mailed Sep. 9, 2024, U.S. Appl. No. 18/070,605.

Office Action, mailed Sep. 29, 2024, U.S. Appl. No. 18/117,505.

Office Action, mailed Oct. 1, 2024, U.S. Appl. No. 18/122,411.

Aboudi, et al.: Big data management for healthcare systems: Architectre, requirements, and implementation; Advances in Bioinformatics, 2018.

Aboudi (Cont.): doi:http://dx.doi.org/10.1155/2018/4059018 (Year: 2018).

* cited by examiner

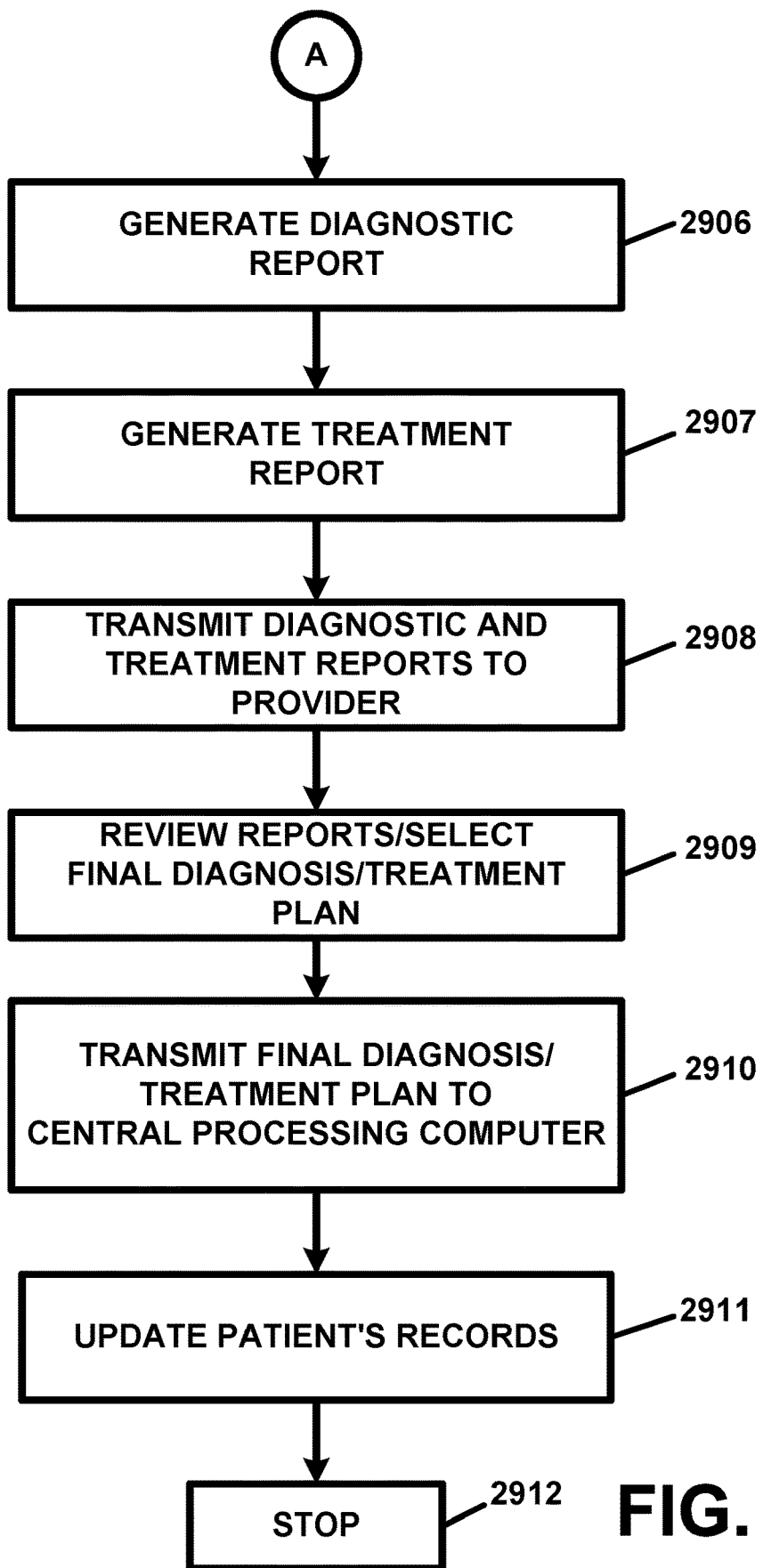

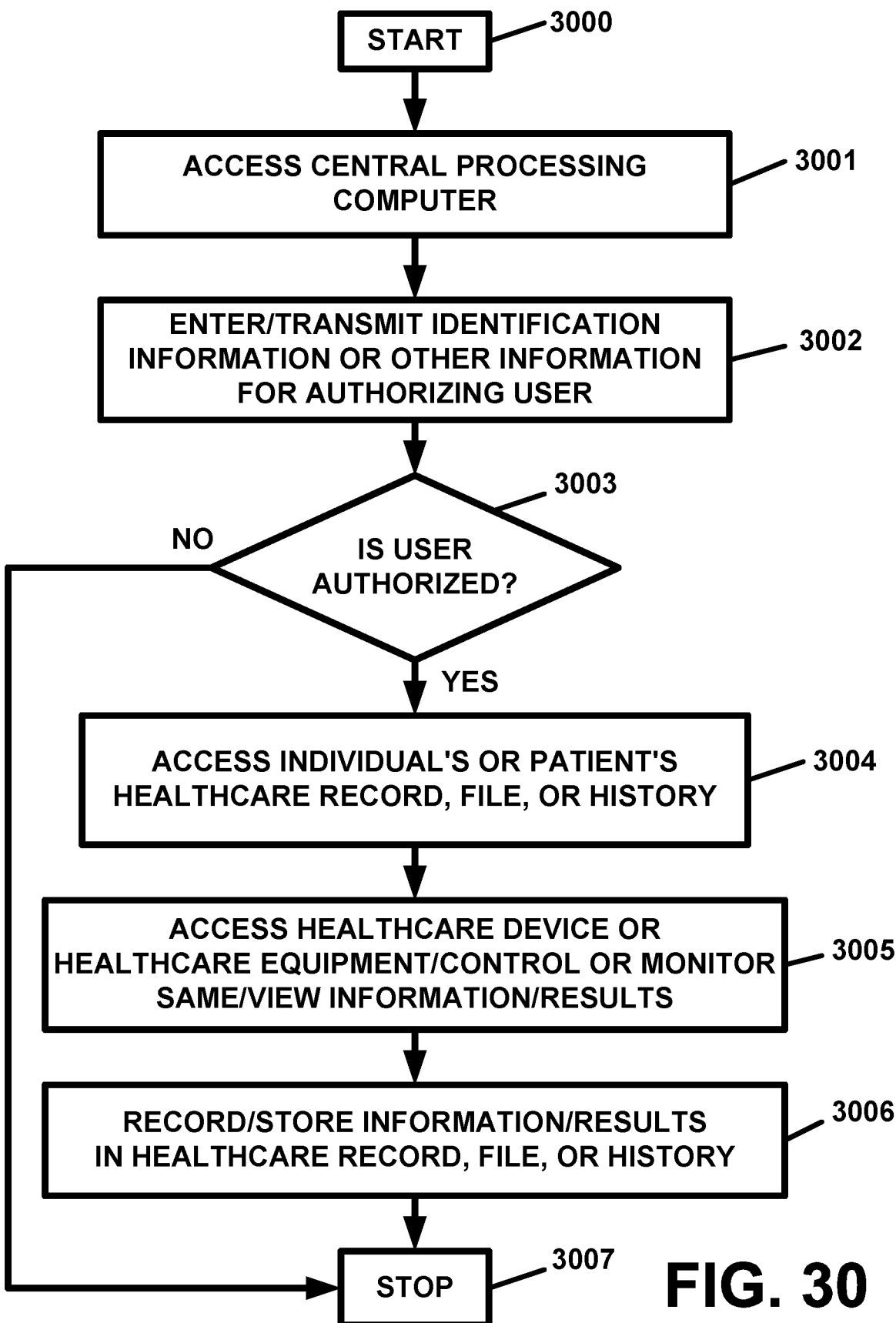

APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK

RELATED APPLICATIONS

This application claims the benefit of the priority of U.S. Provisional Patent Application Ser. No. 63/009,986, filed Apr. 14, 2020, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety. This application also claims the benefit of the priority of U.S. Provisional Patent Application Ser. No. 63/019,410, filed May 3, 2020, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety. This application also claims the benefit of the priority of U.S. Provisional Patent Application Ser. No. 63/038,866, filed Jun. 14, 2020, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

FIELD OF THE INVENTION

The present invention pertains to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional.

BACKGROUND OF THE INVENTION

Healthcare is an area of major concern in the United States. Each year, tens of millions of individuals seek or need the assistance of healthcare professionals. In order to perform proper diagnoses and to prescribe appropriate treatments, healthcare professional or providers typically rely on information which is obtained from patients, relatives of patients, previous providers, and/or healthcare facility and/or hospital staff members. The need to have accurate and/or up-to-date data and/or information, in providing healthcare services and/or healthcare-related services, cannot be emphasized enough.

Stories constantly emerge about patients receiving the wrong treatments, having the wrong surgical procedures performed on themselves, receiving a drug or drugs which fatally and/or otherwise adversely interact with another drug or drugs, etc., with stories going on and on. A 1999 study estimated that between 44,000 and 98,000 individuals die annually in hospitals, in the United States alone, as the result of errors or mistakes made by doctors, healthcare providers, and/or healthcare facility workers. Various other reports also estimate 225,000 deaths annually from medical errors and 180,000 deaths annually from medication errors and adverse reactions. There is no doubt that many of these deaths result from inaccurate and/or erroneous information and/or the lack of the availability of correct and/or up-to-date information.

Another problem lies with the fact that the main source of patient information, medical histories, family histories, etc., upon which doctors or providers may base their diagnoses and/or treatments, are patients who usually supply this information on questionnaires or forms just prior to seeing the healthcare provider and/or during a preliminary interview with the provider. In this regard, information obtained from these questionnaires or forms, as well as from these preliminary interviews with the providers, may not necessarily result in sufficient, comprehensive, and/or accurate, information being obtained regarding the patient. Further, there is no guarantee that the same information will be provided, in a uniform manner, to a next or different provider. As a result, patient information may not be uniformly distributed and/or be available to providers at the point of treatment and/or otherwise.

Another problem which exists in the current healthcare system is that doctors or other providers do not always have the latest information and/or research material available to them prior to, and/or during, the diagnosis and/or treatment process.

Still other problems arise when an individual or a patient, or a caregiver for an individual or a patient, engages in a video call with a healthcare provider in or during a remote or a virtual provider visit or in or during a remote or a distance examination. In such instances, there is no guarantee that the healthcare provider has access to the individual's or the patient's healthcare records, files, or history, before or during the video call and the remote or virtual provider visit or in or during the remote or distance examination. Further, there is no guarantee that the healthcare provider, even if provided with access to the individual's or the patient's healthcare records, files, or history, can access the same, and enter notes, findings, and/or information, into the same in an easy and efficient manner, and/or be able to do so in, during, or after the remote or distance examination. As a result, the healthcare provider may be not be provided with sufficient information to conduct a full and complete examination or evaluation of the individual or the patient, or to make or arrive at a diagnosis based on any and/or all needed and available information regarding the individual or the patient, or to prescribe a treatment based on any and/or all needed or available information regarding the individual or the patient. As a further result, the healthcare provider may not have access to the individual's or the patient's healthcare records, files, or history, in order to properly or completely enter notes or any other information regarding the individual or the patient as well as any information, observations, examination findings, or examinations results, obtained by, made by, or obtained during the remote or the virtual provider visit or in or during the remote or the distance examination.

Another problem associated with healthcare providers and patients who engage in video calls during remote or virtual provider visits or in or during remote or distance examinations lies in the fact that the healthcare provider may not able to control and/or to monitor healthcare equipment, devices, or systems, which is located with the patient. In such instances, patient control and/or operation of such healthcare equipment, devices, or systems, might fail to yield measurements or results if uncalibrated and/or misused by patients or their caregivers.

Another problem also lies in securing data and/or information stored in patient's healthcare records, files, or history, especially when data and/or information may be accessed via the online networks and/or the Internet and/or the World Wide Web.

SUMMARY OF THE INVENTION

The present invention pertains to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional, which overcomes the shortcomings of the prior art.

The present invention is directed to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional for a variety of healthcare and healthcare-related applications.

The apparatus and method of the present invention can be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribe a treatment based on any and/or all any and/or all information regarding the individual or the patient. As a further result, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented in the individual's or the patient's healthcare records, files, or history.

The present invention facilitates improved healthcare quality, efficient information collection, processing and dissemination, efficient diagnosis and treatment, cost efficiency, cost containment, as well as many other benefits and advantages as will be described herein. The apparatus and method of the present invention can also facilitate the distribution and management of healthcare insurance, life insurance, disability insurance, as well as claims processing related thereto.

The present invention also provides an apparatus and a method for providing a comprehensive processing system which incorporates data and/or information from any combination and/or all of the participants in the healthcare field, including patients, providers, payers or insurance companies, and/or brokers, agents and/or other intermediaries who act on behalf of any of the above-identified persons or entities.

The apparatus of the present invention includes a central processing computer or central processing computer system which can be a network or server computer. The apparatus also includes a healthcare provider communication device or computer which is associated with a healthcare provider such as a healthcare professional, a hospital, a clinic, a pharmacy, a treatment center, a treatment facility, and/or any other provider of services described herein. Any healthcare professional, hospital, clinic, pharmacy, treatment center, treatment facility, and/or any other provider of services, healthcare or otherwise, which is described herein can also be referred to herein as a "provider". The healthcare provider computer(s) can communicate with, and operate in conjunction with, the central processing computer and/or any of the other computers and/or computer systems or communication devices described herein.

The apparatus can also include a healthcare payer communication device or computer which is associated with a healthcare payer such as a healthcare insurer, insurance company, health maintenance organization, a clinic, and/or any other payer of healthcare services and products described herein. The healthcare payer computer(s) can communicate with, and operate in conjunction with, central processing computer and/or any of the other computers and/or computer systems or communication devices described herein.

The apparatus can also include a user or patient communication device or computer which is associated with an individual, or patient, or a caregiver of the individual or patient, who seeks or who is provided with healthcare and/or related services, products and/or related information. The user or patient communication device(s) can communicate with, and operate in conjunction with, central processing computer and/or any of the other computers and/or computer systems described herein.

The apparatus can also include an intermediary communication device or computer which is associated with an intermediary, a broker, an agent, and/or any other individual and/or entity, or any third party, that can utilize the present invention in order to act for and/or on behalf of any other individual, party, or entity, described herein. The intermediary computer(s) can communicate with, and operate in conjunction with, central processing computer and any of the other computers and/or computer systems described herein.

The apparatus can also include a healthcare records computer which can be or can include a computer or computer system, or any number of computers or computer systems, or a cloud computer system or cloud system. The healthcare records computer can serve to store and house an electronic healthcare record or electronic healthcare files or any number of electronic healthcare records or electronic healthcare files. The healthcare records computer can be associated with any provider, insurer, payer, intermediary, insurance exchange, or any user, individual, patient, organization, or entity, who or which utilizes the present invention.

Each healthcare records computer can be utilized to store an electronic healthcare record or electronic healthcare file or any number of electronic healthcare records or electronic healthcare files which can be accessed by the central processing computer, by any provider communication device, by any insurer or payer communication device, by any user or patient communication device, by any intermediary communication device, or by any other computer, communication device or other device described herein as being utilized in connection with the present invention. The healthcare records computer can also be utilized to facilitate cloud storage of any electronic healthcare record(s) or electronic healthcare file(s).

The apparatus can also include an insurance exchange computer, or any number of insurance exchange computers which can be utilized to process and store information regarding the selling of healthcare insurance, disability insurance, and life insurance, policies, products, and/or services, to any of the herein-described users, individuals, patients, or entities, who or which utilize the apparatus 100 and method of the present invention. The insurance exchange computer can be utilized to advertise, provide information regarding, sell, and/or maintain records regarding, and process any other information regarding, group insurance as well as individual or family insurance policies, products, or services. The insurance exchange computer can also be utilized to sell automobile, homeowners, business, and/or liability insurance policies, products, or services.

The apparatus can also include a social networking computer. The social networking computer can be linked with, and utilized in connection with, the apparatus so as to allow and/or facilitate integrating the apparatus of the present invention with social networks, social networking, and social media. The social networking computer can be associated with a social networking company, a social networking website, or social networking entity, website, group, organization, or association. The social networking computer can also be associated with any one or any number of social networking companies, social networking websites, or social networking entities, websites, groups, organizations, or associations. The social networking computer can also provide links to any computers associated with any one or any number of social networking companies, social networking websites, or social networking entities, websites, groups, organizations, or associations. The social networking computer can perform any and all of the functions performed by any social networking company, a social networking website, or social networking entity, website, group, organization, or association. Any number of social networking computers can be utilized in connection with the present invention.

The apparatus can also include a media computer. The media computer can provide, and be a source of, news information, current events information, healthcare information, healthcare or healthcare-related news, current events, advertisements, and/or marketing information or materials, which can be disseminated via the present invention. Any number of media computers, with each being dedicated to providing any number, types, or kinds of, news information, current events information, healthcare information, healthcare or healthcare-related news, current events, advertisements, and/or marketing information or materials, can be utilized in connection with the present invention.

Each of the central processing computer(s), the provider communications devices, the payer communication devices, the user or patient communication devices, the intermediary communication devices, the healthcare records computers, the insurance exchange computers, the social networking computers, and the media computers can communication in a bi-directional manner with, and/or can send and/or receive signals, messages, reports, notification messages, alerts, or any other communications or electronic communication transmissions, to, from and/or between, any other, or any number of, other central processing computer(s), if utilized, provider communications devices, payer communication devices, user or patient communication devices, intermediary communication devices, healthcare records computers, insurance exchange computers, social networking computers, and/or the media computers.

Each of the central processing computer(s), the provider communications devices, the payer communication devices, the user or patient communication devices, the intermediary communication devices, the healthcare records computers, the insurance exchange computers, the social networking computers, and the media computers can be linked to or with any other central processing computer(s), if utilized, provider communications devices, payer communication devices, user or patient communication devices, intermediary communication devices, healthcare records computers, insurance exchange computers, social networking computers, and/or the media computers via a wired link or line or a wireless link.

Each of the provider communications devices, payer communication devices, user or patient communication devices, intermediary communication devices, healthcare records computers, insurance exchange computers, social networking computers, and/or the media computers can be connected with or linked with the central processing computer.

Any and/or all of the signals, messages, reports, notification messages, or any other communications, described herein as being transmitted from one device, computer, or communication device, to another, can be, or can be included in, or be attached to, an e-mail message, an instant messaging message, an electronic transmission, or an electronic data transmission or electronic data interchange, or can be transmitted via any other data or information transmission, and can be transmitted via or using any appropriate or necessary computer(s) or device(s).

The present invention can be utilized on, and/or over, the Internet and/or the World Wide Web and/or any other communication network, telecommunication network, telephone network, a line-connected network, or a wireless communication network, or any combination of same. The present invention can also utilize wireless Internet and/or World Wide Web services, equipment and/or devices. The central processing computer(s) and/or any of the herein-described computers or communication devices can have a web site or web sites associated with same.

The present invention can be utilized on, or over, the Internet and/or the World Wide Web and/or on, or over, any other communication network or system, including, but not limited to, a communication network or system, a telecommunication network or system, a telephone communication network or system, a cellular communication network or system, a wireless communication network or system, a wireless Internet network or system, a wireless World Wide Web network or system, a line or wired communication network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, and/or any other communication network or system, and/or any combination of the above communication networks or systems.

The apparatus and method of the present invention can utilize electronic commerce technologies and security methods, techniques and technologies, in any and/or all of the instances of data and/or information processing, and/or data and/or information transmission described herein.

Each of the central processing computer(s), as well as each of the herein-described computers or communication devices can include a central processing unit or CPU, a random access memory device(s) (RAM), a read only memory device(s), and a user input device. Each of the central processing computer(s), as well as each of the herein-described computers or communication devices can also include a display device, a transmitter(s), a receiver, a database(s), and an output device. The database(s) can contain any and/or all of the data and/or information which is needed to perform the various processing methods, services, functions and/or operations, described herein.

The present invention can be utilized in numerous preferred embodiments in order to provide a vast array of healthcare and healthcare-related services for any one or more of the various parties described herein.

The present invention can be utilized to create and maintain a comprehensive and/or a centralized electronic healthcare record system. The present invention can also be utilized to provide for a comprehensive electronic healthcare record, file, or history, for each individual, patient, or caregiver, as well as facilitates access to comprehensive healthcare or healthcare-related data and/or information for or regarding an individual, patient, or caregiver via the central processing computer. An individual's, patient's, or caregiver's, electronic healthcare record, electronic healthcare file or electronic healthcare history, can be contained in any number of electronic healthcare records, electronic medical records, electronic dental records, electronic pharmacy records, and/or electronic behavioral healthcare records, regardless of where each respective record is or may be stored.

A user can access any one or more, or any and/or all of, the electronic healthcare records, electronic medical records, electronic dental records, electronic pharmacy records, and/or electronic behavioral healthcare records, or portion(s) of same which contain data or information for or regarding individual, patient, or caregiver. The present invention can be utilized to provide a comprehensive healthcare record, file, or history, for an individual, patient, or caregiver, by providing any and/or all healthcare or healthcare-related data and/or information, for or regarding an individual, patient, pr caregiver, and/or any and/or all link(s) or hyperlink(s) to any and/or all of the electronic healthcare records, electronic medical records, electronic dental records, electronic pharmacy records, and/or electronic behavioral healthcare records, which contain any and/or all healthcare or healthcare-related data or information for or regarding individual, patient, or caregiver.

The present invention can also be utilized by any individual, patient, caregiver, user, provider, insurer or payer, or third party or intermediary, to create a link or hyperlink to any electronic healthcare record(s), electronic medical record(s), electronic dental record(s), electronic pharmacy record(s), and/or electronic behavioral healthcare record(s), which contain or which are to contain healthcare or healthcare-related data or information for or regarding any individual, patient, or caregiver.

The present invention can also be utilized in order to allow an individual or a patient, or a caregiver, or one responsible for the care of an individual or patient, to enter notes, comments, or messages regarding or relating to the individual or patient into one or more of any of the individual's, patient's, or caregiver's, electronic healthcare record(s), electronic healthcare file(s), electronic medical record(s), electronic dental record(s), electronic pharmacy record(s), and/or electronic behavioral healthcare record(s). Any respective note, comment, or message can be in text form, audio form, or video form, and can contain information regarding a symptom, an illness, an experience, a treatment, a diagnosis, a treatment plan, an activity, a problem, a concern, a thought or an idea, a question, a question for a healthcare provider, or any other information which the individual or patient, or one caring for the individual or patient, may deem important to be recorded or noted in the respective electronic healthcare record(s), electronic medical record(s), electronic dental record(s), electronic pharmacy record(s), and/or electronic behavioral healthcare record(s), or which can be communicated to, or otherwise made available to, a provider or an insurer or payer.

A healthcare provider can access, obtain, and/or use, the information provided or contained in the note, comment, or message, or provided or contained in multiple notes, comments, or messages, for any suitable purpose, such as, but not limited to, for preparing for, or for use during, a remote or virtual office visit with, or a remote or distance examination of, an individual, a patient, or a caregiver for or an individual or a patient, during a video telephone call, a video chat session, or a videoconference, with the individual, the patient, or the caregiver for or the individual or the patient, or for use during a conversation, discussion, or consultation, during a video telephone call, a video chat session, or a videoconference, with the individual, the patient, or the caregiver for the individual or the patient, or for use during a conversation, discussion, or consultation, during a video telephone call, a video chat session, or a videoconference, with and between, the healthcare provider, and the individual, the patient, or the caregiver for or the individual or the patient, or another healthcare provider or any other provider, or an insurer or a payer, or an intermediary, or for use during reviewing, updating, modifying, or performing any other activity in connection with, an individual's or patient's healthcare records, files, or histories, for use while making a diagnosis, for use while formulating a treatment or a treatment plan, for use in reviewing or evaluating an individual's or patient's diagnosis or treatment, for use in treatment planning and/or the evaluating of same, for use in care management, for use in monitoring or evaluating a recovery, for use in providing continuing or on-going care or treatment, for use in connection with the providing of a remote healthcare services or tele-health services, and/or for any other suitable use or purpose.

Any notes, comments or messages, can be provided by the individual, patient, or caregiver, or by any person caring for the individual or patient, while making an appointment, in advance of a video telephone call, a video chat session, or a videoconference, or a remote or virtual office visit with, or a remote or distance examination of, or in advance of a video telephone call, a video chat session, or a videoconference, or a remote or distance examination of, with the individual, the patient, or the caregiver for the individual or the patient, or a video telephone call, a video chat session, or a videoconference, with another provider, or a payer or insurer or any third party or intermediary, in connection with any telehealth related activity, or for the purpose of making and entering a note, comment, or message, into the individual's or patient's respective electronic healthcare record(s), electronic medical record(s), electronic dental record(s), electronic pharmacy record(s), and/or electronic behavioral healthcare record(s). In this regard, the present invention can allow an individual or patient, or a caregiver, or one responsible for caring for the individual or patient, to make and enter any notes, comments, or messages, into the individual's or patient's respective electronic healthcare record(s), electronic medical record(s), electronic dental record(s), electronic pharmacy record(s), and/or electronic behavioral healthcare record(s) so as to facilitate accurate and complete healthcare information record keeping.

Any provider of an individual or patient, any insurer or payer of an individual or patient, any caregiver of an individual or patient, or any other authorized third party, intermediary, person, or entity, can also enter and store any note(s), comment(s), or message(s) in the individual's or patient's electronic healthcare record.

Any insurance claim form or the payment request form can be date stamped and/or time stamped. In this manner, claim or payment request processing can be tracked or monitored so as to facilitate audits of the insurer or payer in order to ascertain if the insurer or payer is properly and/or efficiently handling a claim or payment request for the individual or patient, and/or if the insurer or payer is in compliance with any laws, rules, or regulations, governing claims or payment processing and/or handling. Information regarding the date stamped and/or time stamped claims, including the insurer's or the payer's processing or handling of same, and the response or reply to same, can also be stored by the present invention and can be accessed and/or obtained by any authorized user or entity.

The present invention can also generate a co-payment message or a deductible message containing information regarding a co-payment due by the individual or patient to the provider under the individual's or patient's insurance policy or payment program or a deductible which has to be met by the individual or patient under the individual's or patient's insurance policy or payment program.

The present invention can also be utilized in connection with or in conjunction with a personal healthcare record which an individual or patient can maintain for himself, herself, and/or for any children, parents, relatives, friends, or any other individuals whom the individual or patient may be providing care for as a caregiver or a person assisting a caregiver for another. In a preferred embodiment, the personal healthcare record can be stored on one or more user or patient communication devices which can include, but which are not limited to a personal computer, a laptop computer, a tablet, a cellular telephone, a wireless telephone, a television, a digital television, a personal digital assistant (PDA), a smart phone, a Smartphone, a watch, or any other of the herein-described devices, or other devices, which can be used as a user or patient communication device. The personal healthcare record can be stored in any number of user communication devices.

An individual or patient can utilize the present invention to enter notes, comments, messages, information regarding how they are feeling, information regarding a sickness, an illness, a symptom, information regarding types of medications they must take and time intervals for taking same, information regarding their diet, foods eaten, drinks ingested, exercise activity, provider information, allergies, and/or any other healthcare information, healthcare-related information, wellness information, fitness information, diet information, exercise of fitness information, nutritional information, and/or any other information which can find application in a healthcare or healthcare-related setting or scenario or any other information pertinent to the individual or patient as well as any individual(s) for whom the individual or patient is serving as a caregiver.

An individual or patient can utilize the present invention, at any time and with any suitable user or patient communication device, enter or input, and store in a personal healthcare record, any relevant healthcare information, healthcare-related information, wellness information, fitness information, diet information, exercise of fitness information, nutritional information, and/or any other information which can find application in a healthcare or healthcare-related setting or scenario. The patient communication device can also be programmed to provide timed alerts or messages to remind the individual or patient to take medication, eat certain foods, intake certain liquids, schedule an appointment with a provider, check the status of an insurance claim or a payment claim, to exercise, provide diet or exercise reminders, or to perform any other action or activity for himself or herself or to perform any of the above for a person whom he or she is a caregiver.

The individual or patient can, at any time and from any location, access the present invention and upload or transmit to the central processing computer any and/or all information in his or her personal healthcare record into relevant portions of his or her electronic healthcare record and/or into a portion of same dedicated to receiving and storing the personal healthcare record information. The individual or patient can also download or receive from the central processing computer, any data and/or information that is stored in the individual's or patient's electronic healthcare record(s).

The user or patient communication device can also automatically receive, store or record in the personal healthcare record, and transmit to the central processing computer, and data and/or information which can be obtain with or from a wearable sensor or implantable sensor or device such as a wearable or implantable heart rate monitor, blood pressure monitor, blood sugar monitor, or any other device or monitor which can monitor a physiological parameter(s) or a biometric parameter(s). The user or patient communication device can be linked via a wireless or Bluetooth or other suitable communication link with one or more of these wearable or implantable sensors. Data and/or information obtained from the wearable or implantable sensors can be transmitted to the central processing computer and stored in the individual's or patient's electronic healthcare record(s).

The user or patient communication device and/or the personal health record utilized in connection with same, can be equipped with hardware and/or software for translating any data and/or information from one language into any other language, for translating audio information into text information for storing in the user or patient communication device, for storing audio information, for translating text information into audio information, for providing reminders to schedule appointments with providers, for providing reminders for scheduled appointments with providers, and/or for providing any other functions which are described herein as being performed in connection with the user or patient communication device. The present invention can also be utilized to receive information from an individual or patient regarding a personal healthcare record, store and update an electronic healthcare record with the personal healthcare record information, and thereafter, generate a new personal healthcare record using any new or updated information from the electronic healthcare record(s). The present invention can provide and maintain up-to-date electronic healthcare records and personal healthcare records for individuals or patients.

The user or patient communication device of the present invention can also be utilized to be a personal healthcare monitoring and/or planning tool or device for monitoring and/or planning healthcare and/or healthcare-related activities, events, occurrences, and/or happenings, for the individual or patient, the individual's or patient's children, parents, relatives, or those for whom the individual or patient serves or acts as a caregiver. The user or patient communication device can also be utilized to be a personal wellness, fitness, and/or nutritional monitoring and/or planning tool or device for monitoring and/or planning wellness or wellness-related, fitness or fitness-related, and/or nutritional or nutritional-related, activities, events, occurrences, and/or happenings, for the individual or patient, the individual's or patient's children, parents, relatives, or those for whom the individual or patient serves or acts as a caregiver. The user or patient communication device can also be equipped with any needed or desired software or software application or any number of software applications needed, required, or desired for enabling the user or patient communication device to provide the herein-described features, functions, and/or functionality. The present invention can also be utilized to provide information regarding individual and/or family healthcare planning, and/or monitoring, individual and/or family wellness planning and/or monitoring, individual and/or family fitness planning and/or monitoring, and/or individual and/or family nutritional planning and/or monitoring.

The present invention can also be utilized to schedule appointments, and/or remote or virtual office visits or examinations, with providers and to provide automatically generated appointment reminders.

The present invention can also be utilized to provide social networking functionality and capability via an electronic healthcare record(s) or any. Any of the herein-described individuals, patients, caregivers, providers, insurers, payers, third parties, or other entities, can access a social network via any of the electronic healthcare records described herein. Each and every type or kind of electronic healthcare record utilized in or in connection with the present invention can have information, link(s), or hyperlink(s), to any social networking web sites, web pages, support groups, on-line forums, on-link information services, as well as social networking web sites or social networking web pages to or for social networking members, support groups, information providers, healthcare providers, as well as any of the providers, insurers, payers, individuals, patient, third parties, intermediaries, or any other persons or entities described herein who are or who may be members of any social network.

The present invention can also be utilized to provide an individual or patient with information, or a link(s) or a hyperlink(s) to information, regarding a social networking website or a social networking company, any information provided thereby or thereat, or information regarding any social networking support groups or social networking support group members, on-line seminars, forums, chat room discussions, or others, with which or whom the individual or patient may engage upon the individual or patient being diagnosed with an illness, a sickness, or a condition, or upon the individual or patient about to undergo or undergoing a treatment, a procedure, or an operation, or about to embark upon or already involved in a treatment plan.

The providing of the social networking information to the individual or patient can also serve to allow the individual or patient to learn more about a diagnosis, a treatment, or a treatment plan, to interact with others who have been diagnosed with the same or a similar illness, a sickness, or a condition, or others who may be undergoing the same or a similar treatment or who may be following a same or a similar treatment plan. The present invention can also be utilized so as to identify and provide the individual or patient with information or link(s) or hyperlink(s) to a social networking website, a social networking company, a support group or support groups, a member of the social network members of the social network, social networking lectures, classes, or seminars, social networking sponsored lectures, classes, or seminars, social networking discussions, question and answer sessions, or informational or other forums, or any other social networking or social networking sponsored activities or events, for any number of social networks. The present invention can also be utilized in a same, similar, or analogous manner, in order to process and/or to provide veterinary healthcare information and/or veterinary healthcare-related information for and regarding any kind or type of animal or animals or any type or kind of pet or pets. The present invention can also be utilized as a clearinghouse for facilitating the offering, selling, buying, trading, and/or other commerce and/or transactions, involving healthcare and/or healthcare-related services, products and/or goods.

The present invention can be utilized to allow an individual, a patient, or a caregiver of or for the individual or the patient to engage in a video call, a video chat session, or a videoconference, with a healthcare provider in order to facilitate or to provide for a remote or virtual office visit with the healthcare provider or in order to facilitate or to provided for a remote or distance consultation or examination with or by a healthcare provider.

Any number, kinds, or types, of healthcare providers, who or which have registered with the apparatus of the present invention in order to engage in video calls, video chat sessions, or videoconferences, in order to provide remote or virtual office visits or in order to provide remote or distance consultations or examinations with and for any individuals or patients, or caregivers, can store any data and/or information regarding his or her name, address, telephone number, e-mail address, text messaging information or number(s), or any other contact information, credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

Any of the above-described or herein-described data and/or information regarding the healthcare provider, for any number of healthcare providers, can be stored in, and can be searchable from, the database of the central processing computer. Any of the above-described or herein-described data and/or information regarding the healthcare provider, for any number of healthcare providers, can be also be stored in, and can be searchable from, the database of any provider communication device. Further, any of the above-described or herein-described data and/or information regarding the healthcare provider, for any number of healthcare providers, can be also be stored in, and can be searchable from, the database of any user communication device.

The individual, the patient, or the caregiver of or for the individual or the patient, can access the central processing computer or a respective provider communication device with or using his or her user communication device, or by accessing data and/or information stored in his or her communication device, at any time, in order to search for and/or to select a healthcare provider(s) with whom he or she can schedule a video call, a video chat session, or a videoconference. The individual, the patient, or the caregiver of or for the individual or the patient, can select the individual's or the patient's current healthcare provider, current primary care provider, or a new or different healthcare provider, or a healthcare provider having a certain specialization, or a certain availability. The individual or the patient, or the caregiver of or for the individual or the patient, can make an appointment for a video call, a video chat session, or a videoconference, with the healthcare provider with or using the user communication device. At the time of making the appointment, the individual, patient, or caregiver, can provide a telephone number, a call number, a conference call number, or an IP address, associated with the user communication device which the individual, the patient, or the caregiver, will use for the video call, the video chat session, or the videoconference. At the time of making the appointment, the individual, the patient, or the caregiver, can also be provided with the telephone number, the call number, the conference call number, or the IP address, associated with the provider communication device which will be used by the healthcare provider for the video call, the video chat session, or the videoconference. At the time of making the appointment, the individual, the patient, or the caregiver, can also be provided with an instruction as to whether he or she is to call the healthcare provider at the appointment time, or whether the healthcare provider will call the individual, the patient, or the caregiver, at the appointment time.

In instances when the appointment is being made via the central processing computer, the appointment can be made via the individual's or the patient's electronic medical record, file, or history, which is stored in the database of the central processing computer, and information regarding the appointment can be stored in the individual's or the patient's electronic medical record, file, or history as well as in the healthcare provider's work schedule or in an appointment schedule of the healthcare provider. In instances when the appointment is being made via a provider communication device, the appointment can be made via the individual's or the patient's electronic medical record, file, or history, which is stored in the database of the provider communication device, and information regarding the appointment can be stored in the individual's or the patient's electronic medical record, file, or history as well as in the healthcare provider's work schedule or in an appointment schedule of the healthcare provider. In instances when the appointment is being made via a user communication device, the appointment can be made via the individual's or the patient's electronic medical record, file, or history, or personal healthcare record, which is stored in the database of the user communication device, and information regarding same can be automatically transmitted to and stored in the individual's or the patient's electronic medical record, file, or history in the database of the central processing computer as well as in the healthcare provider's work schedule or in an appointment schedule of the healthcare provider.

The central processing computer can be programmed so that, once an appointment for a video call, a video chat session, or a videoconference, has been made, the central processing computer can automatically generate an appointment message containing information regarding the appointment, and/or the time and date of same, which has been scheduled and will transmit same to the provider communication device of or associated with the healthcare provider with whom the appointment has been made, and will also transmit same to the user communication device(s) of or associated with the individual, the patient, or the caregiver. The provider communication device with which an appointment has been made can also be programmed so that, once an appointment for a video call, a video chat session, or a videoconference, has been made, the provider communication device can automatically generate an appointment message containing information regarding the appointment, and/or the time and date of same, which has been scheduled and will transmit same to any other provider communication device of or associated with the healthcare provider with whom the appointment has been made, and will also transmit same to the user communication device(s) of or associated with the individual, the patient, or the caregiver. The user communication device with which an appointment has been made can also be programmed so that, once an appointment for a video call, a video chat session, or a videoconference, has been made, the user communication device can automatically generate an appointment message containing information regarding the appointment, and/or the time and date of same, which has been scheduled and will transmit same to the central processing computer, to any provider communication device of or associated with the healthcare provider with whom the appointment has been made, and/or to any other user communication device(s) of or associated with the individual, the patient, or the caregiver.

The central processing computer can also be programmed so that, once an appointment for a video call, a video chat session, or a videoconference, has been made, the central processing computer can automatically generate a reminder message(s) containing information for reminding each of the individual, the patient, or the caregiver, and the healthcare provider of the appointment for the video call, the video chat session, or the videoconference. The reminder message or reminder messages can be transmitted to each of the user communication device(s) of or associated with the individual, the patient, or the caregiver, and to the provider communication device of or associated with the healthcare provider.

Any of the appointment messages and/or reminder messages described herein can include the appointment time, the name of the healthcare provider, and the telephone number, the call number, the conference call number, or the IP address, associated with the provider communication device which will be used by the healthcare provider for the video call, the video chat session, or the videoconference, and the name of the individual, the patient, or the caregiver, and the telephone number, the call number, the conference call number, or the IP address, associated with the user communication device which the individual, the patient, or the caregiver, will use for the video call, the video chat session, or the videoconference, and an instruction, if any, as to who is to initiate the video call, the video chat session, or the videoconference, such as, for example, whether the individual, the patient, or the caregiver, is to call the healthcare provider at the appointment time or whether the healthcare provider is to call the individual, the patient, or the caregiver, at the appointment time.

Any of the herein-described appointment messages and/or reminder messages can be stored in the individual's or the patient's electronic healthcare record, file, or history, in the database of the central processing computer and/or in the database of the user communication device, such as in a healthcare provider appointments section or field of same. Likewise, any of the herein-described appointment messages and/or reminder messages can be stored in the healthcare provider's records or files which can also be stored in the database of the central processing computer and/or in the database of the provider communication device such as in an appointments section or field of same.

Any of the herein-described appointment messages or reminder messages can also contain a link or a hyperlink to the electronic healthcare record, file, or history, of the individual or the patient. Any of the herein-described appointment messages or reminder messages can also contain a link or a hyperlink for allowing each of the individual, the patient, or the caregiver of or for the individual or the patient to initiate a video call, a video chat session, or a videoconference, described herein via the link or the hyperlink.

A healthcare provider or any number of healthcare providers can be available for a video call, a video chat session, or a videoconference, at any given time and an individual, a patient, or a caregiver for the individual or the patient, can simply access the central processing computer, see which healthcare provider or healthcare providers are available and can immediately initiate a video call, a video chat session, or a videoconference, with an available healthcare provider.

The apparatus of the present invention can be utilized to in order to allow the healthcare provider to gain authorized access to the individual's or the patient's electronic healthcare records, files, or history, prior to and/or during the video call, the video chat session, or the videoconference, with the individual, the patient, or the caregiver of or for the individual or the patient. In this regard, the healthcare provider can review the individual's or the patient's electronic healthcare records, files, or history, prior to and/or during the video call, the video chat session, or the videoconference, obtain information from same, enter notes, observations, or examination findings, into same, and/or enter information regarding a diagnosis, a treatment, or a treatment plan into same, and/or enter information regarding and/or prescribe a medication or a drug, prescribe a therapy of any kind or type, prescribe a treatment of any kind or kind, and/or make a referral to another healthcare provider. Any and/or all information, including a video or a video clip, and/or an audio, a video, and/or an audio and video recording, of the video call, the video chat session, or the videoconference, can be recorded and stored in the individual's or the patient's electronic healthcare records, files, or history.

The present invention can be utilized in order to allow a healthcare provider to conduct a video call, a video chat session, or a videoconference with an individual, a patient, or a caregiver of the individual or the patient, in order to allow the healthcare provider to conduct a remote or virtual office visit with, or to conduct a remote or distance examination of, the individual or the patient. The healthcare provider can obtain any information, needed or desired for conducting the remote or virtual office visit or the remote or distance examination, from the individual, the patient, or the caregiver, during the video call, the video chat session, or the videoconference. The healthcare provider can also access and/or obtain information from the individual's or the patient's electronic healthcare record, file, or history. The healthcare provider can also obtain information from any healthcare measuring device or equipment, any healthcare measurement device or equipment, or any healthcare monitoring device or equipment, or obtain and/or transmit any data and/or information from any healthcare equipment input device, healthcare measurement input device, or healthcare monitoring input device described herein.

The healthcare provider can enter any notes and/or observations regarding the individual or the patient and/or regarding any data and/or information obtained or reviewed during the video call, the video chat session, or the videoconference, into the individual's or the patient's electronic healthcare record, file, or history.

The healthcare provider can also make or arrive at a diagnosis for the individual or the patient, and/or prescribe a treatment, or a course of treatment, or provide a treatment plan, or generate or issue a prescription for a drug or a medication, or generate or issue a prescription for a test or procedure, or make a referral to another healthcare provider, for the individual or the patient. The healthcare provider can utilize any information contained in the individual's or the patient's electronic healthcare record, file, or history, in order to take into account any allergies, possible drug or medication interactions, or any other information regarding the individual or the patient which must be considered in making a diagnosis, and/or in prescribing a treatment, or a course of treatment, or in providing a treatment plan, or in generating or issuing a prescription for a drug or a medication, or in generating or issuing a prescription for a test or a procedure, or in making a referral to another healthcare provider, for the individual or the patient. Any prescription(s) or referral(s) generated or issued can be electronically sent, such as by e-mail, instant message, SMS message, MMS message, or in any other suitable communication device to any provider communication device of or associated with the individual's or the patient's pharmacy or to any other healthcare provider to whom the respective prescription or referral is to be sent.

The healthcare provider can also enter any information regarding any notes, observations, examination findings, and/or any other information obtained during the video call, the video chat session, or the videoconference, into the individual's or the patient's electronic healthcare record, file, or history, so as to update same to include information regarding the video call, the video chat session, or the videoconference, and the remote office visit or the virtual office visit and/or the remote examination or the distance examination which was conducted during same with the individual, the patient, or the caregiver.

The video call, which can be recorded, can also be stored in the individual's or the patient's electronic healthcare record, file, or history, for retrieval at any time by the healthcare provider or another healthcare provider, or by the individual, the patient, the caregiver, or another caregiver, or by a healthcare insurer or a healthcare payer, or by an intermediary, or by any other authorized person or entity, at any time.

The apparatus or the central processing computer can, after any and/or all information obtained during and/or regarding the video call has been entered by the healthcare provider and stored in the individual's or the patient's electronic healthcare record, file, or history, can generate a video call report and/or a remote or virtual office visit report or a remote or distance examination report, containing information regarding the video call and/or information regarding the video call and/or the remote or virtual office visit or the remote of distance examination, and can transmit the video call report and/or remote or virtual office visit report or a remote or distance examination report in, as, or attached to, an e-mail message or in, as, or attached to, an electronic communication transmission, to the provider communication device of or associated with the individual's or the patient's primary care healthcare provider or any other healthcare provider of the individual or the patient, to a user communication device of or associated with the individual, the patient, or a caregiver of the individual or the patient, to a payer communication device of or associated with a healthcare insurer or a healthcare payer of the individual or the patient, and/or to an intermediary communication device of or associated with an intermediary. Any remote or virtual office visit report or a remote or distance examination report generated by the apparatus of the present invention can also be stored in the individual's or the patient's electronic healthcare record, file, or history.

The apparatus or the central processing computer, which can be programmed to generate and transmit an insurance claim form or a request for payment form, can utilize the information stored by the healthcare provider in order to generate an insurance claim form or a request for payment form. The apparatus or the central processing computer, which can be programmed to generate and transmit a request for payment of co-payment form, can generate a request for payment of co-payment form. The apparatus or the central processing computer can transmit the insurance claim form or a request for payment form, in, as, or attached to, an e-mail message, or in, as, or attached to any other suitable electronic communication transmission, to the payer communication device of or associated with the healthcare insurer or the healthcare payer of the individual or the patient. The apparatus or the central processing computer can also transmit the request for payment of co-payment form in, as, or attached to, an e-mail message, or in, as, or attached to any other suitable electronic communication transmission, to the user communication device.

Any insurance claim form(s) or a request for payment form(s) and any request for payment of co-payment form(s) generated by, and/or transmitted by, the apparatus or the central processing computer can be stored in the individual's or the patient's electronic healthcare record, file, or history.

In this regard, the apparatus and method of the present invention can be utilized to facilitate and/or to conduct remote or virtual healthcare provider visits, consultations, and/or examinations, via and/or through the use of video calls, video chat sessions, and/or videoconferences, with and between an individual, a patient, and/or a caregiver for the individual or the patient. The apparatus and method of the present invention can also be utilized to schedule remote or virtual provider visits, consultations, and/or examinations, via and/or through the use of video calls, video chat sessions, and/or videoconferences, with and between an individual, a patient, and/or a caregiver for the individual or the patient.

The present invention can also be utilized in connection with, or in conjunction with, a distributed ledger and with Blockchain technology. A distributed ledger and Blockchain technology can be utilized along with a central processing computer, in a combined system, wherein certain of the transactions, described herein as being performed by the apparatus, can be processed and/or performed by and/or with a central processing computer and/or certain other transactions can be processed and/or performed by and/or with, and/or using, a distributed ledger and Blockchain technology or Blockchain technologies. Any and/or all transactions, described herein as being performed and/or processed by the apparatus, can also be processed and/or performed by and/or with, and/or using, a distributed ledger and Blockchain technology or Blockchain technologies, and/or using any cryptocurrency Blockchain technology or technologies.

Any type of Blockchain technology can be utilized in connection with the apparatus and methods of the present invention. For example, the apparatus and methods of the present invention can utilize a distributed ledger(s) along with any Blockchain technology or technologies, Bitcoin Blockchain technology or technologies, Ethereum Blockchain technology or technologies, Bitcoin Cash Blockchain technology or technologies, Litecoin Blockchain technology or technologies, Privacy Coin Bitcoin technology or technologies, and/or any other suitable Blockchain technology or technologies, and/or Smart contracts and/or Smart contract technology or technologies and/or decentralized autonomous organizations (DAOs), decentralized autonomous organizations (DAOs) technology or technologies, and/or any combination of same.

Applicant incorporates by reference herein the subject matter and teachings of "Blockchain Technology Explained" by Alan T. Norman, "Blockchain" by Abraham K. White, "Blockchain—A Practical Guide To Developing Business, Law, And Technology Solutions" by Joseph J. Bambara and Paul R. Allen, and "Blockchain—Ultimate Guide To Understanding Blockchain, Bitcoin, Cryptocurrencies, Smart Contracts And The Future of Money" by Mark Gates, in their entirety, for all of their respective subject matter and teachings regarding distributed ledger technology and/or technologies, Blockchain technology and/or technologies, Bitcoin technology and/or technologies, Bitcoin Blockchain technology and/or technologies, Ethereum technology and/or technologies, Ethereum Blockchain technology and/or technologies, cryptocurrencies, cryptocurrency technology and/or technologies, and/or smart contract technology and/or technologies, and/or decentralized autonomous organizations (DAOs) technologies, and/or peer-to-peer technology and/or technologies, and/or any other technology or technologies related thereto or which can be utilized in conjunction distributed ledgers, Blockchain technologies, Smart contracts, decentralized autonomous organizations (DAOs), and/or cryptocurrencies.

By utilizing a distributed ledger and a suitable Blockchain technology, the apparatus and methods of the present invention can reduce the amount of processing performed by, and reliance on, a central processing computer and/or can eliminate the need for a central processing computer and any centralized entity which might operate the central processing computer.

A central processing computer and distributed ledger and Blockchain technology system can be utilized which includes a central processing computer component, which can perform any and/or all of the functions described herein as being performed by the central processing computer, and a distributed ledger and Blockchain technology system component, which can also perform any and/or all of the functions described herein as being performed by the central processing computer.

Any and/or all of the various operations, transactions, functions, and/or functionalities, described herein as being performed by the apparatus can be performed by either a central processing computer component of the central processing computer/distributed ledger/Blockchain technology system and/or by the distributed ledger and Blockchain technology system component of the central processing computer/distributed ledger/Blockchain technology system.

Transactions which are to be processed by the central processing computer component and by the distributed ledger and Blockchain technology system component can be pre-selected or pre-programmed into the central processing computer/distributed ledger/Blockchain technology system, and can be re-programmed at any time. The use of the distributed ledger and Blockchain technology system component can be utilized to provide added security for the individual's or the patient's electronic healthcare record, file, or history, and can also be utilized to prevent healthcare identity theft involving the individual or patient.

The apparatus and method of the present invention can also be utilized to facilitate and/or to conduct remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary. The apparatus and method of the present invention can also be utilized to schedule remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The apparatus and method of the present invention can also be utilized to facilitate healthcare claims processing. Any of the individuals, patients, caregivers, providers, insurers or payers, and/or intermediaries or third parties, or any other users, can file claims with the respective insurer, payer, or party, electronically via the apparatus of the present invention. The apparatus of the present invention can facilitate an expedited and/or a paperless claim process or request for payment process. The apparatus of the present invention can also provide for, or facilitate, automatic claim submission or request for payment submission to an insurer or payer.

The apparatus of the present invention can also be utilized in order to claim or request healthcare insurance benefits, disability insurance benefits, and/or life insurance benefits. The apparatus can also administer and/or maintain financial accounts for, and/or on behalf of, any of the individuals, patients, caregivers, users, providers, insures or payers, and/or intermediaries or third parties, described herein.

The present invention can, in addition, be utilized in order to maintain individual, patient, or caregiver, electronic healthcare records or electronic healthcare files private and/or to safeguard individual, patient, or caregiver, electronic healthcare records or electronic healthcare files, by restricting and/or by limiting access to the respective electronic healthcare records or electronic healthcare files.

The present invention can also be utilized to issue prescriptions or scripts for medicines, medications, or drugs, to pharmacies on an individual's or a patient's behalf, or to issue prescriptions or scripts for procedures, tests, analyses, analysis work-ups, blood work, treatments, therapy, therapy sessions, physical therapy, physical therapy sessions, or any other prescribed goods, services, or activities, or to issue referrals to other healthcare providers or providers of any other goods or services. The apparatus of the present invention can also be utilized to perform drug-drug and drug-allergy interaction checks.

The apparatus and method of the present invention can also be used to provide for the remote control and/or monitoring of any of the herein-described healthcare devices, healthcare equipment, healthcare testing devices or equipment, healthcare information gathering devices or equipment, or healthcare monitoring devices or equipment. The apparatus and method of the present invention can also be utilized in order to perform a remote procedure on an individual or patient, a remote surgery or surgical procedure on an individual or patient, or to remotely administer a treatment to an individual or patient.

The present invention can also be utilized in connection with, or in conjunction with, a distributed ledger and with Blockchain technology and/or with RFID tags and RFID reader systems and/or with various personal monitoring systems, in order to provide for numerous other applications for using, and/or uses for, the present invention.

The apparatus of the present invention can also include any number of RFID reader systems, or any number or RFID tags and RFID readers, which can be utilized as described herein. The apparatus of the present invention can also include any number of governmental entity/intermediary communication device(s) which can be used by governmental entities and/or intermediaries as described herein. The apparatus of the present invention can also include any number of user/patient monitoring systems which can include any number of monitoring devices and/or healthcare measurement tools or devices for use as described herein.

Each or the provider communication devices, the insurer/payer communication devices, the user communication devices, and/or the governmental entity/intermediary communication devices, can include a global positioning device for determining the position or location of the respective device.

The apparatus of the present invention can be utilized in various embodiments to provide a wide range of healthcare and tele-health functionalities as described herein, including, but not limited to remote or virtual office visits and video calls with healthcare providers.

The apparatus of the present invention can also utilize position or location information regarding the position or location of an individual's or patient's user communication device and/or a healthcare provider's provider communication device in processing information for determining if a transaction involving the individual's or patient's healthcare account or involving the individual's or patient's healthcare insurance account is authorized or allowed, or is unauthorized or not allowed, and/or for determining if a video call, a video chat session, or a videoconference, a remote office visit, a virtual office visit, a remote examination, or a distance examination, is authorized or allowed, or is unauthorized or not allowed.

The apparatus of the present invention, can be utilized in order to perform position-based or location-based transaction security, account security, or transaction authentication, for any healthcare transaction(s), healthcare account transaction(s), and/or remote healthcare transaction(s), which authentication can be based on the position, location, or geographic location of the user communication device, and/or of a healthcare provider's provider communication device, and, hence, the individual or patient, or his or her caregiver, and/or a healthcare provider, at a time, or at the time, of any performance, or attempted performance, by the individual or patient, or his or her caregiver, or the healthcare provider, of any healthcare transaction, healthcare account transaction, and/or remote healthcare transaction, involving the individual or patient or any healthcare account(s) or healthcare insurance account(s) of, for, or associated with the individual or patient.

In another preferred embodiment, as well as in any and/or all of the embodiments described herein, the apparatus 300 and methods of the present invention can also be utilized in, in connection with, or in conjunction with, the providing of in-person healthcare services and/or in-person healthcare-related services, and/or in, in connection with, or in conjunction with, any in-person transactions involving individuals or patients and/or healthcare providers. In a preferred embodiment, the apparatus 300 of the present invention can be used to determine and/or verify an identity of an individual or patient and provide a healthcare provider with access to the individual's or patient's healthcare record(s), file(s), or history or histories.

The apparatus of the present invention can also be utilized in order to provide public health and/or public safety services, and/or any other health services to or for any individuals or patients who utilize the same. The apparatus of the present invention can also be utilized in order to detect, store, and provide, data and/or information, to any and/or all users, individuals, or patients, when a person, who has, or who has been determined to be inflicted with, a sickness or an illness, or an adverse or other health condition, or a bacterial infection, a viral infection, or a contagious infection, or who are determined to be in need of an immunization or immunizations, which condition, circumstance, or state of affairs, can or might pose a public health threat to the public at large and/or which can or might pose a particular threat to any user, individual, or patient, enters into or onto any public or private buildings, structures, properties, or venues, and/or any room, area, or section, of the same, and/or of any commercial, public, or private, vehicles. The apparatus of the present invention can also be utilized by governmental entities, public entities, and/or private entities.

The present invention can also be utilized in order to update any and/or all of the electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs), of or for any user, individual, or patient, any time any one such electronic healthcare record (EHR), electronic medical record or electronic healthcare file (EMR), electronic dental record or file (EDR), electronic pharmacy record or file (EPR), electronic behavioral health record or file (EBHR), or personal health record or file (PHR), of a user, individual, or patient, is updated, changed, alerted, or modified.

The present invention can also be utilized in order to allow an individual or patient, or a caregiver of the individual or patient, to have control over the respective individual's or patient's numerous electronic healthcare records (EHRs), electronic medical records or electronic healthcare files (EMRs), electronic dental records or files (EDRs), electronic pharmacy records or files (EPRs), electronic behavioral health records or files (EBHRs), and/or personal health records or files (PHRs). In this regard, the individual or patient can utilize the present invention in order to grant permission, to a healthcare provider, a healthcare provider, a healthcare insurer or a healthcare payer, and/or to an intermediary or governmental entity, and/or to any other person or entity, to access or use, and/or to update, change, alter, or modify, any information or data contained in the individual's or patient's various electronic record(s) or health records.

The present invention can also be utilized by an individual, a patient, or a caregiver for an individual or patient, to schedule an appointment for an in-office visit, an in-office examination, an in-person visit, an in-person examination, a house-call visit, a house-call examination, a tele-health appointment, a tele-health visit, a remote or a virtual provider visit, or a remote or a distance examination.

The present invention can also be utilized in order to allow an individual or patient, or a caregiver of the individual or patient, to identify, and/or to locate, or to allow the apparatus of the present invention, to select, identify, or locate, a healthcare provider who is available for conducting an in-office visit, an in-office examination, an in-person visit, an in-person examination, a house-call visit, a house-call examination, a tele-health appointment, a tele-health visit, a remote or a virtual provider visit, or a remote or a distance examination, with the individual or patient, or the caregiver, at any given moment in time, and/or in an emergency situation and/or on an emergency basis.

Any of the data and/or information, of any type or kind, and including, but not limited to, any and/or all of the data, information, messages, reports, video recordings or video clips, audio recordings, pictures, photographs, and/or other information, described herein as being transmitted to, received by processed by, generated by, transmitted from, or stored by or in, the apparatus of the present invention can also be stored by and in a distributed ledger and Blockchain technology system.

The present invention can also be utilized in order to provide healthcare tracking, healthcare monitoring, treatment tracking, treatment plan tracking, and/or wellness tracking, for individuals or patients.

Intelligent agents, software agents, mobile agents, and/or related technologies, can be utilized in conjunction with the present invention. The respective intelligent agent(s), software agent(s), mobile agent(s), (hereinafter referred to collectively as "intelligent agent" or "intelligent agents") can be programmed and/or designed to act on behalf of the respective users, individuals, patients, caregivers, providers, insurers or payers, and/or intermediaries, so as to act on behalf of the respective party as well as to perform any of processing functions and/or other functions described herein.

In another preferred embodiment, the intelligent agent can act on behalf of the respective person or party in various related interactions and/or other activities which are described as being performed herein and/or which may be incidental and/or related thereto. Therefore, the present invention also provides an agent-based apparatus and method for providing healthcare information and/or healthcare-related information.

The apparatus of the present invention, in any and/or all of the embodiments described herein, can also be programmed to be self-activating and/or activated automatically.

In any and/or all of the embodiments described herein, the apparatus of the present invention can also be utilized in a same, similar, or analogous manner, in order to process and/or to provide veterinary healthcare information and/or veterinary healthcare-related information for and regarding any kind or type of animal or animals or any type or kind of pet or pets. In this regard, it is to be understood that the present invention can be utilized by any user, individual, caregiver, provider, insurer or payer, or intermediary, in order to process healthcare or healthcare-related information for any animals and/or pets.

The present invention can also provide for cloud-based healthcare or healthcare-related data and/or information processing and/or storage, cloud-based electronic healthcare records, cloud-based electronic healthcare records storage and/or retrieval, a cloud-based electronic healthcare records system or platform, and/or cloud based processing and/or storage of any and/or all of the data and/or information described herein as being processed by the apparatus and methods of the present invention.

Any data and/or information regarding any of the herein-described insurance claims, claims for payment, and/or any other request for a payment, for, regarding, or relating to, any video call, video chat session, or videoconference, can contain, or can contain as an attachment, a copy of a recording of the video call, the video chat session, or the videoconference.

Further, any data and/or information regarding any of the herein-described insurance claims, claims for payment, and/or any other request for a payment, for, regarding, or relating to, any video call, video chat session, or videoconference, can be stored in the electronic healthcare record of or for the individual or the patient using the distributed ledger and/or blockchain technology system.

BRIEF DESCRIPTION OF THE DRAWINGS

In the Drawings:

FIGS. 29A and 29B illustrate yet another preferred embodiment method of utilizing the apparatus of the present invention, in flow diagram form; and FIG. 30 illustrates another preferred embodiment method of utilizing the apparatus of the present invention, in flow diagram form.

DESCRIPTION OF THE PREFERRED EMBODIMENTS

Figure 1:
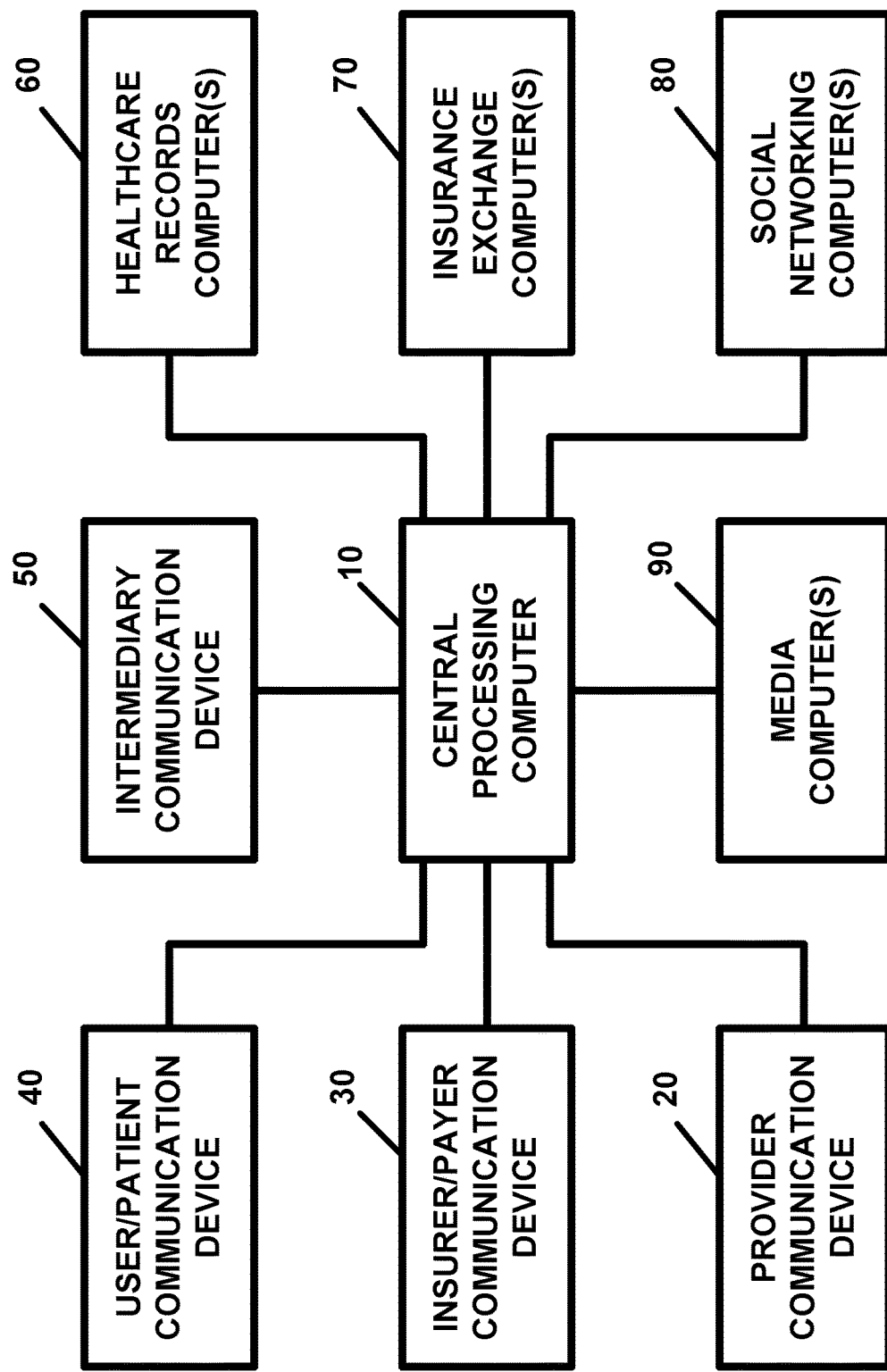
FIG. 1 illustrates a preferred embodiment of the apparatus of the present invention, in block diagram form.

The present invention pertains to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional.

The present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus and method of the present invention can be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribe a treatment based on any and/or all any and/or all information regarding the individual or the patient. As a further result, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented in the individual's or the patient's healthcare records, files, or history.

As used herein, the term "electronic healthcare record" or "EHR" means any electronic healthcare record, electronic healthcare file, electronic medical record, electronic dental record, electronic pharmacy record, electronic behavioral health record, and/or any other record or record keeping system, software, hardware, or device, or any combination of same or group of same, which can contain healthcare information or healthcare-related information.

As used herein, the terms "individual", "patient", "client", "user" or the like, or their plural forms, refers to any person, individual, patient, entity, and/or client, who or which uses the present invention, and/or who seeks and/or who receives healthcare services, healthcare-related services, healthcare-related information, and/or any of the other services and/or products provided by the present invention. The terms "individual", "patient", "client", "user" or the like, or their plural forms, also refer to any athlete or participant of or in any sport or sports or any activity or activities, an athlete or a sports participant of any age, a professional athlete, a minor league athlete, an Olympic athlete, a competitive athlete, a government team athlete, a world class competition athlete, an amateur athlete, a college athlete, a high school age athlete, a child athlete, a secondary school athlete, a recreational organization athlete or member, a child recreational organization athlete or member, an adult recreational organization athlete or member, a little league athlete or member, a boys club athlete or member, a girls club athlete or member, a hobbyist athlete, or any other individual, male or female, who participate in athletic endeavors, sporting events, exercise activities, martial arts, mixed martial arts, boxing, wrestling, or physical activities, or any team sport or activity or individual sport or activity.

As used herein, the term "caregiver" or the plural of same, refers to any parent, child, agent, attorney, representative, guardian, legal guardian, or any other person or entity who or which is responsible for caring for, looking after, or otherwise taking care of any healthcare needs of any individual or patient. The term "caregiver" also refers to any organization, governmental entity, business, team, league, club, network, or any other entity, or any employee or agent of same, which or who oversees, manages, uses, employs, provides oversight over, owns or otherwise has playing or managing rights over, provides control over, or provides or is responsible for the healthcare of, any of the herein-described or other athletes or sports participants.

As used herein, the terms "doctor", "healthcare provider", "provider", "therapist", "healthcare information specialist", etc., or their plural forms, refers to any medical doctor, including any and all of the various medical specialists and/or specialties, including, but not limited to internists, orthopedists, ophthalmologists, cardiologists, hematologists, endocrinologists, oncologists, ears, nose and throat specialists, neurologists, urologists, gastroenterologists, dermatologists, pediatricians), medical specialist, surgeon, surgical specialists, including any and/or forms and/or types of surgeons), physician, dentist, psychiatrist, psychologist, optometrist, podiatrist, osteopath, chiropractor, pharmacist, therapist, physical therapist, respiratory therapist, nurse, healthcare aid, nutritionist, and/or any other person, individual and/or professional who can provide healthcare, healthcare-relate, wellness and/or wellness-related services and/or products.

As used herein, the terms "insurer", "payer", "insurance provider", "heath insurance provider", "life insurance provider", "disability insurance provider", etc., or their plural forms, refers to any insurance companies, healthcare insurance companies, disability insurance companies, property or casualty insurance companies, health maintenance organizations, healthcare providers, and any other payer and/or provider of healthcare services and/or products, who which provide and/or pay for healthcare and/or healthcare-related benefits, services, and/or products, and/or who or which provide respective health insurance, life insurance and/or disability insurance benefits, services and/or products. The terms "insurer" or "payer" can also refer to any government or governmental agency, department, of entity, which provides healthcare services or which provides payment(s) for healthcare and/or healthcare services.

As used herein, the terms "broker", "agent", "billing service", "collection agent", "manager", "intermediary", "assistant", etc., or their plural forms, refer to any broker, insurance broker, agent, insurance agent, intermediary, third party, billing service provider, collection agent, claim processing agent, and/or any other person, individual, and/or entity, which acts on behalf of, or for, any of the individuals, patients, doctors, healthcare providers, insurers, payers, etc., described herein. The terms "telehealth" and "tele-health" are used interchangeably herein.

Applicant hereby incorporates by reference herein the subject matter and teachings of U.S. Provisional Patent Application Ser. No. 63/009,986, filed Apr. 14, 2020, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

Applicant hereby incorporates by reference herein the subject matter and teachings of U.S. Provisional Patent Application Ser. No. 63/019,410, filed May 3, 2020, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

Applicant hereby incorporates by reference herein the subject matter and teachings of U.S. Provisional Patent Application Ser. No. 63/038,866, filed Jun. 14, 2020, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

Applicant hereby incorporates by reference herein the subject matter and teachings of U.S. patent application Ser. No. 16/202,448, filed Nov. 28, 2018, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

Applicant hereby incorporates by reference herein the subject matter and teachings of U.S. patent application Ser. No. 14/638,934, filed Mar. 4, 2015, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

Applicant hereby incorporates by reference herein the subject matter and teachings of U.S. Provisional Patent Application Ser. No. 61/971,225, filed Mar. 27, 2014, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

FIG. 1 illustrates the apparatus of the present invention, in block diagram form. The apparatus of the present invention is denoted generally by the reference numeral 100. In the preferred embodiment, the apparatus 100 of the present invention includes a central processing computer or central processing computer system 10 (hereinafter referred to as the "central processing computer 10"). In the preferred embodiment the central processing computer 10 can be a network or server computer.

In the preferred embodiment, the central processing computer 10 can provide control over the apparatus 100 and can perform any of the various processing services and/or functions described herein. The central processing computer 10 may be a single computer or system of computers and/or may be include a plurality of computers or computer systems which are utilized in conjunction with one another. The central processing computer 10, in the preferred embodiment can provides services for any of the other computers and/or computer systems described herein as being associated with any of the individuals, patients, healthcare providers, insurers, payers, brokers, agents, and/or intermediaries, described herein.

The apparatus 100 also includes a healthcare provider communication device or computer 20 (hereinafter referred to as "provider communication device 20" or "provider computer 20") which is associated with a healthcare provider such as a healthcare professional, a hospital, a clinic, a pharmacy, a treatment center, a treatment facility, and/or any other provider of services described herein. Any healthcare professional, hospital, clinic, pharmacy, treatment center, treatment facility, and/or any other provider of services, healthcare or otherwise, which is described herein can also be referred to herein as a "provider". A provider computer 20 can also be associated with, or can be used by, any research institution, research facility, teaching institution, teaching hospital, college, university, school, or other institution or entity which may perform research, or provide research information or any related information regarding studies, findings, or developments, in the healthcare field or in healthcare-related fields. A provider computer 20 can also be associated with, or can be used by, any public health department, public health agency, public health facility, or other public health entity, on any one or more of a national level, a country level, a state level, a provincial level, a county level, a city level, a municipal level, or any other level, which is entrusted to provide for the public health and/or to perform services or oversight regarding public health. A provider computer 20 can also be associated with, or can be used by, any immunization registry or immunization registries. A provider computer 20 can also be associated with, or can be used by, any source or provider of educational or instructional information, or information regarding instructions or procedures, or links or hyperlinks to same.

Any number or amount of healthcare provider computers 20 can be utilized in conjunction with a healthcare provider and/or group of providers. The healthcare provider communication device(s) 20 can communicate with, and operate in conjunction with, the central processing computer 10 and/or any of the other computers and/or computer systems associated with any of the other individuals and/or entities which utilize and/or operate in conjunction with the present invention.

The apparatus 100 can also include a healthcare insurer or payer communication device or computer 30 (hereinafter referred to as "payer communication device 30" or "payer computer 30") which is associated with a healthcare payer such as a healthcare insurer, insurance company, health maintenance organization, a clinic, and/or any other payer of healthcare services and products described herein. Any number or amount of healthcare payer computers 30 can be utilized in conjunction with a healthcare payer and/or group of payers. The healthcare payer communication device(s) 30 can communicate with, and operate in conjunction with, central processing computer 10 and/or any of the other computers and/or computer systems associated with any of the other individuals and/or entities which utilize and/or operate in conjunction with the present invention.

The apparatus 100 can also include a user, patient, or individual, communication device or computer 40 (which may hereinafter be referred to either as "user communication device 40", "user or patient communication device 40", "user computer 40", "patient computer 40", or "user or patient computer or communication device 40") which is associated with any user of the apparatus 100 or any individual or healthcare patient or client who seeks or who is provided with healthcare and/or related services, products and/or related information. The user or user or patient communication device 40 can also be utilized by any individual, party, or entity, who or which may merely utilize the present invention in order to care or another individual or to obtain information of interest.

A user or user or patient communication device 40 may also be located at public places or locations, such as at kiosks or other publicly available computer or communication devices. Any number or amount of user or patient computers 40 can be utilized in conjunction with a user, patient, group of users, and/or group of patients. The user or patient communication device 40 can communicate with, and operate in conjunction with, the central processing computer 10 and/or any of the other computers and/or computer systems associated with any of the other individuals and/or entities which utilize and/or operate in conjunction with the present invention. The user or patient communication device 40 can also be utilized by any other individual or entity desiring to utilize and/or to obtain information from the apparatus 100.

The apparatus 100 can also include an intermediary communication device or computer 50 (hereinafter referred to as "intermediary communication device 50" or "intermediary computer 50") which is associated with an intermediary, a broker, an agent, and/or any other individual and/or entity, that can utilize the present invention in order to act for and/or on behalf of any other individual, party, or entity, described herein. Any number or amount of intermediary computers 50 can be utilized in conjunction with an intermediary and/or group of intermediaries. The intermediary computer(s) 50 can communicate with, and operate in conjunction with, the central processing computer 10 and any of the other computers and/or computer systems associated with any of the other individuals and/or entities which utilize and/or operate in conjunction with the present invention.

In the preferred embodiment, any of the provider communication device(s) 20, the payer computer(s) 30, the patient computer(s) 40, and/or the intermediary computer(s) 50, can be any computer or communication device, including, but not limited to, a personal computer, a home computer, a server computer, a network computer, a hand-held computer, a palmtop computer, a laptop computer, a personal communication device, a cellular telephone, a wireless telephone, a mobile telephone, a digital television, an interactive television, a digital television, a personal digital assistant, a telephone, a digital telephone, a television, an interactive television, a beeper, a pager, and/or a watch.

Each of the central processing computer(s) 10, the provider communication device(s) 20, the payer communication device(s) 30, the patient computer(s) 40, and/or the intermediary computer(s) 50, can transmit information to, as well as receive information from, any of the computers 10, 20, 30, 40, and 50, described herein. In this regard, each of the computers 10, 20, 30, 40, and 50, can communicate with, process information from, and/or share data and/or information with, each other and/or any other computer or computers 10, 20, 30, 40, and 50, described herein and/or utilized in conjunction with the present invention. In this manner, data and/or information transfer between any of the computers 10, 20, 30, 40, and 50, can communicate with any other computer or computers 10, 20, 30, 40, and 50, in a bi-directional manner.

The central processing computer(s) 10, the provider communication device(s) 20, the payer computers(s) 30, the patient computer(s) 40, and the intermediary computer(s) 50, can communicate with one another, and/or be linked to one another, over a communication network, a telecommunication network, a telephone network, a line-connected network, and/or a wireless communication network. Each of the computers 10, 20, 30, 40, and 50, can be linked with any other computer or computers directly or indirectly directly or indirectly with one another so as to facilitate a direct or indirect bi-directional communication said respective computers. Communications between each of the computers 10, 20, 30, 40, or 50 can also involve an e-mail server or e-mail servers in those instances when e-mails are described as being used to transmit or send any of the information, signals, messages, reports, notification messages, or any other communications, described herein, by or between any of the computers 10, 20, 30, 40, or 50, or when any of the information, signals, messages, reports, notification messages, or any other communications, described herein, are transmitted by and/or between any of the parties described herein and/or by or between any of the computers 10, 20, 30, 40, or 50, or any other computers or communication devices, computer systems, communication network equipment, server computers, etc., or any other devices used or needed in order to facilitate communications or the transmission of any of the herein-described information, signals, messages, reports, notification messages, or any other communications.

The apparatus 100 can also include a healthcare records computer 60 or computers (hereinafter referred to as "healthcare records computer 60" or "healthcare records computer(s) 60) which can be or can include a computer or computer system, or any number of computers or computer systems, or a cloud computer system or cloud system. The healthcare records computer can serve to store and house an electronic healthcare record or electronic healthcare files or any number of electronic healthcare records or electronic healthcare files. In the preferred embodiment, the healthcare records computer 60 can be associated with any provider, insurer, payer, intermediary, insurance exchange, or any user, individual, patient, organization, or entity, who or which utilizes the apparatus 100 and method of the present invention.

Each healthcare records computer 60 can be utilized to store an electronic healthcare record or electronic healthcare file or any number of electronic healthcare records or electronic healthcare files which can be accessed by the central processing computer 10, by any provider communication device 20, by any insurer or payer communication device 30, by any user or patient communication device 40, by any intermediary communication device 50, or by any other computer, communication device or other device described herein as being utilized in connection with the apparatus 100 and method of the present invention. The healthcare records computer 60 can also be utilized to facilitate cloud storage of any electronic healthcare record(s) or electronic healthcare file(s).

The apparatus 100 can also include an insurance exchange computer 70, or any number of insurance exchange computers 70 which can be utilized to process and store information regarding the selling of healthcare insurance, disability insurance, and life insurance, policies, products, and/or services, to any of the herein-described users, individuals, patients, or entities, who or which utilize the apparatus 100 and method of the present invention. The insurance exchange computer 70 can be utilized to advertise, provide information regarding, sell, and/or maintain records regarding, and process any other information regarding, group insurance as well as individual or family insurance policies, products, or services. The insurance exchange computer 70 can also be utilized to sell automobile, homeowners, business, and/or liability insurance policies, products, or services.

The apparatus 100 can also include a social networking computer 80. The social networking computer 80 can be linked with, and utilized in connection with, the apparatus 100 so as to allow and/or facilitate integrating the apparatus 100 of the present invention with social networks, social networking, and social media. In a preferred embodiment, for example, the social networking computer 80 can be associated with a social networking company, a social networking website, or social networking entity, website, group, organization, or association. The social networking computer 80 can be associated with any one or any number of social networking companies, social networking websites, or social networking entities, websites, groups, organizations, or associations. The social networking computer 80 can also provide links to any computers associated with any one or any number of social networking companies, social networking websites, or social networking entities, websites, groups, organizations, or associations. In the preferred embodiment, the social networking computer 80 can perform any and all of the functions performed by any social networking company, a social networking website, or social networking entity, website, group, organization, or association. In a preferred embodiment, any number of social networking computers 80 can be utilized in connection with the apparatus 100 of the present invention.

The apparatus 100 can also include a media computer 90. In the preferred embodiment, the media computer 90 can provide, and be a source of, news information, current events information, healthcare information, healthcare or healthcare-related news, current events, advertisements, and/or marketing information or materials, which can be disseminated via the apparatus 100 of the present invention, In a preferred embodiment, any number of media computers 90, with each being dedicated to providing any number, types, or kinds of, news information, current events information, healthcare information, healthcare or healthcare-related news, current events, advertisements, and/or marketing information or materials, can be utilized in connection with the apparatus 100.

In a preferred embodiment, each of the central processing computer(s) 10, the provider communications devices 20, the payer communication devices 30, the user or patient communication devices 40, the intermediary communication devices 50, the healthcare records computers 60, the insurance exchange computers 70, the social networking computers 80, and the media computers 90 can communication in a bi-directional manner with, and/or can send and/or receive signals, messages, reports, notification messages, alerts, or any other communications or electronic communication transmissions, to, from and/or between, any other, or any number of, other central processing computer(s) 10, if utilized, provider communications devices 20, payer communication devices 30, user or patient communication devices 40, intermediary communication devices 50, healthcare records computers 60, insurance exchange computers 70, social networking computers 80, and/or the media computers 90.

In a preferred, each of the central processing computer(s) 10, the provider communications devices 20, the payer communication devices 30, the user or patient communication devices 40, the intermediary communication devices 50, the healthcare records computers 60, the insurance exchange computers 70, the social networking computers 80, and the media computers 90 can be linked to or with any other central processing computer(s) 10, if utilized, provider communications devices 20, payer communication devices 30, user or patient communication devices 40, intermediary communication devices 50, healthcare records computers 60, insurance exchange computers 70, social networking computers 80, and/or the media computers 90 via a wired link or line or a wireless link.

In a preferred embodiment, each of the provider communications devices 20, payer communication devices 30, user or patient communication devices 40, intermediary communication devices 50, healthcare records computers 60, insurance exchange computers 70, social networking computers 80, and/or the media computers 90 can be connected with or linked with the central processing computer 10 as shown in FIG. 1.

In a preferred embodiment, any and/or all of the signals, messages, reports, notification messages, or any other communications, described herein as being transmitted from one device, computer, or communication device, to another, can be, or can be included in, or be attached to, an e-mail message, an instant messaging message, an electronic transmission, or an electronic data transmission or electronic data interchange, or can be transmitted via any other data or information transmission, and can be transmitted via or using any appropriate or necessary computer(s) or device(s).

In the preferred embodiment, the present invention is utilized on, and/or over, the Internet and/or the World Wide Web. The present invention, in the preferred embodiment, can also utilize wireless Internet and/or World Wide Web services, equipment and/or devices. The central processing computer(s) 10, in the preferred embodiment, has a web site or web sites associated therewith. Each of the other computers or communication devices described herein can also have a web site or web sites associated with same.

Although the Internet and/or the World Wide Web is a preferred communication system and/or medium utilized, the present invention, in all of the embodiments described herein, can also be utilized with any appropriate communication network or system including, but not limited to, a communication network or system, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, a cable television network or system, and/or any other communication network or system, and/or any combination of the above communication networks or systems.

In the preferred embodiment, each of the central processing computer(s) 10, the provider communication device(s) 20, the payer communication device(s) 30, the patient computer(s) 40, the intermediary computer(s) 50, the healthcare records computer(s) 60, the insurance exchange computer(s) 70, the social networking computer(s) 80, and the media computer(s) 90, can transmit data and/or information using TCP/IP, as well as any other Internet and/or World Wide Web, and/or communication, protocols.

The apparatus 100 of the present invention can utilize electronic commerce technologies and security methods, techniques and technologies, in any and/or all of the instances of data and/or information processing, and/or data and/or information transmission described herein.

Figure 2:
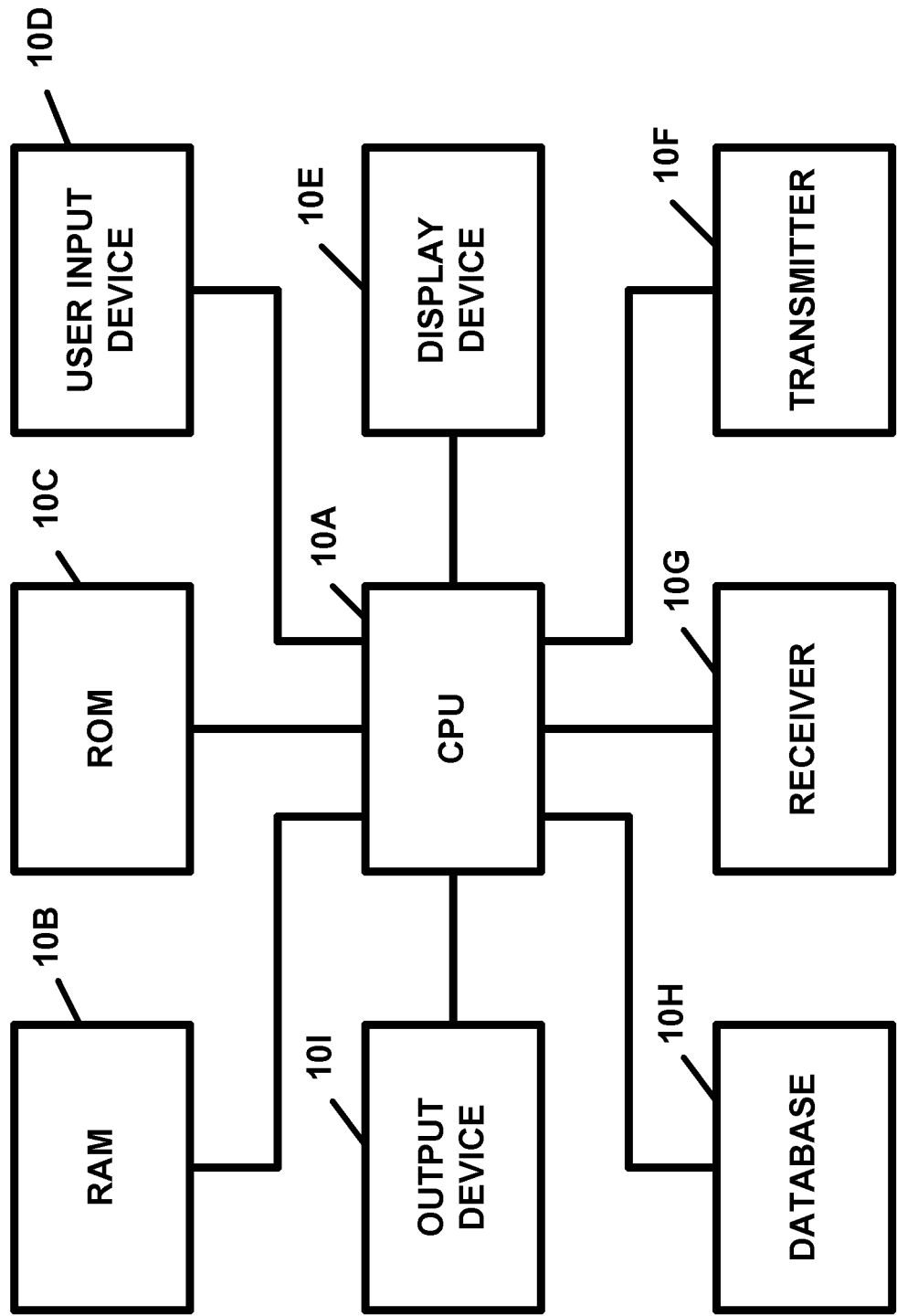
FIG. 2 illustrates the central processing computer of FIG. 1, in block diagram form.

FIG. 2 illustrates the central processing computer 10, in block diagram form. The central processing computer 10, in the preferred embodiment, is a network computer or computer system, or any other communication device which can provide the functionality of, and which can be utilized as a central processing computer such as an Internet server computer and/or a web site server computer. In the preferred embodiment, the central processing computer 10 includes a central processing unit or CPU 10A, which in the preferred embodiment, is a microprocessor. The CPU 10A may also be a microcomputer, a minicomputer, a macro-computer, and/or a mainframe computer, depending upon the application. The central processing computer 10 also includes a random access memory device(s) 10B (RAM) and a read only memory device(s) 10C (ROM), each of which is connected to the CPU 10A, a user input device 10D, for entering data and/or commands into the central processing computer 10, which includes any one or more of a keyboard, a scanner, a user pointing device, such as, for example, a mouse, a touch pad, and/or an audio input device and/or a video input device, a microphone or audio recording device, a camera or a video recording device, and/or any device, electronic and/or otherwise which can be utilized for inputting and/or entering healthcare data and/or information, for example pulse rate monitors, blood pressure monitors, electrocardiograms, glucose monitors, blood-sugars monitors, blood oxygen or percentage oxygen measurement devices, etc., if desired, which input device(s) are also connected to the CPU 10A. The central processing computer 10 also includes a display device 10E for displaying data and/or information to a user or operator.

The central processing computer 10 also includes a transmitter(s) 10F, for transmitting signals and/or data and/or information to any one or more of the central processing computer(s) 10, the provider communication device(s) 20, the payer computers(s) 30, the patient computer(s) 40, and the intermediary computer(s) 50, the healthcare records computer(s) 60, the insurance exchange computer(s) 70, the social networking computer(s) 80, and the media computer(s) 90, or any other individual computer(s), which may be utilized in conjunction with the present invention. The central processing computer 10 also includes a receiver 10G, for receiving signals and/or data and/or information from any one or more of the central processing computer(s) 10, the provider communication device(s) 20, the payer computers(s) 30, the patient computer(s) 40, and the intermediary computer(s) 50, the healthcare records computer(s) 60, the insurance exchange computer(s) 70, the social networking computer(s) 80, and the media computer(s) 90, which may be utilized in conjunction with the present invention.

The central processing computer 10 also includes a database(s) 10H which contains data and/or information pertaining to the patients, providers, payers, and intermediaries who or which are serviced by the present invention and/or who or which utilize the present invention.

The database 10H can contain any one or any number of electronic healthcare records (EHRs), which electronic healthcare records definition includes electronic healthcare records or electronic healthcare files, electronic medical records or electronic healthcare files (EMRs), electronic dental records or files (EDRs), electronic pharmacy records or files (EPRs), electronic behavioral health records or files (EBHRs), as well as any personal health records or files (PHRs). The database 10H can contain any one or any number of electronic healthcare records (EHRs), which electronic healthcare records definition includes electronic healthcare records or electronic healthcare files, electronic medical records or electronic healthcare files (EMRs), electronic dental records or files (EDRs), electronic pharmacy records or files (EPRs), electronic behavioral health records or files (EBHRs), as well as any personal health records or files (PHRs) for each user, individual, or patient, who utilizes the apparatus and methods of the present invention. The database 10H can contain any one or any number of electronic healthcare records (EHRs), which electronic healthcare records definition includes electronic healthcare records or electronic healthcare files, electronic medical records or electronic healthcare files (EMRs), electronic dental records or files (EDRs), electronic pharmacy records or files (EPRs), electronic behavioral health records or files (EBHRs), as well as any personal health records or files (PHRs), of or for any number of users, individuals, or patients.

The database 10H can also contain and/or include, for each individual or patient, and/or in each respective electronic healthcare record or electronic healthcare file, electronic medical record or electronic healthcare file (EMR), electronic dental record or file (EDR), electronic pharmacy record or file (EPR), electronic behavioral health record or file (EBHR), as well as any personal health record or file (PHR), for the respective individual or patient, information regarding any and/or all immunizations previously provided to the individual or patient, information regarding any and/or all immunizations not yet, or not previously, provided to the individual or patient, information regarding any and/or immunizations needed by the individual or patient, and/or any information regarding any previous or current diagnosis, or state of health, regarding any disease, viral infection, bacterial infection, sickness, infirmity, weakness, or ailment, of or regarding the individual or patient, with which the individual or patient has been diagnosed, or which the individual or patient is currently experiencing or enduring.

The database 10H can also contain and/or include, for each user, individual, or patient, a digital certificate or any number of digital certificates which can contain information regarding any and/or all immunizations previously provided to the individual or patient, information regarding any and/or all immunizations not yet, or not previously, provided to the individual or patient, information regarding any and/or immunizations needed by the individual or patient, and/or any information regarding any previous or current diagnosis, or state of health, regarding any disease, viral infection, bacterial infection, sickness, infirmity, weakness, or ailment, of or regarding the individual or patient, with which the individual or patient has been diagnosed, or which the individual or patient is currently experiencing or enduring.

The database 10H can also contain and/or include passport information or other official identification information for any user, individual, or patient. In a preferred embodiment, the passport information or other official identification information for any user, individual, or patient, can also include or contain, or include as an attachment, a digital certificate or any number of digital certificates which can contain information regarding any and/or all immunizations previously provided to the individual or patient, information regarding any and/or all immunizations not yet, or not previously, provided to the individual or patient, information regarding any and/or immunizations needed by the individual or patient, and/or any information regarding any previous or current diagnosis, or state of health, regarding any disease, viral infection, bacterial infection, sickness, infirmity, weakness, or ailment, of or regarding the individual or patient, with which the individual or patient has been diagnosed, or which the individual or patient is currently experiencing or enduring.

The database 10H can also contain any links or hyperlinks to any of the above electronic healthcare records or electronic healthcare files, electronic medical records or files, electronic dental records or files, electronic pharmacy records or files, electronic behavioral health records or files, and/or personal health records or files, which may be located or stored on any computer or computers external from the central processing computer 10, for any number of users, individuals, or patients.

Each of the herein-described electronic healthcare records, electronic medical records, electronic dental records, electronic pharmacy records, and/or electronic behavioral health records can also contain a personal health record portion. The apparatus 100 and method of the present invention can store a personal health record for each individual or patient. The personal health record can be stored in each individual's or patient's respective electronic healthcare record(s), electronic medical record(s), electronic dental record(s), electronic pharmacy record(s), and/or electronic behavioral health record(s), as well as in any user or patient communication device 40. The personal healthcare record can be updated as described herein or in any other appropriate manner.

The database 10H can also contain a look-up table or look-up tables and/or data and/or information relating thereto, for identifying and locating a respective electronic healthcare record(s), an electronic medical record, an electronic dental records, an electronic pharmacy record, an electronic behavioral health record, or a personal health records, for or associated with any user, individual, patient, or person who may utilize the apparatus 100 of the present invention. In this regard, the database 10H can store any healthcare data and/or information or healthcare-related data and/or information for any user, individual, patient, or person who may utilize the apparatus 100 of the present invention, whether that information is stored in the central processing computer 10, the database 10H, or any provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90, regardless of where these computers or communications devices are located and regardless of what data and/or information is stored on same.

In the preferred embodiment, the database 10H contain data and/or information for locating, retrieving, storing, or providing a comprehensive healthcare record of healthcare file for any individual, user, patient, or person. The database 10H can also contain any necessary data or information for locating, identifying, retrieving, storing, any information from any of the various types of kinds of electronic healthcare records or electronic healthcare files regarding of the type, kind, and/or vendor or supplier of same, regardless of where these electronic healthcare records or electronic healthcare files are located or stored. In a preferred embodiment, the database 10H can also contain an index or other information for identifying data fields in the respective databases of the various respective electronic healthcare records for enabling the central processing computer 10 to identify data and/or information in each of the respective electronic healthcare records or electronic healthcare files.

The database 10H can also contain any data and/or information for allowing any herein-described user, individual, patient, person, provider, payer, intermediary, or entity, to access or obtain any of the herein-described data and/or information, wherever such data and/or information is located or stored, as well as to perform any function described herein as being capable of being performed by the apparatus 100 of the present invention.

The database 10H can also contain any data and/or information for integrating, linking to or with, and/or accessing data and/or information stored or located in, any number, type, or kind, of any of the herein-described electronic healthcare records or electronic healthcare files, electronic medical records or files, electronic dental records or files, electronic pharmacy records or files, electronic behavioral health records or files, as well as any personal health records or files.

The database 10H can contain any of the herein-described data and/or information for any number of individuals, users, patients, or persons. The database 10H can also contain data and/or information regarding a name, relationship, and authorization for any parent, relative, legal guardian, caregiver, healthcare proxy holder, or any person, individual, or entity, who or which may be responsible for caring for, accessing, updating, or maintaining healthcare records or files for, making decisions for, or making healthcare-related decisions for, taking actions for, providing care for, or performing any task or activity for, any other individual(s), user(s), patient(s), or person(s). For example, the database 10H can, for a child, contain information regarding the child's parent or legal guardian, and for the database 10H, for an elderly person of any other person, contain information regarding the person's child, caregiver, healthcare proxy holder, or any other authorized person or entity, or for individuals who belong to a school or club's athletic program, or a sports team, a club, a social or other organization, the database 10H can contain information regarding a coach, team doctor, trainer or other authorized individual.

The database 10H can contain any and/or all of the information needed and/or required in order to perform any and/or all of the functions, services and/or operations described herein as being performed by the central processing computer 10 or the apparatus 100 of the present invention. In this regard the database 10H can contain data and/or information regarding patient name, patient identification information, patient social security number or other identification information, date of birth, sex, gender, race, nationality, ethnicity, spoken language, preferred language, other languages, religion or religious affiliation, next-of-kin, relatives, emergency contact person, doctors or providers, therapists, nutritionists, insurance or payer information, group insurance information, group health insurance information, life insurance information, disability insurance information, patient address, phone number, e-mail and/or other contact information, medical history, psychological history, dental history, family history, family medical, psychological, and/or dental history, past and/or current or active symptoms, past and/or current or active diagnoses, past and/or current or active treatments or treatment plans, care management plan or plans, allergies, active or current medications or prescription drugs, active or current medication allergies, past, active, or current allergies, smoking status, insurance coverage, insurance co-payment and/or deductible information, co-payment information regarding any payer or insurer insurance policy or payment plan, deductible information regarding any payer or insurer insurance policy or payment plan, benefit eligibility information, insurance information, insurance claim procedures, insurance claim forms, doctor or provider appointment schedules, past treatments, past diagnosis, symptoms, insurance claim forms, employer information, lifestyle information, treatment plans, treatment progress, broker/agent/intermediary information, education information, age, sex, marital status, employee benefits information, types or services and/or treatments needed, and any other data and/or information regarding the patient which would be needed and/or desired in order to perform any and/or all of the functions, services and/or operations described herein.

The database 10H can also contain provider office visit summaries, hospital discharge summaries, hospital discharge instructions, and/or any examination, treatment, testing, or procedure, summary, and any instructions, treatment plan or instructions, care management plan or instructions, or any other information which can be provided to any individual, patient, provider, payer, insurer, third party or intermediary, or caregiver, described herein as using the apparatus 100 and method of the present invention, or described herein as being able to receive services, provide services, or otherwise use or be serviced by, the apparatus 100 and method of the present invention.

In the case of deceased patients or individuals, the database 10H can contain information regarding date of death, place of death, preliminary cause of death, and/or final determination of cause of death. The database 10H can also contain information regarding any other information regarding a deceased patient or individual and can also contain information regarding final resting place.

The database 10H can also contain, for each patient or individual, information regarding dates of appointments or services with or from healthcare providers or other providers, dates of laboratory tests, dates of treatments, operations, or procedures, dates of doctor visits, therapy sessions, vital signs, healthcare chart changes, or information regarding height, weight, blood pressure, heart rate, pulse rate, body-mass index, growth charts, and/or any other related or pertinent data or information.

The database(s) 10H can also contain healthcare and/or medical video, image, and/or audio, and/or text, data and/or information, and/or surgical video, image, and/or audio, and/or text, data and/or information, and/or dental video, image, and/or audio, and/or text, data and/or information, such as, for example, x-rays, Magnetic Resonant Images (MM), CAT scans, digital x-ray files, digital Magnetic Resonant Imaging (MM) files, digital CAT scan files, and/or any other video, imaging, and/or audio, healthcare data and/or information which can be utilized by healthcare providers, payers, intermediaries, patients, and/or other users of the present invention. In this manner, the present invention can facilitate the availability of any of the above-described video, image, and/or audio, data and/or information in a network environment. For example, a medical specialist can have access to, and/or review, an MM or a CAT scan for a patient, from any location and at any time.

The database 10H can also contain data and/or information regarding providers including provider name, provider social security number or identification number, type of professional or service provider, address, phone number, fax number, e-mail and/or other contact information, experience, specialties, insurances accepted, schedule of charges, financial account identification information, resume information, education, work experience, claim forms, appointment schedules, procedures performed, and/or any other data and/or information concerning the providers for providing any and/or all of the functions, services, and/or operations described herein as being performed by the present invention.

The database 10H can also contain data and/or information regarding all possible fields of medicine, surgery, psychiatry, psychology, dentistry, oral surgery, optometry, podiatry, physical therapy, respiratory therapy, hypnosis, osteopathy, nutrition, wellness, and/or any other possible healthcare fields and/or subject matter which can possibly by utilized in the processing and/or operation of the present invention.

The database 10H can also contain information on illnesses, symptoms, diseases and/or sicknesses, theories, scientific theories, research data and/or information, diagnosis information, treatment information, treatment plans, treatment processes, treatment progresses, treatment interactions, side effects, expected treatment results, treatment providers, treatment durations, treatment costs, pre-treatment information, post-treatment information, treatment monitoring information, statistical information regarding diagnoses, treatments, treatment success rates, treatment failure rates, treatment centers, therapy plans, therapy success rates, therapy failure rates, treatment procedures, medications treatments, non-medication treatments, healthcare institutions, treatment evaluating criteria, treatment mistakes and/or mishaps, indicators of mistakes and/or mishaps, corrective actions, links to providers, links to treatment centers or institutions, reimbursement rates, nutrition information, diet information, exercise information, exercise routines, treatment options, healthcare advise, wellness advice, preventive care, preventive procedure, health maintenance, drug and medication information, drug interaction information, video information, including video files or clips and other information, regarding illnesses, diseases, treatments and follow-up care, audio information, including audio files or clips and other information, regarding illnesses, diseases, treatments and follow-up care, treatment and/or procedure information and/or narratives, treatment analysis, diagnosis analysis, diagnosis monitoring, diagnosis confirmation and/or checking, and/or other information for providing the herein-described functions, services, and/or operations.

The database 10H can also contain information regarding the insurance companies and payers described herein, including, but not limited to, payer name, address, phone number, fax number, e-mail address, identification number(s), coverage types, policies and/or coverages provided, reimbursement rates, patients and/or providers serviced and/or covered by the payer, policy information, claim forms, claim procedures, claim status, claim processing information, claim submission procedures and policies, reasonable and customary charges, co-payment information, pre-approval information and/or procedures, claim form information, electronic form claim forms, insurance and/or coverage requirements, guidelines, and/or triggering events, covered procedures and/or treatments, uncovered procedures and/or treatments, claim approval information, claim approval history, claim approval statistics, claim rejection or denial information, claim rejection or denial history, claim rejection or denial statistics, financial account information, network provider information, network patient information, claim statistics, preventative care and/or benefits information, benefits information, benefits request information and/or claim forms, claim submission information, claim processing information, claim status information, payment information and statistics, and/or any other data and/or information regarding and/or related to payers which are needed and/or desired for providing any and/or all of the functions, services, and/or operations described herein.

The database 10H can also contain data and/or information regarding the brokers, agents and/or intermediaries described herein, including, but not limited to, intermediary name, address, phone number, fax number, e-mail address, clients, patients services, insurance policies, policy information, policy quote information, policy proposal information, any and/or all of the above information described herein regarding patients, providers, payers, etc., which may be of interest to the intermediaries described herein which may be useful and/or beneficial to the intermediaries in providing any of the functions, services, and/or operation described herein.

The database 10H can also contain contact information such as phone numbers, fax numbers, pager numbers, beeper numbers, e-mail addresses, hyperlinks to, and/or any other information which can facilitate contact between any of the parties described herein. The database 10H also includes electronic signature data and/or information for any of the parties, patients, providers, payers, and/or intermediaries, described herein for facilitating transactions, claim submissions, financial transactions, etc., by and/or between any of the above patients, providers, payers, and/or intermediaries.

The database 10H can also contain and notes, comments, or messages, which can be provided by any user, individual, patient, caregiver, provider, insurer, payer, third party, intermediary, or any other person or entity who or which utilizes the apparatus 100 and method of the present invention.

The database 10H can also contain any number of electronic healthcare records, electronic medical records, electronic dental records, electronic pharmacy records, electronic behavioral health records, and/or links to other electronic healthcare records, electronic medical records, electronic dental records, electronic pharmacy records, electronic behavioral health records which might be located in healthcare records computers 60 or other computers or computer systems located remote from the central processing computer 10. Any and/or all of these electronic healthcare records, electronic medical records, electronic dental records, electronic pharmacy records, electronic behavioral health records can contain data and/or information and/or link or hyperlinks to data and/or information regarding any individuals, patients, his or her caregivers, children, parent, relatives, friends, social networking friends, connections, of followers, providers, insurers or payers. The databases 10H can also contain any and/or all information regarding the data and/or information fields in each electronic healthcare record, electronic medical record, electronic dental record, electronic pharmacy record, and/or electronic behavioral health record, information for mapping common or like data fields for each and information or links or hyperlinks for accessing like data or like information fields in each of the different electronic healthcare records, electronic medical records, electronic dental records, electronic pharmacy records, electronic behavioral health records.

The data and/or information in the database 10H can also include links to any other information, information sources, news sources, and/or other information and/or data which can or may be utilized by the present invention and/or by any of the patients, providers, payers, intermediaries and/or any other users of the present invention.

The database 10H can also contain data and/or information regarding healthcare news, healthcare developments, healthcare discoveries, etc., for and including the medical field, surgical field, psychological field, dental field, nutrition field, fitness field, etc., and/or any other healthcare field or fields.

The database 10H, in the preferred embodiment, can also contain video and/or audio files which can be utilized for training of healthcare professionals as well as for providing general information to any user of the present invention. In this manner, and as will be described hereinbelow, the apparatus 100 can be utilized as a simulator for providing training in medical diagnosing, medical training, surgical training, psychiatric training, psychological training, dental training, oral surgery training, therapist training, and/or for training any of the healthcare providers described herein and/or envisioned.

For example, the present invention can be utilized to provide a medical doctor with a set of symptoms, evaluate the diagnosis and treatment prescribed and provide follow-up patient conditions which may or may not call for the medical doctor to re-evaluate his or her diagnosis and/or treatment. In a similar fashion, the present invention can be used for training and continuing education and training for any of the healthcare providers described herein and/or otherwise envisioned utilizing the present invention.

The database 10H can also contain data and/or information restricting access by any of the providers, payers, patients, intermediaries, and/or other users, to any of the data and/or information stored in the database 10H.

The database 10H can also contain information correlating symptoms and/or conditions with diagnoses, prognoses, and/or treatments, treatment methods, procedures, etc. The database 10H also contains any and/or all information needed and/or desired for facilitating the processing of symptoms, conditions, medical histories, family histories, and other information, in order to arrive at diagnoses and/or prognoses, treatments, prescriptions, procedures and/or any other healthcare and/or healthcare-related information.

The database 10H can also contain information regarding medical records, medical charts, x-rays, MRIs, and/or any other information, described herein and/or otherwise, which can be associated with an individual's or patient's medical history, medical record, or medical file, for any individual or patient who utilizes the apparatus 100 and method of the present invention.

The database 10H can also contain information regarding surgical records, surgical charts, x-rays, MRIs, and/or any other information, described herein and/or otherwise, which can be associated with an individual's or patient's surgical history, surgical record, or surgical file, for any individual or patient who utilizes the apparatus 100 and method of the present invention.

The database 10H can also contain information regarding dental records, dental charts, x-rays, and/or any other information, described herein and/or otherwise, which can be associated with an individual's or patient's dental history, dental record, or dental file, for any individual or patient who utilizes the apparatus 100 and method of the present invention.

The database 10H can also contain information regarding a prescription drug record, file, or account, for an individual or patient for any individual or patient who utilizes the apparatus 100 and method of the present invention.

The database 10H can also contain information regarding a healthcare spending account or healthcare spending accounts for any individual or patient, or for any of the individuals or patients, described herein or otherwise, who utilize the apparatus 100 and method of the present invention. For example, the healthcare spending account is or can be an account which can be a deposit account, a credit account, a debit account, an electronic money or an electronic cash account, or any combination of same, which can be held by any individual, patient, employer, bank, credit union, financial institution, investment institution, healthcare insurer, healthcare payer, or any other third party, and which can be used as a source of funds for payment for any type of healthcare service or healthcare product which is provided to, or administered to, or sought by, any individual or patient who utilizes the apparatus 100 and method of the present invention. In a preferred embodiment, the healthcare spending account can be used by the individual or patient to pay for any healthcare service, treatment, procedure, or product, at any time a payment is desired to be made for same.

The database 10H can also contain and/or include, for each individual, patient, caregiver, healthcare provider, or any other provider, healthcare insurer or healthcare payer, or any intermediary, who or which utilizes the apparatus 100 of the present invention, information regarding, or a link or a hyperlink, to any information regarding a telephone number or an IP address, or other contact information, for to regarding any communication device or computer which can be utilized by the respective individual, patient, caregiver, healthcare provider, or any other provider, healthcare insurer or healthcare payer, or any intermediary, in making and/or in engaging in any of the video calls, video chat sessions, or videoconferences, described herein.

The database 10H can also contain and/or include, for each healthcare provider who or which utilizes the apparatus 100 of the present invention and who or which desires to engage in video calls, video chat sessions, or videoconferences, and/or in remote or virtual office visits or in remote or distance examinations, any data and/or information or a link or hyperlink to any data and/or information regarding or containing the healthcare provider's work schedule(s) as well any information for allowing any individual, patient, or caregiver, to schedule and/or conduct a video call, a video chat session, or a videoconference, and/or a remote or a virtual office visit or a remote or a distance examination, with the healthcare provider.

The database 10H can also contain and/or include, for each healthcare provider who or which utilizes the apparatus 100 of the present invention and who or which desires to engage in video calls, video chat sessions, or videoconferences, any data and/or information or a link or hyperlink to any data and/or information regarding or containing the healthcare provider's work schedule(s) as well any information for allowing any healthcare insurer or healthcare payer, or any intermediary, to schedule and/or conduct a video call, a video chat session, or a videoconference, with the healthcare provider.

The database 10H can also contain and/or include, for each healthcare insurer or healthcare payer who or which utilizes the apparatus 100 of the present invention and who or which desires to engage in video calls, video chat sessions, or videoconferences, any data and/or information or a link or hyperlink to any data and/or information regarding or containing the healthcare insurer's or healthcare payer's work schedule(s) as well any information for allowing any individual, patient, or caregiver, or any healthcare provider, or any intermediary, to schedule and/or conduct a video call, a video chat session, or a videoconference, with the healthcare insurer or the healthcare payer.

The database 10H can also contain and/or include, for each intermediary who or which utilizes the apparatus 100 of the present invention, and who or which desires to engage in video calls, video chat sessions, or videoconferences, any data and/or information or a link or hyperlink to any data and/or information regarding or containing the intermediary's work schedule(s) as well any information for allowing any individual, patient, or caregiver, or any healthcare provider, or any healthcare insurer or healthcare payer, to schedule and/or conduct a video call, a video chat session, or a videoconference, with the intermediary.

The database 10H can also contain and/or include, for each healthcare provider who or which has registered with the apparatus 100 in order to engage in video calls, video chat sessions, or videoconferences, in order to provide remote or virtual office visits or in order to provide remote or distance consultations or examinations with and for any individuals or patients, or caregivers, any data and/or information regarding the healthcare provider's name, address, telephone number, e-mail address, text messaging information or number(s), or any other contact information, credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

The database 10H can also contain, for each individual or patient who utilizes the apparatus 100 and method of the present invention, information regarding, or a record of, each and every instance of a provider office visit involving the individual or patient, a communication(s) with a provider or providers involving or regarding the individual or patient, a payment(s) made by or on behalf of the individual or patient, an insurance claim(s) made by a provider or providers on a healthcare insurance policy or account for or regarding the individual or patient, including information regarding date of claim, time of claim, or the provider making the claim, a co-payment(s) made by or on behalf of the individual or patient, a payment(s) made on an insurance claim, a denial(s) of an insurance claim or insurance claims, or a resolution(s) of an insurance claim or insurance claims. The database 10H can also contain information regarding a history or record of insurance claims made by a provider or providers, or made by an individual or patient, for each individual or patient who utilizes the apparatus 100 and method of the present invention.

The database 10H can also contain and/or include, for each individual, patient, or caregiver of or for the individual or the patient, any recordings of any of the herein-described video calls, video chat sessions, or video conferences, in which the individual, patient, or caregiver of or for the individual or the patient, was a party to or participated in.

The database 10H can also contain and/or include for each individual, patient, or caregiver of or for the individual or the patient, any of the herein-described video call reports, remote or virtual office visit reports, remote or distance examination reports, insurance claim forms, request for payment forms, and/or request for payment of co-payment forms, generated for, pertaining to, or associated with, the each individual, patient, or caregiver of or for the individual or the patient.

The database 10H can also contain credit report data or information, a credit report, credit reports, or a credit history, for any individual or patient, or for any of the individuals or patients, described herein or otherwise, who utilize the apparatus 100 and method of the present invention. The credit report or credit reports, or credit history, can contain any of the information which is typically provided by, or which may be provided by, any commercial or other credit reporting company or agency, such as, for example, but not limited to, credit reporting companies such as TransUnion LLC, Experian Information Solutions, Inc., Equifax, Inc., or any other credit reporting company, agency, or bureau, or any credit card company or financial institution. The database 10H can also contain any data or information which is typically found in a credit report database or credit history database, and/or any data and/or information which is, or which can be, utilized in generating, and/or analyzing, a credit report or credit reports, or a credit history, for, or on behalf of, any individual or patient, or for any of the individuals or patients, described herein or otherwise, who utilize the apparatus 100 and method of the present invention. The database 10H can also contain e-mail contact information, telephone contact information, cellular telephone contact information, and/or any other suitable contact information, for an individual or patient which can be utilized to notify the individual or patient when information regarding his or her credit report or credit reports, or credit history, is accessed, obtained, changed, or when a new entry of information is made in same.

The database 10H can also include advertisements, advertisement materials and information, marketing materials or information, commercials, video clips, infomercials, and any other information, which can include text information, video information, audio information, or any combination of same, which can be used to provide an advertisement, or advertisement material or information, to or for any individual, patient, provider, healthcare provider, payer, healthcare payer, insurer, healthcare insurer, product provider, service provider, third party provider, or any other person or entity, who or which utilizes the apparatus 100 and method of the present invention. A respective advertisement, advertisement material and information, marketing material or information, commercial, video clips, infomercials, and/or any other information, can be used to advertise or market any product(s) or service(s) which can be used by, provided to, provided by, advertised to, advertised by, marketed to, or marketed by, any individual, patient, provider, healthcare provider, payer, healthcare payer, insurer, healthcare insurer, product provider, service provider, third party provider, or any other person or entity, who or which utilizes the apparatus 100 and method of the present invention.

The database 10H can also contain news information, news reports, published reports, theses, study reports, or any other data or information regarding health issues, healthcare issues, health conditions, diseases, treatments, drugs, medications, healthcare procedures, medical procedures, surgical procedures, dental procedures, prescription products or services, non-prescription products or services, over-the-counter products or services, health or wellness issues or recommendations, exercise issues or recommendations, alternate therapy or treatment types or recommendations, herbal therapies or recommendations, or any other data or information which can be used by or provided to any individual, patient, provider, healthcare provider, payer, healthcare payer, insurer, healthcare insurer, product provider, service provider, third party provider, or any other person or entity, who or which utilizes the apparatus 100 and method of the present invention. The news information, news reports, published reports, theses, study reports, or any other data or information can include text information, video information, audio information, or any combination of same.

The news information, news reports, published reports, theses, study reports, or any other data or information, stored in the database 10H, can be transmitted to, or fed to, the central processing computer 10, for storage in the database 10H, by or from any appropriate computer or communication device, which is associated with or used by any news source, news organization, research institution, research professional, healthcare facility, an author, researcher, academician, or any other individual, person, or entity. An intermediary communication device 50 can also be utilized to transmit the news information, news reports, published reports, theses, study reports, or any other data or information to the central processing computer 10.

The database 10H can also contain prescription drugs information, prescription medication information, over-the-counter drug or medication information, wellness information, exercise and fitness information, and/or any other information pertinent to an individual's or a patient's heath, well-being, or treatment.

The database 10H can also include language translation information or software so that any of the data or information described herein as being stored in the database 10H, or as being provided in any of the messages, reports, or other communications, described herein can be translated into any language.

The database 10H can also contain, for each individual, patient, provider, and/or insurer or payer who or which utilize the apparatus 100, data and/or information regarding charges made to an individual or patient, charges made by a provider, charges made by an insurer or payer, amounts paid to an individual or patient, amounts paid by an individual or patient to a provider, amounts paid by an insurer or payer to a provider, amounts paid by an insurer or patient to an individual or patient, amounts paid by an individual or patient to an insurer or payer, a charges-back(s) made regarding a payment to, for, or by, a provider, a charge-back(s) made regarding a payment to, for, or by, an individual or patient, and/or a charge-back(s) made regarding a payment to, for, or by, an insurer.

The database 10H can also contain any notes, comments, or messages, which can be provided in text, in audio recordings or audio clips, and/or in video recordings or video clips. The database 10H can also contain any data, information, and/or software programs for translating audio information to text information and for translating test information to audio information. The database 10H can also contain any data, information, and/or software programs for translating text information or audio information from one language to another so as to provide a multi-lingual healthcare information and records keeping system. The database 10H can also contain any notes, comments, or messages, which can be provided by any of the herein-described users, individuals, patients, providers, insurers, payers, third parties, intermediaries, and/or any other person or entity who or which utilizes the apparatus 100 and method of the present invention.

The database 10H can also contain any notes, comments, or messages, which can be stored in any and/or all of the electronic healthcare records or electronic healthcare files, electronic medical records or files, electronic dental records or files, electronic pharmacy records or files, electronic behavioral health records or files, and/or personal health records or files, described herein as being utilized in connection with the apparatus 100 and method of the present invention. In this regard, it is important to note that, in a preferred embodiment of the present invention, any and/or all of the electronic healthcare records or electronic healthcare files, electronic medical records or files, electronic dental records or files, electronic pharmacy records or files, electronic behavioral health records or files, and/or personal health records or files, described herein as being utilized in connection with the apparatus 100 are or can be designed to receive, store, and/or provide, any notes, comments, and/or messages, provided by any of the herein-described users, individuals, patients, providers, insurers, payers, third parties, intermediaries, and/or any other person or entity, as text information or in text form, as audio information or in audio form, or as video information or in video form. Any text or audio information can be translated to from text to audio or from audio to text, and any text or audio information can be translated from one language to any one of more of any other language.

The database 10H can also contain sports medicine-related data and/of information for and including healthcare records, histories, or files, of and for athletes or sports participants of any age and in or for any sport or athletic activity. The database 10H can also contain data and/or information regarding healthcare records, histories, and/or files, for any athletes or sport participants and their respective organizations, teams, clubs, leagues, or other entities. The database 10H can also contain data and/or information for creating and for maintaining a comprehensive and/or centralized sports medicine healthcare record, history, and/or file, system for athletes or participants of any sport or sports or any activity or activities, athletes or sports participants of any age, professional athletes, minor league athletes, Olympic athletes, competitive athletes, government team athletes, world class competition athletes, amateur athletes, college athletes, high school age athletes, children athletes, secondary school athletes, recreational organization athletes or members, child recreational organization athletes or members, adult recreational organization athletes or members, little league athletes or members, boys club athletes or members, girls club athletes or members, hobbyist athletes, or any other individuals, male or female, who participate in athletic endeavors, sporting events, exercise activities or programs, the martial arts, mixed martial arts, boxing and other fighting or combat sports, any and/or all team sports, including but not limited to baseball, football, basketball, hockey, soccer, lacrosse, track and field, gymnastics, car racing, skiing and winter sports, swimming and aquatic sports, weightlifting, dancing, and/or any other sports or sporting activities, and/or other physical activities, or any team sporting activities or individual sporting activities.

The database 10H can also contain data and/or information regarding any organization, governmental entity, business, team, league, club, network, or any other entity, which oversees, manages, uses, employs, provides oversight over, owns or otherwise has playing or managing rights over, provides control over, or provides or is responsible for the healthcare of, any of the herein-described or other athletes or sports participants.

The database 10H can also contain data and/or information for or regarding sports-related injuries or athletic related injuries, or conditions, or other healthcare information relating to sports-related injuries, athletic injuries, sport-related conditions, and/or athletics-related conditions.

The database 10H can also contain data and/or information for diagnosing, treating, treatment planning, curing, rehabilitating, and/or for performing therapy or therapies for, sports-related injuries or conditions or athletic-related injuries or conditions. The database 10H can also contain information regarding diagnoses, treatments, treatment plans, procedures, corrective procedures or surgical procedures, cures, rehabilitation, therapies, physical therapies, exercise therapies, drug or medicinal therapies, diets, nutritional therapies, alternate medicine therapies, herbal therapies, and/or any other information which can or which may be utilized or needed for monitoring and/or managing the health and well-being of athletes or sports participants.

The database 10H can also contain data, information, or algorithms, for devising and planning treatments, treatment plans, procedures, operations, rehabilitation programs, plans, or regimens, physical therapy programs, plans, or regimens, occupational therapy programs, plans, or regimens, exercise programs, plans, or regimens, massage therapy programs, plans, or regimes, and/or any other programs, plans, or regimens for treating, curing, or otherwise dealing with, a sports-related injury or diagnosis.

The database 10H can also contain data and/or information regarding, for identifying or locating, healthcare providers, doctors, specialists, dentists, dental specialists, psychiatrists, psychologists, chiropractors, podiatrists, optometrists, or any other providers, hospitals, treatments facilities, therapists, nurses, physical therapists, massage therapists, occupational therapists, trainers, and/or any other providers or care givers, and/or testing laboratories, who or which can provide services for any other athletes and/or sports participants who may or which my utilize or be serviced by the apparatus 100 and method of the present invention, or any of their respective organizations, teams, clubs, or other entities.

The database 10H can also contain information, text information, audio, audio information or audio clips, video, video information, video clips, audio and video information, audio and video clips, news story, television programs, and/or information in any other form or type regarding fitness, fitness exercises, exercises, fitness routines, fitness regimens, wellness, wellness exercises, wellness routines, wellness regimens, diets, diet exercises, diet or dieting routines, diet ort dieting regimens, training, training principals, training exercises, training routines, training regimens, nutrition, health and well being, meditation and any other information.

The database 10H can also contain statistical and/or other probabilistic and/or mathematical information for assigning and/or correlating certain levels and/or estimates for any and/or all of the information, diagnoses, prognoses, treatments, procedures, and/or any other information processed and/or generated by the central processing computer 10 and/or the apparatus 100.

The database 10H, in the preferred embodiment, can be a database which may include individual databases or collections of databases, with each database being designated to store any and all of the data and/or information described herein. The database 10H, or collection of databases, may be updated by each of the respective patients, providers, payers, users, and/or intermediaries, and/or by any other third party, in real-time, and/or via dynamically linked database management techniques.

The data and/or information stored in the database 10H can also be updated by and/or dynamically linked to, various external sources, including but not limited to news services, research publications, research facilities, healthcare laboratories, providers of healthcare goods and/or services, pharmaceutical companies, research institutions, schools. The database 10H will contain any and all information deemed necessary and/or desirable for providing all of the processing and/or services and/or functions described herein.

The database 10H can also contain data and/or information regarding any and/or all International Classification of Diseases (ICD) codes, ICD-10 codes, ICD-9, or any other ICD codes, or other codes, billing codes, diagnostic codes, treatment codes, or symptom codes, as well as any other codes or coding information which pertains to healthcare, the administration of healthcare services, healthcare record keeping, healthcare billing, healthcare diagnostics, healthcare treatments, or any other healthcare or healthcare-related functions or services, or any information or function, described-herein as capable of being provided by the apparatus 100 and method of the present invention. The database 10H can also contain data and/or information regarding the foreign language translations or conversions of or for, or for the foreign language translation or converting, of any of the herein-described International Classification of Diseases (ICD) codes, ICD-10 codes, ICD-9, any other ICD codes, or other codes, billing codes, diagnostic codes, treatment codes, symptom codes, as well as any other codes or coding information which pertains to healthcare, the administration of healthcare services, healthcare record keeping, healthcare billing, healthcare diagnostics, healthcare treatments, or any of the healthcare or healthcare-related functions or services, or any information or function described-herein as capable of being provided by the apparatus 100 and method of the present invention, into any one or any number of foreign languages.

The database 10H can contain any look-up tables, or information for use in a look table, for translating or converting any of the data, information, or codes, described herein, into any one or any number of foreign languages. The database 10H can also contain any language translation software or language conversion software which can be used to perform any of the foreign language translation or foreign language conversion processing or functionality described as being performed by the apparatus 100 and method of the present invention.

The database 10H can also contain any information or software, or rules algorithms, which can be used in generating insurance claim forms which can be submitted error-free to any of the insurers or payers described herein.

The database 10H can also contain digital pictures, photographs, images, video, or video clips, of individuals or patients, as well as digital pictures, photographs, images, video, or video clips, of physical conditions of or regarding an individual or patient, which can be accessed or retrieved by any of the individuals, patients, providers, payers, or intermediaries, described herein as utilizing the apparatus 100 and method of the present invention.

For example, in instances where photographs or images can be useful to see a state of a physical condition of a patient or individual, or to compare a state of a physical condition from one point in time to another, or to track the state of a physical condition, a photograph(s), picture(s), or image(s), or video clip, can be digitally recorded, with a camera or video recording device, and stored in the database 10H and/or in the patient's or individual's healthcare record or healthcare file for later retrieval, use, and/or review.

For example, a dermatologist seeking to determine if a skin condition has or is changing in size, shape, or color, can take and store, in the database 10H and/or in the patient's or individual's healthcare record or healthcare file, one or more photographs, pictures, or images, or a video clips, of the skin condition. In an analogous manner, a plastic surgeon can obtain and store, in the database 10H and/or in the patient's or individual's healthcare record or healthcare file, photographs, pictures, or images, or video clips, showing physical conditions of an individual or patient before, after, or during a procedure or procedures. A dentist or an oral health professional can obtain and store, in the database 10H and/or in the patient's or individual's healthcare record or healthcare file, in addition to x-rays, a photograph(s), picture(s), or image(s), or a video clip(s), showing physical conditions of an individual's or patient's mouth, teeth, gums, or other physical oral state, for later retrieval, use, or review. In an analogous manner, any healthcare provider can obtain and store, in the database 10H and/or in a patient's or individual's healthcare record or healthcare file, a photograph(s), picture(s), or image(s), or a video clip(s), obtained in or during an office visit, an examination, a procedure, an operation, a treatment, or during any other occasion, event, occurrence, or happening, for later retrieval and use as needed or desired by any provider, payer, patient, individual, or intermediary, described herein as being able to utilize the apparatus 100 and method of the present invention.

The database 10H can also contain video and/or audio clips or recordings of office visits, examinations, procedures, operations, or any other healthcare, healthcare-related, or any other event(s), occurrence(s), or happening(s), which may or which can be of interest to any provider, insurer, payer, patient, individual, or intermediary, described herein as being able to utilize the apparatus 100 and method of the present invention.

The database 10H can also contain transcripts of office visits, examinations, procedures, operations, or any other healthcare, healthcare-related, or any other event(s), occurrence(s), or happening(s), or any video calls, video chat sessions, or videoconferences of any a remote or virtual office visits or any remote or distance examinations, which may or which can be of interest to any provider, insurer, payer, patient, individual, or intermediary, described herein as being able to utilize the apparatus 100 and method of the present invention.

The database 10H can also contain data, information, links, or hyperlinks, which can allow a healthcare provider to create or generate and/or transmit prescriptions or electronic prescriptions, or prescription forms, to pharmacies or other providers, for a patient or individual, or prescriptions or electronic prescriptions for tests, analyses, analysis workups, procedures, therapy, physical therapy, or other healthcare or healthcare-related services, for a patient or individual, or which can allow a healthcare provider to transmit a referral or an electronic referral or referral form to other healthcare providers or other providers of goods or services for a patient or individual.

The database 10H can also contain data, information, links, or hyperlinks, which can allow a healthcare provider to perform remote control or monitoring of healthcare devices or equipment used in the treatment of, a care of, or a monitoring of, a patient or individual, while the patient or individual is at home, in a hospital, in a nursing home, in a care facility, or traveling in or on, respectively, a car, automobile, train, subway train, boat, helicopter, airplane, aircraft, or any other vehicle. The database 10H can also contain data, information, a link(s), or a hyperlink(s) which can allow a healthcare provided to remotely control healthcare devices or equipment, instruments, surgical instruments, and/or any other devices which can be used in performing a procedure, a surgery, or a surgical procedure, on an individual or patient, and/or to administer a treatment to the individual or patient, via data, information, link(s), or a hyperlink(s), contained in the individual's or patient's electronic healthcare record.

The database 10H can also contain data and/or information regarding artificial limbs, artificial organs, implanted or implantable devices, and/or prosthetic devices, and/or dental implants, dental braces, and/or any other devices associated with an individual or patient. The data and/or information regarding artificial limbs, artificial organs, implanted or implantable devices, and/or prosthetic devices, and/or dental implants, dental braces, and/or any other devices associated with an individual or patient can include manufacturer information, model information, date put into use or installed, if applicable, maintenance instructions, provider who or which prescribed, installed, implanted, or fitted same, dates examined or checked, and/or any other data or information regarding same.

The database 10H can also contain data, information, or software, for performing healthcare audits, for performing meaningful use information processing routines, for identifying or selecting individuals for clinical trials, experimental procedures, experimental treatments, healthcare focus groups, healthcare surveys, or other activities or events, or for performing any other processing routines which can advantageously use any of the information stored in the database 10H, any information stored in any of the herein-described healthcare records, files, or histories, described herein, or any other information, stored by the apparatus 100 of the present invention or any of its computers, communication devices, component parts, or devices, or any other information stored in, provided by, generated by, or used by, the apparatus 100 of the present invention. For example, with regards to clinical trials, experimental procedures, experimental treatments, healthcare focus groups, healthcare surveys, or other activities or events, the database 10H can contain information regarding whether or not an individual or patient can or may be a candidate for, be eligible to participate in, has agreed to be candidate for, or has agreed to participate in, clinical trials, experimental procedures, experimental treatments, healthcare focus groups, healthcare surveys, or other activities or events, or has agreed to be candidate for, or has agreed to participate in, a particular clinical trial(s), experimental procedure(s), experimental treatment(s), healthcare focus group(s), healthcare survey(s), or other activities or events.

The database 10H can also contain any data and/or information needed or used to determine or measure the effectiveness of, or side effects experienced or associated with, any medication(s), medicine(s), drug(s), dietary supplement(s), supplement(s), vitamin(s), nutrient(s), over-the-counter product(s) or substance(s), or the effectiveness of a procedure(s), treatment(s), treatment plan(s), care management plan(s), or any other good(s) or service(s) which can be offered in the marketplace.

The database 10H can also contain data and/or information relating to information regarding health conditions, healthcare conditions, illnesses, diagnoses, symptoms, treatments, treatment plans, care management plans, care management practices, insurance information, information regarding type of insurance, wellness information, healthcare practices, healthcare history patterns, healthcare trends, treatment trends, care management trends, statistics, statistical analyses, studies, study trends, or any other healthcare or healthcare-related information, for or regarding any number or type of groups of individuals or patients, and any data or information for determining same. The database 10H can also contain data or information regarding, or for determining, any of the above-described information for any number of groups of individuals or patients based on sex, gender, age, occupation, education, ethnicity, nationality, country of origin, religion, or any demographic or demographics, or any other criteria. The database 10H can also contain data or information regarding, or for determining statistical information or probability information regarding, any of the herein-described information.

The database 10H can also contain data or information for implementing and for performing drug formulary checks or analyses, as well as data or information for performing medication, medicine, or drug, reconciliation.

The database 10H can also contain immunization data or information.

The database 10H can also contain educational or instructional information, links or hyperlinks to same, information regarding instructions or procedures, or links or hyperlinks to same, in order to allow for the providing of patient-specific educational or instructional information or resources to patients or individuals, as well as to any of the herein-described healthcare providers, other providers, payers or insurers, or intermediaries or caregivers.

The database 10H can also contain data or information necessary or desired for administering employee benefits for any of the individuals or patients who utilize the apparatus 100 and method of the present invention.

The database 10H can also contain data or information necessary or desired for purchasing or enrolling in employee benefits for any of the individuals or patients who utilize the apparatus 100 and method of the present invention.

The database 10H can also contain data or information necessary or desired for allowing any individual or patient to make a request or a claim for, or pursuant to, or to file a request or a claim for, an employee benefit or employee benefits, for any of the individuals or patients who utilize the apparatus 100 and method of the present invention.

The database 10H can also contain data or information for facilitating, or for providing for, the portability of healthcare insurance or health insurance benefits, life insurance or life insurance benefits, or disability insurance or disability insurance benefits, or for providing for the portability of any other employee benefit or employee benefits.

The database 10H can also contain any of the messages or reports described herein as being generated by or provided by the apparatus 100 and method of the present invention, for later use by any provider, insurer, payer, patient, individual, or intermediary, or any other person or entity, described herein as being able to utilize the apparatus 100 and method of the present invention.

The database 10H can also contain any data, information, or software, for performing any of the processing routines or functionality described herein as being capable of being performed by, or provided by, the apparatus 100 of the present invention.

The data and/or information which is contained and/or stored in the database 10H as well as any of the other databases 20H, 30H, 40, and 50H, described herein can be obtained from the various patients, individuals, providers, payers, and/or intermediaries, who or which utilize and/or who or which are serviced by the present invention. For example, the respective patients, providers, payers, intermediaries, and/or other users, could fill out questionnaires, forms, narratives, claim forms, and/or any other information medium, in written form, electronically, and/or otherwise.

Data and/or information stored in the database 10H as well as any of the other databases described herein can be updated by multiple parties. For example, a patient may provide a medical history for his or her individual file, and his or her medical doctor can update the medical history information for the patient upon examining and/or treating him or her. The payer may also update the file with any associated payment or payment-related information. Should the patient go to another doctor or different type of doctor, all previous information would be available for, and can be updateable by, the next doctor.

The database 10H can also contain information regarding alternate medicine techniques, herbal techniques, meditation techniques, exercise techniques, self healing, faith healing, and/or other non-medicine treatments and/or techniques.

The database 10H can also include statistical data and/or information regarding diagnoses, and/or alternate diagnoses, treatment success, treatment failure, as well as statistical data and/or information regarding misdiagnoses. The database 10H also contains data and/or information regarding experimental treatments as well as statistical information regarding same, successes of same and failures of same.

The database 10H can also contain any other data and/or information, including software for performing any and all of the operations, routines, processing routines, and other functions and/or functionality described herein as being capable of being performed by the apparatus 100, the central processing computer(s) 10 and any of the herein-described provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90.

The database 10H can also contain any and/or all of the herein-described information for providing electronic veterinary healthcare records or filed (EVHRs) which can be used for maintaining healthcare records or file for any types or kinds f animals, high value animals, exotic animals, pet of any kind or type, or any other types or kinds of animals. For example, electronic veterinary healthcare records or files can be maintained and used for race horses, circus animals, animals used in shows, service animals, animals used for breeding, household pets, dogs, cats, fish, birds, mammals of any kind or types, birds of any kinds or types, and/or any other animal for which an owner, caregiver, or other responsible person or entity, may find it desirable or necessary to keep a healthcare record or file. In a preferred embodiment, the database 10H can also contain, any of the data and/or information, or any analogous data and/or information, described herein as being stored or contained in the database 10H, for any animal for which an electronic veterinary healthcare record or file is maintained.

It is important to note that the apparatus 100 and method of the present invention can be utilized, in any and/or all of the embodiments described herein, in order to process and/or to provide veterinary healthcare information and/or veterinary healthcare-related information for and regarding any kind or type of animal or animals. In this regard, when used in veterinary applications, the terms "individual", "patient", "client", "user" or the like, or their plural forms, also refer to any of the herein-described animals or pets or any other animals or pets.

The database 10H can also contain any data and/or information, as well as any links or hyperlinks to any of the herein-described provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90 described herein as being used in connection with the present invention, and/or can contain data and/or information and/or links or hyperlinks to any data and/or information located or stored on, at, or in any of the provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90 described herein.

The database 10H can also contain information, links and/or hyperlinks, to any social networking web sites, web pages, support groups, on-line forums, on-link information services, as well as social networking web sites or social networking web pages to or for social networking members, support groups, information providers, healthcare providers, as well as any of the providers, insurers, payers, individuals, patient, third parties, intermediaries, or any other persons or entities described herein who are or who may be members of any social network.

The database 10H can also contain data and/or information regarding any animals or pets associated with any individual, patient, or caregiver as well as any data and/or information regarding any electronic healthcare record for respective animal or pet.

The database 10H can also contain, for each or any of the herein-described individuals, patients, or caregiver, or for each provider or payer or insurer of a respective individual, patient, or caregiver, financial information regarding insurance premiums or payments, or premiums or payments for an insurer or payer policy, plan or program, which are or were made by or on behalf of the individual, patient, or caregiver, any and/or any insurance claim(s) or request(s) for payment(s) made by or on behalf of the individual, patient, or caregiver, provider bills or provider charges submitted in an insurance claim or a request for payment, provider amounts or provider charges billed for goods, products, or services, amounts paid by an insurer or payer for the amounts billed or charged by a provider, amounts paid or amounts of co-payments paid by or on behalf of the individual, patient, or caregiver, for the amounts billed, deductibles paid by or on behalf of the individual, patient or caregiver, and/or any other data and/or information regarding charges, bills, insurance claims, requests for payments, amounts paid by insurers or payers, and/or any amounts paid by or on behalf of the respective individual, patient, or caregiver.

The database 10H can also contain, for each individual, patient, or caregiver, any data and/or information regarding any vehicle(s) owned or operated by the individual, patient, or caregiver, along with data and/or information, and/or a link(s) or hyperlink(s) to any manufacturer of the vehicle or to any telematics, on-line service provider, or other services provider for the vehicle, such as for example, a telematics, on-line services provider, or other services provider who or which provides products and services such as those offered and provided in connection with automobiles and other motor vehicles as of the filing data of this application.

In any and/or all of the embodiments described herein, any of the data and/or information which is or which may be stored in the database 10H, and/or any of the other databases described herein, can be utilized and/or can appear in any of the reports, diagnostic reports, treatment reports, evaluation reports, provider reports, payer reports, patient reports, training reports, and/or any other reports, described herein.

In a preferred embodiment, the database 10H can also store a user profile for each user, individual, patient, caregiver, and/or healthcare provider, healthcare professional, hospital, clinic, pharmacy, treatment center, treatment facility, and/or any other provider of services described herein, insurer, payer, insurer employee or agent, payer employee or agent, intermediary, governmental entity employee or agent, who or which utilizes the apparatus 300 of the present invention. In a preferred embodiment, the user profile can contain or include a name, address, email address, telephone number, text message number, cellular telephone number, file photograph, educational information, training information, work experience information, and/or any other information regarding the respective user, individual, patient, caregiver, and/or healthcare provider, healthcare professional, hospital, clinic, pharmacy, treatment center, treatment facility, and/or any other provider of services described herein, insurer, payer, insurer employee or agent, payer employee or agent, intermediary, governmental entity employee or agent, who or which utilizes the apparatus 300 of the present invention.

In a preferred embodiment, database 10H can also contain and/or include video recordings of any and/or all remote healthcare visits, remote doctor visits, and/or tele-health visits, for and/or regarding each user, individual, or patient.

In a preferred embodiment, the database 10H can also contain and/or include educational videos for providing instruction to users, individuals, patients, caregivers, healthcare providers, insurers, payers, governmental entity employees and agents, and intermediaries, as well any other individuals or entities.

The central processing computer 10 also includes an output device 10I for output any data, information, report, etc., described herein. In the preferred embodiment, the output device 10I can be a printer, a display, a transmitter, a modem, a speaker, and/or any other device which can be used to output data.

Any of the data and/or information for any of the patients, individuals, providers, payers, and/or intermediaries, can be updated by different parities and which such updated data and/or information being made available to other respective parties so as to provide and ensure comprehensive and up-to-date healthcare and healthcare-related information.

Figure 3:
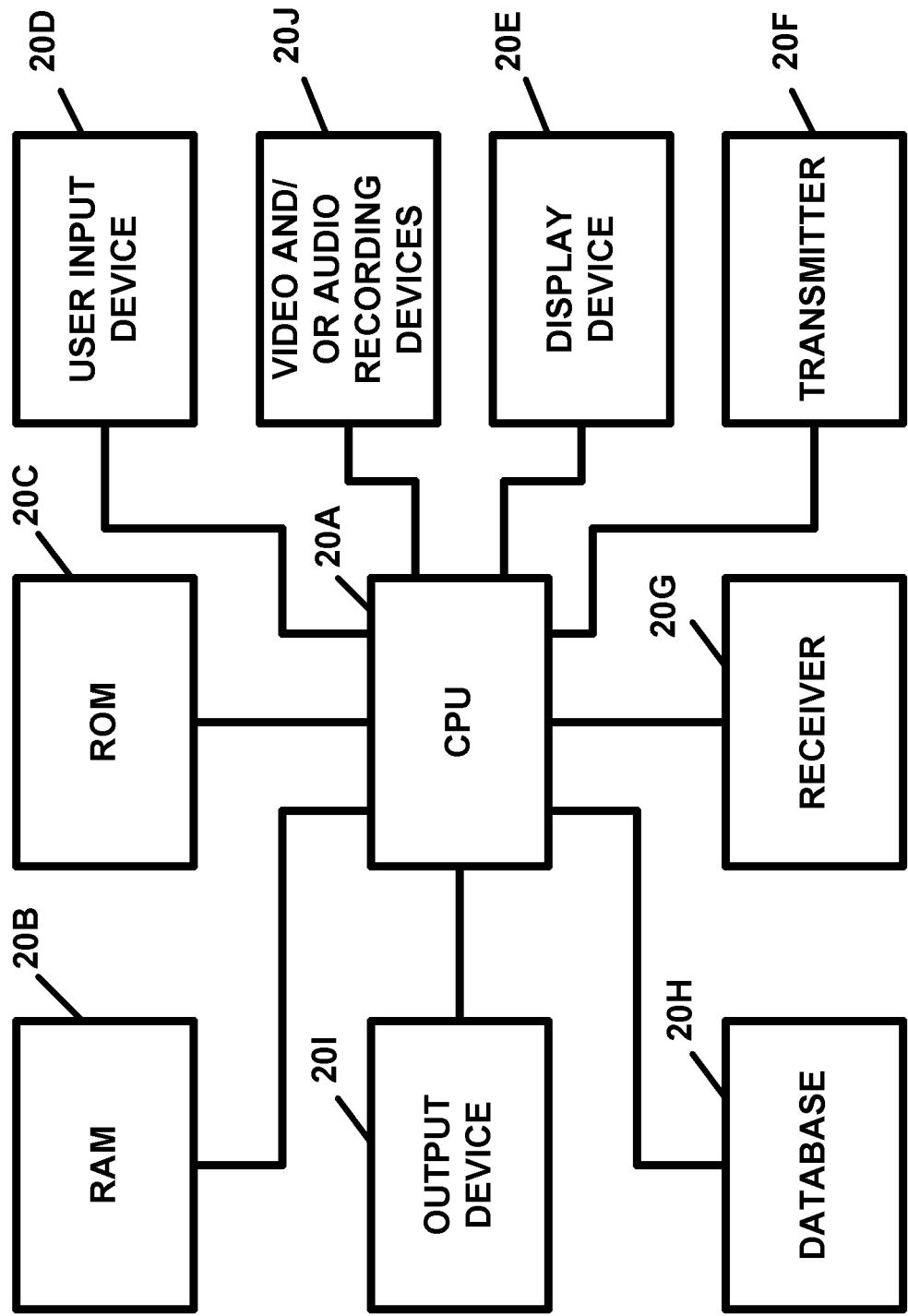
FIG. 3 illustrates the provider communication device of FIG. 1, in block diagram form.

FIG. 3 illustrates the provider communication device 20, in block diagram form. The provider communication device 20, in the preferred embodiment, can be personal computer, a network computer or computer system, or any other computer or communication device, which is utilized as a provider computer 20. In the preferred embodiment, the provider communication device 20 includes a central processing unit or CPU 20A, which in the preferred embodiment, is a microprocessor. The CPU 20A may also be a microcomputer, a minicomputer, a macro-computer, and/or a mainframe computer, depending upon the application.

The provider communication device 20 also includes a random access memory device(s) 20B (RAM) and a read only memory device(s) 20C (ROM), each of which is connected to the CPU 20A, a user input device 20D, for entering data and/or commands into the provider communication device 20, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, which an also include, for example, pulse rate monitors, blood pressure monitors, electrocardiograms, glucose monitors, blood-sugars monitors, blood glucose monitors, blood oxygen percentage level monitors, oximeters, and/or digital finger pulse oximeters, etc., if desired, or any other devices, measuring or measurement devices or equipment, or any other equipment used for obtaining information regarding an individual or patient, which input device(s) are also connected to the CPU 20A. In another preferred embodiment, the pulse rate monitors, blood pressure monitors, electrocardiograms, glucose monitors, blood-sugars monitors, etc., if desired, or any other devices, measuring or measurement devices or equipment, or any other equipment used for obtaining information regarding an individual or patient, can also be integrated into the provider communication device 20.

The user input device 20D can also acquire, receive, generate and/or provide, data which can be entered by a user or individual and/or can be a device which can acquire, receive, generate and/or provide, digital data such as medical, healthcare, bio-metric, physiological, and/or any other kind of healthcare data and/or healthcare-related data. For example, a user input device 20D can be a keyboard for allowing a user to input information into the provider communication device and/or a user input device can, for example, by a heart rate monitor or EKG machine which can receive information from a patient or individual and generate a digital signal, digital data, analog data, and/or any other signal, data, and/or information, which is representative of the patient's or individual's heart rate, pulse rate, and/or cardiac activity.

The user input device 20D can also be, or can include, any one or more of, and/or any combination of, a thermometer, a digital thermometer, a stethoscope, a heart rate monitor or measurement device, a pulse rate monitor or measurement device, a blood pressure monitor or measurement device, a blood oxygen or percentage oxygen measurement device, a blood pressure measurement device, blood analysis device or machine, a respirator, a respiration monitoring or measurement device, a dialysis machine, a dialysis device, electrocardiograph (EKG) machine or device, electroencephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laparoscopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, a PET scan device, an optical metabolism measurement or monitoring device, a radiotelemetric device, a doppler medical device, a mammogram device, a carbon dioxide detection or measurement device, a carbon monoxide detection or measurement device, a transvascular impedence measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, dental probe, microscopic camera probing device, any scope having a camera and/or a light, a laparoscopic device, a laparoscopic camera device, a camera used in or associated with equipment for performing visual probing of the body or any portions, parts, or organs, thereof, such as, but not limited to, a colonoscopy, an endoscopy, an esophagoscopy, a gastroscopy, or any devices used in laparoscopic surgery or other surgeries, an ingestible or implantable pill, capsule, or device, containing a camera and/or a light and equipment or circuitry for transmitting information as well as images to equipment inside or outside the body, and/or any other bio-metric or physiological data measuring device(s) and/or data acquisition device (hereinafter referred to generally or collectively as "healthcare equipment input device", "healthcare measurement input device", or "healthcare monitoring input device").

In a preferred embodiment, any healthcare equipment input device, any healthcare measurement input device, or any healthcare monitoring input device, can also be, and/or can include any of the herein-described components of, a provider communication device 20.

The user input device 20D can also be, or can include, a pacemaker, a device for monitoring blood pressure or blood flow, or an ingestible or implantable pill, capsule, or device, containing a camera and/or a light and equipment or circuitry for transmitting information as well as images to equipment inside or outside the body.

The user input device 20D can also be, or can include, a dental probe which can include, at the very least, a camera or a video recording device and a light, as well as a handle, for allowing the provider to examine the mouth, teeth, and/or gums, of an individual or patient. In a preferred embodiment, the dental probe can be utilized to in order to examine the exterior of the mouth as well as the interior portions of the mouth. In a preferred embodiment, the dental probe can be utilized in order to perform and/or to record a dental examination or an oral care examination by being inserted into, and by being maneuvered inside and/or about the interior of, the mouth, and/or by being maneuvered so as to examine any and/or various areas of the inside or interior of an individual's or patient's mouth, palate, tongue, teeth, and/or gums. In a preferred embodiment, the light of the dental probe can be utilized to provide sufficient lighting for enabling a dental examination or an oral examination as well as for viewing of, and/or the recording of, information obtained by and/or recorded by the camera or the video recording device of the dental probe. In a preferred embodiment, the dental probe can be connected to the provider communication device 20 via a wired connection, via a wireless connection, and/or via Bluetooth connection, or via any combination of the same.

In a preferred embodiment, the dental probe can also be a separate and/or a standalone healthcare device, a piece of healthcare equipment, a healthcare equipment input device, a healthcare measurement input device, or a healthcare monitoring input device.

The user input device 20D can also be, or can include, a global positioning device which can be utilized for determining a position or location of the provider communication device 20 and/or the provider who or which is using the same.

The provider communication device 20 also includes a display device 20E for displaying data and/or information to a user or operator.

The provider communication device 20 also includes a transmitter(s) 20F, for transmitting signals and/or data and/or information to any one or more of the central processing computer(s) 10, any other provider communication device(s) 20, the communication device(s) 30, the user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention. The provider communication device 20 also includes a receiver 20G, for receiving signals and/or data and/or information from any one or more of the central processing computer(s) 10, any other provider communication device(s) 20, the payer communication device(s) 30, the user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention.

The provider communication device 20 also includes a database(s) 20H. The database 20H can contain and/or be linked to any of the data and/or information described herein as being stored in the database 10H.

The provider communication device 20 also includes an output device 20I for output any data, information, report, etc., described herein. In the preferred embodiment, the output device 20I can be a printer, a display, a transmitter, a modem, a speaker, and/or any other device which can be used to output data.

The provider communication device 20 also includes a video and/or audio recording device(s) 20J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

Figure 4:
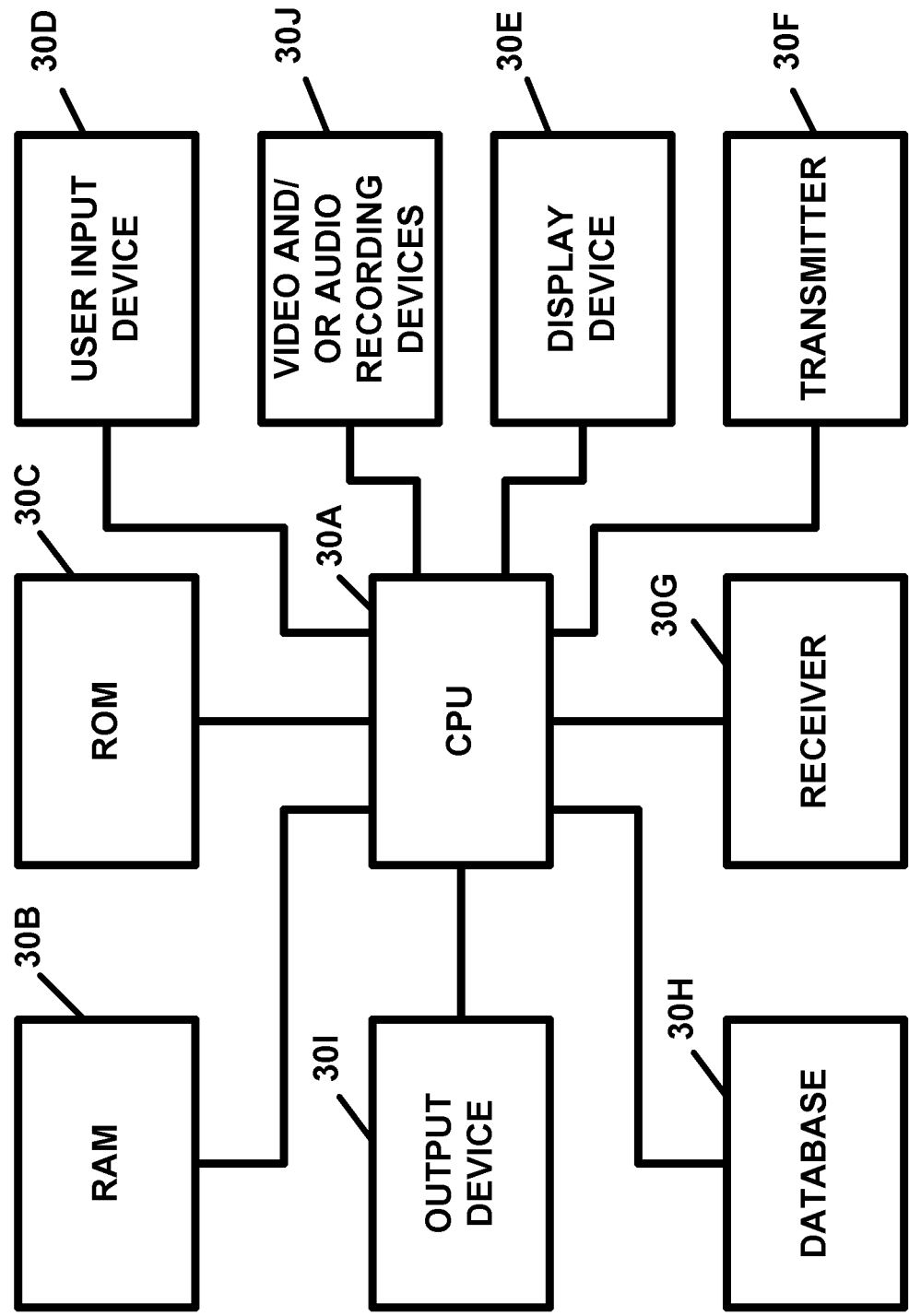
FIG. 4 illustrates the insurer or payer communication device of FIG. 1, in block diagram form.

FIG. 4 illustrates the payer communication device 30, in block diagram form. The payer communication device 30, in the preferred embodiment, can be personal computer, a network computer or computer system, or any other computer or communication device, which is utilized as a payer computer 30. In the preferred embodiment, the payer communication device 30 includes a central processing unit or CPU 30A, which in the preferred embodiment, is a microprocessor. The CPU 30A may also be a microcomputer, a minicomputer, a macro-computer, and/or a mainframe computer, depending upon the application.

The payer communication device 30 also includes a random access memory device(s) 30B (RAM) and a read only memory device(s) 30C (ROM), each of which is connected to the CPU 30A, a user input device 30D, for entering data and/or commands into the payer communication device 30, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electro-cardiograms, glucose monitors, blood-sugars monitors, etc., if desired, which input device(s) are also connected to the CPU 30A. The payer communication device 30 also includes a display device 30E for displaying data and/or information to a user or operator.

The payer communication device 30 also includes a transmitter(s) 30F, for transmitting signals and/or data and/or information to any one or more of the central processing computer(s) 10, the provider communication device(s) 20, any other payer communication device(s) 30, the user or patient communication device(s) 40, and the intermediary computer(s) 50, the healthcare records computer(s) 60, the insurance exchange computer(s) 70, the social networking computer(s) 80, and/or the media computer(s) 90 described herein, which may be utilized in conjunction with the present invention. The payer communication device 30 also includes a receiver 30G, for receiving signals and/or data and/or information from any one or more of the central processing computer(s) 10, the provider communication device(s) 20, any other payer communication device(s) 30, the user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention.

The payer communication device 30 also includes a database(s) 30H. The database 30H can contain and/or be linked to any of the data and/or information described herein as being stored in the database 10H.

The payer communication device 30 also includes an output device 30I for output any data, information, report, etc., described herein. In the preferred embodiment, the output device 30I can be a printer, a display, a transmitter, a modem, a speaker, and/or any other device which can be used to output data.

The payer communication device 30 also includes a video and/or audio recording device(s) 30J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

Figure 5:
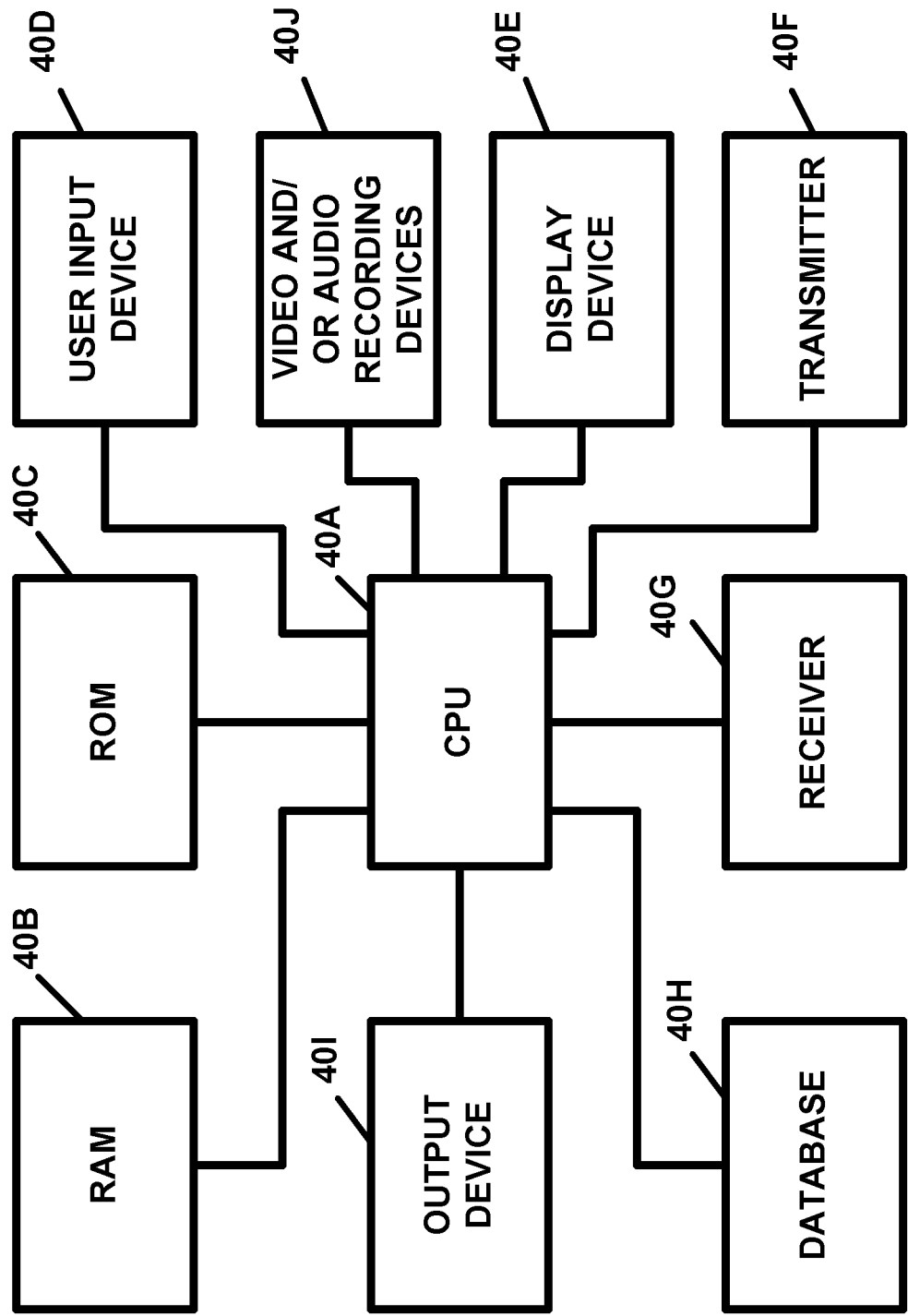
FIG. 5 illustrates the user or patient communication device of FIG. 1, in block diagram form.

FIG. 5 illustrates the user or patient communication device 40, in block diagram form. The user or patient communication device 40, in the preferred embodiment, can be personal computer, a network computer or computer system, or any other computer or communication device, which is utilized as a patient computer. In the preferred embodiment, the user or patient communication device 40 includes a central processing unit or CPU 40A, which in the preferred embodiment, is a microprocessor. The CPU 40A may also be a microcomputer, a minicomputer, a macro-computer, and/or a mainframe computer, depending upon the application.

The user or patient communication device 40 also includes a random access memory device(s) 40B (RAM) and a read only memory device(s) 40C (ROM), each of which is connected to the CPU 40A, a user input device 40D, for entering data and/or commands into the user or patient communication device 40, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electro-cardiograms, glucose monitors, blood-sugars monitors, blood glucose monitors, blood oxygen percentage level monitors, oximeters, and/or digital finger pulse oximeters, etc., if desired, which input device(s) are also connected to the CPU 40A.

The user input device 40D can also acquire, receive, generate and/or provide, data which can be entered by a user or individual and/or can be a device which can acquire, receive, generate and/or provide, digital data such as medical, healthcare, bio-metric, physiological, and/or any other kind of healthcare data and/or healthcare-related data. For example, a user input device 40D can be a keyboard for allowing a user to input information into the patient communication device and/or a user input device can, for example, by a heart rate monitor or EKG machine which can receive information from a patient or individual and generate a digital signal, digital data, analog data, and/or any other signal, data, and/or information, which is representative of the patient's or individual's heart rate, pulse rate, and/or cardiac activity.

The user input device 40D can also be, or can include, or the user or patient communication device 40 can include, any one or more of, and/or any combination of, a thermometer, a digital thermometer, a stethoscope, a heart rate monitor or measurement device, a pulse rate monitor or measurement device, a blood pressure monitor or measurement device, a blood oxygen or percentage oxygen measurement device, a blood pressure measurement device, a blood glucose monitor, a blood oxygen percentage level monitor, an oximeter, a digital finger pulse oximeter, a blood analysis device or machine, a respirator, a respiration monitoring or measurement device, a dialysis machine, a dialysis device, electrocardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laparoscopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedance measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, dental probe, microscopic camera probing device, and/or any other bio-metric or physiological data measuring device(s) and/or data acquisition device data acquisition device (hereinafter referred to generally or collectively as "healthcare equipment input device", "healthcare measurement input device", or "healthcare monitoring input device"). In a preferred embodiment, any healthcare equipment input device, healthcare measurement input device, or healthcare monitoring input device, can be connected to, or linked to, the CPU 40A and/or the user or patient input device 40, via a wired connection, a wireless connection, a Wi-Fi connection, a Bluetooth connection, or any combination of same.

In a preferred embodiment, any healthcare equipment input device, any healthcare measurement input device, or any healthcare monitoring input device, can also be, and/or can include any of the herein-described components of, a user or patient communication device 40.

The user input device 40D can also be, or can include, a dental probe which can include, at the very least, a camera or a video recording device and a light, as well as a handle, for allowing the provider to examine the mouth, teeth, and/or gums, of an individual or patient. In a preferred embodiment, the dental probe can be utilized to in order to examine the exterior of the mouth as well as the interior portions of the mouth. In a preferred embodiment, the dental probe can be utilized in order to perform and/or to record a dental examination or an oral care examination by being inserted into, and by being maneuvered inside and/or about the interior of, the mouth, and/or by being maneuvered so as to examine any and/or various areas of the inside or interior of an individual's or patient's mouth, palate, tongue, teeth, and/or gums. In a preferred embodiment, the light of the dental probe can be utilized to provide sufficient lighting for enabling a dental examination or an oral examination as well as for viewing of, and/or the recording of, information obtained by and/or recorded by the camera or the video recording device of the dental probe. In a preferred embodiment, the dental probe can be connected to the user or patient communication device 40 via a wired connection, via a wireless connection, and/or via Bluetooth connection, or via any combination of the same.

In a preferred embodiment, the dental probe can also be a separate and/or a standalone healthcare device, a piece of healthcare equipment, a healthcare equipment input device, a healthcare measurement input device, or a healthcare monitoring input device.

The user input device 40D can also be, or can include, a global positioning device which can be utilized for determining a position or location of the user or patient communication device 40 and/or the user or operator of the same and/or any individual or healthcare patient or client who uses the same.

The user or patient communication device 40 also includes a display device 40E for displaying data and/or information to a user or operator.

The user or patient communication device 40 also includes a transmitter(s) 40F, for transmitting signals and/or data and/or information to any one or more of the central processing computer(s) 10, the provider communication device(s) 20, the payer communication device(s) 30, any other user or patient communication device(s) 40, and the intermediary computer(s) 50, the healthcare records computer(s) 60, the insurance exchange computer(s) 70, the social networking computer(s) 80, and/or the media computer(s) 90 described herein, which may be utilized in conjunction with the present invention. The user or patient communication device 40 also includes a receiver 40G, for receiving signals and/or data and/or information from any one or more of the central processing computer(s) 10, the provider communication device(s) 20, the payer communication device(s) 30, any other user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention.

The user or patient communication device 40 also includes a database(s) 40H. The database 40H can contain and/or be linked to any of the data and/or information described herein as being stored in the database 10H.

The user or patient communication device 40 also includes an output device 40I for output any data, information, report, etc., described herein. In the preferred embodiment, the output device 40I can be a printer, a display, a transmitter, a modem, a speaker, and/or any other device which can be used to output data.

The user or patient communication device 40 also includes a video and/or audio recording device(s) 40J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

Figure 6:
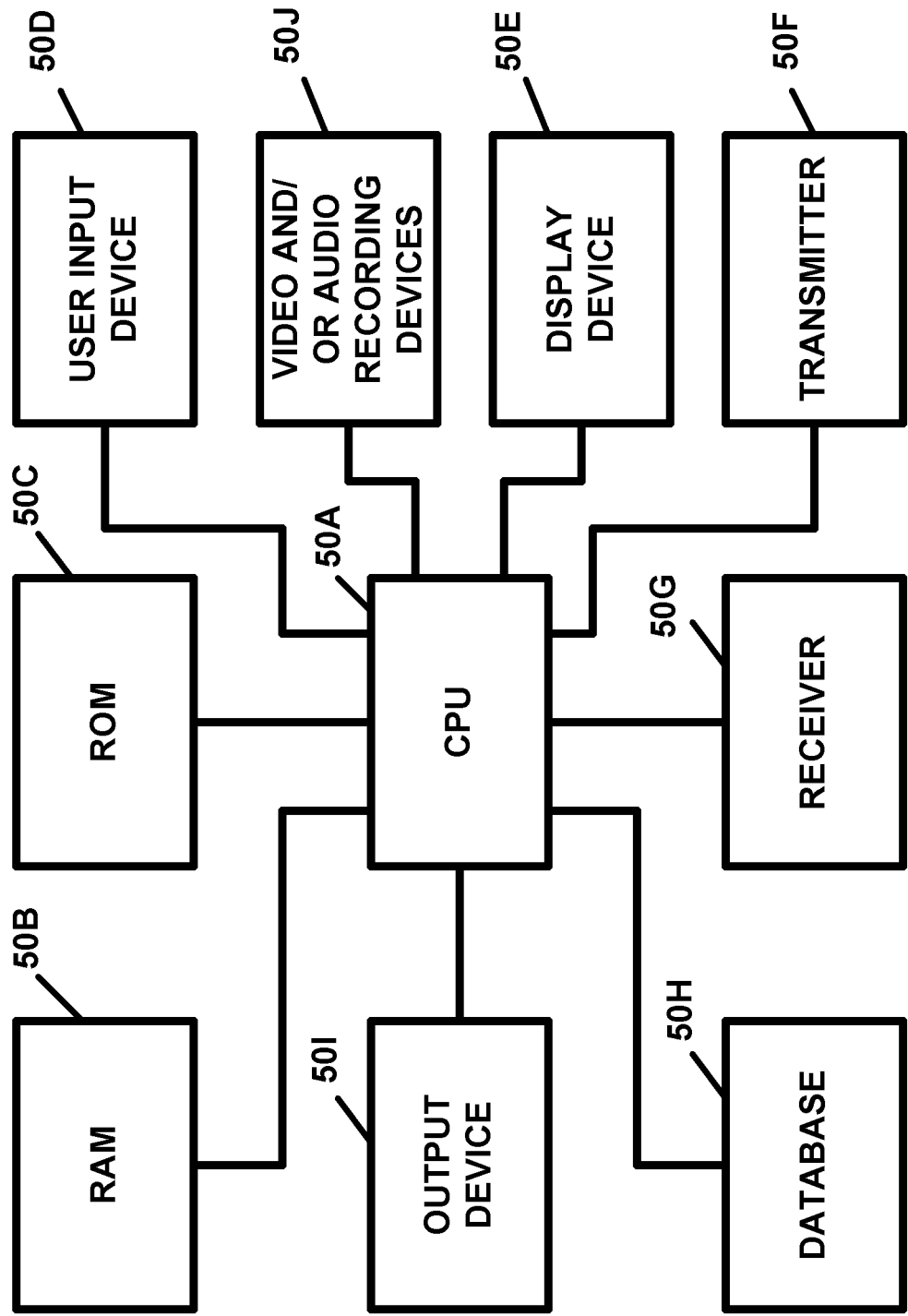
FIG. 6 illustrates the intermediary communication device of FIG. 1, in block diagram form.

FIG. 6 illustrates the intermediary computer 50, in block diagram form. The intermediary computer 50, in the preferred embodiment, can be personal computer, a network computer or computer system, or any other computer or communication device, which is utilized as an intermediary computer 50. In the preferred embodiment, the intermediary computer 50 includes a central processing unit or CPU 50A, which in the preferred embodiment, is a microprocessor. The CPU 50A may also be a microcomputer, a minicomputer, a macro-computer, and/or a mainframe computer, depending upon the application.

The intermediary computer 50 also includes a random access memory device(s) 50B (RAM) and a read only memory device(s) 50C (ROM), each of which is connected to the CPU 50A, a user input device 50D, for entering data and/or commands into the intermediary computer 50, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, glucose monitors, blood-sugars monitors, etc., if desired, which input device(s) are also connected to the CPU 50A. The intermediary computer 50 also includes a display device 50E for displaying data and/or information to a user or operator.

The intermediary computer 50 also includes a transmitter(s) 50F, for transmitting signals and/or data and/or information to any one or more of the central processing computer(s) 10, the provider communication device(s) 20, the payer communication device(s) 30, the user or patient communication device(s) 40, any other intermediary computer(s) 50, the healthcare records computer(s) 60, the insurance exchange computer(s) 70, the social networking computer(s) 80, and/or the media computer(s) 90 described herein, which may be utilized in conjunction with the present invention. The intermediary computer 50 also includes a receiver 50G, for receiving signals and/or data and/or information from any one or more of the central processing computer(s) 10, the provider communication device(s) 20, the payer communication device(s) 30, the user or patient communication device(s) 40, any other intermediary computer(s) 50, the healthcare records computer(s) 60, the insurance exchange computer(s) 70, the social networking computer(s) 80, and/or the media computer(s) 90 described herein, which may be utilized in conjunction with the present invention, which may be utilized in conjunction with the present invention.

The intermediary computer 50 also includes a database(s) 50H. The database 50H can contain and/or be linked to any of the data and/or information described herein as being stored in the database 10H.

The intermediary communication device 50 also includes an output device 50I for output any data, information, report, etc., described herein. In the preferred embodiment, the output device 50I can be a printer, a display, a transmitter, a modem, a speaker, and/or any other device which can be used to output data.

The intermediary communication device 50 also includes a video and/or audio recording device(s) 50J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

In any and/or all of the embodiments described herein, any one of the central processing computers 10, the provider communication devices 20, the payer communication devices 30, the patient communication devices 40, and/or the intermediary communication devices 50, can include input devices (not shown) for facilitating the data entry of a patients vital signs and/or other medical data such as, but not limited to, pulse rate, blood pressure, blood-sugar level, etc., and any other data and/or information which can be input into the respective computer and/or communication device and be transmitted to the central processing computer consistent with the utilization of the present invention as described herein.

Figure 7:
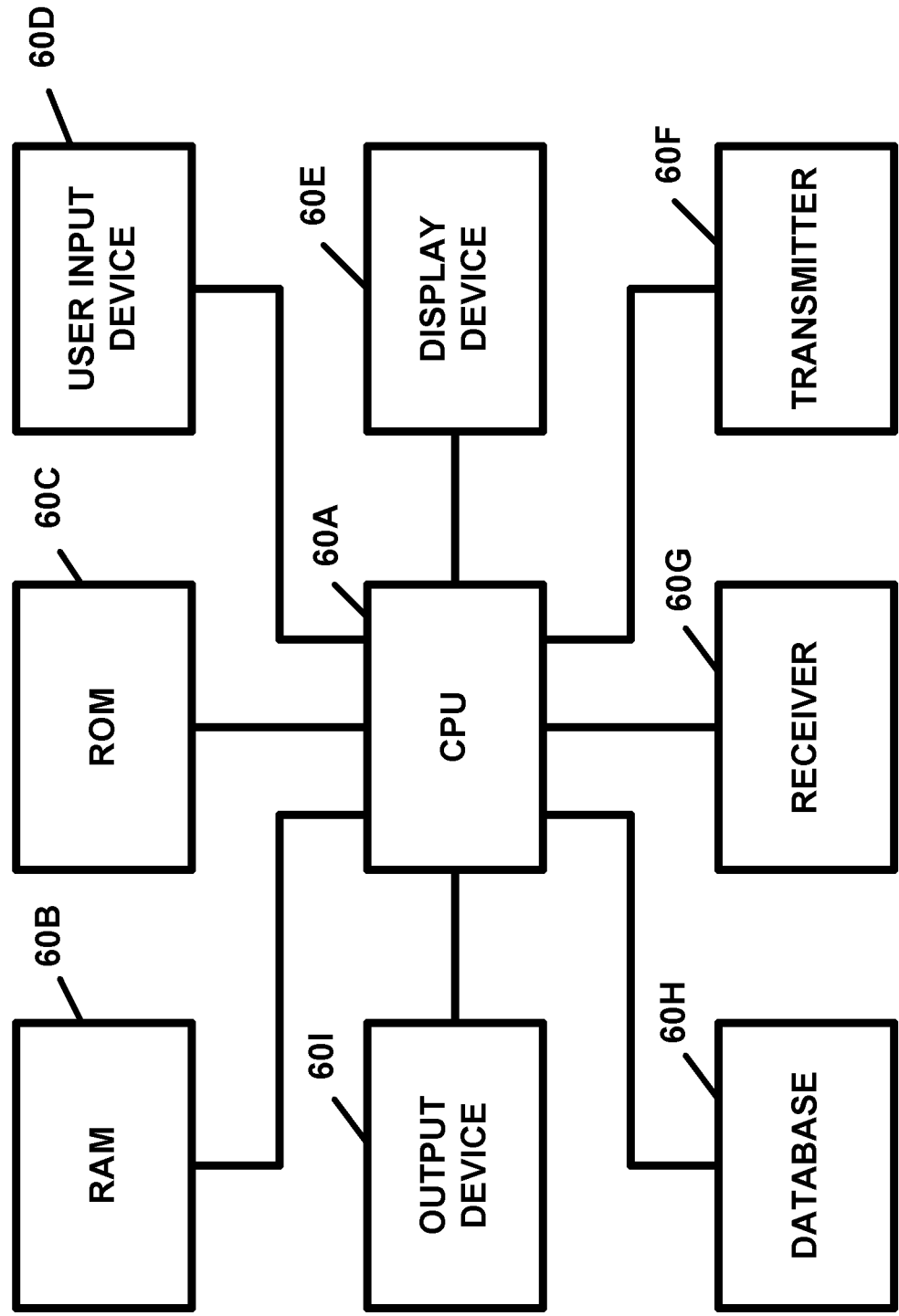
FIG. 7 illustrates an exemplary healthcare records cloud system computer of FIG. 1, in block diagram form.

FIG. 7 illustrates the healthcare records computer 60, in block diagram form. The healthcare records computer 60, in the preferred embodiment, can be server computer or server computer system, a cloud computer or cloud computer system, a network computer or computer system, a personal computer or any other computer or communication device, or any cellular telephone, tablet, personal digital assistant, wireless communication device or wireless computer, a watch, or any other communication device, which is utilized to store an electronic healthcare record, an electronic medical record, an electronic dental record, an electronic pharmacy record, or an electronic behavioral healthcare record or any one or any number of electronic healthcare records, electronic medical records, electronic dental records, electronic pharmacy records, and/or electronic behavioral healthcare records. In a preferred embodiment, the healthcare records computer 60 can be any computer or computer system for storing any electronic healthcare record, an electronic medical record, an electronic dental record, an electronic pharmacy record, or an electronic behavioral healthcare record which is store somewhere else other than the central processing computer. The healthcare records computer 60 can be used by, maintained by, or associated with any individual, provider, user, patient, payer, intermediary, or any other entity or third party.

In the preferred embodiment, the healthcare records computer 60 includes a central processing unit or CPU 60A, which in the preferred embodiment, is a microprocessor. The CPU 60A may also be a microcomputer, a minicomputer, a macro-computer, and/or a mainframe computer, depending upon the application.

The healthcare records computer 60 also includes a random access memory device(s) 60B (RAM) and a read only memory device(s) 60C (ROM), each of which is connected to the CPU 60A, a user input device 60D, for entering data and/or commands into the healthcare records computer 60, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information which input device(s) are also connected to the CPU 60A. The healthcare records computer 60 also includes a display device 60E for displaying data and/or information to a user or operator.

The healthcare records computer 60 also includes a transmitter(s) 60F, for transmitting signals and/or data and/or information to any one or more of the central processing computer(s) 10, the provider communication device(s) 20, the payer computers(s) 30, the user or patient communication device(s) 40, and the intermediary computer(s) 50, any other healthcare records computer(s) 60, the insurance exchange computer(s) 70, the social networking computer(s) 80, and/or the media computer(s) 90 described herein, which may be utilized in conjunction with the present invention. The healthcare records computer 60 also includes a receiver 60G, for receiving signals and/or data and/or information from any one or more of the central processing computer(s) 10, the provider communication device(s) 20, the payer computers(s) 30, the user or patient communication device(s) 40, the intermediary computer(s) 50, any other healthcare records computer(s) 60, the insurance exchange computer(s) 70, the social networking computer(s) 80, and/or the media computer(s) 90 described herein, which may be utilized in conjunction with the present invention.

The healthcare records computer 60 also includes a database(s) 60H. The database 60H can contain and/or be linked to any of the data and/or information described herein as being stored in the database 10H and can also contain any data and/or information regarding and including any of the of electronic healthcare records, electronic medical records, electronic dental records, electronic pharmacy records, and/or electronic behavioral healthcare records which are stored in the healthcare records computer 60.

The healthcare records computer 60 also includes an output device 60I for output any data, information, report, etc., described herein. In the preferred embodiment, the output device 60I can be a printer, a display, a transmitter, a modem, a speaker, and/or any other device which can be used to output data.

Figure 8:
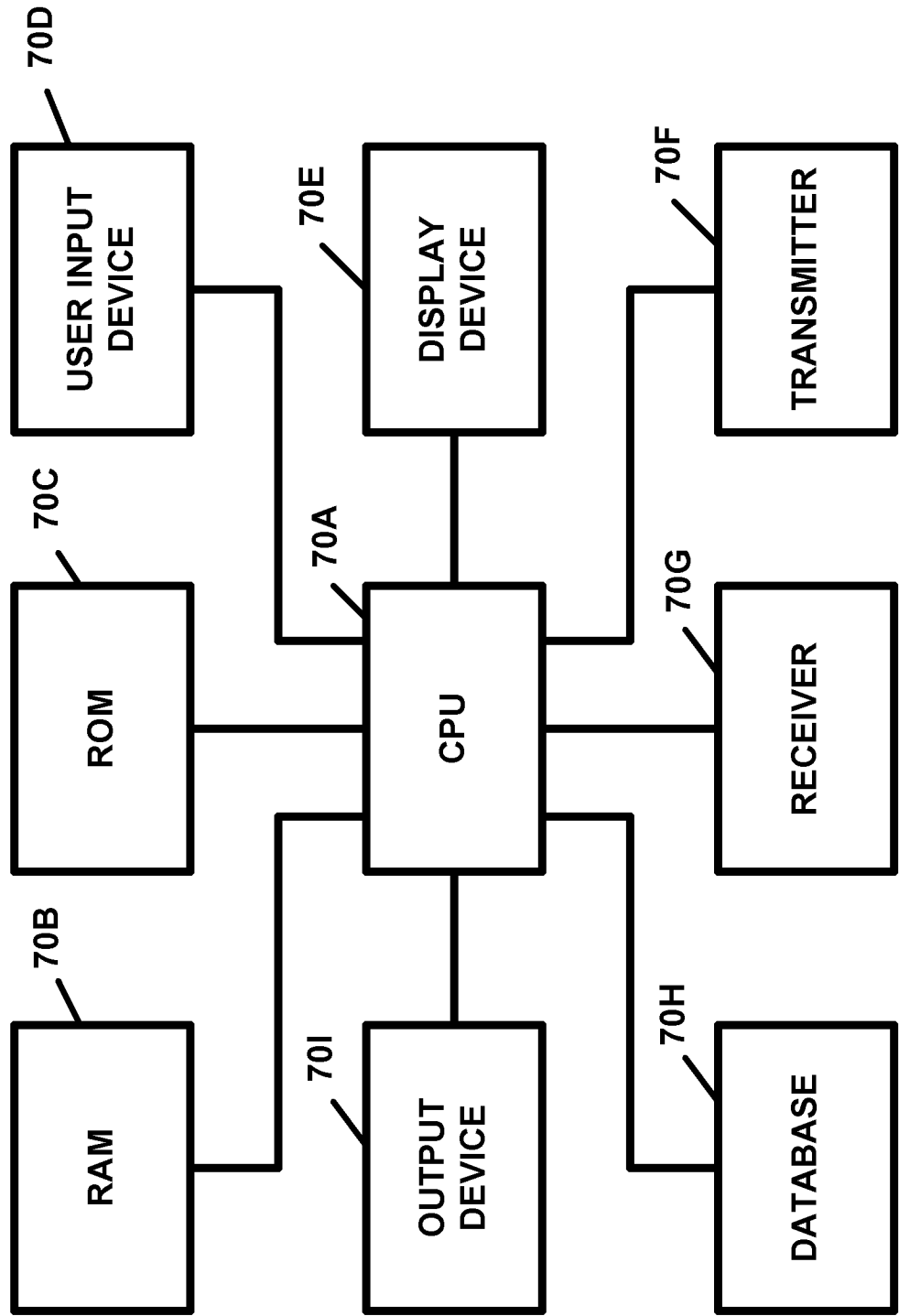
FIG. 8 illustrates the an exemplary insurance exchange computer of FIG. 1, in block diagram form.

FIG. 8 illustrates the insurance exchange computer 70, in block diagram form. The insurance exchange computer 70, in the preferred embodiment, can be server computer or server computer system, a cloud computer or cloud computer system, a network computer or computer system, a personal computer or any other computer or communication device, or any cellular telephone, tablet, personal digital assistant, wireless communication device or wireless computer, a watch, or any other communication device, which is utilized to function as an insurance exchange computer 70.

In a preferred embodiment, the insurance exchange computer 70 can be any computer or computer system for providing the functionality described herein as being provided by the insurance exchange computer 70.

The insurance exchange computer 70 can be used by, maintained by, or associated with any provider of any of the herein-described insurance policies, products, or services, described herein as being provided via the apparatus 100 and method of the present invention.

In the preferred embodiment, the insurance exchange computer 70 includes a central processing unit or CPU 70A, which in the preferred embodiment, is a microprocessor. The CPU 70A may also be a microcomputer, a minicomputer, a macro-computer, and/or a mainframe computer, depending upon the application.

The insurance exchange computer 70 also includes a random access memory device(s) 70B (RAM) and a read only memory device(s) 70C (ROM), each of which is connected to the CPU 70A, a user input device 70D, for entering data and/or commands into the insurance exchange computer 70, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information which input device(s) are also connected to the CPU 70A. The insurance exchange computer 70 also includes a display device 70E for displaying data and/or information to a user or operator.

The insurance exchange computer 70 also includes a transmitter(s) 70F, for transmitting signals and/or data and/or information to any one or more of the central processing computer(s) 10, the provider communication device(s) 20, the payer communication device(s) 30, the user or patient communication device(s) 40, and the intermediary computer(s) 50, the healthcare records computer(s) 60, any other insurance exchange computer(s) 70, the social networking computer(s) 80, and/or the media computer(s) 90 described herein, which may be utilized in conjunction with the present invention. The insurance exchange computer 70 also includes a receiver 70G, for receiving signals and/or data and/or information from any one or more of the central processing computer(s) 10, the provider communication device(s) 20, the payer communication device(s) 30, the user or patient communication device(s) 40, the intermediary computer(s) 50, the healthcare records computer(s) 60, any other insurance exchange computer(s) 70, the social networking computer(s) 80, and/or the media computer(s) 90 described herein, which may be utilized in conjunction with the present invention.

The insurance exchange computer 70 also includes a database(s) 70H. The database 70H can contain and/or be linked to any of the data and/or information described herein as being stored in the database 10H and can also contain any data and/or information regarding and including any of the various insurance policies, products, or service, which can be offered for sale by the insurance exchange computer 70, as well as any data and/or information regarding insured individuals or entities, their insurance policies, products, and/or services, claims made, claims paid, and any other records typically stored or maintained by an insurance company computer, an insurance exchange computer, an electronic commerce computer or any other data and/or information for providing any of the functions or functionality described herein as being performed by the insurance exchange computer 70.

The insurance exchange computer 70 also includes an output device 701 for output any data, information, report, etc., described herein. In the preferred embodiment, the output device 701 can be a printer, a display, a transmitter, a modem, a speaker, and/or any other device which can be used to output data.

Figure 9:
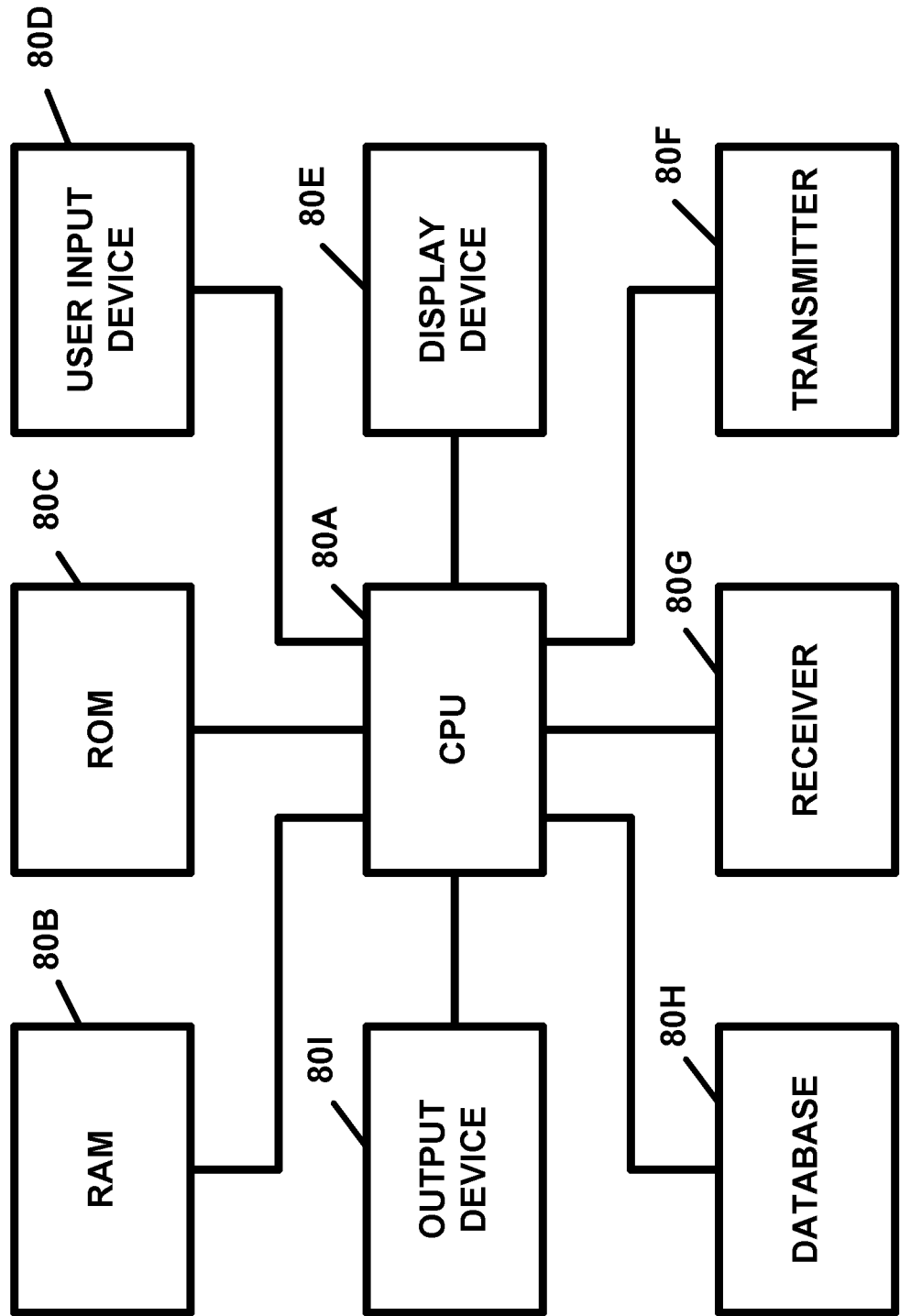
FIG. 9 illustrates an exemplary social networking computer of FIG. 1, in block diagram form.

FIG. 9 illustrates the social networking computer 80, in block diagram form. The social networking computer 80, in the preferred embodiment, can be any social networking computer or computer system or any computer or computer system used by or associated with any social networking company or social networking website, or can be any suitable server computer or server computer system, a cloud computer or cloud computer system, a network computer or computer system, a personal computer or any other computer or communication device, or any cellular telephone, tablet, personal digital assistant, wireless communication device or wireless computer, a watch, or any other communication device, which is utilized to function as a social networking computer 80. In a preferred embodiment, the social networking computer 80 can be any computer of computer system for providing the functionality described herein as being provided by the social networking computer 80 or any social networking computer or website.

The social networking computer 80 can be used by, maintained by, or associated with social networking company, website, or other entity and can provide any of the herein-described social networking information, activities, and/or functionality, described herein as being provided via the apparatus 100 and method of the present invention and which can be provided by any social networking company, website, or other entity.

In the preferred embodiment, the social networking computer 80 includes a central processing unit or CPU 80A, which in the preferred embodiment, is a microprocessor. The CPU 80A may also be a microcomputer, a minicomputer, a macro-computer, and/or a mainframe computer, depending upon the application.

The social networking computer 80 also includes a random access memory device(s) 80B (RAM) and a read only memory device(s) 80C (ROM), each of which is connected to the CPU 80A, a user input device 80D, for entering data and/or commands into the social networking computer 80, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information which input device(s) are also connected to the CPU 80A. The social networking computer 80 also includes a display device 80E for displaying data and/or information to a user or operator.

The social networking computer 80 also includes a transmitter(s) 80F, for transmitting signals and/or data and/or information to any one or more of the central processing computer(s) 10, the provider communication device(s) 20, the payer communication device(s) 30, the user or patient communication device(s) 40, and the intermediary computer(s) 50, the healthcare records computer(s) 60, the insurance exchange computer(s) 70, any other social networking computer(s) 80, and/or the media computer(s) 90 described herein, which may be utilized in conjunction with the present invention. The social networking computer 80 also includes a receiver 80G, for receiving signals and/or data and/or information from any one or more of the central processing computer(s) 10, the provider communication device(s) 20, the payer communication device(s) 30, the user or patient communication device(s) 40 the intermediary computer(s) 50, the healthcare records computer(s) 60, the insurance exchange computer(s) 70, any other social networking computer(s) 80, and/or the media computer(s) 90 described herein, which may be utilized in conjunction with the present invention.

The social networking computer 80 also includes a database(s) 80H. The database 80H can contain and/or be linked to any of the data and/or information described herein as being stored in the database 10H and can also contain any data and/or information typically found in or utilized by a social networking computer or any members of the social network serviced thereby as well as any data and/or information typically utilized in providing or performing the functionality and/or services provided or offered by the social network associated with the social networking computer 80.

The social networking computer 80 also includes an output device 801 for output any data, information, report, etc., described herein. In the preferred embodiment, the output device 801 can be a printer, a display, a transmitter, a modem, a speaker, and/or any other device which can be used to output data.

Figure 10:
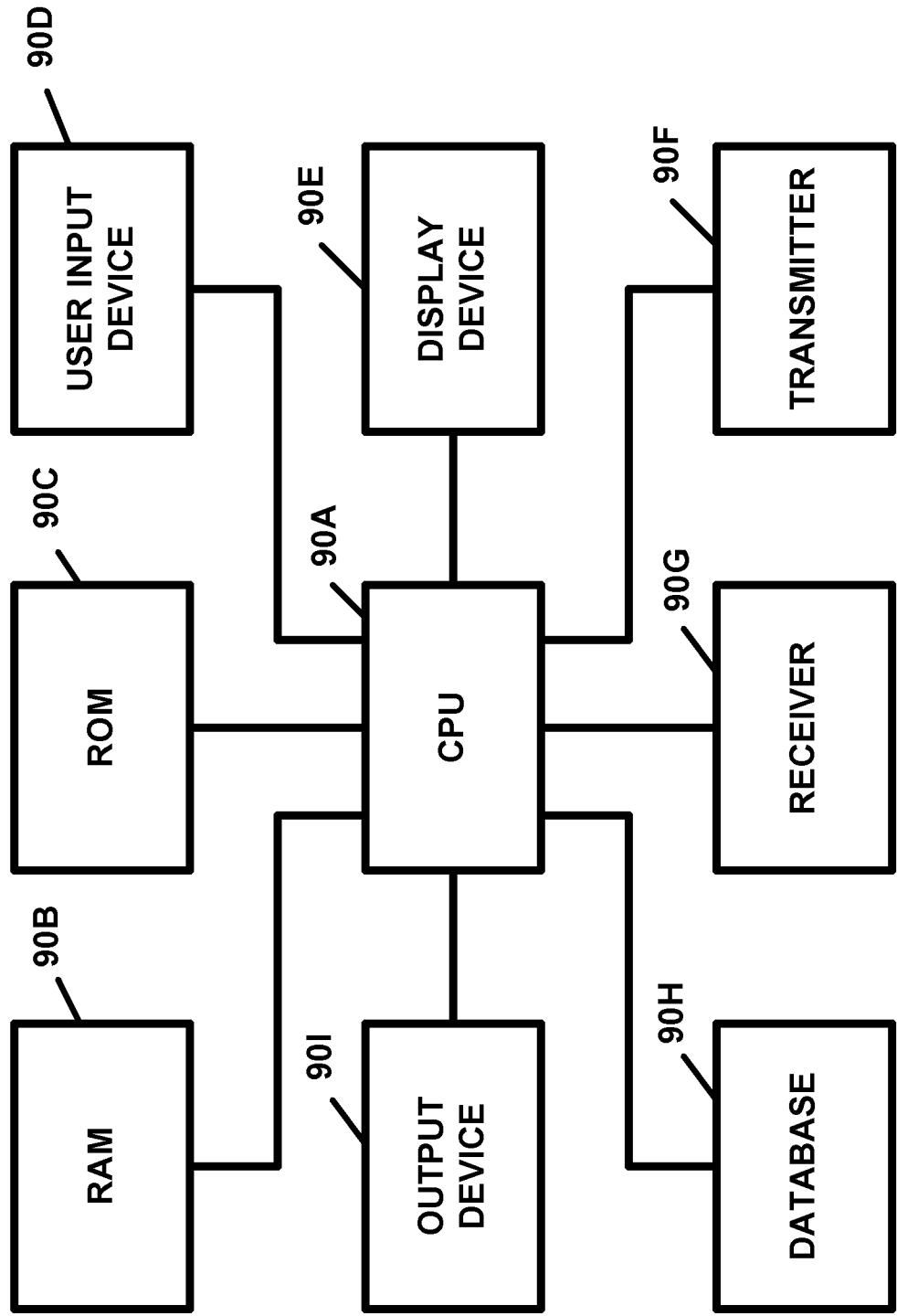
FIG. 10 illustrates an exemplary media computer of FIG. 1, in block diagram form.

FIG. 10 illustrates the media computer 90, in block diagram form. The media computer 90, in the preferred embodiment, can be any computer or computer system used by or associated with any news information source, individual, company, or entity, any external information source, individual, company, or entity, any advertiser or advertisement source, individual, company or entity, or any marketing materials source, individual, company, or entity.

The media computer 90 can be any computer or computer system which can provide, to any of the herein-described users, individuals, patients, providers, payers, intermediaries, third parties, and/or entities who or which utilized the apparatus 100 and method of the present invention, any news, information, advertisements, or marketing materials, of any kind, nature, or type, which can include, but which is not limited to, any healthcare or healthcare-related news, information, advertisements, or marketing materials, any fitness or fitness-related news, information, advertisements, or marketing materials, any wellness or wellness-related news, information, advertisements, or marketing materials, as well as any non-healthcare or non-healthcare-related news, information, advertisements, or marketing materials. The media computer 90 provides news, information, advertisements, or marketing materials, via the apparatus 100 and method of the present invention. In a preferred embodiment, the media computer 90 can be any computer or computer system for providing the functionality described herein as being provided by the media computer 90.

The media computer 90 can be used by, maintained by, or associated with a media company or entity, a news service, information source or service, an advertiser, an advertisement company, agency, or entity, a marketer, a marketing company or entity, or any individual providing a media, news, information, advertisements, or marketing materials of or on behalf of themselves or another, The media computer 90 can provide any of the herein-described media, news, information, advertisements, or marketing materials, and/or any other information and/or can provide any o the functionality described herein as being provided via the apparatus 100 and method of the present invention.

In the preferred embodiment, the media computer 90 includes a central processing unit or CPU 90A, which in the preferred embodiment, is a microprocessor. The CPU 90A may also be a microcomputer, a minicomputer, a macrocomputer, and/or a mainframe computer, depending upon the application.

The media computer 90 also includes a random access memory device(s) 90B (RAM) and a read only memory device(s) 90C (ROM), each of which is connected to the CPU 90A, a user input device 90D, for entering data and/or commands into the media computer 90, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information which input device(s) are also connected to the CPU 90A. The media computer 90 also includes a display device 90E for displaying data and/or information to a user or operator.

The media computer 90 also includes a transmitter(s) 90F, for transmitting signals and/or data and/or information to any one or more of the central processing computer(s) 10, the provider communication device(s) 20, the payer communication device(s) 30, the user or patient communication device(s) 40, and the intermediary computer(s) 50, the healthcare records computer(s) 60, the insurance exchange computer(s) 70, the social networking computer(s) 80, and/or any other media computer(s) 90 described herein, which may be utilized in conjunction with the present invention. The media computer 90 also includes a receiver 90G, for receiving signals and/or data and/or information from any one or more of the central processing computer(s) 10, the provider communication device(s) 20, the payer communication device(s) 30, the user or patient communication device(s) 40 the intermediary computer(s) 50, the healthcare records computer(s) 60, the insurance exchange computer(s) 70, the social networking computer(s) 80, and/or any other media computer(s) 90 described herein, which may be utilized in conjunction with the present invention.

The media computer 90 also includes a database(s) 90H. The database 90H can contain and/or be linked to any of the data and/or information described herein as being stored in the database 10H and can also contain any data and/or information typically found in or utilized by a media computer as well as any of the respective media, news, information, advertisements, or marketing materials, and/or any data and/or information typically utilized in providing or performing the functionality and/or services provided or offered by the media computer 90.

The media computer 90 also includes an output device 901 for output any data, information, report, etc., described herein. In the preferred embodiment, the output device 901 can be a printer, a display, a transmitter, a modem, a speaker, and/or any other device which can be used to output data.

The apparatus and method of the present invention can be utilized in numerous preferred embodiments in order to provide a vast array of healthcare and healthcare-related services for any one or more of the various parties described herein. While certain of the preferred embodiments may be described with regards to utilization by a particular party, it is important to note that any individual, patient, user, provider, payer, and/or intermediary or third party, may utilize the present invention in the same, similar, and/or analogous, manner. For example, a preferred embodiment for determining and/or ascertaining a medical diagnosis can be described as being utilized by a treating physician as well as be utilized by a provider to verify and/or check a diagnosis as well as by a patient or other user or individual in order to perform a self-diagnosis or double check a doctors diagnosis. In the same manner, any other preferred embodiment and/or other uses of the present invention can be utilized by any of the parties described herein.

The apparatus 100 of the present invention can also be utilized in order to allow an individual or a patient, or a caregiver, or one responsible for the care of an individual or patient, to enter notes, comments, or messages regarding or relating to the individual or patient into one or more of any of the individual's, patient's, or caregiver's, electronic healthcare record(s), electronic healthcare file(s), electronic medical record(s), electronic dental record(s), electronic pharmacy record(s), and/or electronic behavioral healthcare record(s). Any respective note, comment, or message can be in text form, audio form, or video form, and can contain information regarding a symptom, an illness, an experience, a treatment, a diagnosis, a treatment plan, an activity, a problem, a concern, a thought or an idea, a question, a question for a healthcare provider, or any other information which the individual or patient, or one caring for the individual or patient, may deem important to be recorded or noted in the respective electronic healthcare record(s), electronic medical record(s), electronic dental record(s), electronic pharmacy record(s), and/or electronic behavioral healthcare record(s), or which can be communicated to, or otherwise made available to, a provider or an insurer or payer.

A healthcare provider can access, obtain, and/or use, the information provided or contained in the note, comment, or message, or provided or contained in multiple notes, comments, or messages, for any suitable purpose, such as, but not limited to, for preparing for, or for use during, a remote or virtual office visit with, or a remote or distance examination of, an individual, a patient, or a caregiver for or an individual or a patient, during a video telephone call, a video chat session, or a videoconference, with the individual, the patient, or the caregiver for or the individual or the patient, or for use during a conversation, discussion, or consultation, during a video telephone call, a video chat session, or a videoconference, with the individual, the patient, or the caregiver for the individual or the patient, or for use during a conversation, discussion, or consultation, during a video telephone call, a video chat session, or a videoconference, with and between, the healthcare provider, and the individual, the patient, or the caregiver for or the individual or the patient, or another healthcare provider or any other provider, or an insurer or a payer, or an intermediary, or for use during reviewing, updating, modifying, or performing any other activity in connection with, an individual's or patient's healthcare records, files, or histories, for use while making a diagnosis, for use while formulating a treatment or a treatment plan, for use in reviewing or evaluating an individual's or patient's diagnosis or treatment, for use in treatment planning and/or the evaluating of same, for use in care management, for use in monitoring or evaluating a recovery, for use in providing continuing or on-going care or treatment, for use in connection with the providing of a remote healthcare services or tele-health services, and/or for any other suitable use or purpose.

Any notes, comments or messages, can be provided by the individual, patient, or caregiver, or by any person caring for the individual or patient, while making an appointment, in advance of a video telephone call, a video chat session, or a videoconference, or a remote or virtual office visit with, or a remote or distance examination of, or in advance of a video telephone call, a video chat session, or a videoconference, or a remote or distance examination of, with the individual, the patient, or the caregiver for the individual or the patient, or a video telephone call, a video chat session, or a videoconference, with another provider, or a payer or insurer or any third party or intermediary, in connection with any tele-health related activity, or for the purpose of making and entering a note, comment, or message, into the individual's or patient's respective electronic healthcare record(s), electronic medical record(s), electronic dental record(s), electronic pharmacy record(s), and/or electronic behavioral healthcare record(s). In this regard, the present invention can allow an individual or patient, or a caregiver, or one responsible for caring for the individual or patient, to make and enter any notes, comments, or messages, into the individual's or patient's respective electronic healthcare record(s), electronic medical record(s), electronic dental record(s), electronic pharmacy record(s), and/or electronic behavioral healthcare record(s) so as to facilitate accurate and complete healthcare information record keeping.

The apparatus 100 of the present invention can be utilized to provide healthcare services, such as, but not limited to, a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The apparatus 100 of the present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus 100 and method of the present invention can also be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus 100 and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The apparatus 100 of the present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The apparatus 100 of the present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus 100 of the present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribe a treatment based on any and/or all any and/or all information regarding the individual or the patient. As a further result, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented in the individual's or the patient's healthcare records, files, or history.

In a preferred embodiment, the apparatus 100 and method of the present invention can be utilized to allow an individual, a patient, or a caregiver of or for the individual or the patient to engage in a video call, a video chat session, or a videoconference, with a healthcare provider in order to facilitate or to provide for a remote or virtual office visit with the healthcare provider or in order to facilitate or to provided for a remote or distance consultation or examination with or by a healthcare provider.

In a preferred embodiment, it is envisioned that any number, kinds, or types, of healthcare providers, who or which have registered with the apparatus 100 in order to engage in video calls, video chat sessions, or videoconferences, in order to provide remote or virtual office visits or in order to provide remote or distance consultations or examinations with and for any individuals or patients, or caregivers, can store any data and/or information regarding his or her name, address, telephone number, e-mail address, text messaging information or number(s), or any other contact information, credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

In a preferred embodiment, any of the above-described or herein-described data and/or information regarding the healthcare provider, for any number of healthcare providers, can be stored in, and can be searchable from, the database 10H of the central processing computer 10. In the preferred embodiment, any of the above-described or herein-described data and/or information regarding the healthcare provider, for any number of healthcare providers, can be also be stored in, and can be searchable from, the database 20H of any provider communication device 20. In the preferred embodiment, any of the above-described or herein-described data and/or information regarding the healthcare provider, for any number of healthcare providers, can be also be stored in, and can be searchable from, the database 40H of any user communication device 40.

In a preferred embodiment, it is envisioned that the individual, the patient, or the caregiver of or for the individual or the patient, can access the central processing computer 10 or a respective provider communication device 20 with or using his or her user communication device 40, or by accessing data and/or information stored in his or her communication device 40, at any time, in order to search for and/or to select a healthcare provider(s) with whom he or she can schedule a video call, a video chat session, or a videoconference. The individual, the patient, or the caregiver of or for the individual or the patient, can select the individual's or the patient's current healthcare provider, current primary care provider, or a new or different healthcare provider, or a healthcare provider having a certain specialization, or a certain availability. The individual or the patient, or the caregiver of or for the individual or the patient, can make an appointment for a video call, a video chat session, or a videoconference, with the healthcare provider with or using the user communication device 40. At the time of making the appointment the individual, patient, or caregiver, can provide a telephone number, a call number, a conference call number, or an IP address, associated with the user communication device 40 which the individual, the patient, or the caregiver, will use for the video call, the video chat session, or the videoconference. At the time of making the appointment, the individual, the patient, or the caregiver, can also be provided with the telephone number, the call number, the conference call number, or the IP address, associated with the provider communication device 20 which will be used by the healthcare provider for the video call, the video chat session, or the videoconference. At the time of making the appointment, the individual, the patient, or the caregiver, can also be provided with an instruction as to whether he or she is to call the healthcare provider at the appointment time, or whether the healthcare provider will call the individual, the patient, or the caregiver, at the appointment time.

In instances when the appointment is being made via the central processing computer 10, the appointment can be made via the individual's or the patient's electronic medical record, file, or history, which is stored in the database 10H of the central processing computer 10, and information regarding the appointment can be stored in the individual's or the patient's electronic medical record, file, or history as well as in the healthcare provider's work schedule or in an appointment schedule of the healthcare provider. In instances when the appointment is being made via a provider communication device 20, the appointment can be made via the individual's or the patient's electronic medical record, file, or history, which is stored in the database 20H of the provider communication device 20, and information regarding the appointment can be stored in the individual's or the patient's electronic medical record, file, or history as well as in the healthcare provider's work schedule or in an appointment schedule of the healthcare provider. In instances when the appointment is being made via a user communication device 40, the appointment can be made via the individual's or the patient's electronic medical record, file, or history, or personal healthcare record, which is stored in the database 40H of the user communication device 40, and information regarding same can be automatically transmitted to and stored in the individual's or the patient's electronic medical record, file, or history in the database 10H of the central processing computer 10 as well as in the healthcare provider's work schedule or in an appointment schedule of the healthcare provider.

In a preferred embodiment, the central processing computer 10 can be programmed so that, once an appointment for a video call, a video chat session, or a videoconference, has been made, the central processing computer 10 can automatically generate a message (hereinafter an "appointment message") containing information regarding the appointment, and/or the time and date of same, which has been scheduled and will transmit same to the provider communication device 20 of or associated with the healthcare provider with whom the appointment has been made, and will also transmit same to the user communication device(s) 40 of or associated with the individual, the patient, or the caregiver. In a preferred embodiment, the provider communication device 20 with which an appointment has been made can also be programmed so that, once an appointment for a video call, a video chat session, or a videoconference, has been made, the provider communication device 20 can automatically generate a message (hereinafter an "appointment message") containing information regarding the appointment, and/or the time and date of same, which has been scheduled and will transmit same to any other provider communication device 20 of or associated with the healthcare provider with whom the appointment has been made, and will also transmit same to the user communication device(s) 40 of or associated with the individual, the patient, or the caregiver. In a preferred embodiment, the user communication device 40 with which an appointment has been made can also be programmed so that, once an appointment for a video call, a video chat session, or a videoconference, has been made, the user communication device 40 can automatically generate a message (hereinafter an "appointment message") containing information regarding the appointment, and/or the time and date of same, which has been scheduled and will transmit same to the central processing computer 10, to any provider communication device 20 of or associated with the healthcare provider with whom the appointment has been made, and/or to any other user communication device(s) 40 of or associated with the individual, the patient, or the caregiver.

In a preferred embodiment, the central processing computer 10 can also be programmed so that, once an appointment for a video call, a video chat session, or a videoconference, has been made, the central processing computer 10 can automatically generate a reminder message(s) (hereinafter an "reminder message") containing information for reminding each of the individual, the patient, or the caregiver, and the healthcare provider of the appointment for the video call, the video chat session, or the videoconference. The reminder message or reminder messages can be transmitted to each of the user communication device(s) 40 of or associated with the individual, the patient, or the caregiver, and to the provider communication device 20 of or associated with the healthcare provider.

In a preferred embodiment, any of the appointment messages and/or reminder messages described herein can include the appointment time, the name of the healthcare provider, and the telephone number, the call number, the conference call number, or the IP address, associated with the provider communication device 20 which will be used by the healthcare provider for the video call, the video chat session, or the videoconference, and the name of the individual, the patient, or the caregiver, and the telephone number, the call number, the conference call number, or the IP address, associated with the user communication device 40 which the individual, the patient, or the caregiver, will use for the video call, the video chat session, or the videoconference, and an instruction, if any, as to who is to initiate the video call, the video chat session, or the videoconference, such as, for example, whether the individual, the patient, or the caregiver, is to call the healthcare provider at the appointment time or whether the healthcare provider is to call the individual, the patient, or the caregiver, at the appointment time.

In a preferred embodiment, any of the herein-described appointment messages and/or reminder messages can be stored in the individual's or the patient's electronic healthcare record, file, or history, in the database 10H of the central processing computer 10 and/or in the database 40H of the user communication device 40, such as in a healthcare provider appointments section or field of same. Likewise, any of the herein-described appointment messages and/or reminder messages can be stored in the healthcare provider's records or files which can also be stored in the database 10H of the central processing computer 10 and/or in the database 20H of the provider communication device 20 such as in an appointments section or field of same.

In a preferred embodiment, any of the herein-described appointment messages or reminder messages can also contain a link or a hyperlink to the electronic healthcare record, file, or history, of the individual or the patient. Any of the herein-described appointment messages or reminder messages can also contain a link or a hyperlink for allowing each of the individual, the patient, or the caregiver of or for the individual or the patient to initiate a video call, a video chat session, or a videoconference, described herein via the link or the hyperlink.

In another preferred embodiment, a healthcare provider or any number of healthcare providers can be available for a video call, a video chat session, or a videoconference, at any given time and an individual, a patient, or a caregiver for the individual or the patient, can simply access the central processing computer 10, see which healthcare provider or healthcare providers are available and can immediately initiate a video call, a video chat session, or a videoconference, with an available healthcare provider.

In a preferred embodiment, the apparatus 100 can be utilized to in order to allow the healthcare provider to gain authorized access to the individual's or the patient's electronic healthcare records, files, or history, prior to and/or during the video call, the video chat session, or the videoconference, with the individual, the patient, or the caregiver of or for the individual or the patient. In this regard, the healthcare provider can review the individual's or the patient's electronic healthcare records, files, or history, prior to and/or during the video call, the video chat session, or the videoconference, obtain information from same, enter notes, observations, or examination findings, into same, and/or enter information regarding a diagnosis, a treatment, or a treatment plan into same, and/or enter information regarding and/or prescribe a medication or a drug, prescribe a therapy of any kind or type, prescribe a treatment of any kind or kind, and/or make a referral to another healthcare provider. In a preferred embodiment, any and/or all information, including a video or a video clip, and/or an audio, a video, and/or an audio and video recording, of the video call, the video chat session, or the videoconference, can be recorded and stored in the individual's or the patient's electronic healthcare records, files, or history.

Figure 11:
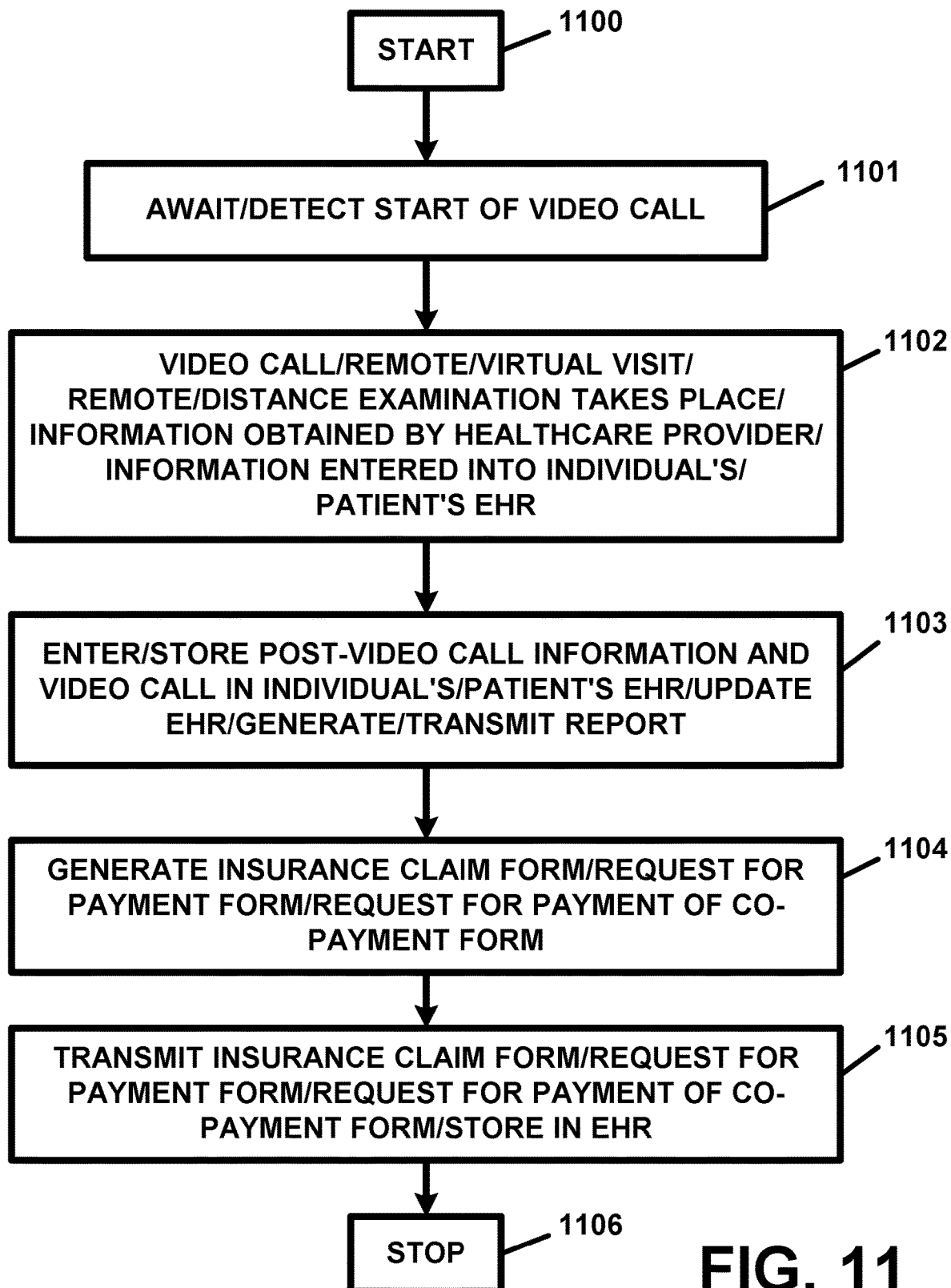
FIG. 11 illustrates a preferred embodiment method of utilizing the apparatus of the present invention, in flow diagram form.

FIG. 11 illustrates a preferred embodiment method for utilizing the apparatus 100 and method of the present invention, in flow diagram form. The preferred embodiment of FIG. 11 will be described as being utilized in connection with a video call between an individual, a patient, or a caregiver, and a healthcare provider. However, it is to be understood, and it is important to note, that the preferred embodiment of FIG. 11 can also be utilized in a same, a similar, and/or an analogous, manner in connection with a video chat session or a videoconference with and/or between an individual, a patient, or a caregiver, and a healthcare provider, a healthcare professional, a healthcare insurer, a healthcare payer, an intermediary, and/or any other provider of any healthcare or other service. It is also to be understood, and it is important to note, that, although described as being utilized in connection with a video call between an individual, a patient, or a caregiver, and a healthcare provider, the embodiment of FIG. 11 can also be utilized in a same, a similar, and/or an analogous, manner in connection with any video call, video chat session, or videoconference, involving and/or with and/or between any of the herein-described individuals, patients, caregivers, healthcare providers, other providers, healthcare insurers, healthcare payers, and/or intermediaries.

With reference to FIG. 11, the operation of the apparatus 100 commences at step 1100. At step 1101, the apparatus 100 will await and detect the start of the video call. In a preferred embodiment, depending on what may be pre-arranged or pre-selected, the individual, the patient, or the caregiver, can call the healthcare provider by using the his or her user communication device 40 to call the provider communication device 20 of or associated with the healthcare provider, or the healthcare provider can call the individual, the patient, or the caregiver, by using his or her provider communication device 20 to call the user communication device 40 of or associated with the individual, the patient, or the caregiver of or for the individual or the patient. In another preferred embodiment, the video call can be initiated and/or can take place via the central processing computer 10. In another preferred embodiment, the video call can be initiated via a link or a hyperlink in any of the herein-described appointment messages or reminder messages. Any of the herein-described links or hyperlinks, in any of the herein-described appointment messages or reminder messages, can provide, or can be, a link or a hyperlink to, for, or associated with the telephone number, the call number, the conference call number, or the IP address, associated with the provider communication device 20 which will be used by the healthcare provider for the video call, as well as the telephone number, the call number, the conference call number, or the IP address, associated with the user communication device 40 which will be used by the individual, the patient, or the caregiver.

In another preferred embodiment, the database 10H of the central processing computer 10 can contain, in the electronic healthcare record, file, or history, of the individual or the patient, and/or in the records or files of the healthcare provider, a link or a hyperlink to, for, or associated with the telephone number, the call number, the conference call number, or the IP address, associated with the provider communication device 20 which will be used by the healthcare provider for the video call as well as the telephone number, the call number, the conference call number, or the IP address, associated with the user communication device 40 which will be used by the individual, the patient, or the caregiver.

In this preferred embodiment, the video call can be initiated by either the individual, the patient, or the caregiver of or for the individual or the patient, using either the telephone number, the call number, the conference call number, or the IP address, associated with the provider communication device 20 or by using the link or the hyperlink provided in the electronic healthcare record, file, or history, of the individual or the patient, or by using the link or the hyperlink provided in the records or files of the healthcare provider, and/or by using the link or the hyperlink provided in the appointment message or any reminder message. In this preferred embodiment, the video call can be initiated by either the healthcare provider using either the telephone number, the call number, the conference call number, or the IP address, associated with the user communication device 40 of or associated with the individual, the patient, or the caregiver, or by using the link or the hyperlink provided in the electronic healthcare record, file, or history, of the individual or the patient, or by using the link or the hyperlink provided in the records or files of the healthcare provider.

Once the video call has been initiated and detected by the apparatus 100 and/or the central processing computer 10, at step 1101, the operation of the apparatus 100 will proceed to step 1102 and the video call can proceed. In a preferred embodiment, the video call can take place with a cellular telephone, a smart phone, a Smartphone, or a personal digital assistant being utilized as the user communication device 40 used by the individual, the patient, or the caregiver, and/or as the provider communication device 20 used by the healthcare provider. In another preferred embodiment, the video call can take place with a personal computer, a laptop computer, a tablet, a tablet computer, a cellular telephone, a smart phone, a Smartphone, or a personal digital assistant, or a watch being utilized as the user communication device 40 used by the individual, the patient, or the caregiver, and/or as the provider communication device 20 used by the healthcare provider. In a preferred embodiment, the video call can take place, and any and/or all data and information can be provided, via the display device 20E of the healthcare provider communication device 20 and via the display device 40E of the user communication device 40.

In a preferred embodiment, the video call can be initiated via a link or a hyperlink contained in the individual's or the patient's electronic healthcare record, file, or history, and the video call can take place via the central processing computer 10 and/or via the individual's or the patient's electronic healthcare record, file, or history, so that information regarding the time and date of the video call, and/or any information regarding any actions taken by the individual, the patient, or the caregiver, or the healthcare provider, and/or any information regarding any information accessed from or in the individual's or the patient's electronic healthcare record, file, or history, and/or any information regarding any notes or information or data entered into, recorded by, or stored in, the individual's or the patient's electronic healthcare record, file, or history, by the individual, the patient, or the caregiver, or the healthcare provider, and/or the video call itself, can be monitored, recorded, and/or stored, in the individual's or the patient's electronic healthcare record, file, or history. In another preferred embodiment, the video call can also take place by and between the provider communication device 20 and the user communication device 40, with each of the healthcare provider communication device 20 and/or the user communication device 40 being in communication with, and/or having access to, the central processing computer 10 and/or being in communication with and/or having access to, the individual's or the patient's electronic healthcare record, file, or history, in the database 10H of the central processing computer 10.

In a preferred embodiment, at the start of the video call, and at or during step 1102, the healthcare provider can take a picture or photograph of the individual, the patient, or the caregiver, using the healthcare provider communication device 20, which picture or photograph can be stored and can be used for verifying the identity of the individual, the patient, or the caregiver as descried herein. In a preferred embodiment, at or during step 1102, the healthcare provider can also take a picture or photograph of himself or herself, which picture or photograph can be stored and can be used for verifying the identity of the healthcare provider as described herein.

Thereafter, at step 1102, the video call can then proceed and the healthcare provider can conduct the remote office visit or the virtual office visit and/or the remote examination or the distance examination with the individual, the patient, or the caregiver. In instances where the individual or the patient is on the video call without a caregiver, then the video call can take place between the individual or the patient and the healthcare provider. In instances where a caregiver is on the video call, then the video call can take place with the individual or the patient, the caregiver and the healthcare provider. In instances where only the caregiver is on the video call without the individual or the patient, then the video call can take place with the caregiver and the healthcare provider. In a preferred embodiment, the video call can be recorded by or with the central processing computer 10, by or with the provider communication device 20, and/or by or with the user communication device 40 for storage in each of the central processing computer 10, the provider communication device 20, and/or the user communication device 40. In this regard, the healthcare provider or another healthcare provider, or the individual, the patient, the caregiver, or another caregiver, can replay or review same at any time.

At step 1102, the healthcare provider can conduct the remote office visit or the virtual office visit and/or the remote examination or the distance examination with the individual, the patient, or the caregiver, by ascertaining the individual's or the patient's condition, symptoms, or the nature of the individual's or the patient's illness, sickness or state of health. At step 1102, the healthcare provider can also obtain information regarding a healthcare history of or for the individual or the patient or any information regarding a family healthcare history of or for the individual or the patient. At step 1102, the healthcare provider can also obtain information regarding any allergies the individual or the patient may have, or any prescription medications or drugs the individual or the patient may be taking. At step 1102, the healthcare provider can also obtain any other information needed or desired for diagnosing and/or treating the individual or the patient during the video call.

At step 1102, the individual or the patient, or the caregiver, can also, if not previously provided to the healthcare provider, provide the healthcare provider with authorization and/or permission to access and review the individual's or the patient's electronic healthcare record, file, or history, and/or to review any data and/or information contained therein. In a preferred embodiment, the healthcare provider can also be provided with authorization or permission to access and review the individual's or the patient's electronic healthcare record, file, or history, prior to the video call. Such authorization or permission can also be provided at the time the appointment is scheduled by the individual, the patient, or the caregiver of or for the individual or the patient.

At step 1102, the healthcare provider can access, and can review or can obtain any data and/or information contained in, the individual's or the patient's electronic healthcare record, file, or history. At step 1102, the healthcare provider can also request and/or conduct a visual examination of the individual or the patient or of a body part of the individual or the patient in and/or under appropriate circumstances by asking the individual or the patient, or the caregiver, to use and/or position the camera associated with the user communication device 40 in order to allow the healthcare provider to look at or view the individual or the patient or any body part of the individual or the patient. At step 1102, the individual, the patient, or the caregiver, can also transmit any data and/or information stored in any personal health record of or for the individual or the patient which might be stored on or in the user communication device 40 which is being utilized for the video call. At step 1102, the individual, the patient, or the caregiver, can also transmit any data and/or information stored in any electronic healthcare record, file, or history, of or for the individual or the patient which might be stored on or in the user communication device 40 which is being utilized for the video call.

At step 1102, the healthcare provider can also ask that the individual, the patient, or the caregiver, obtain and/or transmit any data and/or information from any healthcare measuring device or equipment, any healthcare measurement device or equipment, or any healthcare monitoring device or equipment, or obtain and/or transmit any data and/or information from any healthcare equipment input device, healthcare measurement input device, or healthcare monitoring input device described herein, which can be utilized in connection or in conjunction with the user communication device 40 and/or which has been described herein as being utilized as an input device for or in connection with the user communication device 40. In this regard, the healthcare provider can also request that the individual, the patient, or the caregiver, obtain and/or transmit data and/or information obtained by a pulse rate monitor, a blood pressure monitor, a blood oxygen or percentage oxygen measurement device, an electro-cardiogram, a glucose monitor, a blood-sugars monitor, any device which can acquire, receive, generate and/or provide, digital data such as medical, healthcare, bio-metric, physiological, and/or any other kind of healthcare data and/or healthcare-related data, a heart rate monitor, a pulse rate monitor, or EKG machine, a thermometer, a digital thermometer, a stethoscope, a heart rate monitor or measurement device, a pulse rate monitor or measurement device, a blood pressure monitor or measurement device, a blood pressure measurement device, a blood glucose monitor, a blood oxygen percentage level monitor, an oximeter, a digital finger pulse oximeter, a blood analysis device or machine, a respirator, a respiration monitoring or measurement device, a dialysis machine, a dialysis device, electro-cardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laparoscopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedence measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, dental probe, microscopic camera probing device, or any other bio-metric or physiological data measuring device(s) and/or data acquisition device (each of which can be hereinafter also referred to herein as "healthcare equipment" or as a "healthcare measurement device").

At step 1102, the healthcare provider can also perform, during the video call, a remote control operation and/or a remote monitoring operation of, for, or regarding, any of the above-noted items of healthcare equipment or of any healthcare measurement device(s) via a respective link or hyperlink provided in the individual's or the patient's electronic healthcare record, file, or history. Any results or measurements obtained from any healthcare equipment or from any healthcare measurement device(s) can be provided to the healthcare provider via the display device 20E of the healthcare provider communication device 20.

At step 1102, the individual, the patient, or the caregiver, can also access the individual's or the patient's electronic healthcare record, file, or history, during the video call in order to view same along with the healthcare provider. In a preferred embodiment, any video call video and/or any electronic healthcare record, file, or history information, can be presented on the respective provider communication device 20 and/or the user communication device 40 in a split screen format so as to ensure that as much information as possible can be provided to the healthcare provider and/or to the individual, the patient, or the caregiver, during the video call. In a preferred embodiment, any video call video and/or audio and/or any electronic healthcare record, file, or history information, can be presented on the respective provider communication device 20 by being displayed, in a split screen format or other suitable format, on the display device 20E and/or by being presented via a speaker of the output device 20I of the provider communication device 20 so as to ensure that as much information as possible can be provided to the healthcare provider during the video call. In a preferred embodiment, and any video call video and/or audio and/or any electronic healthcare record, file, or history information, can be presented on the respective user communication device 40 by being displayed, in a split screen format or other suitable format, on the display device 40E and/or by being presented via a speaker of the output device 40I of the user communication device 40 so as to ensure that as much information as possible can be provided to the individual, the patient, or the caregiver, during the video call.

At step 1102, the healthcare provider can obtain any other information from the individual, the patient, or the caregiver, or from the individual's or the patient's electronic healthcare record, file, or history, and/or any other data and/or information which the healthcare provider deems to be needed or desired during the video call and/or during the remote office visit or the virtual office visit and/or the remote examination or the distance examination with the individual, the patient, or the caregiver. At step 1102, the healthcare provider can enter any notes, comments, and/or observations, and/or any examination findings, regarding the individual or the patient and/or regarding any data and/or information obtained or reviewed during the video call, into the individual's or the patient's electronic healthcare record, file, or history. At step 1102, the healthcare provider can also make or arrive at a diagnosis for the individual or the patient, and/or can prescribe a treatment, or a course of treatment, or can provide a treatment plan, or can generate or issue a prescription for a drug or a medication, or can generate or issue a prescription for a test or procedure, or can make a referral to another healthcare provider, for the individual or the patient. In a preferred embodiment, the healthcare provider can utilize any information contained in the individual's or the patient's electronic healthcare record, file, or history, in order to take into account any allergies, possible drug or medication interactions, or any other information regarding the individual or the patient which must be considered in making or in arriving at a diagnosis, and/or in prescribing a treatment, or a course of treatment, or in providing a treatment plan, or in generating or issuing a prescription for a drug or a medication, or in generating or issuing a prescription for a test or a procedure, or in making a referral, to another healthcare provider, for the individual or the patient. In a preferred embodiment, any prescription(s) or referral(s) generated or issued during step 1102 can be electronically sent, such as by e-mail, instant message, SMS message, MMS message, or in any other suitable communication device to any provider communication device 20 of or associated with the individual's or the patient's pharmacy or to any other healthcare provider to whom the respective prescription or referral is to be sent.

The healthcare provider can also, as step 1102, recommend that the individual or the patient, or the caregiver of or for the individual or the patient, obtain information from, and/or join or participate in or with, any social network or social networks associated with any of the herein-described social networking computers 80 which are described herein as being utilized in connection with the apparatus 100 of the present invention. The healthcare provider can also, as step 1102, recommend that the individual or the patient, or the caregiver of or for the individual or the patient, obtain information from and/or subscribe to any of the herein-described media computers 90 which are described herein as being utilized in connection with the apparatus 100 of the present invention. Thereafter, the video call can end and the operation of the apparatus 100 will proceed to step 1103.

At step 1103, the healthcare provider can enter any information regarding any notes, comments, observations, examination findings, and/or any other information obtained during the video call into the individual's or the patient's electronic healthcare record, file, or history, so as to update same to include information regarding the video call and the remote office visit or the virtual office visit and/or the remote examination or the distance examination which was conducted during same with the individual, the patient, or the caregiver. At step 1103, the healthcare provider can also store the picture or photograph of the individual, the patient, or the caregiver, which was taken during the video call along with any other information regarding the video call and the remote office visit, for the video call and the remote office visit, in order provide verification regarding the identity of the individual, the patient, or the caregiver.

At step 1103, the healthcare provider can also store the picture or photograph of the healthcare provider, which was taken during the video call along with any other information regarding the video call and the remote office visit, for the video call and the remote office visit, in order provide verification regarding the identity of the healthcare provider.

At step 1103, the video call, which can be recorded, can also be stored in the individual's or the patient's electronic healthcare record, file, or history, for retrieval at any time by the healthcare provider or another healthcare provider, or by the individual, the patient, the caregiver, or another caregiver, or by a healthcare insurer or a healthcare payer, or by an intermediary, or by any other authorized person or entity, at any time.

At step 1103, the central processing computer 10 can, after any and/or all information obtained during and/or regarding the video call has been entered by the healthcare provider and stored in the individual's or the patient's electronic healthcare record, file, or history, can generate a video call report and/or a remote or virtual office visit report or a remote or distance examination report, containing information regarding the video call and/or information regarding the remote or virtual office visit or the remote of distance examination, any data and information obtained or entered or recorded during the video call, and/or the photograph of the individual, the patient, or the caregiver and/or the picture or photograph of the healthcare provider, and/or any other data and/or information regarding the video call and the remote office visit, and can transmit the video call report and/or the remote or virtual office visit report or a remote or distance examination report in, as, or attached to, an e-mail message or in, as, or attached to, an electronic communication transmission, to the provider communication device 20 of or associated with the individual's or the patient's primary care healthcare provider or any other healthcare provider of the individual or the patient, to a user communication device 40 of or associated with the individual, the patient, or the caregiver or any other caregiver of the individual or the patient, to a payer communication device 30 of or associated with a healthcare insurer or a healthcare payer of the individual or the patient, and/or to an intermediary communication device 50 of or associated with an intermediary.

In a preferred embodiment, the video call report and/or the remote or virtual office visit report or a remote or distance examination report, can contain or include any of the data and/or information obtained from the individual, the patient, or the caregiver, prior to, during or after, the video call, any other information obtained from the individual, the patient, or the caregiver, or any information obtained from the individual's or the patient's electronic healthcare record, file, or history, and/or any other data and/or information which the healthcare provider deems to be needed or desired during the video call and/or during the remote office visit or the virtual office visit and/or the remote examination or the distance examination with the individual, the patient, or the caregiver, any information regarding any of the healthcare provider's notes, comments, observations, or examination findings, regarding the individual or the patient and/or any information regarding any data and/or information obtained or reviewed during the video call, and/or entered into the individual's or the patient's electronic healthcare record, file, or history, or any information regarding any diagnosis arrived or made for the individual or the patient, and/or any information regarding any prescribed treatment or course of treatment, any treatment plan, or any prescription for a drug or a medication, or any prescription for a test or procedure, or any referral to another healthcare provider, for the individual or the patient. In a preferred embodiment, the video call report and/or the remote or virtual office visit report or a remote or distance examination report, can contain or include any information regarding any recommendation that the individual or the patient, or the caregiver of or for the individual or the patient, obtain information from, and/or join or participate in or with, any social network or social networks associated with any of the herein-described social networking computers 80 and/or any recommendation that the individual or the patient, or the caregiver of or for the individual or the patient, obtain information from and/or subscribe to any of the herein-described media computers 90.

In a preferred embodiment, any remote or virtual office visit report or a remote or distance examination report generated at step 1103 can also be stored in the individual's or the patient's electronic healthcare record, file, or history.

At step 1104, the central processing computer 10, which can be programmed to generate and transmit an insurance claim form or a request for payment form, can utilize the information stored at step 1103 in order to generate an insurance claim form or a request for payment form. At step 1104, the central processing computer 10, which can be programmed to generate and transmit a request for payment of co-payment form, can generate a request for payment of co-payment form. In a preferred embodiment, the insurance claim form or a request for payment form and/or the request for payment of co-payment form, can also include, or include as an attachment(s), any one or more of the photograph of the individual, the patient, or the caregiver, the picture or photograph of the healthcare provider, any data and/or information regarding the video call and the remote office visit, the video call report and/or the remote or virtual office visit report or a remote or distance examination report.

At step 1105, the central processing computer 10 can transmit the insurance claim form or a request for payment form, in, as, or attached to, an e-mail message, or in, as, or attached to any other suitable electronic communication transmission, to the payer communication device 30 of or associated with the healthcare insurer or the healthcare payer of the individual or the patient. At step 1105, the central processing computer 10 can also transmit the request for payment of co-payment form in, as, or attached to, an e-mail message, or in, as, or attached to any other suitable electronic communication transmission, to the user communication device 40.

At step 1105, any insurance claim form(s) or a request for payment form(s) and any request for payment of co-payment form(s) generated by, and/or transmitted by, the central processing computer 10, and any attachments, if applicable, can be stored in the individual's or the patient's electronic healthcare record, file, or history. Thereafter, the operation of the apparatus 100 will cease at step 1106.

In this regard, the apparatus 100 and method of the present invention can be utilized to facilitate and/or to conduct remote or virtual healthcare provider visits, consultations, and/or examinations, via and/or through the use of video calls, video chat sessions, and/or videoconferences, with and between an individual, a patient, and/or a caregiver for the individual or the patient. The apparatus 100 and method of the present invention can also be utilized to schedule remote or virtual provider visits, consultations, and/or examinations, via and/or through the use of video calls, video chat sessions, and/or videoconferences, with and between an individual, a patient, and/or a caregiver for the individual or the patient.

In another preferred embodiment, as well as in any and/or all of the embodiments described herein, the apparatus and methods of the present invention can also be utilized in connection with, or in conjunction with, a distributed ledger and with Blockchain technology. In a preferred embodiment, a distributed ledger and Blockchain technology can be utilized along with a central processing computer, in a combined system, wherein certain of the transactions, described herein as being performed by the apparatus, can be processed and/or performed by and/or with a central processing computer and/or certain other transactions can be processed and/or performed by and/or with, and/or using, a distributed ledger and Blockchain technology or Blockchain technologies. In another preferred embodiment, any and/or all transactions, described herein as being performed and/or processed by the apparatus, can also be processed and/or performed by and/or with, and/or using, a distributed ledger and Blockchain technology or Blockchain technologies, and/or using any cryptocurrency Blockchain technology or technologies.

In a preferred embodiment, any type of Blockchain technology can be utilized in connection with the apparatus and methods of the present invention. In a preferred embodiment, for example, the apparatus and methods of the present invention can utilize a distributed ledger(s) along with any Blockchain technology or technologies, Bitcoin Blockchain technology or technologies, Ethereum Blockchain technology or technologies, Bitcoin Cash Blockchain technology or technologies, Litecoin Blockchain technology or technologies, Privacy Coin Bitcoin technology or technologies, and/or any other suitable Blockchain technology or technologies, and/or Smart contracts and/or Smart contract technology or technologies and/or decentralized autonomous organizations (DAOs), decentralized autonomous organizations (DAOs) technology or technologies, and/or any combination of same.

Applicant incorporates by reference herein the subject matter and teachings of "Blockchain Technology Explained" by Alan T. Norman, "Blockchain" by Abraham K. White, "Blockchain—A Practical Guide To Developing Business, Law, And Technology Solutions" by Joseph J. Bambara and Paul R. Allen, and "Blockchain—Ultimate Guide To Understanding Blockchain, Bitcoin, Cryptocurrencies, Smart Contracts And The Future of Money" by Mark Gates, in their entirety, for all of their respective subject matter and teachings regarding distributed ledger technology and/or technologies, Blockchain technology and/or technologies, Bitcoin technology and/or technologies, Bitcoin Blockchain technology and/or technologies, Ethereum technology and/or technologies, Ethereum Blockchain technology and/or technologies, cryptocurrencies, cryptocurrency technology and/or technologies, and/or smart contract technology and/or technologies, and/or decentralized autonomous organizations (DAOs) technologies, and/or peer-to-peer technology and/or technologies, and/or any other technology or technologies related thereto or which can be utilized in conjunction distributed ledgers, Blockchain technologies, Smart contracts, decentralized autonomous organizations (DAOs), and/or cryptocurrencies.

By utilizing a distributed ledger and a suitable Blockchain technology, the apparatus and methods of the present invention can reduce the amount of processing performed by, and reliance on, a central processing computer and/or can eliminate the need for a central processing computer and any centralized entity which might operate the central processing computer.

It is important to note that the distributed ledger and the Blockchain technology utilized with same can also be referred to herein as a "distributed ledger/Blockchain technology", "distributed ledger and Blockchain technology", "distributed ledger/Blockchain technology system", or "distributed ledger and Blockchain technology system", or that the distributed ledger and the Blockchain technology utilized with same can also be referred by using any suitable phrase or terminology indicative of an application or system which utilizes or which includes a distributed ledger which is used with any Blockchain technology or which is used in connection, or in conjunction, with any Blockchain technology.

Figure 12:
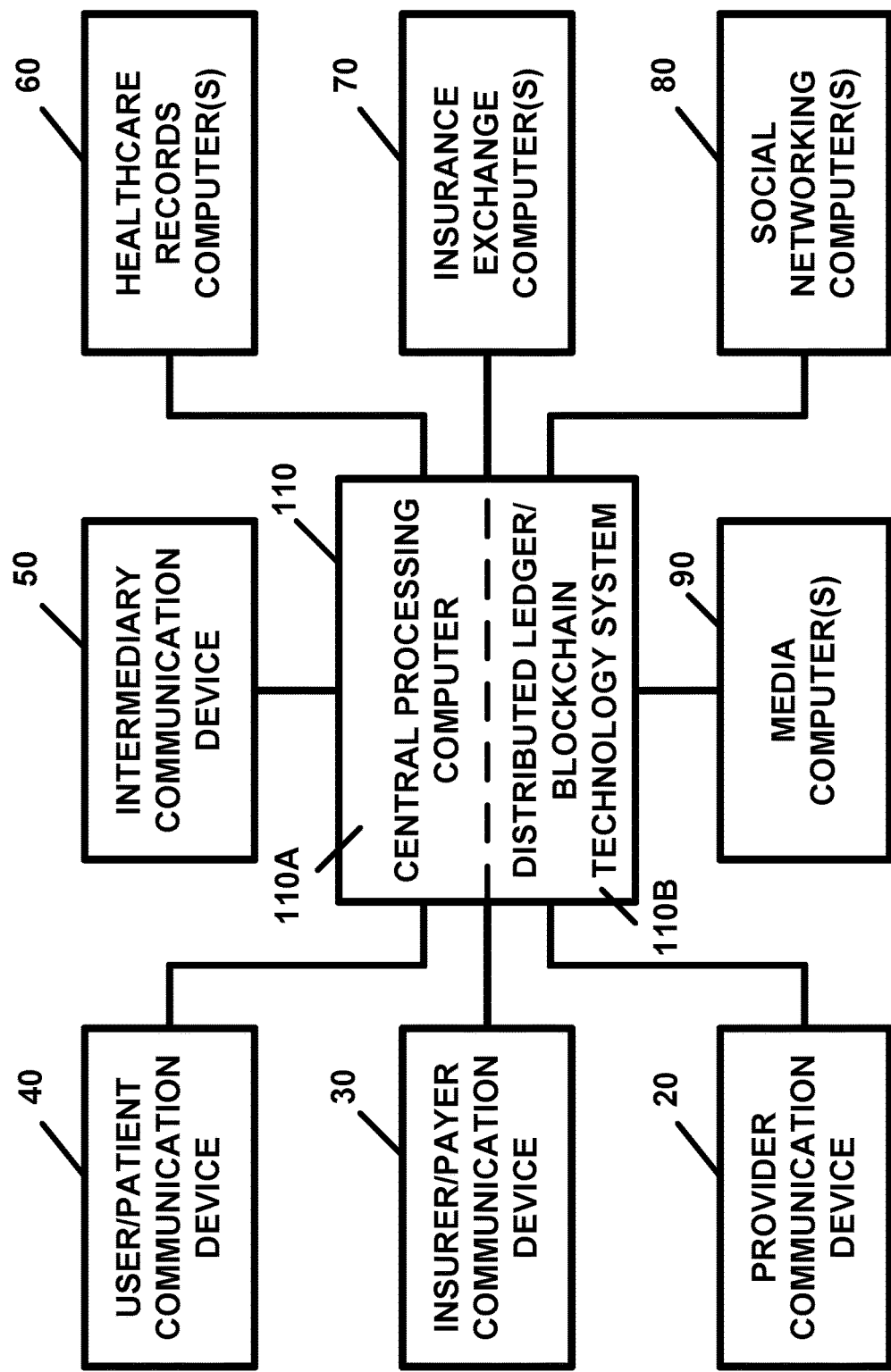
FIG. 12 illustrates another preferred embodiment of the apparatus of the present invention, in block diagram form.

FIG. 12 illustrates another preferred embodiment apparatus of the present invention, which is designated by the reference numeral 200, in block diagram form. With reference to FIG. 12, the apparatus 200 includes a central processing computer and distributed ledger and Blockchain technology system 110 (hereinafter "central processing computer/distributed ledger/Blockchain technology system 110") as well as any of, or each of, the other noted components of the apparatus 100 of FIG. 1. The central processing computer/distributed ledger/Blockchain technology system 110 includes a central processing computer component 110A, which can perform any and/or all of the functions described herein as being performed by the central processing computer 10 and/or the apparatus 100 of FIG. 1, and a distributed ledger and Blockchain technology system component 110B, which can also perform any and/or all of the functions described herein as being performed by the central processing computer 10 and/or the apparatus 100 of FIG. 1.

With reference once again to FIG. 12, the apparatus 200 can also include any number of provider communication devices 20, insurer/payer communication devices 30, user communication devices 40, intermediary communication devices 50, healthcare records computers 60, insurance exchange computers 70, social networking computers 80, and/or media computers 90.

In a preferred embodiment, any and/or all of the various operations, transactions, functions, and/or functionalities, described herein as being performed by the apparatus 100 in the preferred embodiment of FIG. 11 can also be performed by the apparatus 200 of FIG. 12 and, in particular, can be performed by either the central processing computer component 110A of the central processing computer/distributed ledger/Blockchain technology system 110 and/or by the distributed ledger and Blockchain technology system component 110B of the central processing computer/distributed ledger/Blockchain technology system 110. In a preferred embodiment, for example, any and/or all transactions involving any storing of any of the herein-described data and/or information, and/or any data and/or information regarding any video call(s) and/or remote office visit(s), and/or any video call reports and/or any of the remote or virtual office visit reports or any remote or distance examination reports, in the individual's or the patient's electronic healthcare record, file, or history, can be performed by the distributed ledger and Blockchain technology system component 110B of the central processing computer/distributed ledger/Blockchain technology system 110. In a preferred embodiment, any data and/or information regarding any transactions processed via the distributed ledger and Blockchain technology system component 110B can also be stored in the central processing computer component 110A.

In a preferred embodiment, transactions which are to be processed by the central processing computer component 110A and by the distributed ledger and Blockchain technology system component 110B can be pre-selected or pre-programmed into the central processing computer/distributed ledger/Blockchain technology system 110, and can be re-programmed at any time. In a preferred embodiment, the use of the distributed ledger and Blockchain technology system component 110B can be utilized to provide added security for the individual's or the patient's electronic healthcare record, file, or history, and can also be utilized to prevent healthcare identity theft involving the individual or patient.

Figure 13:
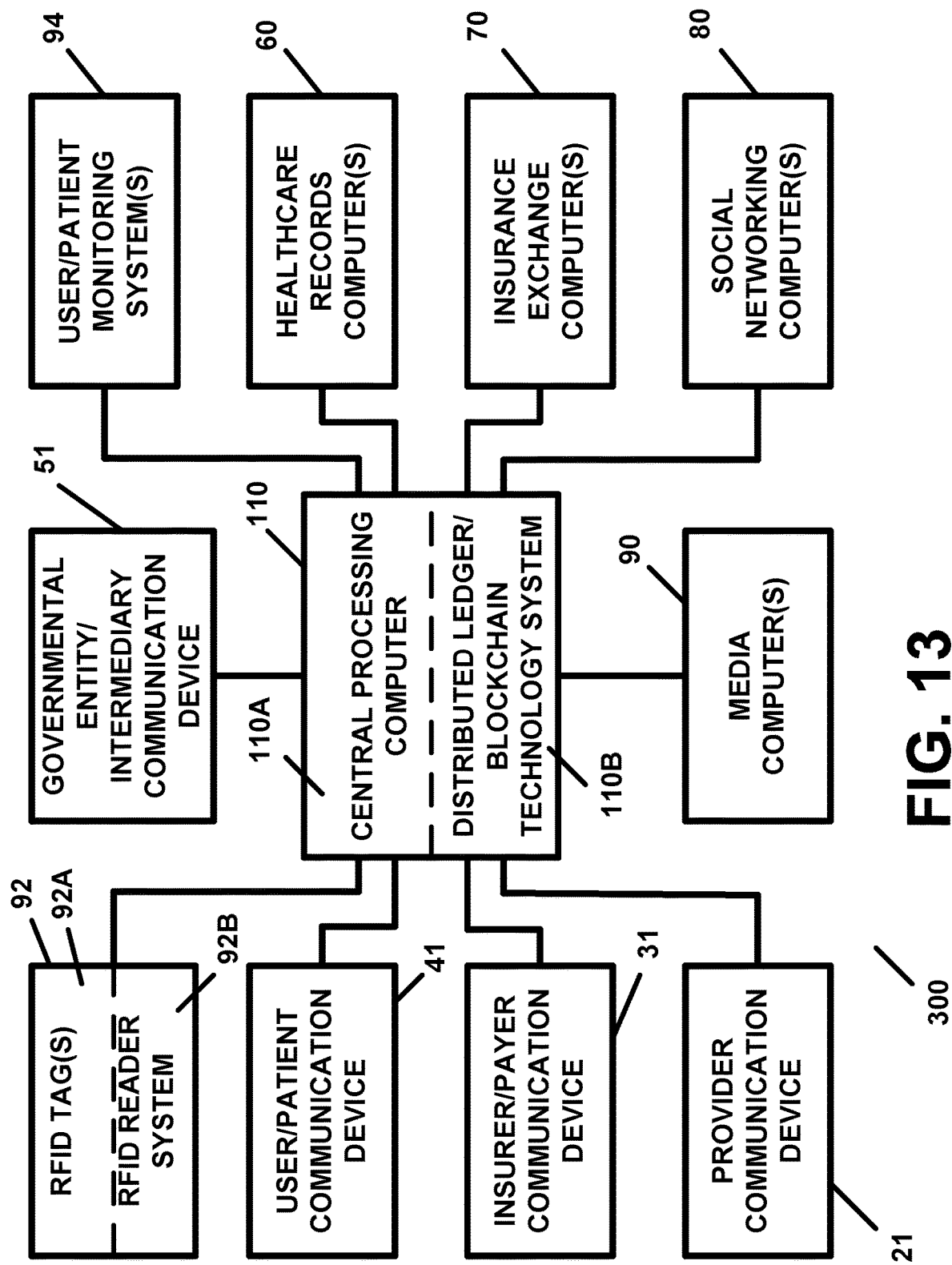
FIG. 13 illustrates another preferred embodiment of the apparatus of the present invention, in block diagram form.

In another preferred embodiment, as well as in any and/or all of the embodiments described herein, the apparatus and methods of the present invention can also be utilized in connection with, or in conjunction with, a distributed ledger and with Blockchain technology and/or with RFID tags and RFID tag reader systems and/or with various personal monitoring systems, in order to provide for numerous other applications for using and/or uses for the present invention. The terms "RFID tag reader" and "RFID reader" can be used interchangeably herein. FIG. 13 illustrates another preferred embodiment of the apparatus of the present invention, in block diagram form. The apparatus of FIG. 13 is denoted generally by the reference numeral 300.

With reference to FIG. 13, the apparatus 300 includes a central processing computer and distributed ledger and Blockchain technology system 110 (hereinafter "central processing computer/distributed ledger/Blockchain technology system 110"). In a preferred embodiment, the central processing computer/distributed ledger/Blockchain technology system 110 includes a central processing computer component 110A, which can perform any and/or all of the functions described herein as being performed by the central processing computer 10 and/or the apparatus 100 of FIG. 1, and a distributed ledger and Blockchain technology system component 110B, which can also perform any and/or all of the functions described herein as being performed by the central processing computer 10 and/or the apparatus 100 of FIG. 1.

With reference once again to FIG. 13, in a preferred embodiment, the apparatus 300 of FIG. 13 also includes any number of provider communication device(s) 21, any number of insurer/payer communication device(s) 31, any number of user/patient communication device(s) 41 (also referred to as "user communication device 41"), any number of healthcare records computer(s) 60, any number of insurance exchange computer(s) 70, any number of social networking computer(s) 80, and/or any number of media computer(s) 90. In a preferred embodiment, each of the provider communication device(s) 21, the insurer/payer communication device(s) 31, and/or the user/patient communication device(s) 41, can be connected to, and/or linked with, the central processing computer/distributed ledger/Blockchain technology system 110, using any suitable and/or appropriate wired connection, wireless connection, or any combination of same, on, via, or using, any suitable and/or appropriate communication network or any combination of communication networks.

In a preferred embodiment, each of the provider communication device(s) 21, the insurer/payer communication device(s) 31, and/or the user/patient communication device(s) 41, of the apparatus 300, can include any and/or all of the components of the respective provider communication device(s) 20, the insurer/payer communication device(s) 30, and/or the user/patient communication device(s) 40, of the apparatus 100 of FIG. 1 and/or the apparatus 200 of FIG. 12. In a preferred embodiment, each of the provider communication device(s) 21, the insurer/payer communication device(s) 31, and/or the user/patient communication device(s) 41, can also include a global positioning device which can be utilized in order to determine the position or location of each of the respective provider communication device(s) 21, insurer/payer communication device(s) 31, and/or user/patient communication device(s) 41.

With reference once again to FIG. 13, in a preferred embodiment, the apparatus 300 can also include any number of RFID tags/RFID reader system(s) 92, each of which can include any number of RFID tags 92A and RFID reader systems 92B. In a preferred embodiment, the RFID tags/RFID reader system(s) 92 can be utilized in or for any number of a variety ways as described herein and/or otherwise. In a preferred embodiment, the RFID tags/RFID reader system(s) 92 can be connected to, and/or linked with, the central processing computer/distributed ledger/Blockchain technology system 110, using any suitable and/or appropriate wired connection, wireless connection, or any combination of same, on, via, or using, any suitable and/or appropriate communication network or any combination of communication networks.

In a preferred embodiment, any user, individual, patient, caregiver, and/or any healthcare provider, healthcare professional, hospital, clinic, pharmacy, treatment center, treatment facility, and/or any other provider of services, healthcare or otherwise, described herein, who or which uses the apparatus 300 of the present invention, can be assigned a healthcare account or any number of healthcare accounts. Any user, individual, patient, caregiver, and/or any healthcare provider, healthcare professional, hospital, clinic, pharmacy, treatment center, treatment facility, and/or any other provider of services, healthcare or otherwise, described herein can also be assigned any number of types or kinds of healthcare accounts depending upon how they respectively utilize the apparatus 300 of the present invention. As and for an example, an individual who might be a healthcare provider or a physician, can be assigned one or more healthcare accounts for use as a patient, who utilizes the apparatus 300 for his or her own healthcare purposes, and one of more healthcare accounts for use as a healthcare provider or physician who utilizes the apparatus 300 for providing healthcare services to or for patients.

Any of the herein-described insurers, payers, intermediaries, governmental entities, an/or any other persons or entities who or which utilize the apparatus 300 for his, her, or its, respective purposes can also be assigned one or more healthcare accounts.

In a preferred embodiment, an RFID tag 92A can be assigned to any user, individual, patient, caregiver, and/or any healthcare provider, healthcare professional, hospital, clinic, pharmacy, treatment center, treatment facility, and/or any other provider of services described herein, healthcare or otherwise, who or which uses the apparatus 300 of the present invention. In a preferred embodiment the RFID tag 92A can also be assigned to a healthcare account which is assigned to or for the respective user, individual, patient, caregiver, healthcare provider, healthcare professional, hospital, clinic, pharmacy, treatment center, treatment facility, and/or any other provider of services described herein, who or which uses the apparatus 300 of the present invention.

In a preferred embodiment, the RFID tag 92A can be provided in or as a physical identification card or other physical item or device, and/or can be attached to, or located within, an article of clothing, a watch, a necklace, a bracelet, an ankle bracelet, a ring, an article of jewelry, or any other wearable article or item. In a preferred embodiment, the RFID tag 92A can also be implantable within an individual or patient. In a preferred embodiment, the RFID tag 92A can also be provided in or as a physical identification card, attached to, or located on or within, a cellular telephone, a smart phone, a Smartphone, a personal digital assistant, or any other personal article or item. In a preferred embodiment, any number of RFID tags 92A can be assigned to or associated with any respective user, individual, patient, caregiver, healthcare provider, healthcare professional, hospital, clinic, pharmacy, treatment center, treatment facility, and/or any other provider of services described herein, who or which uses the apparatus 300 of the present invention, and/or to any healthcare account or healthcare accounts associated with the respective user, individual, patient, caregiver, healthcare provider, healthcare professional, hospital, clinic, pharmacy, treatment center, treatment facility, and/or any other provider of services described herein.

In a preferred embodiment, an RFID reader system 92B, or any RFID reader or RFID readers of same, can be located at any facility or office, or in a room or venue therein, of any user, individual, patient, caregiver, and/or healthcare provider, healthcare professional, hospital, clinic, pharmacy, treatment center, treatment facility, and/or any other provider of services described herein, who or which utilizes the apparatus 300 of the present invention. In another preferred embodiment, an RFID reader system 92B, or any RFID reader or RFID readers of same, can also be located on or implemented with any communication device, computer, computer peripheral device, cellular telephone, smart phone, personal digital assistant, or any other device of or associated with, any user, individual, patient, caregiver, and/or healthcare provider, healthcare professional, hospital, clinic, pharmacy, treatment center, treatment facility, and/or any other provider of services described herein, who or which utilizes the apparatus 300 of the present invention.

In a preferred embodiment, the RFID tag/RFID reader system(s) 92, and any RFID tags 92A and any RFID reader system(s) 92B of same, can be utilized for identifying, verifying the identification of, and/or for accessing, any data and/or information, and/or any account(s) or any healthcare account(s) of, associated with, corresponding to, or regarding, any user, individual, patient, caregiver, and/or healthcare provider, healthcare professional, hospital, clinic, pharmacy, treatment center, treatment facility, and/or any other provider of services described herein, who or which utilizes the apparatus 300 of the present invention.

With reference once again to FIG. 13, in a preferred embodiment, the apparatus 300 can also include any number of governmental entity/intermediary communication device(s) 51. In a preferred embodiment, the governmental entity/intermediary communication device(s) 51 can be the same as, similar to, or analogous to, the intermediary communication device(s) 50 of the apparatus 100 of FIG. 1 and/or the apparatus 200 of FIG. 2. The governmental entity/intermediary communication device(s) 51 can be used by any of the herein-described intermediaries as well as by any governmental entities and/or any governmental entity employees, agents, personnel, or any other authorized individuals or entities. In a preferred embodiment, the governmental entity/intermediary communication device(s) 51 can be utilized in or for any number of a variety ways as described herein and/or otherwise. In a preferred embodiment, the governmental entity/intermediary communication device(s) 51 can be connected to, and/or linked with, the central processing computer/distributed ledger/Blockchain technology system 110, using any suitable and/or appropriate wired connection, wireless connection, or any combination of same, on, via, or using, any suitable and/or appropriate communication network or any combination of communication networks.

With reference once again to FIG. 13, in a preferred embodiment, the apparatus 300 can also include any number of user/patient monitoring systems 94 which can include any number of monitoring devices and/or healthcare measurement tools or devices for detecting, recording, measuring, and/or monitoring, an individual's or patient's heart rate, pulse rate, blood pressure, blood oxygen level(s), blood sugar level(s), or any other biometric measure, measurement, or metric, as well as can include any number of performance measurement devices or tools for detecting, recording, measuring, and/or monitoring, an individual's or patient's physical performance in or during any type or kind of activity, such as, but not limited to, the individual's or patient's rate of speed, rate of acceleration, rate of deceleration, rate of changing direction of movement, distance traveled, speed of travel, and/or any other physical performance measure, measurement, or metric.

In a preferred embodiment, the user/patient monitoring systems 94 can be, or can include, any wearable or non-wearable device or equipment which can be utilized to measure biological, physiological, or any other, data and/or information of, for, or related to, an individual or patient. For example, the user/patient monitoring systems 94 can be, or can include, equipment for measuring pulse rate, heart rate, blood pressure, blood-sugar level, blood oxygen levels or percentages, blood glucose level or blood-sugar level, speed of movement, steps taken, distance traveled, or any other data and/or information regarding the individual or patient, his or her biometric data, and/or a measure of or regarding his or her performance of or in certain physical and/or non-physical tasks or activities.

In a preferred embodiment, the user/patient monitoring systems 94 can be or can include, a thermometer, a digital thermometer, a stethoscope, a heart rate monitor or measurement device, a pulse rate monitor or measurement device, a blood pressure monitor or measurement device, a blood oxygen or percentage oxygen measurement device, a blood pressure measurement device, blood analysis device or machine, a respirator, a respiration monitoring or measurement device, a dialysis machine, a dialysis device, electrocardiograph (EKG) machine or device, electroencephalograph (EEG) machine or device, electromyograph (EMG) machine or device, a magnetic resonance imaging (MM) machine or device, X-ray machine or device, medical imaging machine or device, thermal imaging machine or device, a heart sound monitor or measurement device, a lung sound monitoring or measurement device, respiration rate monitoring or measurement device, a laparoscopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, a PET scan device, an optical metabolism measurement or monitoring device, a radiotelemetric device, a doppler medical device, a mammogram device, a carbon dioxide detection or measurement device, a carbon monoxide detection or measurement device, a transvascular impedence measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, dental probe, microscopic camera probing device, any scope having a camera and/or a light, a laparoscopic device, a laparoscopic camera device, a camera used in or associated with equipment for performing visual probing of the body or any portions, parts, or organs, thereof, such as, but not limited to, a colonoscopy, an endoscopy, an esophagoscopy, a gastroscopy, or any devices used in laparoscopic surgery or other surgeries, an ingestible or implantable pill, capsule, or device, containing a camera and/or a light and equipment or circuitry for transmitting information as well as images to equipment inside or outside the body, and/or any other bio-metric or physiological data measuring device(s) and/or data acquisition device.

In a preferred embodiment, the user/patient monitoring systems 94 can also be or can also include, a gyroscope, an accelerometer, a decelerometer, a magnetometer, an RFID tag(s), a thermometer for measuring temperature of the environment, a device for measuring body temperature, a device for measuring speed of movement, a device for measuring distance traveled, or any other device or devices which can measure and record information regarding three-dimensional movements of the individual or patient. In a preferred embodiment, and depending upon the application, the user/patient monitoring systems 94 can also be, or include, any devices or equipments which are needed, required, or desired, for measuring, monitoring, and/or tracking individual or patient activity or performance using any type or kind of optical-based camera (OBC) tracking systems, local positioning system (LPS) tracking systems, and/or global positioning system/global navigation satellite system (GPS/GNSS) tracking systems, and/or any other tracking system, which are or can be utilized to track players or athletes during sporting or athletic competitions or training.

In a preferred embodiment, the respective optical-based camera (OBC) tracking systems, local positioning system (LPS) tracking systems, and/or global positioning system/global navigation satellite system (GPS/GNSS) tracking systems, which are utilized to track individual or patient activity or performance can also utilize or include any of the herein-described RFID tags/RFID reader system(s) 92.

In a preferred embodiment, the user/patient monitoring systems 94 can be utilized in or for any number of a variety ways as described herein and/or otherwise. In a preferred embodiment, the user/patient monitoring systems 94 can be connected to, and/or linked with, the central processing computer/distributed ledger/Blockchain technology system 110, using any suitable and/or appropriate wired connection, wireless connection, or any combination of same, on, via, or using, any suitable and/or appropriate communication network or any combination of communication networks.

In a preferred embodiment, any and/or all of the various operations, transactions, functions, and/or functionalities, described herein as being performed by the apparatus 100 in the preferred embodiment of FIG. 11 can also be performed by the apparatus 300 of FIG. 13 and/or, in particular, can be performed by either the central processing computer component 110A of the central processing computer/distributed ledger/Blockchain technology system 110 and/or by the distributed ledger and Blockchain technology system component 110B of the central processing computer/distributed ledger/Blockchain technology system 110. In a preferred embodiment, for example, any and/or all transactions involving any storing of any of the herein-described data and/or information, and/or any data and/or information regarding any video call(s) and/or remote office visit(s), and/or any video call reports and/or any of the remote or virtual office visit reports or any remote or distance examination reports, in the individual's or the patient's electronic healthcare record, file, or history, can be performed by the distributed ledger and Blockchain technology system component 110B of the central processing computer/distributed ledger/Blockchain technology system 110. In a preferred embodiment, any data and/or information regarding any transactions processed via the distributed ledger and Blockchain technology system component 110B can also be stored in the central processing computer component 110A.

In a preferred embodiment, transactions which are to be processed by the central processing computer component 110A and by the distributed ledger and Blockchain technology system component 110B can be pre-selected or pre-programmed into the central processing computer/distributed ledger/Blockchain technology system 110, and can be re-programmed at any time. In a preferred embodiment, the use of the distributed ledger and Blockchain technology system component 110B can be utilized to provide added security for the individual's or the patient's electronic healthcare record, file, or history, and can also be utilized to prevent healthcare identity theft involving the individual or patient.

Figure 14:
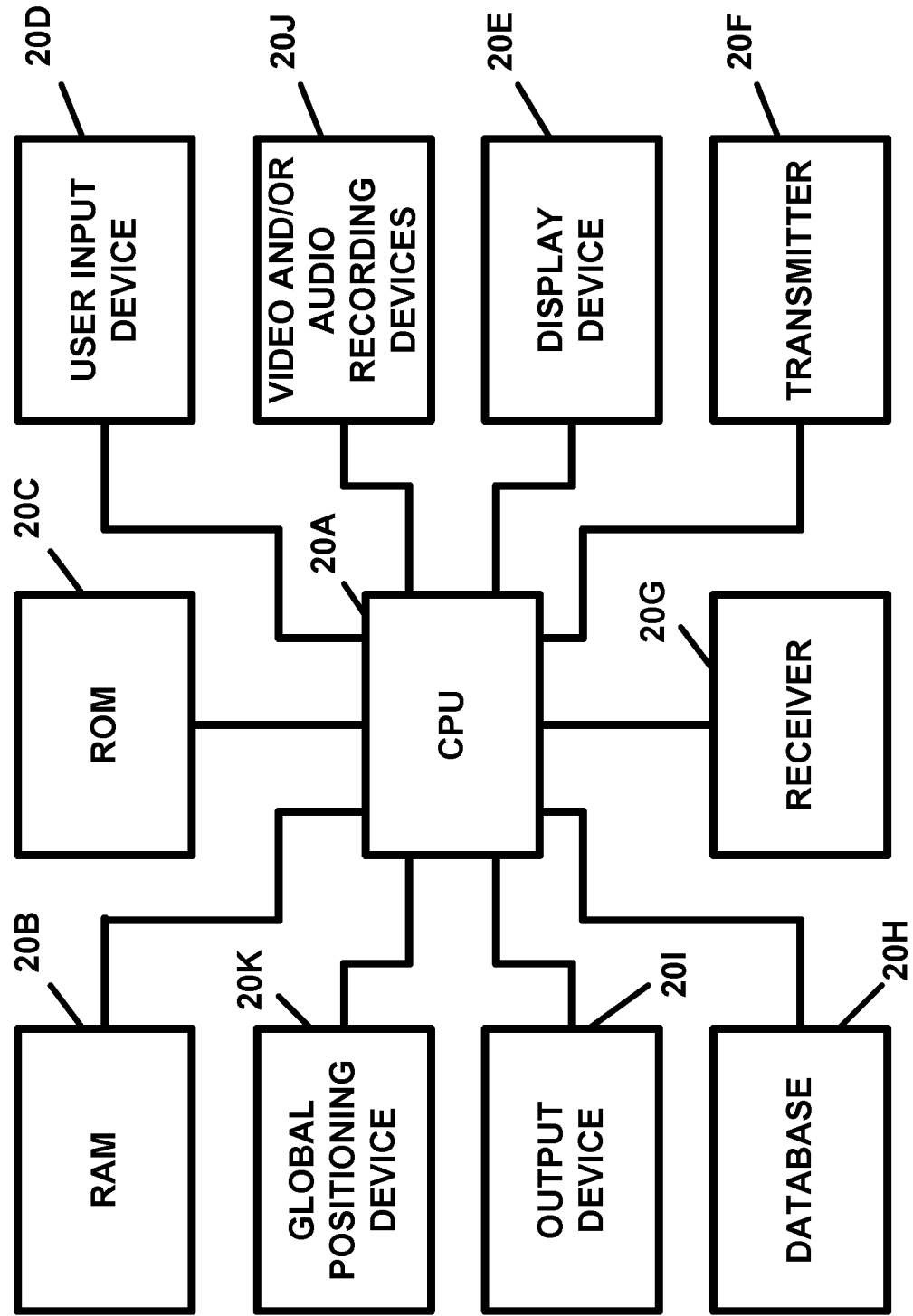
FIG. 14 illustrates the provider communication device of FIG. 13, in block diagram form.

FIG. 14 illustrates a preferred embodiment of the provider communication device 21 of FIG. 13, in block diagram form. With reference to FIG. 14, the provider communication device 21 includes any and/or all of the components of the provider communication device 20 of FIG. 3 and, in addition, the provider communication device 21 also includes a global positioning device 20K. In this regard, the provider communication device 21 includes a CPU 20A, and a RAM 20B, a ROM 20C, a user input device 20D, video and/or audio recording devices 20J, a display device 20E, a transmitter 20F, a receiver 20G, a database 20H, an output device 20I, and a global positioning device 20K, each of which is connected with or linked to the CPU 20A. In a preferred embodiment, the global positioning device 20K determines a position or location of the provider communication device 21. In a preferred embodiment, the provider communication device 21, as well as the provider communication device 20, can be equipped and/or can be programmed for voice activation operation and/or voice control operation of and/or regarding any and/or all of the herein-described operations and functions which are capable of being performed by the provider communication device 21 and/or the provider communication device 20.

Figure 15:
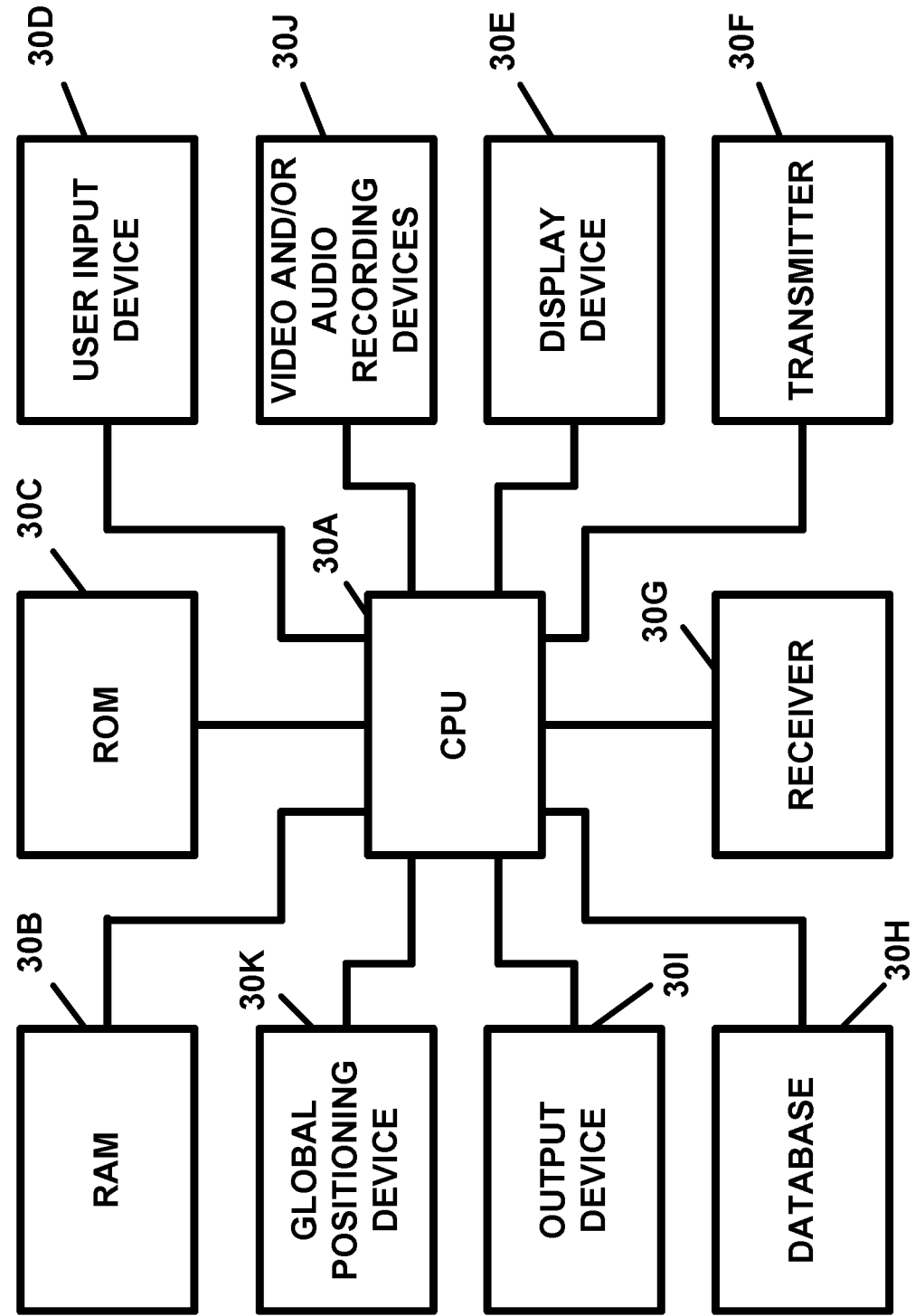
FIG. 15 illustrates the insurer or payer communication device of FIG. 13, in block diagram form.

FIG. 15 illustrates a preferred embodiment of the insurer or payer communication device 31 of FIG. 13, in block diagram form. With reference to FIG. 15, the insurer or payer communication device 31 includes any and/or all of the components of the insurer or payer communication device 30 of FIG. 4 and, in addition, the insurer or payer communication device 31 also includes a global positioning device 30K. In this regard, the insurer or payer communication device 31 includes a CPU 30A, and a RAM 30B, a ROM 30C, a user input device 30D, video and/or audio recording devices 30J, a display device 30E, a transmitter 30F, a receiver 30G, a database 30H, an output device 301, and a global positioning device 30K, each of which is connected with or linked to the CPU 30A. In a preferred embodiment, the global positioning device 30K determines a position or location of the insurer or payer communication device 31.

Figure 16:
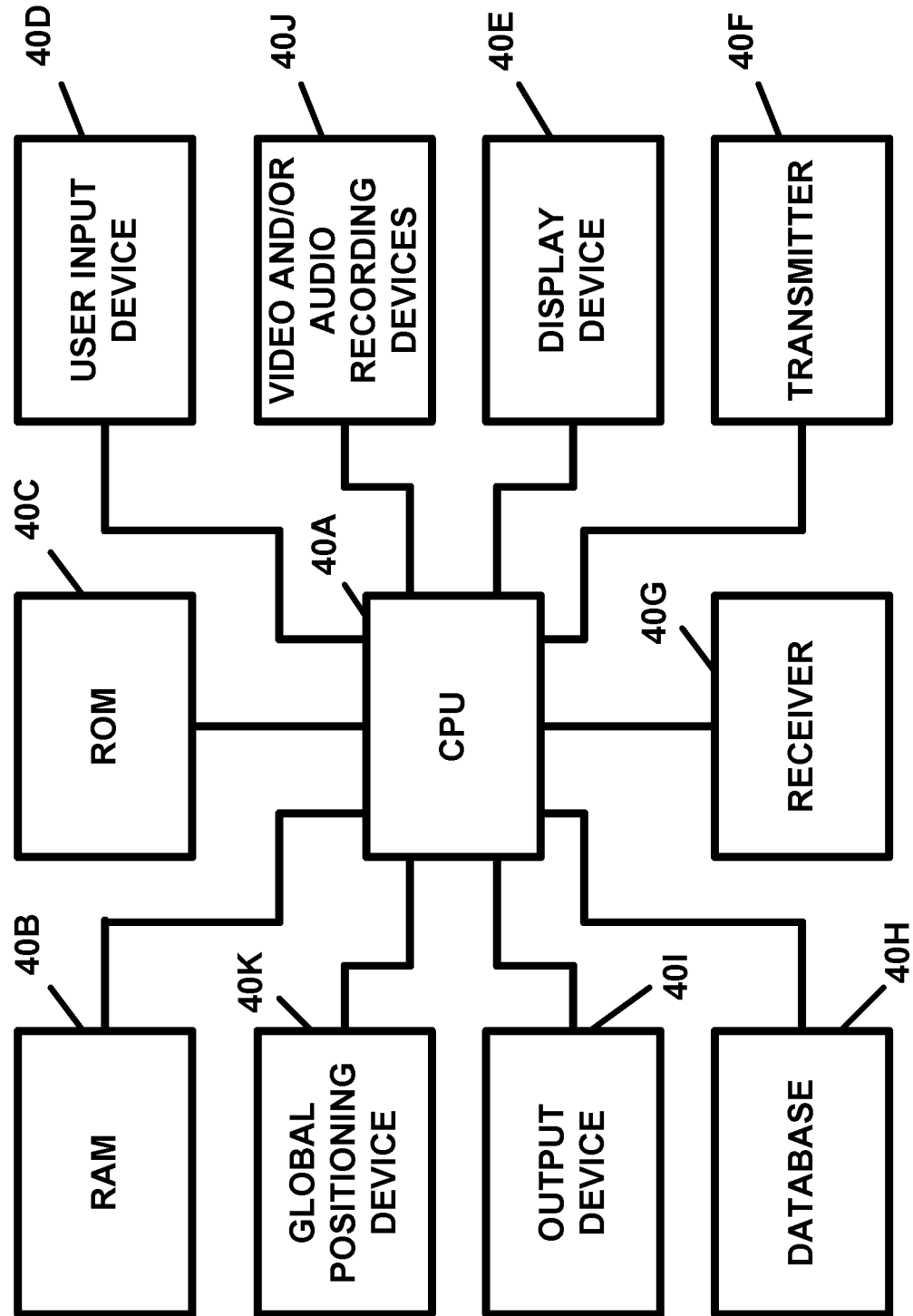
FIG. 16 illustrates the user or patient communication device of FIG. 13, in block diagram form.

FIG. 16 illustrates a preferred embodiment of the user communication device 41 of FIG. 13, in block diagram form. With reference to FIG. 16, the user communication device 41 includes any and/or all of the components of the user communication device 40 of FIG. 5 and, in addition, the user communication device 41 also includes a global positioning device 40K. In this regard, the user communication device 41 includes a CPU 40A, and a RAM 40B, a ROM 40C, a user input device 40D, video and/or audio recording devices 40J, a display device 40E, a transmitter 40F, a receiver 40G, a database 40H, an output device 40I, and a global positioning device 40K, each of which is connected with or linked to the CPU 40A. In a preferred embodiment, the global positioning device 40K determines a position or location of the user communication device 41. In a preferred embodiment, the user communication device 41, as well as the user communication device 40, can be suitably equipped and/or can be programmed for voice activation operation and/or voice control operation of and/or regarding any and/or all of the herein-described operations and functions which are capable of being performed by the user communication device 41 and/or by the user communication device 40.

Figure 17:
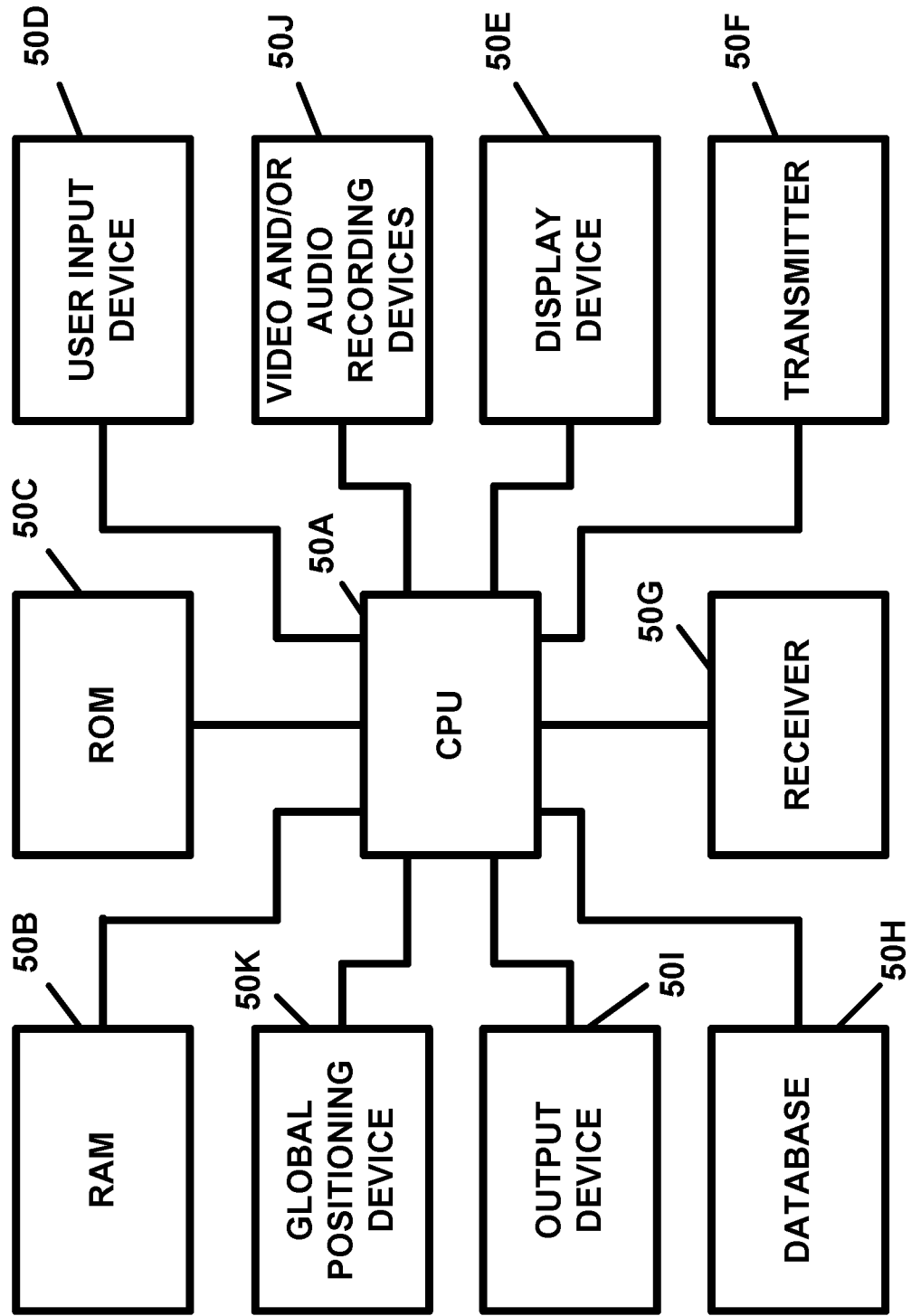
FIG. 17 illustrates the governmental entity/intermediary communication device of FIG. 13, in block diagram form.

FIG. 17 illustrates a preferred embodiment of the governmental entity/intermediary communication device 51 of FIG. 13, in block diagram form. With reference to FIG. 17, the governmental entity/intermediary communication device 51 includes any and/or all of the components of the intermediary communication device 50 of FIG. 6 and, in addition, the governmental entity/intermediary communication device 51 also includes a global positioning device 50K. In this regard, the governmental entity/intermediary communication device 51 includes a CPU 50A, and a RAM 50B, a ROM 50C, a user input device 50D, video and/or audio recording devices 50J, a display device 50E, a transmitter 50F, a receiver 50G, a database 50H, an output device 50I, and a global positioning device 50K, each of which is connected with or linked to the CPU 50A. In a preferred embodiment, the global positioning device 50K determines a position or location of the governmental entity/intermediary communication device 51.

The apparatus 300 of the present invention can be utilized in numerous preferred embodiments in order to provide a vast array of healthcare and healthcare-related services, and/or provide remote healthcare services, and/or tele-health services, for any one or more of the users, individuals, patients, caregivers, and/or healthcare providers, healthcare professionals, hospitals, clinics, pharmacies, treatment centers, treatment facilities, and/or any other providers of services described herein, and/or other various parties described herein. While certain of the preferred embodiments may be described with regards to utilization by a particular party, it is important to note that any individual, patient, user, provider, payer, governmental entity and/or intermediary or third party, may utilize the present invention in the same, similar, and/or analogous, manner.

The apparatus 300 of the present invention can also be utilized in order to allow an individual or a patient, or a caregiver, or one responsible for the care of an individual or patient, to enter notes, comments, or messages regarding or relating to the individual or patient into one or more of any of the individual's, patient's, or caregiver's, electronic healthcare record(s), electronic healthcare file(s), electronic medical record(s), electronic dental record(s), electronic pharmacy record(s), and/or electronic behavioral healthcare record(s). As noted herein, any respective note, comment, or message, can be in text form, audio form, or video form, and can contain information regarding a symptom, an illness, an experience, a treatment, a diagnosis, a treatment plan, an activity, a problem, a concern, a thought or an idea, a question, a question for a healthcare provider, or any other information which the individual or patient, or one caring for the individual or patient, may deem important to be recorded or noted in the respective electronic healthcare record(s), electronic medical record(s), electronic dental record(s), electronic pharmacy record(s), and/or electronic behavioral healthcare record(s), or which can be communicated to, or otherwise made available to, a provider or an insurer or payer.

A healthcare provider can access, obtain, and/or use, any of the information provided or contained in any note, comment, or message, or provided or contained in multiple notes, comments, or messages, and/or can view or review any previously recorded videos of any one or more previous remote healthcare visits, remote examinations, remote or virtual visits, or tele-health visits, involving the individual or patient and the healthcare provider and/or involving the individual or patient and any other healthcare provider(s), for any suitable purpose, such as, but not limited to, for preparing for, or for use during, a remote or virtual office visit with, or a remote or distance examination of, an individual, a patient, or a caregiver for or an individual or a patient, during a video telephone call, a video chat session, or a videoconference, with the individual, the patient, or the caregiver for or the individual or the patient, or for use during a conversation, discussion, or consultation, during a video telephone call, a video chat session, or a videoconference, with the individual, the patient, or the caregiver for the individual or the patient, or for use during a conversation, discussion, or consultation, during a video telephone call, a video chat session, or a videoconference, with and between, the healthcare provider, and the individual, the patient, or the caregiver for or the individual or the patient, or another healthcare provider or any other provider, or an insurer or a payer, or an intermediary, or for use during reviewing, updating, modifying, or performing any other activity in connection with, an individual's or patient's healthcare records, files, or histories, for use while making a diagnosis, for use while formulating a treatment or a treatment plan, for use in reviewing or evaluating an individual's or patient's diagnosis or treatment, for use in treatment planning and/or the evaluating of same, for use in care management, for use in monitoring or evaluating a recovery, for use in providing continuing or on-going care or treatment, for use in connection with the providing of a remote healthcare services or tele-health services, and/or for any other suitable use or purpose.

A healthcare provider can view or review any previously recorded videos of any one or more previous remote healthcare visits, remote examinations, remote or virtual visits, or tele-health visits, involving the individual or patient and the healthcare provider and/or involving the individual or patient and any other healthcare provider(s), prior to, during, or after, any remote healthcare visit, remote examination, remote or virtual visit, or tele-health visit, with the individual or patient, in order to note and/or to assess the individual's or patient's physical appearance, body language, reactions, responses, and/or any differences and/or changes in same, from and/or between a given remote healthcare visit, remote examination, remote or virtual visit, or tele-health visit, and another remote healthcare visit, remote examination, remote or virtual visit, or tele-health visit. In this regard, the healthcare provider can ascertain differences and/or similarities in the appearance, behavior, and/or condition, of the individual or patient from one remote healthcare visit, remote examination, remote or virtual visit, or tele-health visit, to another. In a preferred embodiment, the healthcare provider can, at any time before, during, or after, any remote healthcare visit, remote examination, remote or virtual visit, or tele-health visit, be provided with, and can view, via the display device 20E of his or her provider communication device 21, any previously recorded videos of one or more previous remote healthcare visits, remote examinations, remote or virtual visits, or tele-health visits, involving the individual or patient, and/or any current remote healthcare visit, remote examination, remote or virtual visit, or tele-health visit, involving the individual or patient, in a multiple screen format or display or in a split-screen format or display. The use of previously recorded videos of one or more previous remote healthcare visits, remote examinations, remote or virtual visits, or tele-health visits, can also be utilized to provide visual documentation of an individual's or patient's condition, or changes in the same, from time to time.

Any notes, comments, or messages, which can be provided by the individual, patient, or caregiver, or by any person caring for the individual or patient, while making an appointment, in advance of a video telephone call, a video chat session, or a videoconference, or a remote or virtual office visit with, or a remote or distance examination of, or in advance of a video telephone call, a video chat session, or a videoconference, or a remote or distance examination of, with the individual, the patient, or the caregiver for the individual or the patient, or a video telephone call, a video chat session, or a videoconference, with another provider, or a payer or insurer or any third party or intermediary, in connection with any tele-health related activity, or for the purpose of making and entering a note, comment, or message, into the individual's or patient's respective electronic healthcare record(s), electronic medical record(s), electronic dental record(s), electronic pharmacy record(s), and/or electronic behavioral healthcare record(s), can also include a video message or a video clip of a message provided by the individual or patient or a caregiver of the individual or patient.

The apparatus 300 of the present invention can be utilized to provide healthcare services, such as, but not limited to, a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The apparatus 300 of the present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus 300 and method of the present invention can be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus 300 and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The apparatus 300 of the present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The apparatus 300 of the present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus 300 of the present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribe a treatment based on any and/or all any and/or all information regarding the individual or the patient. In a preferred embodiment, the healthcare provider can also be provided with any notes, comments, or messages, which was provided by the individual, patient, or caregiver, or by any person caring for the individual or patient, when making or scheduling the appointment with the healthcare provider and in advance of a video telephone call, a video chat session, a videoconference, a remote or virtual office visit with, or a remote or distance examination. In this manner, the healthcare provider can be made aware, and be informed, of any possible reason(s) for the video telephone call, a video chat session, a videoconference, a remote or virtual office visit with, or a remote or distance examination, and can be better prepared for the same.

In a preferred embodiment, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented and recorded in the individual's or the patient's healthcare records, files, or history. A video and audio recording of the remote or the distance examination, the individual or patient and healthcare provider during the same, any information exchanged, and any statements, verbal or non-verbal statements or gestures, can be stored in the individual's or the patient's healthcare records, files, or history.

As noted herein, it is envisioned that any number, kinds, or types, of healthcare providers, who or which have registered with the apparatus 300 in order to engage in video calls, video chat sessions, or videoconferences, in order to provide remote or virtual office visits or in order to provide remote or distance consultations or examinations with and for any individuals or patients, or caregivers, can store in the database 10H, any data and/or information regarding his or her name, address, telephone number, e-mail address, text messaging information or number(s), or any other contact information, his or her photograph, and information regarding his or her credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

In a preferred embodiment, any of the above-described or herein-described data and/or information regarding the healthcare provider, for any number of healthcare providers, can be stored in, and can be searchable from, the database 10H of the central processing computer component 110A of the central processing computer/distributed ledger/Blockchain technology system 110. In the preferred embodiment, any of the above-described or herein-described data and/or information regarding the healthcare provider, for any number of healthcare providers, can be also be stored in, and can be searchable from, the database 20H of any provider communication device 21. In the preferred embodiment, any of the above-described or herein-described data and/or information regarding the healthcare provider, for any number of healthcare providers, can be also be stored in, and can be searchable from, the database 40H of any user communication device 41.

In a preferred embodiment, it is envisioned that the individual, the patient, or the caregiver of or for the individual or the patient, can access the central processing computer component 110A of the central processing computer/distributed ledger/Blockchain technology system 110 or a respective provider communication device 21 with or using his or her user communication device 41, or by accessing data and/or information stored in his or her communication device 41, at any time, in order to search for and/or to select a healthcare provider(s) with whom he or she can schedule a video call, a video chat session, or a videoconference.

In a preferred embodiment, the individual, the patient, or the caregiver of or for the individual or the patient, using his or her user communication device 41, can access the central processing computer component 110A of the central processing computer/distributed ledger/Blockchain technology system 110 in order to access the healthcare provider for the individual or patient. In this regard, the individual, the patient, or the caregiver of or for the individual or the patient, can simply make an appointment, in a manner described herein and/or otherwise, with a particular healthcare provider. In cases when the individual or patient is searching for a healthcare provider, the individual or patient, or the caregiver, can enter search criteria and/or keywords regarding a healthcare provider they are seeking. In a preferred embodiment, the search criteria and/or keywords can be transmitted from the user communication device 41 to, and received at and by, the central processing computer component 110A of the central processing computer/distributed ledger/Blockchain technology system 110.

The central processing computer component 110A of the central processing computer/distributed ledger/Blockchain technology system 110 can, thereafter, process the search criteria and/or keywords and generate a healthcare provider search report containing information regarding one or more healthcare providers who match any of the search criteria and/or keywords. In a preferred embodiment, the healthcare provider search report can contain a user profile for each identified healthcare provider and/or any other information described herein as being stored in the databases 10H, 20H, 30H, 40H, and/or 50H, and/or the apparatus, 100, 200, or 200, for or regarding the healthcare provider. Thereafter, the individual, the patient, or the caregiver of or for the individual or the patient, can simply make an appointment with the desired healthcare provider.

In the manner described herein, and/or otherwise, the individual, the patient, or the caregiver of or for the individual or the patient, can select the individual's or the patient's current healthcare provider, current primary care provider, or a new or different healthcare provider, or a healthcare provider having a certain specialization, or a certain availability. The individual or the patient, or the caregiver of or for the individual or the patient, can make an appointment for a video call, a video chat session, or a videoconference, with the healthcare provider with or using the user communication device 41. At the time of making the appointment the individual, patient, or caregiver, can provide a telephone number, a call number, a conference call number, or an IP address, associated with the user communication device 41 which the individual, the patient, or the caregiver, will use for the video call, the video chat session, or the videoconference. At the time of making the appointment, the individual, the patient, or the caregiver, can also be provided with the telephone number, the call number, the conference call number, or the IP address, associated with the provider communication device 21 which will be used by the healthcare provider for the video call, the video chat session, or the videoconference. At the time of making the appointment, the individual, the patient, or the caregiver, can also be provided with an instruction as to whether he or she is to call the healthcare provider at the appointment time, or whether the healthcare provider will call the individual, the patient, or the caregiver, at the appointment time.

In instances when the appointment is being made via the central processing computer component 110A of the central processing computer/distributed ledger/Blockchain technology system 110, the appointment can be made via the individual's or the patient's electronic medical record, file, or history, which is stored in the database 10H of the central processing computer component 110A of the central processing computer/distributed ledger/Blockchain technology system 110, and information regarding the appointment can be stored in the individual's or the patient's electronic medical record, file, or history, as well as in the healthcare provider's work schedule or in an appointment schedule of the healthcare provider. In instances when the appointment is being made via a provider communication device 21, the appointment can be made via the individual's or the patient's electronic medical record, file, or history, which is stored in the database 20H of the provider communication device 21, and information regarding the appointment can be stored in the individual's or the patient's electronic medical record, file, or history as well as in the healthcare provider's work schedule or in an appointment schedule of the healthcare provider. In instances when the appointment is being made via a user communication device 41, the appointment can be made via the individual's or the patient's electronic medical record, file, or history, or personal healthcare record, which is stored in the database 40H of the user communication device 41, and information regarding same can be automatically transmitted to and stored in the individual's or the patient's electronic medical record, file, or history in the database 10H of the central processing computer component 110A of the central processing computer/distributed ledger/Blockchain technology system 110 as well as in the healthcare provider's work schedule or in an appointment schedule of the healthcare provider.

In a preferred embodiment, central processing computer component 110A of the central processing computer/distributed ledger/Blockchain technology system 110 can be programmed so that, once an appointment for a video call, a video chat session, or a videoconference, has been made, the central processing computer component 110A of the central processing computer/distributed ledger/Blockchain technology system 110 can automatically generate a message (hereinafter an "appointment message") containing information regarding the appointment, and/or the time and date of same, which has been scheduled and will transmit same to the provider communication device 21 of or associated with the healthcare provider with whom the appointment has been made, and will also transmit same to the user communication device(s) 41 of or associated with the individual, the patient, or the caregiver.

In a preferred embodiment, the provider communication device 21, with which an appointment has been made, can also be programmed so that, once an appointment for a video call, a video chat session, or a videoconference, has been made, the provider communication device 20 can automatically generate a message (hereinafter an "appointment message") containing information regarding the appointment, and/or the time and date of same, which has been scheduled and will transmit same to any other provider communication device 21 of or associated with the healthcare provider with whom the appointment has been made, and will also transmit same to the user communication device(s) 41 of or associated with the individual, the patient, or the caregiver. In a preferred embodiment, the user communication device 41 with which an appointment has been made can also be programmed so that, once an appointment for a video call, a video chat session, or a videoconference, has been made, the user communication device 41 can automatically generate a message (hereinafter an "appointment message") containing information regarding the appointment, and/or the time and date of same, which has been scheduled and will transmit same to the central processing computer component 110A of the central processing computer/distributed ledger/Blockchain technology system 110, to any provider communication device 21 of or associated with the healthcare provider with whom the appointment has been made, and/or to any other user communication device(s) 41 of or associated with the individual, the patient, or the caregiver.

In a preferred embodiment, the central processing computer component 110A of the central processing computer/distributed ledger/Blockchain technology system 110 can also be programmed so that, once an appointment for a video call, a video chat session, or a videoconference, has been made, the central processing computer component 110A of the central processing computer/distributed ledger/Blockchain technology system 110 can automatically generate a reminder message(s) (hereinafter an "reminder message") containing information for reminding each of the individual, the patient, or the caregiver, and the healthcare provider of the appointment for the video call, the video chat session, or the videoconference. The reminder message or reminder messages can be transmitted to each of the user communication device(s) 41 of or associated with the individual, the patient, or the caregiver, and to the provider communication device 21 of or associated with the healthcare provider.

In a preferred embodiment, any of the appointment messages and/or reminder messages described herein can include the appointment time, the name of the healthcare provider, and the telephone number, the call number, the conference call number, or the IP address, associated with the provider communication device 21 which will be used by the healthcare provider for the video call, the video chat session, or the videoconference, and the name of the individual, the patient, or the caregiver, and the telephone number, the call number, the conference call number, or the IP address, associated with the user communication device 41 which the individual, the patient, or the caregiver, will use for the video call, the video chat session, or the videoconference, and an instruction, if any, as to who is to initiate the video call, the video chat session, or the videoconference, such as, for example, whether the individual, the patient, or the caregiver, is to call the healthcare provider at the appointment time or whether the healthcare provider is to call the individual, the patient, or the caregiver, at the appointment time.

In a preferred embodiment, any of the herein-described appointment messages and/or reminder messages can be stored in the individual's or the patient's electronic healthcare record, file, or history, in the database 10H of the central processing computer component 110A of the central processing computer/distributed ledger/Blockchain technology system 110 and/or in the database 40H of the user communication device 41, such as in a healthcare provider appointments section or field of same. Likewise, any of the herein-described appointment messages and/or reminder messages can be stored in the healthcare provider's records or files which can also be stored in the database 10H of the central processing computer component 110A of the central processing computer/distributed ledger/Blockchain technology system 110 and/or in the database 20H of the provider communication device 21 such as in an appointments section or field of same.

In a preferred embodiment, any of the herein-described appointment messages or reminder messages can also contain a link or a hyperlink to the electronic healthcare record, file, or history, of the individual or the patient. Any of the herein-described appointment messages or reminder messages can also contain a link or a hyperlink for allowing each of the individual, the patient, or the caregiver of or for the individual or the patient to initiate a video call, a video chat session, or a videoconference, described herein via the link or the hyperlink.

In another preferred embodiment, a healthcare provider, or any number of healthcare providers, can be available, or can be "on-call" for a video call, a video chat session, or a videoconference, at any given time and with any given individual, patient, or caregiver, and an individual, a patient, or a caregiver for the individual or the patient, can simply access the central processing computer component 110A of the central processing computer/distributed ledger/Blockchain technology system 110, see which healthcare provider or healthcare providers are available, and can immediately initiate a video call, a video chat session, or a videoconference, with an available healthcare provider. In this regard, the apparatus 300 can allow any individual, patient, or caregiver, to have or to engage in a video call, a video chat session, or a videoconference, with any suitable and/or available healthcare provider regarding or involving an emergency situation or matter or an urgent care situation or matter, or at any other time, with the healthcare provider being provided with access to the individual's or the patient's healthcare records, files, or history, so as to best provide care for, or assist, the individual or patient.

In a preferred embodiment, the apparatus 300 can be utilized to in order to allow the healthcare provider to gain authorized access to the individual's or the patient's electronic healthcare records, files, or history, prior to and/or during the video call, the video chat session, or the videoconference, with the individual, the patient, or the caregiver of or for the individual or the patient. In this regard, the healthcare provider can review the individual's or the patient's electronic healthcare records, files, or history, prior to and/or during the video call, the video chat session, or the videoconference, obtain information from same, enter notes, observations, or examination findings, into same, and/or enter information regarding a diagnosis, a treatment, or a treatment plan into same, and/or to enter information regarding and/or to prescribe a medication or a drug, prescribe a therapy of any kind or type, prescribe a treatment of any kind or kind, and/or make a referral to another healthcare provider. In a preferred embodiment, any and/or all information, including a video or a video clip, and/or an audio, a video, and/or an audio and video recording, of the video call, the video chat session, or the videoconference, can be recorded and can be stored in the individual's or the patient's electronic healthcare records, files, or history.

Figure 18:
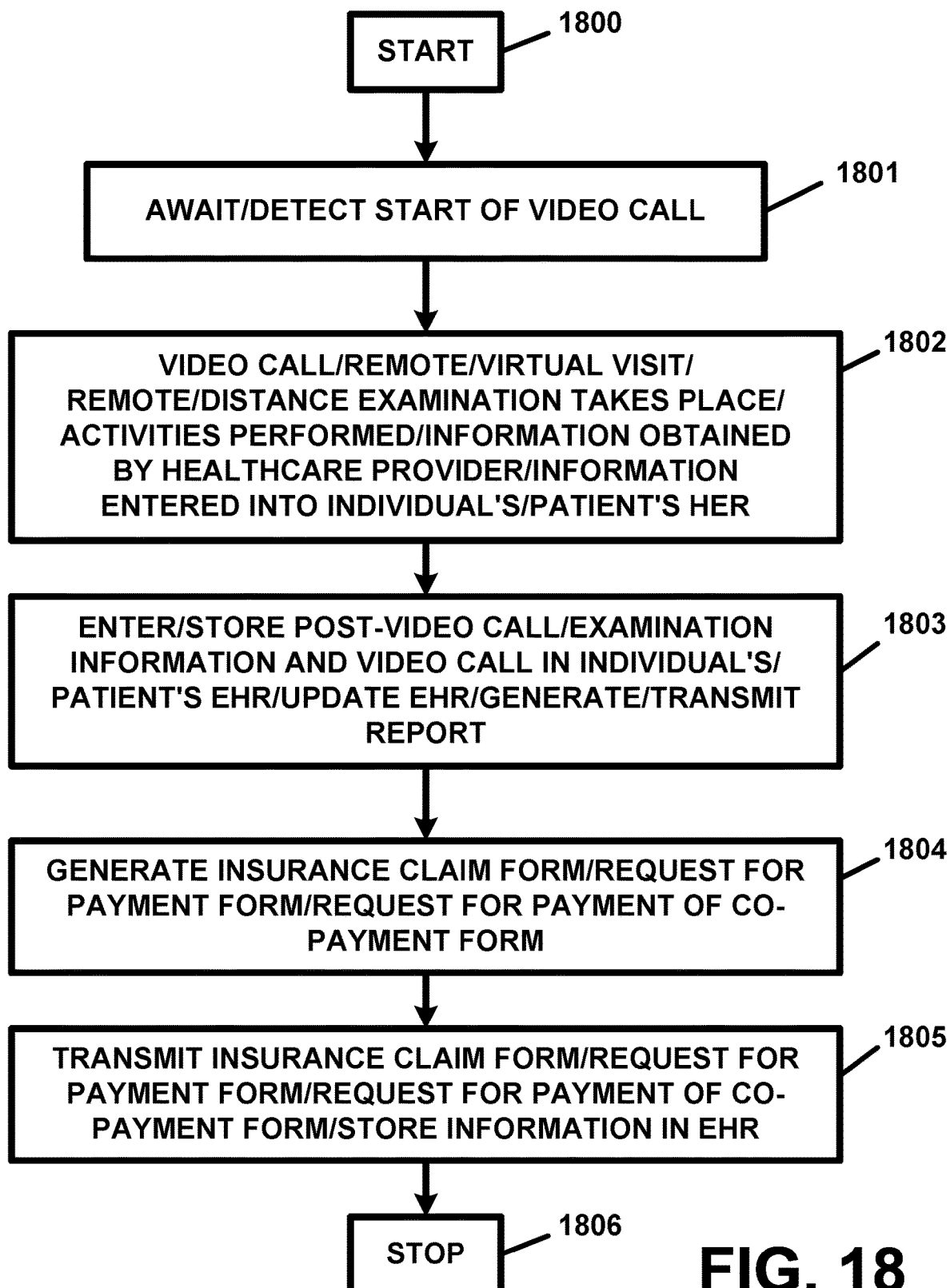
FIG. 18 illustrates another preferred embodiment method of utilizing the apparatus of the present invention, in flow diagram form.

FIG. 18 illustrates a preferred embodiment method for utilizing the apparatus 300 and method of the present invention, in flow diagram form. The preferred embodiment of FIG. 18 will be described as being utilized in connection with a video call between an individual, a patient, or a caregiver, and a healthcare provider. However, it is to be understood, and it is important to note, that the preferred embodiment of FIG. 18 can also be utilized in a same, a similar, and/or an analogous, manner in connection with a video chat session or a videoconference with and/or between an individual, a patient, or a caregiver, and any healthcare provider, healthcare professional, any healthcare insurer, any healthcare payer, any intermediary, and/or any other provider of healthcare or other services. It is also to be understood, and it is important to note that, although described as being utilized in connection with a video call between an individual, a patient, or a caregiver, and a healthcare provider, the embodiment of FIG. 18 can also be utilized in a same, a similar, and/or an analogous, manner in connection with any video call, video chat session, or videoconference, involving and/or with and/or between any of the herein-described individuals, patients, caregivers, healthcare providers, other providers, healthcare insurers, healthcare payers, and/or intermediaries.

With reference to FIG. 18, the operation of the apparatus 100 commences at step 1800. At step 1801, the apparatus 300 will await and detect the start of the video call. In a preferred embodiment, depending on what may be pre-arranged or pre-selected, the individual, the patient, or the caregiver, can call the healthcare provider by using the his or her user communication device 41 to call the provider communication device 21 of or associated with the healthcare provider, or the healthcare provider can call the individual, the patient, or the caregiver, by using his or her provider communication device 21 to call the user communication device 41 of or associated with the individual, the patient, or the caregiver of or for the individual or the patient. In another preferred embodiment, the video call can be initiated and/or can take place via the central processing computer component 110A of the central processing computer/distributed ledger/Blockchain technology system 110. In another preferred embodiment, the video call can be initiated via a link or a hyperlink in any of the herein-described appointment messages or reminder messages. Any of the herein-described links or hyperlinks, in any of the herein-described appointment messages or reminder messages, can provide, or can be, a link or a hyperlink to, for, or associated with, the telephone number, the call number, the conference call number, or the IP address, associated with the provider communication device 21 which will be used by the healthcare provider for the video call, as well as the telephone number, the call number, the conference call number, or the IP address, associated with the user communication device 41 which will be used by the individual, the patient, or the caregiver.

In another preferred embodiment, the database 10H of the central processing computer component 110A of the central processing computer/distributed ledger/Blockchain technology system 110 can contain, in the electronic healthcare record, file, or history, of the individual or the patient, and/or in the records or files of the healthcare provider, a link or a hyperlink to, for, or associated with the telephone number, the call number, the conference call number, or the IP address, associated with the provider communication device 21 which will be used by the healthcare provider for the video call, as well as the telephone number, the call number, the conference call number, or the IP address, associated with the user communication device 41 which will be used by the individual, the patient, or the caregiver.

In this preferred embodiment, the video call can be initiated by either the individual, the patient, or the caregiver of or for the individual or the patient, using either the telephone number, the call number, the conference call number, or the IP address, associated with the provider communication device 21 or by using the link or the hyperlink provided in the electronic healthcare record, file, or history, of the individual or the patient, or by using the link or the hyperlink provided in the records or files of the healthcare provider, and/or by using the link or the hyperlink provided in the appointment message or any reminder message. In this preferred embodiment, the video call can be initiated by either the healthcare provider using either the telephone number, the call number, the conference call number, or the IP address, associated with the user communication device 41 of or associated with the individual, the patient, or the caregiver, or by using the link or the hyperlink provided in the electronic healthcare record, file, or history, of the individual or the patient, or by using the link or the hyperlink provided in the records or files of the healthcare provider.

Once the video call has been initiated and detected by the apparatus 100 and/or the central processing computer component 110A of the central processing computer/distributed ledger/Blockchain technology system 110, at step 1801, the operation of the apparatus 100 will proceed to step 1802 and the video call can proceed. In a preferred embodiment, the video call can take place with a cellular telephone, a smart phone, a Smartphone, or a personal digital assistant being utilized as the user communication device 41 used by the individual, the patient, or the caregiver, and/or as the provider communication device 21 used by the healthcare provider. In another preferred embodiment, the video call can take place with a personal computer, a laptop computer, a tablet, a tablet computer, a cellular telephone, a smart phone, a Smartphone, or a personal digital assistant, or a watch, being utilized as the user communication device 41 used by the individual, the patient, or the caregiver, and/or as the provider communication device 21 used by the healthcare provider. In a preferred embodiment, the video call can take place, and any and/or all data and information can be provided, via the display device 20E of the healthcare provider communication device 21 and via the display device 40E of the user communication device 41.

In another preferred embodiment, the video call can take place, and any and/or all data and information can be provided, via a user communication device 41 and/or any appropriate display device both of which can be located in, on, or at, any type or kind of land vehicle, motor vehicle, automobile, truck, train, subway train, bus, boat, marine vehicle or marine vessel, aircraft, airplane, jet, spacecraft, space shuttle, or any other type or kind of vehicle. In a preferred embodiment, the user communication device 41 can be located in, on, or at, the respective vehicle, and/or any of the herein-described user communication devices 41 can be utilized with any suitable display device in or of the vehicle (also referred to as a "vehicle display device"). In this regard, for example, the user communication device 41 can be linked to the vehicle display device via a wired connection, a wireless connection, a Bluetooth connection, or any combination of same.

In a preferred embodiment, the video call can be initiated via a link or a hyperlink contained in the individual's or the patient's electronic healthcare record, file, or history, and the video call can take place via the central processing computer component 110A of the central processing computer/distributed ledger/Blockchain technology system 110 and/or via the individual's or the patient's electronic healthcare record, file, or history, so that information regarding the time and date of the video call, and/or any information regarding any actions taken by the individual, the patient, or the caregiver, or the healthcare provider, and/or any information regarding any information accessed from or in the individual's or the patient's electronic healthcare record, file, or history, and/or any information regarding any notes or information or data entered into, recorded by, or stored in, the individual's or the patient's electronic healthcare record, file, or history, by the individual, the patient, or the caregiver, or the healthcare provider, and/or the video call itself, can be monitored, recorded, and/or stored, in the individual's or the patient's electronic healthcare record, file, or history. In another preferred embodiment, the video call can also take place by and between the provider communication device 21 and the user communication device 41, with each of the healthcare provider communication device 21 and/or the user communication device 41 being in communication with, and/or having access to, the central processing computer component 110A of the central processing computer/distributed ledger/Blockchain technology system 110 and/or being in communication with and/or having access to, the individual's or the patient's electronic healthcare record, file, or history, in the database 10H of the central processing computer component 110A of the central processing computer/distributed ledger/Blockchain technology system 110.

In a preferred embodiment, at the start of the video call, and at or during step 1802, the healthcare provider can take a picture or photograph, or record a video clip, of the individual, the patient, or the caregiver, using the healthcare provider communication device 21, which picture or photograph, or video clip, can be stored and can be used for verifying the identity of the individual, the patient, or the caregiver as descried herein. In a preferred embodiment, at or during step 1802, the healthcare provider can also take a picture or photograph, or record a video clip, of himself or herself, which picture or photograph, or video clip, can be stored and can be used for verifying the identity of the healthcare provider as described herein.

In a preferred embodiment, at step 1802, a profile photograph or picture of the healthcare provider, such a photograph or picture from the healthcare provider's user profile, can also be, but need not be, transmitted to the user's user communication device 41 along with the video which is transmitted from the provider's provider communication device 21 during the video call, and can be displayed via the display device 40E. In a preferred embodiment, the provider's photograph or picture can be displayed in such a way so as not to interfere with the video call and so as to allow the individual, patient, or caregiver, to verify the identity of the healthcare provider. In a similar manner, at step 1802, a profile photograph or picture of the individual or patient, such a photograph or picture from the individual's r patient's user profile, can also be, but need not be, transmitted to the provider's communication device 21 along with the video which is transmitted from the user's user communication device 41 during the video call, and can be displayed via the display device 20E. In a preferred embodiment, the individual's or patient's photograph or picture can be displayed in such a way so as not to interfere with the video call and so as to allow the healthcare provider to verify the identity of the individual or patient.

Thereafter, at step 1802, the video call can then proceed and the healthcare provider can conduct the remote office visit or the virtual office visit, and/or the remote examination, or the distance examination, with the individual, the patient, or the caregiver. In instances where the individual or the patient is on the video call without a caregiver, then the video call can take place between the individual or the patient and the healthcare provider. In instances where a caregiver is on the video call, then the video call can also take place with the individual or the patient, the caregiver, and the healthcare provider. In instances where only the caregiver is on the video call without the individual or the patient, then the video call can take place with the caregiver and the healthcare provider.

In a preferred embodiment, at step 1802, the video and audio of the video call can be recorded by or with the central processing computer component 110A of the central processing computer/distributed ledger/Blockchain technology system 110, by or with the provider communication device 21, and/or by or with the user communication device 41, or by or with the respective video and/or audio recording devices 20J, 30J, and/or 40J, of same for storage in each of the central processing computer component 110A of the central processing computer/distributed ledger/Blockchain technology system 110, and Blockchain technology system component 110B of the central processing computer/distributed ledger/Blockchain technology system 110, the provider communication device 21, and/or the user communication device 41. In a preferred embodiment, the recording of the video call can include a recording of the entirety of the video call and/or certain portions of the same. In a preferred embodiment, the entire video call is recorded.

In a preferred embodiment, the recording of the video call can be stored in the individual's or patient's electronic healthcare record, file, or history, in the database 10H of the central processing computer component 110A of the central processing computer/distributed ledger/Blockchain technology system 110, in the Blockchain technology system component 110B of the central processing computer/distributed ledger/Blockchain technology system 110, in the database 20H of the provider communication device 21, and/or in the database 40H of the user communication device 41.

The video and audio recording of the video call can retrieved and viewed by the healthcare provider, by the individual or patient, or a caregiver of the individual or patient, by an insurer or payer, by any intermediary, or by any other authorized individual. In a preferred embodiment, the healthcare provider can retrieve recordings of previously video calls with the individual or patient, as well as previously recorded video calls between the individual or patient and other healthcare providers, before, during, or after, the video call so as to observe and take note of any similarities or changes in the individual's or patient's condition, state of being, physical appearance, mannerisms, body language, or any other behavior, which might be useful or beneficial in evaluation, examining, caring for, and/or treating, the individual or the patient. In a preferred embodiment, any suitable number of recorded video calls can be provided on and/or via the display device 20E of the provider communication device 20.

In this regard, the healthcare provider or another healthcare provider, or the individual, the patient, the caregiver, or another caregiver, or any other authorized person, can replay or review the recordings of any number of video calls involving the individual or patient at any time and for any purpose.

At step 1802, the healthcare provider can conduct the remote office visit or the virtual office visit, and/or the remote examination, or the distance examination, with the individual, the patient, or the caregiver, by ascertaining the individual's or the patient's condition, symptoms, or the nature of the individual's or the patient's illness, sickness, or state of health. At step 1802, the healthcare provider can also obtain information regarding a healthcare history of or for the individual or the patient or any information regarding a family healthcare history of or for the individual or the patient. At step 1802, the healthcare provider can also obtain information regarding any allergies the individual or the patient may have, or any prescription medications or drugs the individual or the patient may be taking. At step 1802, the healthcare provider can also obtain any other information needed or desired for diagnosing and/or for treating the individual or the patient during the video call.

At step 1802, the individual or the patient, or the caregiver, can also, if not previously provided to the healthcare provider, provide the healthcare provider with authorization and/or permission to access and review the individual's or the patient's electronic healthcare record, file, or history, and/or to review any data and/or information contained therein. In a preferred embodiment, the healthcare provider can also be provided with authorization or permission to access and review the individual's or the patient's electronic healthcare record, file, or history, prior to the video call. Such authorization or permission can also be provided at the time the appointment is scheduled by the individual, the patient, or the caregiver of or for the individual or the patient. Such authorization and also be a standing authorization such as when the healthcare provider cares for the individual or patient on an ongoing manner or continuing manner.

At step 1802, the healthcare provider can access, and can review or can obtain any data and/or information contained in, the individual's or the patient's electronic healthcare record, file, or history. In a preferred embodiment, various sections of the individual's or the patient's electronic healthcare record, file, or history, can be displayed on the display device 20E of the provider communication device 21 along with the video of the individual or patient, or the caregiver, during the video call. In a preferred embodiment, any section or sections of the individual's or the patient's electronic healthcare record, file, or history, can be simultaneously displayed via the display device in a split-screen format, or in a multiple screen format, or via multiple viewing windows. At step 1802, the healthcare provider can also request and/or conduct a visual examination of the individual or the patient or of a body part of the individual or the patient in and/or under appropriate circumstances by asking the individual or the patient, or the caregiver, to use and/or position the camera associated with the user communication device 41, such as a camera of the video and/or audio recording devices 40J, in order to allow the healthcare provider to look at or view the individual or the patient or any body part of the individual or the patient. At step 1802, the individual, the patient, or the caregiver, can also transmit any data and/or information stored in any personal health record of or for the individual or the patient which might be stored on or in the user communication device 41 which is being utilized for the video call. At step 1802, the individual, the patient, or the caregiver, can also transmit any data and/or information stored in any electronic healthcare record, file, or history, of or for the individual or the patient which might be stored on or in the user communication device 41 which is being utilized for the video call.

At step 1802, the healthcare provider can also ask that the individual, the patient, or the caregiver, obtain and/or transmit any data and/or information, and/or transmit any previously obtained, recorded, and/or stored, data and/or information, from any healthcare measuring device or equipment, any healthcare measurement device or equipment, or any healthcare monitoring device or equipment, or obtain and/or transmit any data and/or information from any healthcare equipment input device, healthcare measurement input device, or healthcare monitoring input device described herein, which can be utilized in connection or in conjunction with the user communication device 41 and/or which has been described herein as being utilized as an input device for or in connection with the user communication device 41. In this regard, the healthcare provider can also request that the individual, the patient, or the caregiver, obtain and/or transmit data and/or information obtained by a pulse rate monitor, a blood pressure monitor, a blood oxygen or percentage oxygen measurement device, an electro-cardiogram, a glucose monitor, a blood-sugars monitor, any device which can acquire, receive, generate and/or provide, digital data such as medical, healthcare, bio-metric, physiological, and/or any other kind of healthcare data and/or healthcare-related data, a heart rate monitor, a pulse rate monitor, or EKG machine, a thermometer, a digital thermometer, a stethoscope, a heart rate monitor or measurement device, a pulse rate monitor or measurement device, a blood pressure monitor or measurement device, a blood pressure measurement device, a blood glucose monitor, a blood oxygen percentage level monitor, an oximeter, a digital finger pulse oximeter, a blood analysis device or machine, a respirator, a respiration monitoring or measurement device, a dialysis machine, a dialysis device, electrocardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laparoscopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedance measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, dental probe, microscopic camera probing device, or any other bio-metric or physiological data measuring device(s) and/or data acquisition device (each of which can be hereinafter also referred to herein as "healthcare equipment" or as a "healthcare measurement device").

Any data and/or information transmitted at or during step 1802 can be transmitted from the user communication device 41, and/or from each respective healthcare measuring device or equipment, each healthcare measurement device or equipment, or each healthcare monitoring device or equipment. Any data and/or information transmitted at or during step 1802 can be transmitted from the user communication device 41, and/or from each respective healthcare measuring device or equipment, healthcare measurement device or equipment, or healthcare monitoring device or equipment, can be transmitted to and stored at provider communication device 21 and/or the central processing computer component 110A of the central processing computer/distributed ledger/Blockchain technology system 110. Any data and/or information obtained, recorded, and/or transmitted, at or during step 1802 can be real-time data and/or information, live data and/or information, or previously recorded or previously stored data and/or information.

At step 1802, the healthcare provider can also perform, during the video call, a remote control operation and/or a remote monitoring operation of, for, or regarding, any of the above-noted or herein-described items of healthcare equipment, healthcare monitoring devices, or of any healthcare measurement device(s) or any healthcare devices or healthcare equipment via a respective link or hyperlink provided in the individual's or the patient's electronic healthcare record, file, or history. Any results or measurements obtained from any healthcare equipment or from any healthcare measurement device(s) or healthcare equipment can be provided to the healthcare provider via the display device 20E of the healthcare provider communication device 21.

At step 1802, the healthcare provider can also request that the individual or patient, or the caregiver, obtain and/or record, and transmit to the provider communication device 21 from the user communication device 41, any biometric data, and/or any performance tracking data and/or information, of, for, or regarding, the individual or patient which can be obtained by, from, or via, any of the herein-described user/patient monitoring system(s) 94 and/or any of the herein-described tracking systems, such as, for example, any of the herein-described healthcare measurement device(s) or any healthcare devices or healthcare equipment, a gyroscope, an accelerometer, a decelerometer, a magnetometer, an RFID tag(s), a thermometer for measuring temperature of the environment, a device for measuring body temperature, a device for measuring speed of movement, a device for measuring distance traveled, or any other device or devices which can measure and record information regarding three-dimensional movements of the individual or patient, and/or any device or equipment used for measuring, monitoring, and/or tracking individual or patient activity or performance using any type or kind of optical-based camera (OBC) tracking systems, local positioning system (LPS) tracking systems, and/or global positioning system/global navigation satellite system (GPS/GNSS) tracking systems, and/or any other tracking system, which are or can be utilized to track players or athletes during sporting or athletic competitions or training.

At step 1802, the healthcare provider can also control or monitor the operation, and obtain data and/or information from any of the herein-described healthcare measurement device(s) or any healthcare devices or healthcare equipment, user/patient monitoring system(s), and/or tracking systems 94. At step 1802, any data and/or information requested by the healthcare provider can be transmitted to, and received by and stored at, the provider communication device 21.

In another preferred embodiment, any and/or all of the herein-described healthcare measurement device(s) or any healthcare devices or healthcare equipment, user/patient monitoring system(s), and/or tracking systems 94, can be equipped with its own, or with their own, global positioning device (not shown), for determining the position of location of the same, a receiver (not shown), for receiving control or monitoring signals from the user communication device 41, from the provider communication device 21, from the central processing computer component 110A of the central processing computer/distributed ledger/Blockchain technology system 110, from the central processing computer 10 of FIGS. 1 and 12, and/or from any other computer or communication device utilized by any authorized individual or entity, a central processing unit (CPU) or controller (not shown), for controlling the operation of the respective healthcare measurement device, healthcare device, healthcare equipment, user/patient monitoring system(s), or tracking system 94, a memory or database (not shown), for storing any data and/or information obtained, acquired, or recorded, by the respective healthcare measurement device(s), healthcare device, healthcare equipment, user/patient monitoring system, and/or tracking system 94, and/or a transmitter (not shown) for transmitting any data and/or information to the user communication device 41, to the provider communication device 21, to the central processing computer component 110A of the central processing computer/distributed ledger/Blockchain technology system 110, to the central processing computer 10 of FIGS. 1 and 12, and/or to any other computer or communication device utilized by any authorized individual or entity. In another preferred embodiment, any and/or all of the herein-described healthcare measurement device(s) or any healthcare devices or healthcare equipment, user/patient monitoring system(s), and/or tracking systems 94, can also be assigned an IP address or one or more IP addresses for use in identifying the same.

In another preferred embodiment, the user communication device 41 can be linked to any and/or each healthcare measurement device, healthcare device, healthcare equipment, user/patient monitoring system, and/or tracking system 94 described herein, via a wired connection, via a wireless connection, via a Bluetooth connection, or via any combination of same. In a preferred embodiment the user communication device 41 can be programmed to automatically obtain, collect, and store, any data and/or information obtained by, acquired by, or recorded by, any and/or each healthcare measurement device, healthcare device, healthcare equipment, user/patient monitoring system, and/or tracking system 94 described herein, at any desired or selected time, or at any desired or selected time intervals, and to transmit any such data and/or information, at any desired or selected time, or at any desired or selected time intervals, to each of the provider communication device 21, to the central processing computer component 110A of the central processing computer/distributed ledger/Blockchain technology system 110, to the central processing computer 10 of FIGS. 1 and 12, and/or to any other computer or communication device utilized by any authorized individual or entity. In this regard, the user communication device 41 can be programmed to obtain, collect, and report on, data and/or information, obtained by, acquired by, or recorded by, any and/or each healthcare measurement device, healthcare device, healthcare equipment, user/patient monitoring system, and/or tracking system 94 described herein.

In another preferred embodiment, the user communication device 41 can also be programmed to detect instances when any data and/or information, obtained by, acquired by, or recorded by, any and/or each healthcare measurement device, healthcare device, healthcare equipment, user/patient monitoring system, and/or tracking system 94 described herein, is indicative of an healthcare irregularity or an healthcare emergency for or regarding the individual or patient, or is indicative of a need for the individual or patient to seek healthcare provider intervention, or to seek to see or be examined by a healthcare provider. In such an instance, the user communication device 41 and generate and can provide, at any time, a visual, audio, and/or text, alert message or indication which can be provided via the respective display device 40E and/or output device 40I of the user communication device 40. In such an instance, the user communication device 41 and generate an emergency or other alert message containing information regarding the need see or be examined by a healthcare provider and can transmit the emergency or other alert message to the provider communication device 21, to the central processing computer component 110A of the central processing computer/distributed ledger/Blockchain technology system 110, to the central processing computer 10 of FIGS. 1 and 12, and/or to any other computer or communication device utilized by any authorized individual or entity. In a preferred embodiment, any emergency or other alert message can also contain any data and/or information which is the subject of the an healthcare irregularity or an healthcare and information regarding the position or location of the individual or patient, as determined by the global positioning device 40K of the user communication device or as determined by the respective global positioning device of the respective healthcare measurement device, healthcare device, healthcare equipment, user/patient monitoring system, and/or tracking system 94 from which the data and/or information, which is the subject of the emergency or other alert message, was acquired, obtained, or collected.

With reference once again to FIG. 18, at step 1802, the individual, the patient, or the caregiver, can also access the individual's or the patient's electronic healthcare record, file, or history, during the video call in order to view same along with the healthcare provider. In a preferred embodiment, any video call video and/or any electronic healthcare record, file, or history, information, can be presented on the display device 20E of the respective provider communication device 21 and/or on the display device 40E of the user communication device 41 in a split screen format, or in a multiple-screen format, and/or by using multiple viewing windows, so as to ensure that as much information as possible can be provided to healthcare provider and/or to the individual, the patient, or the caregiver, during the video call. In a preferred embodiment, any video call video and/or audio and/or any electronic healthcare record, file, or history information, can be presented on the respective provider communication device 21 by being displayed, in a split screen format, multiple screen format, multiple viewing window format, or any other suitable format, on or via the display device 20E and/or by being presented via a speaker of the output device 20I of the provider communication device 21 so as to ensure that as much information as possible can be provided to the healthcare provider during the video call. In a preferred embodiment, any video call video and/or audio and/or any electronic healthcare record, file, or history, information, can be presented on or via the respective user communication device 41 by being displayed, in a split screen format, in a multiple screen format, in a multiple viewing window format, or in any other suitable format, on or via the display device 40E and/or by being presented via a speaker of the output device 40I of the user communication device 41 so as to ensure that as much information as possible can be provided to the individual, the patient, or the caregiver, during the video call.

At step 1802, the healthcare provider can obtain any other information from the individual, the patient, or the caregiver, or from the individual's or the patient's electronic healthcare record, file, or history, and/or any other data and/or information which the healthcare provider deems to be needed or desired during the video call and/or during the remote office visit or the virtual office visit and/or the remote examination or the distance examination with the individual, the patient, or the caregiver. In another preferred embodiment, the healthcare provider can also, at step 1802, as well as before and after the video call, retrieve and review previously recorded videos of any previous video calls in which the individual, patient, or caregiver, has engaged, or been involved in, with the healthcare provider or with any other healthcare provider. In a preferred embodiment, the healthcare provider can utilize the previous recordings of previous video calls to obtain additional information, to confirm previous information, and/or to examine, note, or evaluate, the individual's or patient's physical appearance, body language, reactions, responses, and/or any differences and/or changes in same.

At step 1802, the healthcare provider can enter any notes, comments, and/or observations, and/or any examination findings, regarding the individual or the patient and/or regarding any data and/or information obtained or reviewed during the video call, into the individual's or the patient's electronic healthcare record, file, or history. At step 1802, the healthcare provider can also make or arrive at a diagnosis for the individual or the patient, and/or can prescribe a treatment, or a course of treatment, or can provide a treatment plan, or can prescribe a therapy or can provide a therapy plan, or can prescribe an immunization, or can generate or issue a prescription for a drug or a medication, or can generate or issue a prescription for a test or procedure, or can make a referral to another healthcare provider, for the individual or the patient.

In a preferred embodiment, the healthcare provider can utilize any information contained in the individual's or the patient's electronic healthcare record, file, or history, in order to take into account any allergies, possible drug or medication interactions, or any other information regarding the individual or the patient which must be considered in making or in arriving at a diagnosis, and/or in prescribing a treatment, or a course of treatment, or in providing a treatment plan, or in prescribing a therapy or in providing a therapy plan, or in prescribing an immunization, or in generating or issuing a prescription for a drug or a medication, or in generating or issuing a prescription for a test or a procedure, or in making a referral, to another healthcare provider, for the individual or the patient. In a preferred embodiment, any prescription(s) or referral(s) generated or issued at or during step 1802 can be electronically sent, such as by e-mail, instant message, SMS message, MMS message, or in any other suitable communication device to any provider communication device 21 of or associated with the individual's or the patient's pharmacy or to any other healthcare provider to whom the respective prescription or referral is to be sent.

The healthcare provider can also, as step 1802, recommend that the individual or the patient, or the caregiver of or for the individual or the patient, obtain information from, and/or join or participate in or with, any social network or social networks associated with any of the herein-described social networking computers 80 which are described herein as being utilized in connection with the apparatus 100 of the present invention. The healthcare provider can also, at step 1802, recommend or prescribe that the individual or the patient, or the caregiver of or for the individual or the patient, obtain information from and/or subscribe to any of the herein-described media computers 90 which are described herein as being utilized in connection with the apparatus 100 of the present invention.

In a preferred embodiment, the healthcare provider can recommend or prescribe the viewing of video recordings, video clips, news clips, instructional video presentations, classes, seminars, or courses, educational video presentations, classes, seminars, or courses, video presentations, classes, seminars, or courses explaining healthcare issues, diagnoses, treatments, therapies, and other information, and/or any other presentations, classes, seminars, or courses which can provide the individual, patient, or caregiver, with information pertinent to the health, fitness, well-being, treatment, or therapy, of the individual or patient. In a preferred embodiment, the herein-described media computers 90 can transmit any of the herein-described video recordings, video clips, news clips, instructional video presentations, classes, seminars, or courses, educational video presentations, classes, seminars, or courses, video presentations, classes, seminars, or courses explaining healthcare issues, diagnoses, treatments, therapies, and other information, and/or any other presentations, classes, seminars, or courses, to any user communication device 41 of or associated with the individual, patient, or caregiver.

In another preferred embodiment, the media computer 90 can also transmit, to the user communication device 41, news stories or news alerts which can contain information which can provide the individual, patient, or caregiver, with information pertinent to the health, fitness, well-being, treatment, or therapy, of the individual or patient. In another preferred embodiment, the media computer 90 can also transmit, to the provider communication device 21 and/or to any user communication device(s) 41, any video recordings, or live video transmissions, of courses, classes, or seminars, for providing education and/or training, to and/or for any of the herein-described healthcare providers and/or individuals, patients, or caregivers, or any other individuals or entities who or which utilize the apparatus 300 of the present invention. Thereafter, the video call can end and the operation of the apparatus 100 will proceed to step 1803.

At step 1803, the healthcare provider can enter any information regarding any notes, comments, observations, examination findings, and/or any other information, obtained during the video call, into the individual's or the patient's electronic healthcare record, file, or history, so as to update the same so as to include information regarding the video call and the remote office visit or the virtual office visit, and/or the remote examination, or the distance examination, which was conducted with and/or involving the individual, the patient, or the caregiver. At step 1803, the healthcare provider can also store the picture or photograph, or video clip, of the individual, the patient, the caregiver, which was taken during the video call along with any other information regarding the video call and the remote office visit, for the video call and for the remote office visit, in order provide verification regarding the identity of the individual, the patient, or the caregiver.

At step 1803, the healthcare provider can also store the picture or photograph, or the video clip, of the healthcare provider, which was taken during the video call along with any other information regarding the video call and the remote office visit, for the video call and the remote office visit, in order provide verification regarding the identity of the healthcare provider.

At step 1803, the video call, which can be recorded, can also be stored in the individual's or the patient's electronic healthcare record, file, or history, for retrieval at any time by the healthcare provider or another healthcare provider, or by the individual, the patient, the caregiver, or another caregiver, or by a healthcare insurer or a healthcare payer, or by an intermediary, or by any other authorized person or entity, at any time.

At step 1803, the central processing computer component 110A of the central processing computer/distributed ledger/Blockchain technology system 110 can, after any and/or all information obtained during and/or regarding the video call has been entered by the healthcare provider and stored in the individual's or the patient's electronic healthcare record, file, or history, can generate a video call report and/or a remote or virtual office visit report or a remote or distance examination report, containing information regarding the video call, and/or information regarding the remote or virtual office visit, or the remote of distance examination, any data and/or information obtained or entered or recorded during the video call, and/or the picture, photograph, or video clip, of the individual, the patient, or the caregiver and/or the picture. photograph, or video clip, of the healthcare provider, and/or any other data and/or information regarding the video call and the remote office visit, and can transmit the video call report, and/or the remote or virtual office visit report, or a remote or distance examination report, in, as, or attached to, an e-mail message or in, as, or attached to, an electronic communication transmission, to the provider communication device 21 of or associated with the individual's or the patient's primary care healthcare provider or any other healthcare provider of the individual or the patient, to a user communication device 41 of or associated with the individual, the patient, or the caregiver or any other caregiver of the individual or the patient, to a payer communication device 30 of or associated with a healthcare insurer or a healthcare payer of the individual or the patient, and/or to an intermediary communication device 50 of or associated with an intermediary.

In a preferred embodiment, the video call report, and/or the remote or virtual office visit report, or a remote or distance examination report, can contain or include a recording of the video call, any of the data and/or information obtained from the individual, the patient, or the caregiver, prior to, during or after, the video call, any other information obtained from the individual, the patient, or the caregiver, or any information obtained from the individual's or the patient's electronic healthcare record, file, or history, and/or any other data and/or information which the healthcare provider deems to be needed or desired during the video call, and/or during the remote office visit, or the virtual office visit, and/or the remote examination or the distance examination, with or of the individual, the patient, or the caregiver, any information obtained and/or reviewed from any of the herein-described healthcare measurement device(s) or any healthcare devices or healthcare equipment, before, during, or after, the video call, any data and/or information regarding any biometric data or performance tracking information regarding the individual or patient obtained and/or reviewed from any of the herein-described user/patient monitoring system(s) 94, before, during, or after, the video call, any information regarding any of the healthcare provider's notes, comments, observations, or examination findings, regarding the individual or the patient and/or any information regarding any data and/or information obtained or reviewed during the video call, and/or entered into the individual's or the patient's electronic healthcare record, file, or history, or any information regarding any diagnosis arrived or made for the individual or the patient, and/or any information regarding any prescribed treatment or course of treatment, any treatment plan, or any prescription for a drug or a medication, or any prescription for a test or procedure, or any referral to another healthcare provider, for the individual or the patient. In a preferred embodiment, the video call report and/or the remote or virtual office visit report or a remote or distance examination report, can contain or include any information regarding any recommendation that the individual or the patient, or the caregiver of or for the individual or the patient, obtain information from, and/or join or participate in or with, any social network or social networks associated with any of the herein-described social networking computers 80 and/or any recommendation that the individual or the patient, or the caregiver of or for the individual or the patient, obtain information from and/or subscribe to any of the herein-described media computers 90.

In a preferred embodiment, the video call report and/or the remote or virtual office visit report, or a remote or distance examination report, can also contain or include any information regarding the time of the video call, the time duration of the video call, participants or other individuals, other than the individual or patient and the healthcare provider, who listened to or participated in, or who attempted to listen in on, the video call, and/or any other information regarding the video call which can or may be deemed to be useful or beneficial to any healthcare provider, a healthcare insurer or payer, a healthcare intermediary, or any other individual or entity, in monitoring, assessing, auditing, and/or reviewing, the healthcare of the individual or patient, the activity or activities of, or the healthcare services provided by, the healthcare provider, in reviewing, processing, or auditing a healthcare insurance claim or a claim for payment for healthcare services, and/or for any other reason.

In a preferred embodiment, any remote or virtual office visit report or the remote or distance examination report generated at step 1803, and/or any other data and/or information regarding the remote or virtual office visit or the remote or distance examination, can also be stored in the individual's or the patient's electronic healthcare record, file, or history.

In a preferred embodiment, the remote or virtual office visit report, or the remote or distance examination report, generated at step 1803, and/or any other data and/or information regarding the remote or virtual office visit or the remote or distance examination, can be stored in patient's electronic healthcare record, file, or history, which is stored in the database 10H of the central processing computer component 110A of the central processing computer/distributed ledger/Blockchain technology system 110, which is stored in the Blockchain technology system component 110B of the central processing computer/distributed ledger/Blockchain technology system 110, which is stored in the database 20H of the provider communication device 21, and/or which is stored in the database 40H of the user communication device 41.

It is important to note that any and/or all data and/or information, described herein as being stored in the database 10H of the central processing computer component 110A of the central processing computer/distributed ledger/Blockchain technology system 110, as well as described as being stored in any of the databases 20H, 30H, 40H, 50H, 60H, and 70H, of their respective devices 20, 30, 40, 50, 60, and 70, is also, or can also, be stored in the Blockchain technology system component 110B of the central processing computer/distributed ledger/Blockchain technology system 110. It is also important to note that any and/or all video call reports, and/or the remote or virtual office visit reports, or a remote or distance examination reports, and any and/or all data and/or information contained therein, and/or any data and/or information obtained during the remote or virtual office visit, or the remote or distance examination, is also, or can also, be stored in the Blockchain technology system component 110B of the central processing computer/distributed ledger/Blockchain technology system 110. In this regard, individual's or the patient's electronic healthcare record, file, or history, for each individual or patient who utilizes the apparatus 300, is also, or can also, be stored in the Blockchain technology system component 110B of the central processing computer/distributed ledger/Blockchain technology system 110.

In a preferred embodiment, in instances where the individual or patient has a multiple electronic healthcare records, files, or histories, then, at step 1803, the central processing computer component 110A of the central processing computer/distributed ledger/Blockchain technology system 110, can update each of all of the individual's or patient's electronic healthcare records, files, or histories, to reflect any and/or all of the herein-described data and/or information obtained, noted, reported, and/or acted on, by the healthcare provider in, as a result of, and/or pursuant to, the video call. In this regard, all of the individual's or patient's electronic healthcare records, files, or histories, can be updated to correspond with the individual's or patient's electronic healthcare record, file, or history, accessed and used by the healthcare provider in and during the video call.

In a preferred embodiment, all updates and/or changes to all of the individual's or patient's electronic healthcare records, files, or histories, can be stored in the database 10H of the central processing computer component 110A of the central processing computer/distributed ledger/Blockchain technology system 110, can be stored in the database 20H of the provider communication device 21 of or associated with the healthcare provider, can be stored in the database 40H of the user communication device(s) 41 of or associated with the individual or patient, and can be stored in the Blockchain technology system component 110B of the central processing computer/distributed ledger/Blockchain technology system 110.

At step 1804, the central processing computer component 110A of the central processing computer/distributed ledger/Blockchain technology system 110, which can be programmed to generate and transmit an insurance claim form or a request for payment form, can utilize the information stored at step 1803 in order to generate an insurance claim form or a request for payment form. At step 1804, the central processing computer component 110A of the central processing computer/distributed ledger/Blockchain technology system 110, which can be programmed to generate and transmit a request for payment of co-payment form, can generate a request for payment of co-payment form. In a preferred embodiment, the insurance claim form or a request for payment form and/or the request for payment of co-payment form, can also include, or include as an attachment(s), any one or more of the picture, photograph, or video clip, of the individual, the patient, or the caregiver, the picture, photograph, or video clip, of the healthcare provider, and/or any data and/or information regarding the video call and the remote office visit, the video call report and/or the remote or virtual office visit report, or the remote or distance examination report, and/or any information obtained or derived from the same.

At step 1805, the central processing computer component 110A of the central processing computer/distributed ledger/Blockchain technology system 110 can transmit the insurance claim form or a request for payment form, in, as, or attached to, an e-mail message, or in, as, or attached to any other suitable electronic communication transmission, to the payer communication device 30 of or associated with the healthcare insurer or the healthcare payer of the individual or the patient. At step 1805, the central processing computer component 110A of the central processing computer/distributed ledger/Blockchain technology system 110 can also transmit the request for payment of co-payment form in, as, or attached to, an e-mail message, or in, as, or attached to any other suitable electronic communication transmission, to the user communication device 41.

At step 1805, any insurance claim form(s) or any request for payment form(s) and any request for payment of co-payment form(s) generated by, and/or transmitted by, the central processing computer component 110A of the central processing computer/distributed ledger/Blockchain technology system 110, and any attachments, if applicable, can be stored in the individual's or the patient's electronic healthcare record, file, or history, and can be stored in the database 10H of the central processing computer component 110A of the central processing computer/distributed ledger/Blockchain technology system 110, as well as in the databases 20H, 30H, 40H, 50H, 60H, and 70H, of the respective devices 20, 21, 30, 31, 40, 41, 50, 51, 60, and 70, as well as in the Blockchain technology system component 110B of the central processing computer/distributed ledger/Blockchain technology system 110. Thereafter, the operation of the apparatus 100 will cease at step 1806.

In another preferred embodiment, the apparatus 300 of the embodiment of FIG. 18 can also be utilized in a same, a similar, and/or an analogous, manner in order to provide a tele-health dental visit or remote or online dental visit or dental examination with a dentist, a dental assistant, a dental hygienist, or any other dental healthcare provider. In such a preferred embodiment, a dentist, dental assistant, dental hygienist, or any other dental healthcare provider, can conduct a video call, and/or an online dental examination or dental visit, with an individual or patient so as to thereby perform a remote dental examination. In such a preferred embodiment, the dentist, dental assistant, dental hygienist, or other dental healthcare provider, can instruct the individual, the patient, or a caregiver, to utilize and/or to manipulate or position the herein-described dental probe, which can be used as a user input device 40D of the user communication device 41, and which is equipped with light and a camera or a video recording device, inside and/or outside the individual's or patient's mouth, as needed and/or as desired, in order to perform a visual dental examination of the individual's or patient's mouth, teeth, gums, palate, or tongue. In such a preferred embodiment, any picture(s) or video information obtained by, or recorded by or with, the camera or the video recording device of the dental probe can be provided to the dentist, dental assistant, dental hygienist, or other dental healthcare provider, before, during, or after, the video call and/or at or during any of steps 1802 or 1803, and/or at or during any of the other herein-described steps of the embodiment of FIG. 18. In this regard, the herein-described dental probe can be utilized as any other piece of healthcare equipment or any healthcare devices described herein which can be utilized to obtain information regarding an individual or patient before, during, or after, a video call and to provide that information to the respective provider conducting the video call.

In a preferred embodiment, any picture(s) or video information obtained by, or recorded by or with, the camera or the video recording device of the dental probe, or obtained by, or recorded by or with, any other item or piece of healthcare equipment or any healthcare device described herein, can also be provided in, as, or via, a separate screen on the display device 20E of the provider communication device 20 and/or on the display device 40E of the user communication device 40 during the video call. In a similar manner, any picture(s) or video information obtained by, or recorded by or with, a camera or a video recording device of any healthcare equipment input device, any healthcare measurement input device, or any healthcare monitoring input device, described herein, can also be provided in, as, or via, a separate screen on the display device 20E of the provider communication device 20 and/or on the display device 40E of the user communication device 40 during the video call.

In a preferred embodiment, any picture(s) or video information obtained by, or recorded by or with, the camera or the video recording device of the dental probe, or obtained by, or recorded by or with, any other item or piece of healthcare equipment, or any healthcare device, described herein, or any healthcare equipment input device, any healthcare measurement input device, or any healthcare monitoring input device, described herein, can also be stored in the individual's or the patient's electronic healthcare record, file, or history, and can also be stored in the database 10H of the central processing computer component 110A of the central processing computer/distributed ledger/Blockchain technology system 110, as well as in the databases 20H, 30H, 40H, 50H, and 60H, of the respective devices 20, 21, 30, 31, 40, 41, 50, 51, and 60, as well as in the Blockchain technology system component 110B of the central processing computer/distributed ledger/Blockchain technology system 110.

In this regard, the apparatus 300 and method of the present invention can be utilized to facilitate and/or to conduct remote or virtual healthcare provider visits, consultations, and/or examinations, via and/or through the use of video calls, video chat sessions, and/or videoconferences, with and between an individual, a patient, and/or a caregiver for the individual or the patient. The apparatus 300 and method of the present invention can also be utilized to schedule remote or virtual provider visits, consultations, and/or examinations, via and/or through the use of video calls, video chat sessions, and/or videoconferences, with and between an individual, a patient, and/or a caregiver for the individual or the patient.

As described herein, in a preferred embodiment, as well as in any and/or all of the embodiments described herein, the apparatus 300 and methods of the present invention can utilize the centralized processing capabilities of a central processing computer, which is provided by the central processing computer component 110A of the central processing computer/distributed ledger/Blockchain technology system 110, in combination with the distributed processing capabilities and security benefits which can be provided by using a distributed ledger and with Blockchain technology, which is provided by the Blockchain technology system component 110B of the central processing computer/distributed ledger/Blockchain technology system 110. In a preferred embodiment, any and/or all of the herein-described data and/or information, reports, messages, video and audio recordings, video recordings, audio recordings, pictures, photographs, video clips, used, processed, or generated with or using the apparatus 300, or the apparatus 100, or the apparatus 200, can be processed, generated, and/or store, and/or secured, using the Blockchain technology system component 110B of the central processing computer/distributed ledger/Blockchain technology system 110 and/or any other suitable, appropriate, or equivalent, distributed ledger and Blockchain technology system and/or with a distributed ledger and with Blockchain technology. In a preferred embodiment, a distributed ledger and Blockchain technology can be utilized along with a central processing computer, in a combined system, wherein certain of the transactions, described herein as being performed by the apparatus 100, 200, or 300, can be processed and/or can be performed by and/or with a central processing computer and/or wherein certain other transactions can be processed and/or performed by and/or with, and/or using, a distributed ledger and Blockchain technology or Blockchain technologies.

In another preferred embodiment, as well as in any and/or all of the embodiments described or disclosed herein, any and/or all transactions, described herein as being performed and/or processed by the apparatus 300, or the apparatus 100 or 200, can also be processed and/or can be performed by and/or with, and/or using, a distributed ledger and Blockchain technology or Blockchain technologies, and/or using any cryptocurrency Blockchain technology or technologies.

In another preferred embodiment, at step 1802, the provider communication device 21 or the central processing computer component 110A of the central processing computer/distributed ledger/Blockchain technology system 110 can generate a video call alert message containing information regarding the start of the video call, including the date and time of same, the healthcare provided involved, a video clip of the individual or patient, and/or a video clip of the healthcare provider, along with any other information regarding the individual or patient and/or any information regarding the individual's or patient's healthcare account. At step 1802, the provider communication device 21 or the central processing computer component 110A of the central processing computer/distributed ledger/Blockchain technology system 110 the can transmit the video call alert message to any one or more of the user communication devices 41 which can be registered to, or associated with, the individual or patient or a healthcare account assigned to, or associated with, the individual or patient.

In a preferred embodiment, if the video call alert message is generated by the provider communication device 21, the provider communication device 21 can transmit the same to any one or more of the user communication devices 41 of or associated with the individual or patient, or the provider communication device 21 can transmit the video call alert message to the central processing computer component 110A of the central processing computer/distributed ledger/Blockchain technology system 110, which can then transmit the same to any one or more of the user communication devices 41 of or associated with the individual or patient. If the video call alert message is generated by the central processing computer component 110A of the central processing computer/distributed ledger/Blockchain technology system 110, the central processing computer component 110A of the central processing computer/distributed ledger/Blockchain technology system 110, can then transmit the same to any one or more of the user communication devices 41 of or associated with the individual or patient.

In a preferred embodiment, the individual or patient, or a caregiver for the individual or patient, can review information contained in the video call alert message and, if the same is an authorized video call, that is, involving the individual or patient, then the individual or patient, or a caregiver for the individual or patient, can transmit a video call authorized message or signal from the user communication device 41 to the provider communication device 21 and/or to the central processing computer component 110A of the central processing computer/distributed ledger/Blockchain technology system 110. Information regarding the video call alert message, the video call alert message, and the video call authorized message or signal can be stored in the individual's or the patient's electronic healthcare record, file, or history, in the database 10H of the central processing computer component 110A of the central processing computer/distributed ledger/Blockchain technology system 110 and/or in the database 20H of the healthcare provider's provider communication device 21.

In a preferred embodiment, if the video call is not an authorized video call, that is, that the video call does not involve the individual or patient, such as in instances of healthcare identify theft and/or other possible fraudulent use of the individual's or patient's healthcare account or healthcare insurance, then the individual or patient, or a caregiver for the individual or patient, can transmit a video call not authorized message or signal from the user communication device 41 to the provider communication device 21 and/or the central processing computer component 110A of the central processing computer/distributed ledger/Blockchain technology system 110. In such an instance, either the provider communication device 21 or the central processing computer component 110A of the central processing computer/distributed ledger/Blockchain technology system 110 can process information regarding the video call not authorized message or signal, and can terminate the video call and operation of the apparatus 300 will cease at step 1806. Information regarding the video call alert message, the video call alert message, and the video call not authorized message or signal, can thereafter be stored in the individual's or the patient's electronic healthcare record, file, or history, in the database 10H of the central processing computer component 110A of the central processing computer/distributed ledger/Blockchain technology system 110 and/or in the database 20H of the healthcare provider's provider communication device 21.

In a preferred embodiment, any type of Blockchain technology can be utilized in connection with the apparatus 300 and methods of the present invention. In a preferred embodiment, for example, the apparatus 300 and methods of the present invention can utilize a distributed ledger(s) along with any Blockchain technology or technologies, Bitcoin Blockchain technology or technologies, Ethereum Blockchain technology or technologies, Bitcoin Cash Blockchain technology or technologies, Litecoin Blockchain technology or technologies, Privacy Coin Bitcoin technology or technologies, and/or any other suitable Blockchain technology or technologies, and/or Smart contracts and/or Smart contract technology or technologies and/or decentralized autonomous organizations (DAOs), decentralized autonomous organizations (DAOs) technology or technologies, and/or any combination of same.

By utilizing a distributed ledger and a suitable Blockchain technology, the apparatus 300 and methods of the present invention can reduce the amount of processing performed by, and reliance on, a central processing computer and/or can eliminate the need for a central processing computer and/or any centralized entity which might operate the central processing computer. The use of a distributed ledger and a suitable Blockchain technology can also provide for less reliance on a central processing computer for certain tasks and functions. By utilizing a central processing computer in connection with a distributed ledger and a suitable Blockchain technology, the apparatus 200 and 300 allows for certain functions to be performed by and with the central processing computer or central processing computer component and allows for certain functions to be performed by the distributed ledger and a suitable Blockchain technology.

It is important to note that the distributed ledger and the Blockchain technology utilized with same can also be referred to herein as a "distributed ledger/Blockchain technology", "distributed ledger and Blockchain technology", "distributed ledger/Blockchain technology system", or "distributed ledger and Blockchain technology system", or that the distributed ledger and the Blockchain technology utilized with same can also be referred by using any suitable phrase or terminology indicative of an application or system which utilizes or which includes a distributed ledger which is used with any Blockchain technology or which is used in connection, or in conjunction, with any Blockchain technology.

In another preferred embodiment, as well as in any and/or all of embodiments disclosed herein, the apparatus 300 and methods of the present invention can also utilize position or location information regarding the position or location of a user communication device 41 and/or a provider communication device 21 in processing information for determining if a transaction involving the individual's or patient's healthcare account or involving the individual's or patient's healthcare insurance account (hereinafter referred to as a "healthcare transaction" or a "healthcare account transaction"), is authorized or allowed, or is unauthorized or not allowed, and/or for determining if a video call, a video chat session, or a videoconference, a remote office visit, a virtual office visit, a remote examination, or a distance examination, (hereinafter collectively referred to as a "remote healthcare transaction") is authorized or allowed, or is unauthorized or not allowed.

In such a preferred embodiment, the apparatus 300 and/or methods of the present invention, can be utilized in order to perform position-based or location-based transaction security, account security, or transaction authentication, for any healthcare transaction(s), healthcare account transaction(s), and/or remote healthcare transaction(s), which authentication can be based on the position, location, or geographic location (also referred to herein as the "geolocation"), of the user communication device 41, and/or of a healthcare provider's provider communication device 21, and, hence, the individual or patient, or his or her caregiver, and/or a healthcare provider, at a time, or at the time, of any performance, or attempted performance, by the individual or patient, or his or her caregiver, or the healthcare provider, of any healthcare transaction, healthcare account transaction, and/or remote healthcare transaction, involving the individual or patient or any healthcare account(s) or healthcare insurance account(s) of, for, or associated with the individual or patient.

In a preferred embodiment, it is envisioned that each individual or patient can be assigned one or more healthcare accounts and/or one or more healthcare insurance accounts. It is also envisioned that each individual or patient can also be assigned one or more healthcare identity cards ("healthcare ID card") which can be linked to any one or more of the individual's or patient's healthcare account(s) and/or healthcare insurance account(s). In a preferred embodiment, each healthcare ID card can contain or include, or have attached thereon or thereto, an RFID tag 92A which is assigned to, or for, the individual or patient.

In a preferred embodiment, the central processing computer and distributed ledger and Blockchain technology system 110, and the central processing computer component 110A and the distributed ledger and Blockchain technology system component 110B, of same, the provider communication devices 21, and the user communication devices 41, can be equipped with any and/or all necessary hardware and/or software needed or required, and/or can be capable or configured, for performing all of the functions and/or functionalities described herein.

In a preferred embodiment, the position, location, or geographic location, information for, or associated with, the user communication device 41, or the provider communication device 21, can be obtained, in the case of stationary communication devices 41 or 21, such as, for example, home, work, or personal, computers, by determining the position or location of, for, or associated with, the IP address of, for, associated with, or assigned to, the respective user communication device 41 or the respective provider communication device 21, or, in the case of mobile communication devices 41 or 21, such as, for example, cellular telephones, Smartphones or smart phones, personal digital assistants, tablets, tablet computers, laptop computers, notebook computers, handheld computers, or other mobile devices, by determining the position or location of the respective user communication device 41 by using the global positioning device 40K of the user communication device 41, or by determining the position or location of the respective provider communication device 21 by using the global positioning device 20K of the provider communication device 21.

In another preferred embodiment, and under certain circumstances, it may also be possible to determine or ascertain the position or location of the mobile communication device 41 or 21 via an IP address or by "pinging" the same. By "pinging", Applicant refers to the technique(s) known and used by those skilled in the art, at the time of the filing of this application, to request, obtain, and/or determine, the position or location of a mobile communication device, such as mobile user communication device 41 or a mobile provider communication device 21.

In a preferred embodiment, the central processing computer component 110A of the central processing computer/distributed ledger/Blockchain technology system 110 and/or the central processing computer/distributed ledger/Blockchain technology system 110, can determine or can ascertain, or can look-up, the position, location, or geographic location, of a stationary user communication device 41 or stationary provider communication device 21, which is utilized in or involving any healthcare transaction, any healthcare account transaction, and/or any remote healthcare transaction, and/or any attempted healthcare transaction, any attempted healthcare account transaction, and/or any attempted remote healthcare transaction, on, with, using, or involving, any of the herein-described healthcare accounts, healthcare insurance accounts, or healthcare ID cards, associated with an individual or patient, at a time, or at the time, of the same, by using the IP address of the respective user communication device 41 or provider communication device 21.

In a preferred embodiment, the central processing computer component 110A of the central processing computer/distributed ledger/Blockchain technology system 110 and/or the central processing computer/distributed ledger/Blockchain technology system 110, can also determine or can ascertain, or can look-up, the position, location, or geographic location, of a mobile user communication device 41 or mobile provider communication device 21, which is utilized in or involving any healthcare transaction, any healthcare account transaction, and/or any remote healthcare transaction, and/or any attempted healthcare transaction, any attempted healthcare account transaction, and/or any attempted remote healthcare transaction, on, with, using, or involving, any of the herein-described healthcare accounts, healthcare insurance accounts, or healthcare ID cards, associated with an individual or patient, at a time, or at the time, of the same, by using global positioning system data and/or information, which can be obtained with or using the global positioning device 40K of the user communication device 41, and/or data and/or information obtained via the global positioning device 40K, of the respective mobile user communication device 41, or by using global positioning system data and/or information, which can be obtained with or using the global positioning device 20K of the provider communication device 21, and/or data and/or information obtained via the global positioning device 20K, of the respective mobile provider communication device 21, and which can be transmitted to and processed by the central processing computer component 110A of the central processing computer/distributed ledger/Blockchain technology system 110.

In a preferred embodiment, the central processing computer component 110A of the central processing computer/distributed ledger/Blockchain technology system 110 can also determine or can ascertain, or can look-up, the position, location, or geographic location, of a mobile user communication device 41 or a mobile provider communication device 21 by transmitting a request for position or location information of or for the same (also referred to as "pinging" the respective communication device), and by receiving information in response to that request. In another preferred embodiment, if the respective stationary user communication device 41 or stationary provider communication device 21 is equipped with a respective global positioning device 40K or 20K, the central processing computer component 110A of the central processing computer/distributed ledger/Blockchain technology system 110 can also determine or can ascertain, or can look-up, the position, location, or geographic location, of that stationary user communication device 41 or that stationary provider communication device 21 by "pinging" the same as well.

In a preferred embodiment, once the position, location, or geographic location, of the respective user communication device 41, or the respective provider communication device 21, is determined or ascertained, then the central processing computer component 110A of the central processing computer/distributed ledger/Blockchain technology system 110, can compare the position, location, or geographic location, of the respective user communication device 41, or the respective provider communication device 21, with an expected location of the respective individual or patient, or the respective healthcare provider, using the same at a time, or at the time, of any such healthcare transaction, healthcare account transaction, and/or remote healthcare transaction, and/or an attempted healthcare transaction, an attempted healthcare account transaction, and/or an attempted remote healthcare transaction, on, with, using, or involving, any of the herein-described healthcare accounts, healthcare insurance accounts, or healthcare ID cards, associated with the individual or patient.

In a preferred embodiment, it is envisioned that any individual or patient, or any healthcare provider, who utilizes the apparatus 300 of the present invention in order to perform, or to engage in, any healthcare transaction, healthcare account transaction, and/or remote healthcare transaction, and/or who uses or accesses a healthcare account, a healthcare insurance account, or a healthcare ID card, can have stored for or on his or her behalf, in the central processing computer component 110A of the central processing computer/distributed ledger/Blockchain technology system 110, or in the database 10H of the same, information regarding his or her typical or usual itinerary or schedule, including any typical or usual traveling itinerary or schedule (hereinafter also referred to as an "itinerary" or "schedule").

In a preferred embodiment, the information regarding the individual's or patient's, or the healthcare provider's, itinerary or schedule can include information regarding the individual's or patient's, or the healthcare provider's typical or regular itinerary or schedule for any and/or all days of the individual's or patient's, or the healthcare provider's, typical week, work week, weekend, or any trips, vacations, or any deviations from the individual's or patient's, or the healthcare provider's, typical or regular itinerary or schedule. In a preferred embodiment, the information regarding the individual's or patient's, or the healthcare provider's, itinerary or schedule can be entered into a respective user communication device 41 or the respective provider communication device 21 used by, or associated with, the respective individual or patient, or healthcare provider, and can be transmitted to, and received at, the central processing computer component 110A of the central processing computer/distributed ledger/Blockchain technology system 110, and can be stored in the respective database 10H of same.

In a preferred embodiment, information regarding the individual's or patient's, or the healthcare provider's, itinerary or schedule, for given times during given days of the week, can also be monitored and recorded automatically by the his or her respective user communication device 41 or his or her respective provider communication device 21, data and/or information regarding or corresponding to same can be stored in the database 40H of the respective user communication device 41 or the respective provider communication device 21, and/or can be automatically transmitted to, and received at, the central processing computer component 110A of the central processing computer/distributed ledger/Blockchain technology system 110, and can be stored in the respective database 10H of same.

In this regard, in a preferred embodiment, the respective user communication device 41 or the respective provider communication device 21 can be programmed to periodically and/or continuously, and automatically, monitor the position or location and/or the global positioning position or location, as determined by the respective global positioning device 40K or 20K, of the individual's or patient's, or the healthcare provider's, travels and/or movement, at pre-determined and/or at pre-selected time intervals, in order to record the individual's or patient's, or the healthcare provider's, travels or movements during certain times and/or days of the week so as to determine, ascertain, or predict, an expected itinerary or schedule, or an expected travel itinerary or schedule, for the individual or patient, or the healthcare provider, for a given day or for given days. This information can thereafter be utilized as, or to supplement, to complement, or to modify, any data and/or information regarding a previously stored itinerary or schedule of or for the individual or patient's, or the healthcare provider.

In a preferred embodiment, information recorded automatically by the respective user communication device 41 or the respective provider communication device 21 can also be utilized for determining and/or for storing an expected itinerary or schedule for the respective individual or patient, or healthcare provider. In another preferred embodiment, the apparatus 300, the central processing computer component 110A of the central processing computer/distributed ledger/Blockchain technology system 110, the user communication device 41, and/or the provider communication device 21, can utilize any software, programs, or algorithms, or any artificial intelligence (AI) or machine learning software, programs, or algorithms, for recording, for storing, and/or for predicting, and/or for updating, any itinerary or schedule, for determining, for ascertaining, or for predicting, an individual's or patient's, or a healthcare provider's, position, location, or geographic location, at any given time during any given day. In a preferred embodiment, the respective databases 10H, 40H, and 20H, of the central processing computer component 110A of the central processing computer/distributed ledger/Blockchain technology system 110, the user communication device 41, and/or the provider communication device 21, can include or contain any itinerary or schedule information for the individual or patient, or the healthcare provider, as well as any software, programs, or algorithms, or any artificial intelligence (AI) or machine learning software, programs, or algorithms, for recording, storing, and/or predicting, and/or for updating, the itinerary or schedule of or for the individual or patient, or for the healthcare provider.

In a preferred embodiment, and as an example, the database 10H of the central processing computer component 110A of the central processing computer/distributed ledger/Blockchain technology system 110, the database 40H of the user communication device 41, and/or the database 20H of the provider communication device 21, can contain and/or can include, as part of the information regarding the individual's or patient's, or the healthcare provider's, itinerary or schedule, information regarding places, locations, or venues, to which the individual or patient, or healthcare provider, travels or spends time, data and/or information regarding the daily schedule or daily schedules of or for the individual or patient, or for the healthcare provider, and/or any data and/or information regarding the daily routine or daily routines of or for the individual or patient, or the healthcare provider, any places where the individual or patient, or the healthcare provider, is or has to be at a given time(s), and/or any other data and/or information regarding the individual's or patient's, or for the healthcare provider's, daily routines, weekly routines, travel routines, travel routes used, alternate travel routes used, travel times, and/or time of travel regarding any travel by the individual or patient, or the healthcare provider, and/or any other data and/or information regarding the individual's or patient's, or the healthcare provider's, activities or routines that can be stored or recorded and which can be utilized to predict a position, location, or geographic location, of or for the individual or patient, or the healthcare provider, at a certain or given instant in time.

The database 10H of the central processing computer component 110A of the central processing computer/distributed ledger/Blockchain technology system 110, the database 40H of the user communication device 41, and/or the database 20H of the provider communication device 21, can also contain and/or include data and/or information regarding past travels, movements, or activities, including, but not limited to, travel routes and dates and/or times of same, as well as future travel plans, movements, or activities, for the individual or patient, or the healthcare provider.

In a preferred embodiment, the database 10H of the central processing computer component 110A of the central processing computer/distributed ledger/Blockchain technology system 110, the database 40H of the user communication device 41, and/or the database 20H of the provider communication device 21, can also contain and/or can include, as part of the information regarding the individual's or patient's, or the healthcare provider's, itinerary or schedule, information regarding travel itineraries and/or travel schedules for traveling to and between one address, place, or location, to another address, place, or location, and information regarding travel routes or directions for traveling to and between one address, place, or location, to another address, place, or location. In a preferred embodiment, the database 10H of the central processing computer component 110A of the central processing computer/distributed ledger/Blockchain technology system 110, the database 40H of the user communication device 41, and/or the database 20H of the provider communication device 21, can also contain and/or can include software programs, navigation programs, or any algorithms or software applications, for identifying, determining, ascertaining, or calculating, any travel routes or directions for traveling to and between one address, place, or location, to another address, place, or location.

As and for another example, in a preferred embodiment, the database 10H of the central processing computer component 110A of the central processing computer/distributed ledger/Blockchain technology system 110, the database 40H of the user communication device 41, and/or the database 20H of the provider communication device 21, as part of the information regarding the individual's or patient's, or the healthcare provider's, itinerary or schedule, can also contain and/or include any data and/or information regarding the daily weekday schedule for the individual or patient, or the healthcare provider, such as, for example, the individual's or patient's, or the healthcare provider's, home address, the time or approximate time when the individual or patient, or the healthcare provider, leaves home for work or some other activity or venue, a preferred travel route the individual or patient, or the healthcare provider, typically takes to go to work or to some other activity or venue, any typical alternate travel routes to work, to the activity, or to the venue, the time or the approximate time the individual or patient, or the healthcare provider, arrives at work, the activity, or the venue, the time or the approximate time the individual or patient, or the healthcare provider, leaves work, the activity, or the venue, a typical travel route to another activity or venue, if applicable, a typical travel route to the other activity or venue, a typical alternate travel route to the other activity or venue, a time or an approximate time of a travel to the other activity or venue, a time or an approximate time when the individual or patient, or the healthcare provider, leaves the other activity or venue, a typical travel route from the other activity or venue back to the individual's or patient's, or the healthcare provider's, home, a typical travel route to the individual's or patient's, or the healthcare provider's, home, a typical alternate travel route to the individual's or patient's, or the healthcare provider's, home, and/or a typical time or an approximate time when the individual or patient, or the healthcare provider, is expected to arrive at home.

The database 10H of the central processing computer component 110A of the central processing computer/distributed ledger/Blockchain technology system 110, the database 40H of the user communication device 41, and/or the database 20H of the provider communication device 21, can also contain and/or can include, as part of the information regarding the individual's or patient's, or the healthcare provider's, itinerary or schedule, any data and/or information regarding any school(s), workplace(s), club(s), activity venue(s), recreational venue(s), entertainment venue(s), or any other place(s), location(s), and/or other venue(s), of the individual or patient, or the healthcare provider, and/or to which the individual or patient, or the healthcare provider, travels and/or at which the individual or patient, or the healthcare provider, is known to spend time. The database 10H of the central processing computer component 110A of the central processing computer/distributed ledger/Blockchain technology system 110, the database 40H of the user communication device 41, and/or the database 20H of the provider communication device 21, as part of the information regarding the individual's or patient's, or the healthcare provider's, itinerary or schedule, can also contain and/or can include any data and/or information regarding the location(s) of any school(s), workplace(s), club(s), activity venue(s), recreational venue(s), entertainment venue(s), or any other place(s), location(s), and/or other venue(s), of the individual or patient, or the healthcare provider, which data and/or information can include the name, the address, the telephone number, the website address, the IP address, a description of same, schedule information of or for same, and/or any other information regarding same.

The database 10H of the central processing computer component 110A of the central processing computer/distributed ledger/Blockchain technology system 110, the database 40H of the user communication device 41, and/or the database 20H of the provider communication device 21, can also contain and/or can include, as part of the information regarding the individual's or patient's, or the healthcare provider's, itinerary or schedule, any data and/or information regarding any weekday or weekend day schedules or itineraries of the individual or patient, or the healthcare provider. The database 10H of the central processing computer component 110A of the central processing computer/distributed ledger/Blockchain technology system 110, the database 40H of the user communication device 41, and/or the database 20H of the provider communication device 21, can also contain and/or can include, as part of the information regarding the individual's or patient's, or the healthcare provider's, itinerary or schedule, any data and/or information regarding the daily schedule for each weekday or for each weekend day for the individual or patient, or the healthcare provider, travel routes traveled for each day and/or for any trip or expected travel, and/or time(s) associated with each trip or travel segment of each trip or expected travel.

The database 10H of the central processing computer component 110A of the central processing computer/distributed ledger/Blockchain technology system 110, the database 40H of the user communication device 41, and/or the database 20H of the provider communication device 21, can also contain and/or include, as part of the information regarding the individual's or patient's, or the healthcare provider's, itinerary or schedule, data and/or information regarding travel records for the individual or patient, or the healthcare provider, which can contain and/or include data and/or information regarding a date and/or time of travel and/or travel routes taken or traveled by, and/or any other data and/or information regarding, the individual or patient, or the healthcare provider for or during any period of time or during and/or for or relating to any schedule or routine.

The database 10H of the central processing computer component 110A of the central processing computer/distributed ledger/Blockchain technology system 110, the database 40H of the user communication device 41, and/or the database 20H of the provider communication device 21, can also contain and/or include, as part of the information regarding the individual's or patient's, or the healthcare provider's, itinerary or schedule, any other data and/or information, software, programs, and/or algorithms, needed, required, or desired, for performing any and/or all of the functions, functionalities, and/or operations, described herein as being performed by the apparatus 300, and/or by the central processing computer component 110A of the central processing computer/distributed ledger/Blockchain technology system 110, the central processing computer/distributed ledger/Blockchain technology system 110, the user communication device 41, and/or the provider communication device 21, of the present invention.

In a preferred embodiment, the apparatus 300 and/or methods of the present invention can be utilized in order to authenticate an individual or patient, or a healthcare provider, who is engaged in, or involved in, any healthcare transaction, healthcare account transaction, and/or remote healthcare transaction, and/or in any attempt to engage in a healthcare transaction, a healthcare account transaction, and/or a remote healthcare transaction, and/or who uses, or attempts to use, any healthcare account, healthcare insurance account, or healthcare ID card, associated with an individual or patient, or associated with a healthcare provider, by using and processing information regarding the position, location, or geographic location, of the respective user communication device 41 which is being used by the respective individual or patient, the respective provider communication device 21 which is being used by the respective healthcare provider and, hence, the position, location, or geographic location, of the respective individual or patient, or of the respective healthcare provider.

In a preferred embodiment, the apparatus 300 and/or methods of the present invention can be utilized in order to authenticate a respective individual or patient, or healthcare provider, by the position, location, or geographic location, of the individual's or patient's user communication device 41, or the healthcare provider's provider communication device 21, (also referred to herein as "location-based authentication") each time and/or any time the respective individual or patient, or healthcare provider, engages in, or attempts to engage in, a healthcare transaction, a healthcare account transaction, and/or a remote healthcare transaction, and/or who uses, or attempts to use, any healthcare account, healthcare insurance account, or healthcare ID card, associated with a respective individual or patient, or associated with a respective healthcare provider.

In a preferred embodiment, the apparatus 300 of the present invention can perform location-based authentication for or regarding any healthcare transaction, healthcare account transaction, and/or a remote healthcare transaction, described herein, or for or regarding any attempt to perform the same, as well as any transaction, or any attempt to perform a transaction with, on, or involving, any healthcare account, healthcare insurance account, or healthcare ID card, associated with a respective individual, patient, or healthcare provider, described herein.

In a preferred embodiment, the central processing computer component 110A of the central processing computer/distributed ledger/Blockchain technology system 110 can perform processing routines to determine whether or not the individual or patient, or the healthcare provider, is authorized for, or is authenticated in or for, engaging in any healthcare transaction, healthcare account transaction, and/or a remote healthcare transaction, described herein, and/or is authorized for, or is authenticated in or for, performing or engaging in a transaction with, on, or involving, any healthcare account, healthcare insurance account, or healthcare ID card, associated with a respective individual, patient, or healthcare provider, described herein. If determined to be authorized or authenticated, the central processing computer component 110A of the central processing computer/distributed ledger/Blockchain technology system 110 can authenticate and allow the respective, healthcare transaction, healthcare account transaction, and/or remote healthcare transaction, or can allow the transaction with, on, or involving, the healthcare account, the healthcare insurance account, or the healthcare ID card. If determined to be not authorized or not authenticated, the central processing computer component 110A of the central processing computer/distributed ledger/Blockchain technology system 110 can disallow the respective, healthcare transaction, healthcare account transaction, and/or remote healthcare transaction, or can disallow the transaction with, on, or involving, the healthcare account, the healthcare insurance account, or the healthcare ID card.

In a preferred embodiment, the central processing computer component 110A of the central processing computer/distributed ledger/Blockchain technology system 110 can also determine whether or not the determined and authenticated position, location, or geographic location, is located within the geographic limits of a jurisdiction, state, province, region, or country, so as to ensure and/or to document, in any appropriate manner, that any respective action, transaction, or activity, such as, for example, the healthcare transaction, the healthcare account transaction, and/or the remote healthcare transaction, or the transaction with, on, or involving, the healthcare account, the healthcare insurance account, or the healthcare ID card, is legally performed within the geographic limits of a jurisdiction, state, province, region, or country.

Figure 19:
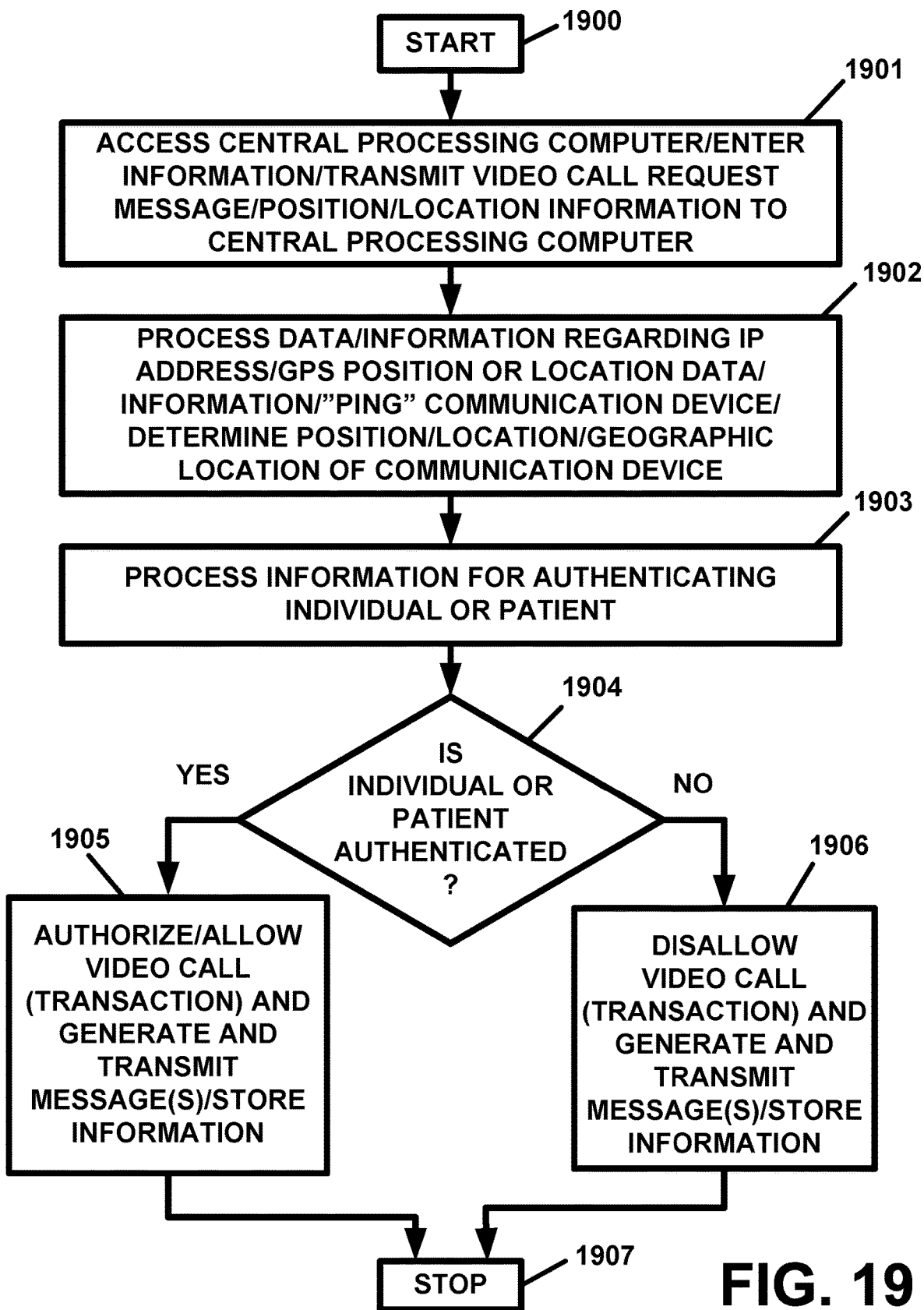
FIG. 19 illustrates yet another preferred embodiment method of utilizing the apparatus of the present invention, in flow diagram form.

FIG. 19 illustrates another preferred embodiment method for utilizing the apparatus 300 of the present invention, in flow diagram form. In the preferred embodiment of the method of FIG. 19, and as and for an exemplary embodiment, the apparatus 300 is described as being utilized in connection with a remote healthcare transaction, which can be a video call as described herein with regards to the embodiment of FIG. 18, and in connection with authenticating the individual or patient in same so as to allow the individual or patient to engage in the video call. It is important to note, however, that the method of the embodiment of FIG. 19 can also be utilized in a same, a similar, and/or an analogous, manner for and/or in any type or kind of healthcare transaction, the healthcare account transaction, and/or the remote healthcare transaction, and/or for or in any transaction with, on, or involving, a healthcare account, a healthcare insurance account, or an healthcare ID card, and so as to authenticate any individual or patient, or any healthcare provider, so as to ascertain if the respective transaction or activity is allowed, authenticated, or disallowed.

With reference to FIG. 19, the operation of the apparatus 300 commences at step 1900 when the individual or patient attempts to initiate or engage in a video call with a healthcare provider. It is envisioned that the individual or patient can establish a healthcare account with the apparatus 300 which can allow the individual or patient to engage in remote healthcare transactions such as the video call. At step 1901, the user or individual can access the central processing computer component 110A of the central processing computer/distributed ledger/Blockchain technology system 110 in order to initiate the video call.

In a preferred embodiment, at step 1901, the individual or patient can enter, into his or her user communication device 41, any information regarding his or her healthcare account and any other information regarding his or her request, or attempt, to initiate or engage in the video call, and can transmit the information in, or as, a video call request message, from the user communication device 41 to the central processing computer component 110A of the central processing computer/distributed ledger/Blockchain technology system 110.

In a preferred embodiment, at step 1901, the video call request message, which is transmitted from the user communication device 41 to the central processing computer component 110A of the central processing computer/distributed ledger/Blockchain technology system 110, can also include or contain information needed for performing the location-based authentication of or for the communication device 41 and, hence, the individual or patient. In a preferred embodiment, for stationary user communication devices 41, the video call request message can contain the IP address of, or information regarding the IP address of, the stationary user communication device 41 from which the video call request message is transmitted. In a preferred embodiment, for mobile user communication devices 41 having an assigned IP address, the video call request message can contain the IP address of, or information regarding the IP address of, the mobile user communication device 41 from which the video call request message is transmitted.

In a preferred embodiment, for mobile user communication devices 41, the video call request message can contain or include position or location data and/or information, as obtained from the global positioning device 40K, at the time of the transmission of the video call request message from the mobile user communication device 41. In a preferred embodiment, for stationary user communication devices 41 having a global positioning device 40K, the video call request message can also contain or include position or location data and/or information, as obtained from the global positioning device 40K, at the time of the transmission of the video call request message from the stationary user communication device 41.

At step 1901, the central processing computer component 110A of the central processing computer/distributed ledger/Blockchain technology system 110, can receive the video call request message which is transmitted from the user communication device 41. In a preferred embodiment, any data and/or information contained in any video call request message transmitted to, and received by, the central processing computer component 110A of the central processing computer/distributed ledger/Blockchain technology system 110 can be time-stamped and/or data stamped and/or can be stored in the database 10H of the central processing computer component 110A of the central processing computer/distributed ledger/Blockchain technology system 110, and/or can be used for any appropriate purpose thereafter.

At step 1902, the central processing computer component 110A of the central processing computer/distributed ledger/Blockchain technology system 110 can process information regarding the IP address, or the position or location information which was determined by the global positioning device 40K of the respective user communication device 41, or any combination of information regarding the IP address and any position or location information which was determined by the global positioning device 40K of the respective user communication device 41, in order to determine the position, location, or geographic location, of the user communication device 41 at the time of the transmission of the above-referenced video call request message from the user communication device 41 to the central processing computer component 110A of the central processing computer/distributed ledger/Blockchain technology system 110. At step 1902, the central processing computer component 110A of the central processing computer/distributed ledger/Blockchain technology system 110 can determine the position, location, or geographic location, of the user communication device 41 at the time of the transmission of the video call request message to the central processing computer component 110A of the central processing computer/distributed ledger/Blockchain technology system 110.

In another preferred embodiment, at step 1902, the central processing computer component 110A of the central processing computer/distributed ledger/Blockchain technology system 110 can also transmit, to the user communication device 41, a request for the user communication device's 41 position or location information, and can receive data and/or information, in response to the request, from the user communication device 41 regarding its position or location, as determined by the global positioning device 40K of the user communication device 41, in order to, or so as to, "ping" the user communication device 41, or so as to effectuate a "pinging" operation of or for the user communication device 41. By performing such a "pinging" operation, the central processing computer component 110A of the central processing computer/distributed ledger/Blockchain technology system 110 can independently obtain position or location information from the user communication device 41. In this regard, by "pinging" the user communication device 41, either directly or by using a cellular, wireless, or other, telecommunication or other provider or service, the central processing computer component 110A of the central processing computer/distributed ledger/Blockchain technology system 110 can validate, confirm, or re-confirm, the position, location, or geographic location, of the user communication device 41.

In a preferred embodiment, at step 1902, if an IP address, or information regarding an IP address, is received by the central processing computer component 110A of the central processing computer/distributed ledger/Blockchain technology system 110, the central processing computer component 110A of the central processing computer/distributed ledger/Blockchain technology system 110 can determine or can ascertain the position, location, or geographic location, of, for, or associated with, the IP address of, for, or assigned to, the user communication device 41 by performing any appropriate IP address look-up processing routine(s) or by using any other appropriate processing routine(s) for determining or for ascertaining the position or location information of or associated with the IP address.

At step 1902, the central processing computer component 110A of the central processing computer/distributed ledger/Blockchain technology system 110 can also utilize the services of any IP address look-up service provider to determine or ascertain the position, location, or geographic location, of, for, or associated with, the IP address. In a preferred embodiment, any position, location, or geographic location, information for or associated with the IP address can include information regarding the IP address, the IP address itself, and information regarding the Internet Service Provider (ISP) servicing the user communication device 41, information regarding the network service provider servicing the user communication device 41, information regarding street address for or associated with the IP address (and the user communication device 41), information regarding map address, position, or location, for or associated with the IP address (and the user communication device 41), information regarding the latitude or the latitude for or associated with the IP address (and the user communication device 41), information regarding the longitude or the longitude for or associated with the IP address (and the user communication device 41), information regarding the locality or municipality, state or province, and/or country or territory, in which the user communication device 41 is located, a digitized map or information for providing a digitized map showing the position or location of the IP address (and the user communication device 41) on the same, and/or any other information for or associated with the IP address.

In a preferred embodiment, at step 1902, if global positioning device information is received by the central processing computer component 110A of the central processing computer/distributed ledger/Blockchain technology system 110 from the user communication device 41, such as when the user communication device 41 transmits the same in or along with the video call request message described herein, or when the user communication device 41 responds to a "pinging" request made by, or initiated by, the central processing computer component 110A of the central processing computer/distributed ledger/Blockchain technology system 110, the central processing computer component 110A of the central processing computer/distributed ledger/Blockchain technology system 110 can determine or can ascertain the position, location, or geographic location, of the user communication device 41, from or using the global positioning device information received by performing any appropriate processing routine(s) in order to determine or ascertain the position, location, or geographic location, of the user communication device 41.

In a preferred embodiment, any position, location, or geographic location, information for or associated with the global positioning information can include information regarding the actual global positioning information received, information regarding the Internet Service Provider (ISP) servicing the user communication device 41, information regarding the network service provider servicing the user communication device 41, information regarding the street address of the user communication device 41, information regarding map address, position, or location, for or associated with the IP address, information regarding the latitude or the latitude of the user communication device 41, information regarding the longitude or the longitude of the user communication device 41, information regarding the locality or municipality, state or province, and/or country or territory, in which the user communication device 41 is located, a digitized map or information for providing a digitized map showing the position or location of the user communication device 41 on the same, and/or any other information for or associated with the position or location of the user communication device 41.

At step 1903, the central processing computer component 110A of the central processing computer/distributed ledger/

Blockchain technology system 110 can perform a processing routine, or any number of processing routines, for authenticating the individual or patient based on the determined position, location, or geographic location, of the user communication device 41 at the time of the transmission of the video call request message from the user communication device 41 to the central processing computer component 110A of the central processing computer/distributed ledger/Blockchain technology system 110. In a preferred embodiment, the central processing computer component 110A of the central processing computer/distributed ledger/Blockchain technology system 110 can compare the determined position, location, or geographic location, of the user communication device 41, at the time of the transmission of the video call request message, from the user communication device 41 to the central processing computer component 110A of the central processing computer/distributed ledger/Blockchain technology system 110, to, with, or against, an expected position, location, or geographic location, of or for the individual or patient, for that time of transmission, based on information regarding the individual's or patient's itinerary or schedule.

In a preferred embodiment, the central processing computer component 110A of the central processing computer/distributed ledger/Blockchain technology system 110 can determine the individual's or patient's expected position, location, or geographic location, from or using any of the herein-described or other information stored in the database 10H regarding the individual's or patient's itinerary or schedule and/or his or her expected position, location, or geographic location, for the day and the time of the transmission.

In a preferred embodiment, the central processing computer component 110A of the central processing computer/distributed ledger/Blockchain technology system 110 can, at step 1903, determine whether or not the determined position, location, or geographic location, of the user communication device 41, at the time of the transmission of the video call request message from the user communication device 41 to the central processing computer component 110A of the central processing computer/distributed ledger/Blockchain technology system 110, is the same as, or is within a pre-selected, pre-defined, and/or pre-determined, distance differential, or distance differential factor, of, from, or relative to, or is within a pre-defined distance differential allowance of, from, or relative to, the individual's or patient's expected position, location, or geographic location. If, at step 1903, the determined position, location, or geographic location, of the user communication device 41, at the time of the transmission of the video call request message from the user communication device 41 to the central processing computer component 110A of the central processing computer/distributed ledger/Blockchain technology system 110, is the same as, or is within a pre-selected, pre-defined, and/or pre-determined, distance differential, or distance differential factor, of, from, or relative to, or is within a pre-defined distance differential allowance of, from, or relative to, the individual's or patient's expected position, then the transmission of the video call request message from the user communication device 41, and the individual or patient, are deemed to be authentic and/or authenticated.

If, however, it is determined that the determined position, location, or geographic location, of the user communication device 41, at the time of the transmission of the video call request message from the user communication device 41 to the central processing computer component 110A of the central processing computer/distributed ledger/Blockchain technology system 110, is not the same as, and is not within a pre-selected, pre-defined, and/or pre-determined, distance differential, or distance differential factor, of, from, or relative to, and is not within a pre-defined distance differential allowance of, from, or relative to, the individual's or patient's expected position, then the transmission of the video call request message from the user communication device 41, and the individual or patient, are deemed to be not authentic and/or not authenticated. In a preferred embodiment, the pre-selected, pre-defined, and/or pre-determined, distance differential, or distance differential factor, or pre-defined distance differential allowance, can be chosen or selected and/or can be pre-programmed, or re-programmed at any time, by or for the individual or patient or for the healthcare account which is sought to be accessed and/or used by the individual or patient.

In a preferred embodiment, the pre-selected, pre-defined, and/or pre-determined, distance differential, or distance differential factor, or pre-defined distance differential allowance, is utilized and/or employed in order to, or so as to account for, and/or to provide reconciliation regarding, the fact that differences in distances can and will typically and normally exist, between the determined positions, locations, or geographic locations, and the expected positions, locations, or geographic locations, in most instances of everyday life and in use of the apparatus 300 when the individual or patient can or may be using his or her user communication device 41 in performing any actions or transactions with, in conjunction with, or in connection with, the apparatus 300 and/or the central processing computer component 110A of the central processing computer/distributed ledger/Blockchain technology system 110. Further, it is understood that such differences, between the determined positions, locations, or geographic locations, and the expected positions, locations, or geographic locations, can be typical in most cases in which the individual or patient utilizes the apparatus 300 and methods of the present invention.

As and for an example, an individual's or patient's positions, locations, or geographic locations, while within his or her home, place of work, or other place, can and/or will be different as the individual or patient moves about inside or within his or her home, place of work, or other place, and/or as the individual or patient can or may deviate in his or her position within a vehicle, and/or as the individual or patient deviates from or while on a travel route or travel plan or itinerary. In a preferred embodiment, for example, the pre-selected, pre-defined, and/or pre-determined, distance differential, distance differential factor, or pre-defined distance differential allowance, can be defined to be any distance or distances, such as, for example, 100 feet, 250 feet, 1000 feet, or any other pre-selected or pre-defined amount, and such can be changed at any time by programming or by re-programming the same with the central processing computer component 110A of the central processing computer/distributed ledger/Blockchain technology system 110 for or by the individual or patient for or regarding a healthcare account with the central processing computer component 110A of the central processing computer/distributed ledger/Blockchain technology system 110 and/or apparatus 300 or for or regarding the healthcare account of or associated with individual or patient.

In a preferred embodiment, artificial intelligence (AI) and/or machine learning techniques and/or routines can also be utilized by the central processing computer component 110A of the central processing computer/distributed ledger/Blockchain technology system 110 in determining or ascertaining expected positions, locations, or geographic locations, and/or in determining and/or in reconciling any differences between determined positions, locations, or geographic locations, and expected positions, locations, or geographic locations, for or regarding the individual or patient and/or his or her itinerary or schedule.

At step 1903, if the transmission of the video call request message from the user communication device 41, and the individual or patient, are deemed by the central processing computer component 110A of the central processing computer/distributed ledger/Blockchain technology system 110 to be not authentic and/or not authenticated, then the central processing computer component 110A of the central processing computer/distributed ledger/Blockchain technology system 110 can, at step 1903, attempt to authenticate the transmission of the video call request message, and/or the individual or patient, by utilizing one or more of a number of alternate authentication routines or means, which authentication routines or means are known by those individuals who are skilled in the relevant art at the time of the filing of this application.

In a preferred embodiment, at step 1903, the central processing computer component 110A of the central processing computer/distributed ledger/Blockchain technology system 110 can attempt to authenticate the transmission of the video call request message from the user communication device 41, and/or the individual or patient, by requiring that the individual or patient correctly answer security questions, the answers for which were previously provided by the individual or patient in and when previously establishing his or her healthcare account with the central processing computer component 110A of the central processing computer/distributed ledger/Blockchain technology system 110 and/or the apparatus 300 and/or in establishing and/or in registering his or her healthcare account with the apparatus 300.

In a preferred embodiment, examples of such security questions can be questions for which the answers to same can be, or can include, a name, an email address, a mother's maiden name, a password, favorite school subject, a make and model of first car, or any other answer to any other subject or question, which can be a response to a security question. At step 1903, the central processing computer component 110A of the central processing computer/distributed ledger/Blockchain technology system 110 can also prompt and/or require the individual or patient to record, at the user communication device 41 (via a microphone of the video and/or audio recording device 40J), and to transmit to the central processing computer component 110A of the central processing computer/distributed ledger/Blockchain technology system 110, a voice sample which can be compared to a previously provided voiceprint for the individual or patient which can be stored in the database 10H of the central processing computer component 110A of the central processing computer/distributed ledger/Blockchain technology system 110.

At step 1903, the central processing computer component 110A of the central processing computer/distributed ledger/Blockchain technology system 110 can also prompt the individual or patient to provide, and/or require that the individual or patient provide, and transmit to the central processing computer component 110A of the central processing computer/distributed ledger/Blockchain technology system 110, any one or more of a retinal scan, a fingerprint, a handprint, or a facial picture, or any other biometric feature or measurement, as obtained and/or as recorded by a respective retinal scanner, fingerprint device, handprint device, camera, or other biometric device, of or associated with the user input device 40D of the user communication device 41.

In a preferred embodiment, the user input device 40D can include a retinal scanner, a fingerprint scanning or reading device, a handprint scanning or reading device, a camera, or any other biometric measurement or reading device.

At step 1903, the central processing computer component 110A of the central processing computer/distributed ledger/Blockchain technology system 110 can process any information provided by the individual or patient in an attempt to authenticate the transmission of the video call request message and/or the individual or patient using any of the herein-described alternative authentication routines. For example, at step 1903, the central processing computer component 110A of the central processing computer/distributed ledger/Blockchain technology system 110 can compare the individual's or patient's answers to his or her security questions, which were previously provided during the healthcare account setup, or can compare the individual's or patient's voice sample to a pre-stored voiceprint of or for the individual or patient, or can compare the individual's or patient's retinal scan, fingerprint, handprint, or facial picture, or any other biometric feature or measurement, with or against a respective and/or pre-stored retinal scan information, fingerprint information, handprint information, facial recognition information, or biometric feature or measurement information, which can be stored in the database 10H for the individual or patient. In a preferred embodiment, the central processing computer component 110A of the central processing computer/distributed ledger/Blockchain technology system 110 and/or the user communication device 41 can also be equipped with any software algorithms and/or programs for processing retinal scan information, fingerprint information, handprint information, facial recognition information, or biometric feature or measurement information.

In a preferred embodiment, if the central processing computer component 110A of the central processing computer/distributed ledger/Blockchain technology system 110 can ascertain matches between any one or more of the respective answers, data, or information, provided by the individual or patient in the above-described alternate authentication operation, then the central processing computer component 110A of the central processing computer/distributed ledger/Blockchain technology system 110 can and will deem the transmission of the video call request message from the user communication device 41, and the individual or patient, as being authentic or authenticated. If, however, the central processing computer component 110A of the central processing computer/distributed ledger/Blockchain technology system 110 does not ascertain any matches between any one or more of the respective answers, data, or information, provided by the individual or patient in the above-described alternate authentication operation, then the central processing computer component 110A of the central processing computer/distributed ledger/Blockchain technology system 110 can and will deem the transmission of the video call request message from the user communication device 41, and the individual or patient, as being not authentic or not authenticated.

At step 1904, the central processing computer component 110A of the central processing computer/distributed ledger/Blockchain technology system 110 will determine whether or not the transmission of the video call request message from the user communication device 41, and the individual or patient, has been authenticated. If at step 1904, the central processing computer component 110A of the central processing computer/distributed ledger/Blockchain technology system 110 determines that the transmission of the video call request message from the user communication device 41, and the individual or patient, has been authenticated, then the operation of the apparatus 300 will proceed to step 1905.

At step 1905, the central processing computer component 110A of the central processing computer/distributed ledger/Blockchain technology system 110, having authenticated the transmission of the video call request message, and the individual or patient, will authorize and/or allow the video call. At step 1905, the central processing computer component 110A of the central processing computer/distributed ledger/Blockchain technology system 110 can generate a transaction authorized message which can include information indicating that the video call is authorized and/or any other information needed or desired for informing the healthcare provider that the video call has been, and is, authorized. At step 1905, the central processing computer component 110A of the central processing computer/distributed ledger/Blockchain technology system 110 can transmit the transaction authorized message to the provider communication device 21 of, associated with, or used by, the healthcare provider who is to be engage with the individual or patient in the video call.

At step 1905, the central processing computer component 110A of the central processing computer/distributed ledger/Blockchain technology system 110 can also transmit the transaction authorized message to the user communication device 41 and/or to any other user communication device(s) 41 of, associated with, or used by, the individual or patient.

At step 1905, the central processing computer component 110A of the central processing computer/distributed ledger/Blockchain technology system 110 can also generate an authentication alert message which can contain information regarding the individual's or patient's authenticated ability to engage in the video call and/or to use his or her healthcare account in doing so, and/or information regarding the date and time of the video call, or attempted video call, information regarding the healthcare provider, and/or any other information regarding the video call. In a preferred embodiment, the authentication alert message can also contain or include any of the herein-described position, location, or geographic location, IP address information, global positioning information, "pinging" information, and/or any other information described herein as being received, processed, utilized, and/or generated, by the central processing computer component 110A of the central processing computer/distributed ledger/Blockchain technology system 110 at steps 1901, 1902, and 1903, in performing the herein-described location-based authentication and/or in performing any of the herein-described alternative authentication processing operations or routines described as being performed at step 1903.

In this regard, it is to be understood, that any data and/or information described as being received, processed, utilized, and/or generated, by the central processing computer component 110A of the central processing computer/distributed ledger/Blockchain technology system 110 at steps 1901, 1902, and 1903, can be included in the authentication alert message. In a preferred embodiment, the authentication alert message can also contain date-stamped and/or time-stamped data and/or information regarding any performance of, or any attempt to perform, the video call and/or the individual's or patient's healthcare account.

Thereafter, at step 1905, the central processing computer component 110A of the central processing computer/distributed ledger/Blockchain technology system 110 can transmit the authentication alert message to the user communication device 41, or to any number of user communication devices 41 of, associated with, or used by, the individual or patient.

In a preferred embodiment, the authentication alert message can be transmitted as, in, or as an attachment to, an email message, an SMS message, an instant message, a text message, an electronic transmission of any kind or type, a pre-recorded telephone call, or any other electronic communication. Thereafter, at step 1905, the central processing computer component 110A of the central processing computer/distributed ledger/Blockchain technology system 110 can store any and/or all of the data and/or information described herein as being provided by the individual or patient and/or any information regarding any action or transaction performed by, and/or with, the individual or patient in any of steps 1901 through 1903, and/or any and/or all data and/or information regarding any of the herein-described processing operations or routines performed by the central processing computer component 110A of the central processing computer/distributed ledger/Blockchain technology system 110 at steps 1901 through 1905, and/or the authentication alert message, in the database 10H.

In a preferred embodiment, at step 1905, any and/or all of the data and/or information described herein as being provided by the individual or patient and/or any information regarding any action or transaction performed by, and/or with, the individual or patient in any of steps 1901 through 1903, and/or any and/or all data and/or information regarding any of the herein-described processing operations or routines performed by the central processing computer component 110A of the central processing computer/distributed ledger/Blockchain technology system 110 at steps 1901 through 1905, can also be stored by and in the distributed ledger and Blockchain technology system component 110B of the central processing computer/distributed ledger/Blockchain technology system 110.

In another preferred embodiment, at step 1905, prior to authorizing or allowing the video call, the central processing computer component 110A of the central processing computer/distributed ledger/Blockchain technology system 110 can also determine whether or not the determined and authenticated position, location, or geographic location, is located within the geographic limits of a jurisdiction, state, province, region, or country, so as to ensure and/or document that the transaction is being legally performed within the respective jurisdiction, state, province, region, or country. In a preferred embodiment, in a situation in which the video call, or any other transaction, is determined to have been performed within the respective jurisdiction, state, province, region, or country, and is legal therein, the central processing computer component 110A of the central processing computer/distributed ledger/Blockchain technology system 110 can allow the video call or any other transaction. In a preferred embodiment, in a situation in which the video call, or any other transaction, is determined to have not been performed within the respective jurisdiction, state, province, region, or country, and is, therefore, deemed to be illegal or prohibited, the central processing computer component 110A of the central processing computer/distributed ledger/Blockchain technology system 110 can disallow the video call or other transaction.

If, at step 1904, the central processing computer component 110A of the central processing computer/distributed ledger/Blockchain technology system 110 determines that the transmission of the video call request message, from the user communication device 41, and the individual or patient, has not been authenticated, then the operation of the apparatus 300 will proceed to step 1906.

At step 1906, the central processing computer component 110A of the central processing computer/distributed ledger/

Blockchain technology system 110, having not authenticated the transmission of the video call request message, and the individual or patient, will reject the video call request message, and the video call, and will deny, disallow, or prevent, the individual or patient from performing the video call with the healthcare provider.

At step 1906, the central processing computer component 110A of the central processing computer/distributed ledger/Blockchain technology system 110 can also generate a failed authentication alert message which can contain information regarding the individual's or patient's attempt to engage in the video call, and/or to use his or her healthcare account in doing so. In the preferred embodiment, the failed authentication alert message can contain information regarding the individual's or patient's attempt to engage in the video call, and/or the individual's or patient's attempt to use his or her healthcare account in doing so, and/or information regarding the date and time of the attempted video call, information regarding the healthcare provider who was to engage in the video call, and/or any other information regarding the video call.

In a preferred embodiment, the failed authentication alert message can also contain or include any of the herein-described position, location, or geographic location, IP address information, global positioning information, "pinging" information, and/or any other of the information described herein as being received, processed, utilized, and/or generated, by the central processing computer component 110A of the central processing computer/distributed ledger/Blockchain technology system 110 at steps 1901, 1902, and 1903 in performing the herein-described location-based authentication and/or in performing any of the herein-described alternative authentication processing operations or routines described as being performed at step 1903.

In this regard, it is to be understood, that any data and/or information described as being received, processed, utilized, and/or generated, by the central processing computer component 110A of the central processing computer/distributed ledger/Blockchain technology system 110 at steps 1901, 1902, and 1903, can be included in the failed authentication alert message. In a preferred embodiment, the failed authentication alert message can also contain date-stamped and/or time-stamped data and/or information regarding the attempt to perform the video call and/or use the individual's or patient's healthcare account.

Thereafter, at step 1906, the central processing computer component 110A of the central processing computer/distributed ledger/Blockchain technology system 110 can transmit the failed authentication alert message to the user communication device 41, or to any number of user communication devices 41 of, associated with, or used by, the individual or patient. The central processing computer component 110A of the central processing computer/distributed ledger/Blockchain technology system 110 can, at step 1906, also transmit the failed authentication alert message to the provider communication device 21 of the healthcare provider who was to be engaged in the video call. In a preferred embodiment, the failed authentication alert message can be transmitted as, in, or as an attachment to, an email message, an SMS message, an instant message, a text message, an electronic transmission of any type or kind, a pre-recorded telephone call, or any other electronic communication. Thereafter, at step 1906, the central processing computer component 110A of the central processing computer/distributed ledger/Blockchain technology system 110 can store any and/or all of the data and/or information described herein as being provided by individual or patient, and/or any information regarding the attempted video call, in any of steps 1901 through 1903, and/or any and/or all data and/or information regarding any of the herein-described processing operations or routines performed by the central processing computer component 110A of the central processing computer/distributed ledger/Blockchain technology system 110 at steps 1901 through 1904 and 1906, and/or the failed authentication alert message, in the database 10H.

In a preferred embodiment, at step 1906, any and/or all of the data and/or information described herein as being provided by the individual or patient and/or any information regarding any action or transaction performed by, and/or with, the individual or patient in any of steps 1901 through 1903, and/or any and/or all data and/or information regarding any of the herein-described processing operations or routines performed by the central processing computer component 110A of the central processing computer/distributed ledger/Blockchain technology system 110 at steps 1901 through 1904 and 1906, can also be stored by and in the distributed ledger and Blockchain technology system component 110B of the central processing computer/distributed ledger/Blockchain technology system 110. Thereafter, the operation of the apparatus 100 will cease at step 1907.

Although described as being used to authenticate an individual or patient in attempting to engage in a video call, the apparatus 300 of the preferred embodiment of FIG. 19 can be utilized in a same, a similar, and/or an analogous, manner in order to authenticate any individual or patient, or any healthcare provider, any insurer or payer or any employee or agent of same, any governmental entity or any employee or agent of same, or any intermediary or any employee or agent of same, when the same is attempting to engage in any type or kind of healthcare transaction, healthcare account transaction, and/or remote healthcare transaction, and/or when the same is attempting to engage in any transaction with, on, or involving, a healthcare account, a healthcare insurance account, or an healthcare ID card, for any individual or patient who utilizes the apparatus 300. In this regard, the apparatus 300 can be utilized to authenticate and/or to allow authorized activities and/or transactions, and/or can be utilized to disallow unauthorized activities and/or transactions, using the position-based or location-based authentication techniques described herein.

In another preferred embodiment of the embodiment of FIG. 19, the video and/or audio recording device 40K, of the user communication device 41, can record a video recording or a video clip and/or an audio recording or an audio clip of the individual or patient during any portion, or during the entire portion, of the video call or any other transaction, or the attempted video call or other transaction, with or without the healthcare provider. In a preferred embodiment, the respective video recording or video clip and/or audio recording or audio clip can be attached to the respective authentication alert message or failed authentication alert message, and can be stored in a healthcare account transaction statement for the individual or patient, in the database 10H of the central processing computer component 110A of the central processing computer/distributed ledger/Blockchain technology system 110 and/or in the distributed ledger and Blockchain technology system component 110B of the central processing computer/distributed ledger/Blockchain technology system 110.

In another preferred embodiment, as well as in any and/or all of the embodiments described herein, the apparatus 300 and methods of the present invention can also be utilized in, in connection with, or in conjunction with, the providing of in-person healthcare services and/or in-person healthcare-related services, and/or in, in connection with, or in conjunction with, any in-person transactions involving individuals or patients and/or healthcare providers. In a preferred embodiment, the apparatus 300 of the present invention can be used to determine and/or verify an identity of an individual or patient and provide a healthcare provider with access to the individual's or patient's healthcare record(s), file(s), or history or histories.

In a preferred embodiment, it is envisioned that an RFID tag 92A can be assigned to any user, individual, patient, caregiver, and/or any healthcare provider, healthcare professional, hospital, clinic, pharmacy, treatment center, treatment facility, and/or any other provider of services described herein, healthcare or otherwise, who or which uses the apparatus 300 of the present invention. In a preferred embodiment, the RFID tag 92A can also be assigned to a healthcare account which is assigned to or for the respective user, individual, patient, caregiver, healthcare provider, healthcare professional, hospital, clinic, pharmacy, treatment center, treatment facility, and/or any other provider of services described herein, who or which uses the apparatus 300 of the present invention.

In a preferred embodiment, the RFID tag 92A can be provided in or as a physical identification card, such as healthcare ID card or a healthcare account card, or any other physical item or device, and/or can be attached to, or located within, an article of clothing, a watch, a necklace, a bracelet, an ankle bracelet, a ring, an article of jewelry, or any other wearable article or item. In a preferred embodiment, the RFID tag 92A can also be implantable within an individual or patient. In a preferred embodiment, the RFID tag 92A can also be provided in or as a physical identification card, attached to, or located on or within, a cellular telephone, a smart phone, a Smartphone, a personal digital assistant, or any other personal article or item. In a preferred embodiment, any number of RFID tags 92A can be assigned to or associated with any respective user, individual, patient, caregiver, healthcare provider, healthcare professional, hospital, clinic, pharmacy, treatment center, treatment facility, and/or any other provider of services described herein, who or which uses the apparatus 300 of the present invention, and/or to any healthcare account or healthcare accounts associated with the respective user, individual, patient, caregiver, healthcare provider, healthcare professional, hospital, clinic, pharmacy, treatment center, treatment facility, and/or any other provider of services described herein.

In a preferred embodiment, it is also envisioned that an RFID reader system 92B, or any RFID reader or RFID readers of same, can be located at any facility or office, or in a room or venue therein, of any user, individual, patient, caregiver, and/or healthcare provider, healthcare professional, hospital, clinic, pharmacy, treatment center, treatment facility, and/or any other provider of healthcare or other services described herein, who or which utilizes the apparatus 300 of the present invention. In another preferred embodiment, an RFID reader system 92B, or any RFID reader or RFID readers of same, can also be located on or implemented with any communication device, computer, computer peripheral device, cellular telephone, smart phone, personal digital assistant, or any other device of or associated with, any user, individual, patient, caregiver, and/or healthcare provider, healthcare professional, hospital, clinic, pharmacy, treatment center, treatment facility, and/or any other provider of services described herein, who or which utilizes the apparatus 300 of the present invention.

In a preferred embodiment, the RFID tag/RFID reader system(s) 92, and any RFID tags 92A and any RFID reader system(s) 92B of same, can be utilized for identifying, verifying the identification of, and/or for accessing, any data and/or information, and/or any account(s) or any healthcare account(s) of, associated with, corresponding to, or regarding, any user, individual, patient, caregiver, and/or healthcare provider, healthcare professional, hospital, clinic, pharmacy, treatment center, treatment facility, and/or any other provider of services described herein, who or which utilizes the apparatus 300 of the present invention.

Figure 20:
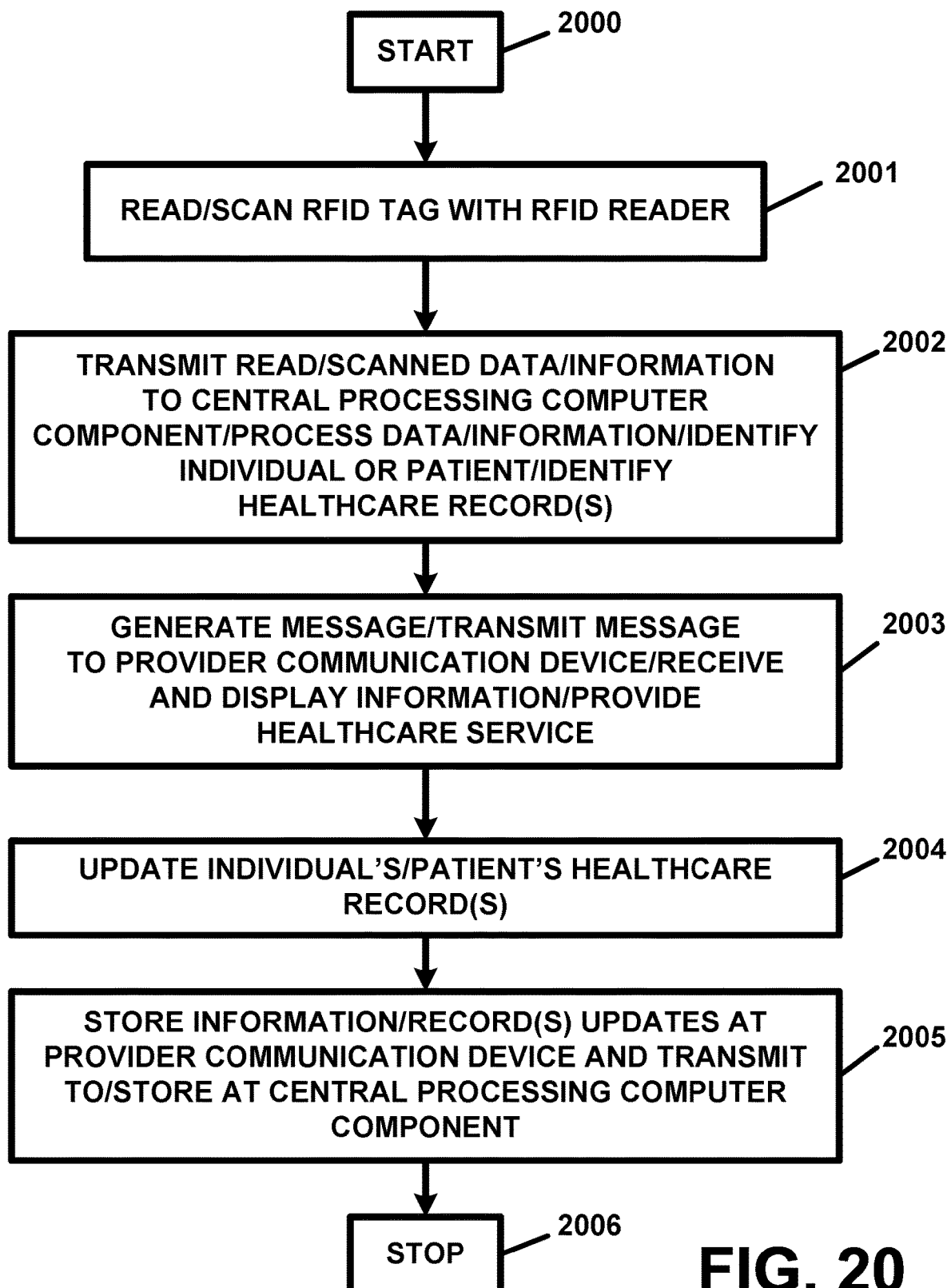
FIG. 20 illustrates still another preferred embodiment method of utilizing the apparatus of the present invention, in flow diagram form.

FIG. 20 illustrates another preferred embodiment method of utilizing the apparatus 300 of the present invention, in flow diagram form. Although the preferred embodiment of FIG. 20 is described and illustrated as being used in order to verify an identify of an individual or patient and to provide a healthcare provider with access to the individual's or patient's healthcare record(s), file(s), or history, during an office visit and/or for a diagnosis or a treatment, the apparatus 300 of the present invention can also be utilized in a same, a similar, and/or an analogous, manner in order to verify an identity of any user, individual, patient, caregiver, and/or any healthcare provider, healthcare professional, or any other individual or entity who or which utilizes the apparatus 300 and to provide an authorized their party with access to a healthcare record(s), file(s), or history, or any other information which can be processed by or stored in the apparatus 300 or any of its component computers or communication devices.

With reference to FIG. 20, the operation of the apparatus 300 commences at step 2000. At step 2001, in a preferred embodiment, the individual or patient can present his or her RFID tag 92A for reading or scanning, by the RFID reader 92B, which is located at, or which is used by or associated with, the healthcare provider. In a preferred embodiment, the individual's or patient's RFID tag 92 can be read or scanned by the RFID reader 92B upon registration in a reception area, upon being engaged by the healthcare provider or by an authorized employee or agent of same, or at any other time while in or at the office or premises of the healthcare provider. At step 2001, the RFID reader 92B can read or scan the individual's or patient's RFID tag 92A.

At step 2002, the data and/or information obtained by the RFID reader 92B can be transmitted, from the RFID reader 92B, or from any other computer or communication device (such as, for example, the provider communication device 21), to the central processing computer component 110A of the central processing computer/distributed ledger/Blockchain technology system 110. At step 2002, the central processing computer component 110A of the central processing computer/distributed ledger/Blockchain technology system 110 can process the data and/or information received and determine the identification of the individual or patient. In a preferred embodiment, at step 2002, the central processing computer component 110A of the central processing computer/distributed ledger/Blockchain technology system 110 can also identify any and/or all of the individual's or patient's healthcare record(s), file(s), or histories.

At step 2003, the central processing computer/distributed ledger/Blockchain technology system 110 can generate a message containing information regarding the individual or patient, the identity of the individual or patient, and a link or links to, or a hyperlink or hyperlinks to, or any other means for opening and/or accessing, the individual's or patient's healthcare record(s), file(s), or history or histories. At step 2003, the central processing computer/distributed ledger/Blockchain technology system 110 can transmit the message to the healthcare provider's provider communication device 21. At step 2003, the healthcare provider's provider communication device 21 can receive the message and can display any information contained therein on or via the display device 20E of the healthcare provider's provider communication device 21. Thereafter, at step 2003, the healthcare provider can conduct the healthcare visit or examination with the individual or patient, or can perform a diagnosis, administer a treatment, or perform any other service for the individual or patient.

At step 2004, the healthcare provider can update the individuals or patient's healthcare record(s), file(s), or history or histories, so as to include information obtained or acquired during the individual's or patient's visit. At step 2004, the healthcare provider can update the individuals or patient's healthcare record(s), file(s), or history or histories, by utilizing the healthcare provider's provider communication device 21.

Thereafter, at step 2005, the healthcare provider can store information regarding the updates to the individual's or patient's healthcare record(s), file(s), or history or histories, along with any other information regarding the individual's or patient's visit, in the database 20H of the healthcare provider's provider communication device 21. At step 2005, the provider communication device 21 can transmit the information regarding the updates to the individual's or patient's healthcare record(s), file(s), or history or histories, along with any other information regarding the individual's or patient's visit, to the central processing computer/distributed ledger/Blockchain technology system 110 and. in particular, to the central processing computer component 110A of the central processing computer/distributed ledger/Blockchain technology system 110. At step 2005, the central processing computer component 110A of the central processing computer/distributed ledger/Blockchain technology system 110 can receive the information regarding the updates to the individual's or patient's healthcare record(s), file(s), or history or histories, along with any other information regarding the individual's or patient's visit, can process the same if needed, and can store the same in the database 10H of the central processing computer component 110A of the central processing computer/distributed ledger/Blockchain technology system 110, and in the individual's or patient's healthcare record(s), file(s), or history or histories, stored therein. At step 2005, the information regarding the updates to the individual's or patient's healthcare record(s), file(s), or history or histories, along with any other information regarding the individual's or patient's visit, can also be stored in the distributed ledger and Blockchain technology system component 110B of the central processing computer/distributed ledger/Blockchain technology system 110.

Thereafter, the operation of the apparatus 300 will cease at step 2006.

In another preferred embodiment, the apparatus 300 of the embodiment of FIG. 20 can dispense with the need to access and use the central processing computer component 110A of the central processing computer/distributed ledger/Blockchain technology system 110 in order to determine the individual's or patient's identify and in order to gain access to the individual's or patient's healthcare record(s), file(s), or history or histories. In such a preferred embodiment, the RFID reader 92B can be linked to the provider communication device 21, or the RFID reader 92B can be a component of, or can be, a user input device 20D of the provider communication device 21. In such a preferred embodiment, the individual's or patient's healthcare record(s), file(s), or history or histories, can be stored in the database 20H of the provider communication device 21. Further, in such a preferred embodiment, the provider communication device 21 can process the data and/or information read or scanned from the individual's or user's RFID tag 92A, and can determine the identify of the individual or user and provide the healthcare provider with access to the individual's or patient's healthcare record(s), file(s), or history or histories.

In another preferred embodiment, the apparatus 300 of the present invention of FIG. 20 can also be utilized in a same, a similar, and/or an analogous, manner in order to verify an identity of any user, individual, patient, caregiver, and/or any healthcare provider, healthcare professional, or any other individual or entity who or which utilizes the apparatus 300, and to provide an authorized their party with access to a healthcare record(s), file(s), or history, or any other information, which can be processed by or stored in the apparatus 300 or any of its component computers or communication devices, for any desired use, application, or purpose.

In another preferred embodiment, as well as in any and/or all of the embodiments described herein, the apparatus 300 of the present invention can also be utilized in order to provide public health and/or public safety services, and/or any other health services to or for any individuals or patients who utilize the apparatus 300. In particular, in a preferred embodiment, the apparatus 300 of the present invention can be utilized in order to detect, store, and provide, data and/or information, to any and/or all users, individuals, or patients, when a person, who has been determined to have, or to be inflicted with, a sickness or an illness, or an adverse or other health condition, or a bacterial infection, a viral infection, or a contagious infection, or who are determined to be in need of an immunization or immunizations, which condition, circumstance, or state of affairs, can or might pose a public health threat to the public at large and/or which can or might pose a particular threat to any user, individual, or patient, enters into or onto any public or private buildings, structures, properties, or venues, and/or any room, area, or section, of the same, and/or of any commercial, public, or private, vehicles. In a preferred embodiment, the apparatus 300 can also be utilized by governmental entities, public entities, and/or private entities.

In a preferred embodiment, it is envisioned that an RFID tag 92A can be assigned to any user, individual, or patient, who uses the apparatus 300 of the present invention. In a preferred embodiment, the RFID tag 92A can also be assigned to a healthcare account which is assigned to or for the respective user, individual, or patient, who uses the apparatus 300 of the present invention.

In a preferred embodiment, the RFID tag 92A can be provided in or as a physical identification card, such as healthcare ID card or a healthcare account card, or any other physical item or device, and/or can be attached to, or located within, an article of clothing, a watch, a necklace, a bracelet, an ankle bracelet, a ring, an article of jewelry, or any other wearable article or item. In a preferred embodiment, the RFID tag 92A can also be implantable within an individual or patient. In a preferred embodiment, the RFID tag 92A can also be provided in or as a physical identification card, attached to, or located on or within, a cellular telephone, a smart phone, a Smartphone, a personal digital assistant, or any other personal article or item. In a preferred embodiment, any number of RFID tags 92A can be assigned to or associated with any respective user, individual, or patient.

In a preferred embodiment, it is also envisioned that an RFID reader system 92B, or any RFID reader or RFID readers of same, can be located at, or stationed at, the entrances to, the exits from, or any designated area(s), security check point(s), or check point(s), of or within, any public buildings, structures, properties, or venues, and/or any room, area, or section, of the same, and/or of any commercial or public vehicles of all types or kinds, and/or of any private buildings, structures, properties, or venues, and/or any room, area, or section, of the same, and/or of any private vehicles of all types or kinds. In a preferred embodiment, public buildings, structures, properties, or venues, and/or commercial or public vehicles, can, for example, include, but not be limited to, any government buildings, public parks, arenas, stadiums, theme parks, airports, train stations, bus terminals, marine terminals, shopping malls, indoor shopping malls, stores of any type or kind, retail stores, wholesale stores, apartment buildings, cooperative buildings, condominiums, town houses, hospitals, nursing homes, doctor's offices, healthcare provider's offices, gyms, urgent care facilities, assisted living facilities, senior citizen residential buildings, professional offices, parking lots, concert halls, movie theaters, schools, colleges, universities, churches and other places of worship, hotels, casinos, racetracks, restaurants, catering halls, public gathering areas which have dedicated entrances, dedicated exits, or dedicated entrances and/or exits, buses, trains, subway trains, cruise ships, ferries, commercial boats or ships, airplanes and/or any type or kind of aircraft, and/or any other building, structure, or venue, or any vehicle, in or at which members of the public, or other large groups, can gather, enjoy, occupy, or utilize, for any type or kind of purpose, and/or can utilize as a mode or transportation.

In a preferred embodiment, private buildings, structures, properties, or venues, and/or vehicles, can, for example, include, but not be limited to, any private building, private office building, residential building, residential apartment, residential coop apartment, residential condominium apartment, private office, private vehicle, or any other building, structure, or venue, or any vehicle, in or on which people can gather, enjoy, occupy, or utilize, in an occupant-controlled manner for any type or kind of purpose, and/or can utilize as a mode or transportation.

In a preferred embodiment, any time any user, individual, or patient, enters an entrance of, enters a designated area of, or exits from, any public building, structure, property, or venue, and/or any room, area, or section, of the same, and/or of any commercial or public vehicle, and/or of any private building, structure, property, or venue, and/or any room, area, or section, of the same, and/or of any private vehicle, their RFID tag 92A can be read or scanned by the RFID reader 92B located at or assigned to that respective entrance, designated area, or exit.

The data and/or information read or scanned by the respective RFID reader 92B can be transmitted to, and processed at, the central processing computer component 110A of the central processing computer/distributed ledger/Blockchain technology system 110. The central processing computer component 110A of the central processing computer/distributed ledger/Blockchain technology system 110 can process the read or scanned data and/or information and can determine the identity of the user, individual, or patient, access his or her individual or patient healthcare record(s), file(s), or history or histories, and determine whether or not the user, individual, or patient, has been determined to have, or to be inflicted with, a sickness or an illness, or an adverse or other health condition, or a bacterial infection, a viral infection, or a contagious infection, or determined to be in need of an immunization or immunizations, which condition, circumstance, or state of affairs, can or might pose a public health threat to the public at large and/or which can or might pose a particular threat to any user, individual, or patient, who utilizes the apparatus 300.

The apparatus 300 of the present invention can thereafter generate a health warning or other alert message, and can transmit the same to each user communication device 41 of or associated with any individual or patient who utilizes the apparatus 300, so as to apprise him or her of the possible or potential public health threat or threat particular to them. Any individual or patient can also, at any time, access the central processing computer component 110A of the central processing computer/distributed ledger/Blockchain technology system 110 in order to ascertain, for any particular public building, structure, property, or venue, and/or any room, area, or section, of the same, and/or for any commercial or public vehicle, and/or for any private building, structure, property, or venue, and/or any room, area, or section, of the same, and/or for any private vehicle.

Figure 21:
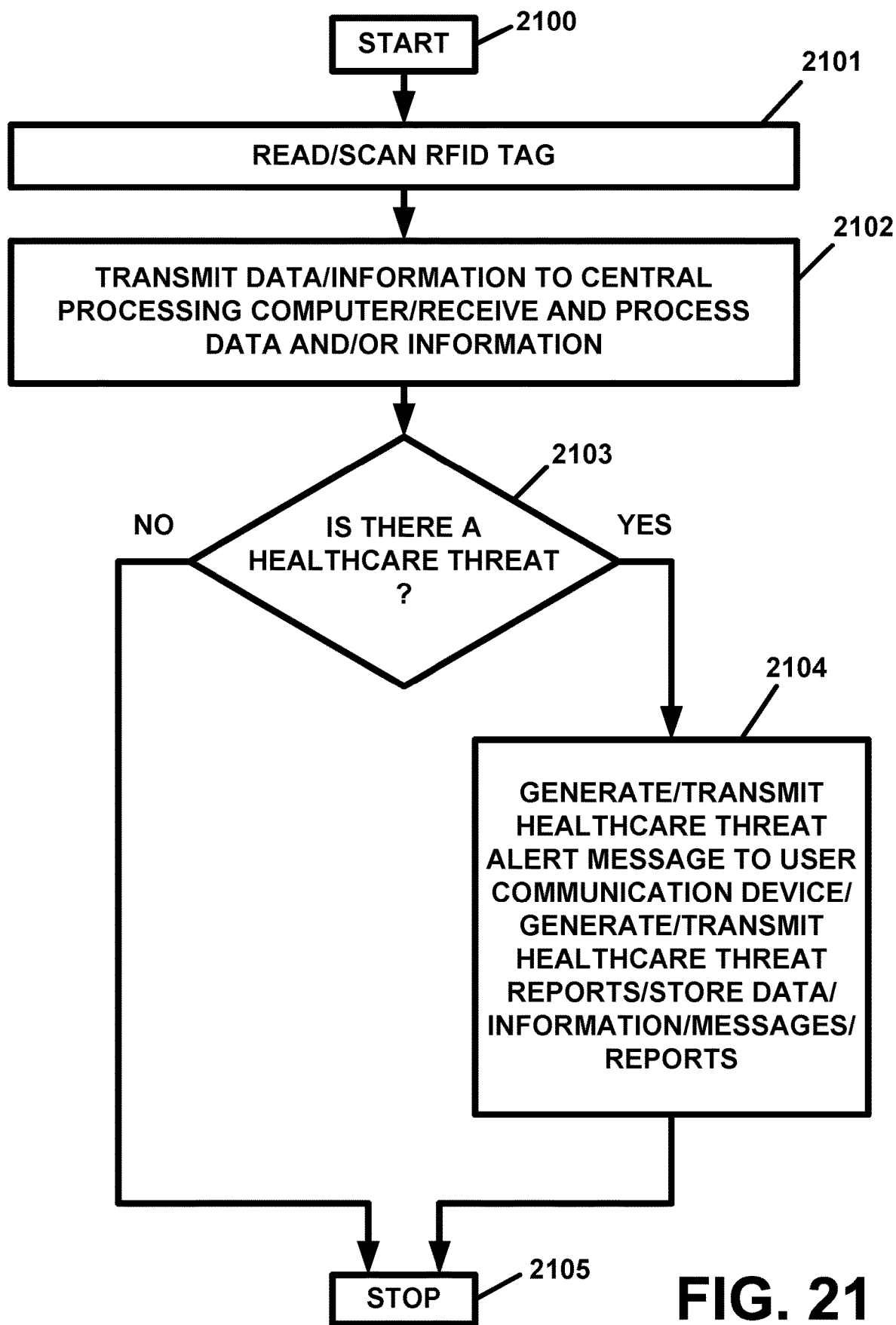
FIG. 21 illustrates another preferred embodiment method of utilizing the apparatus of the present invention, in flow diagram form.

FIG. 21 illustrates another preferred embodiment method for utilizing the apparatus 300, in flow diagram form. In the preferred embodiment of FIG. 21, the apparatus 300 is described as being utilized so as to alert individuals or patients regarding a detection that a person having a contagious infection is or has been present in or at a public building such as an airport or a retail store. It is, however, important to note that the apparatus 300, of the embodiment of FIG. 21, can also be utilized in a same, a similar, and/or an analogous, manner, in order to detect when any person, who may have, or who may be inflicted with, a sickness or illness, or an adverse or other health condition, or a bacterial infection, a viral infection, or a contagious infection, or who is determined to be in need of an immunization or immunizations, which condition, circumstance, or state of affairs, can or might pose a public health threat to the public at large and/or to any individual or patient, enters or has entered into or onto any public or private buildings, structures, properties, or venues, and/or any room, area, or section, of the same, and/or of any commercial, public, or private, vehicles, described herein or otherwise, and in order to provide information regarding the same to any individual or patient, and/or to any healthcare provider(s), healthcare insurer(s), healthcare payer(s), governmental entity or governmental entities, and/or intermediary or intermediaries.

In a preferred embodiment, information can be provided to any individual(s) or patient(s) via alert messages which can be transmitted sent to the respective user communication device(s) 41 of the respective individual(s) or patient(s). In a preferred embodiment, information can be provided upon request to a respective individual's or patient's user communication device(s) 41, such as when a request is transmitted from the user communication device 41 to the central processing computer component 110A of the central processing computer/distributed ledger/Blockchain technology system 110 and when a message responsive to the request is transmitted to the user communication device 41. In a preferred embodiment, it is envisioned that any individual or patient can request to receive alert messages for certain geographical areas or for certain public or private buildings, structures, properties, or venues, and/or vehicles.

With reference to FIG. 21, the operation of the apparatus 300 commences at step 2100. At step 2101, in a preferred embodiment, the person entering the airport or the retail store can present his or her RFID tag 92A for reading or scanning by the RFID reader 92B which is located at a designated entrance of the airport or the retail store. In a preferred embodiment, at step 2101, the RFID reader 92B can read or scan the person's RFID tag 92A.

At step 2102, the data and/or information obtained by the RFID reader 92B can be transmitted, from the RFID reader 92B, or from any other computer or communication device (such as, for example, the governmental entity/intermediary communication device 51), to the central processing computer component 110A of the central processing computer/distributed ledger/Blockchain technology system 110. At step 2002, the central processing computer component 110A of the central processing computer/distributed ledger/Blockchain technology system 110 can process the data and/or information received and can determine the identification of the person. In a preferred embodiment, at step 2002, the central processing computer component 110A of the central processing computer/distributed ledger/Blockchain technology system 110 can also identify any and/or all of the person's healthcare record(s), file(s), or histories, and can process information contained in, or regarding, the same, in order to determine whether or not the person is, or has been, determined to have, or to be inflicted with, a sickness or an illness, or an adverse or other health condition, or a bacterial infection, a viral infection, or a contagious infection, or whether or not the person is determined to be in need of an immunization or immunizations, any of which condition(s), circumstance(s), or state(s) of affairs, can or might pose a public health threat to the public at large and/or to the individual or patient, or any number of individuals or patients (hereinafter referred to as a "healthcare threat").

At step 2103, the central processing computer component 110A of the central processing computer/distributed ledger/Blockchain technology system 110 can determine if the person poses a healthcare threat to the public or to any individual or patient, or any number of individuals or patients. If, at step 2103, the central processing computer component 110A of the central processing computer/distributed ledger/Blockchain technology system 110 determines that the person poses a healthcare threat, then the operation of the apparatus 300 will proceed to step 2104.

At step 2104, the central processing computer component 110A of the central processing computer/distributed ledger/Blockchain technology system 110 can generate a healthcare threat alert message. In a preferred embodiment, the healthcare threat alert message can contain or include information regarding the identify and/or the name of the airport or the retail store, the address of same, the city or municipality, the state or province, and/or the country in which the airport or the retail store is located, the date and time of the detection of the healthcare threat, the nature of the healthcare threat, such as for example, whether the healthcare threat is detection of a person having a contagious viral infection, and/or any other information regarding the detected healthcare threat, and/or any information regarding the same and/or relating to the same.

At step 2104, the central processing computer component 110A of the central processing computer/distributed ledger/Blockchain technology system 110 can transmit the healthcare threat alert message to the user communication device 41 of or associated with the individual or patient and/or can transmit the healthcare threat alert message to any number of user communications device(s) 41 associated with any number of individuals or patients. At step 2104, the central processing computer component 110A of the central processing computer/distributed ledger/Blockchain technology system 110 can also transmit the healthcare threat alert message to any number of provider communication device(s) 21 associated with any number of healthcare providers. At step 2104, the central processing computer component 110A of the central processing computer/distributed ledger/Blockchain technology system 110 can also transmit the healthcare threat alert message to ay number of governmental entity/intermediary communication device(s) 51 associated with any number of governmental entities or intermediaries.

In a preferred embodiment, at or during step 2104, and/or at or during any time before, during, or after step 2104, or at or during any other time, any individual or patient can also access the central processing computer component 110A of the central processing computer/distributed ledger/Blockchain technology system 110, with using his or her user communication device 41, and can transmit, to the central processing computer component 110A of the central processing computer/distributed ledger/Blockchain technology system 110, a request for information regarding any detected healthcare threat(s), and/or any detected healthcare threat(s) regarding any public or private building(s), structure(s), property or properties, or venue(s), and/or vehicle(s), and/or any detected healthcare threat(s) regarding any sickness or illness, or an adverse or other health condition, or a bacterial infection, a viral infection, or a contagious infection, or any threat regarding an unimmunized person, or any other condition(s), circumstance(s), or state(s) of affairs, which can or might pose a public health threat to the public at large and/or to the individual or patient.

In a preferred embodiment, the central processing computer component 110A of the central processing computer/distributed ledger/Blockchain technology system 110 can generate a healthcare threat report containing or including information and/or data and/or information responsive to the request for information, as well as any data and/or information regarding each detected healthcare threat, including any data and/or information which can be contained in each healthcare alert message responsive to the request for information, and can transmit the same to the user communication device 41 of the individual or patient. In another preferred embodiment, the central processing computer component 110A of the central processing computer/distributed ledger/Blockchain technology system 110 can receive and respond to requests for information received from any of the herein-described healthcare providers, healthcare insurers, healthcare payers, and/or governmental entities and/or intermediaries, can generate healthcare threat report messages, and can transmit the same to the respective communication devices 21, 31, and/of 51 of each of the respective requesting healthcare provider(s), healthcare insurer(s), healthcare payer(s), governmental entity or governmental entities, and/or intermediary or intermediaries.

At step 2104, the user communication device 41 can receive the healthcare threat report message and the individual or patient can view or review the data and/or information contained in the same via the display device 40E of the user communication device 41. At step 2104, the central processing computer component 110A of the central processing computer/distributed ledger/Blockchain technology system 110 can store any and/or all information regarding processed by the central processing computer component 110A of the central processing computer/distributed ledger/Blockchain technology system 110 during steps 2101 through 2104, information regarding any detected healthcare threats as well as any generated healthcare threat alert messages, and/or any healthcare threat report messages, in the database 10H of the central processing computer component 110A of the central processing computer/distributed ledger/Blockchain technology system 110. At step 2104, any and/or all information regarding processed by the central processing computer component 110A of the central processing computer/distributed ledger/Blockchain technology system 110 during steps 2101 through 2104, information regarding any detected healthcare threats as well as any generated healthcare threat alert messages, and/or any healthcare threat report messages, can also be stored in the distributed ledger and Blockchain technology system component 110B of the central processing computer/distributed ledger/Blockchain technology system 110. Thereafter, the operation of the apparatus 300 will cease at step 2105.

If, however, at step 2103, the central processing computer component 110A of the central processing computer/distributed ledger/Blockchain technology system 110 determines that the person does not poses any healthcare threat, then the operation of the apparatus 300 will cease at step 2105.

It is important to note that the database 10H of the central processing computer component 110A of the central processing computer/distributed ledger/Blockchain technology system 110 can store any data and/or information need or desired for performing the functionalities of FIG. 21. In this regard, for example, the database 10H can contain and/or include information regarding the identities, names, and addresses, of or for any and/or all of the various public and private buildings, structures, properties, or venues, and/or any room, area, or section, of the same, and/or of any commercial, public, or private, vehicles, described herein or otherwise, the RFID readers 92B used at the same, any information needed for detecting the herein-described sicknesses or illnesses, or adverse or other health conditions, bacterial infections, viral infections, contagious infections, needs for immunizations, and/or any condition(s), circumstance(s), or state(s) of affairs, can or might pose a public health threat to the public at large and/or to the individual or patient, or any number of individuals or patients.

Although the embodiment of FIG. 21 has been described as being used in connection with an airport or a retail store, it is important to note that the apparatus 300 of the embodiment of FIG. 21, can also be utilized in a same, a similar, and/or an analogous, manner, in order to detect, when any person, who may have, or who may be inflicted with, a sickness or illness, or an adverse or other health condition, or a bacterial infection, a viral infection, or a contagious infection, or who is determined to be in need of an immunization or immunizations, which condition, circumstance, or state of affairs, can or might pose a public health threat to the public at large and/or to any individual or patient, enters or has entered into or onto any public or private buildings, structures, properties, or venues, and/or any room, area, or section, of the same, and/or of any commercial, public, or private, vehicles, described herein or otherwise, and in order to provide information regarding the same to any individual or patient, and/or to any healthcare provider(s), healthcare insurer(s), healthcare payer(s), governmental entity or governmental entities, and/or intermediary or intermediaries.

In a preferred embodiment, it is important to note that the database 10H of the central processing computer 10 of the apparatus 100 and the database 10H of the central processing computer component 110A of the central processing computer/distributed ledger/Blockchain technology system 110, of the apparatus 200 and the apparatus 300 contains and/or includes any and/or all data and/or information needed or desired for performing any and/or all of the functions described herein for performing all of the functionalities of all of the preferred embodiments described herein, including the embodiments of FIGS. 11, 13, 18, 19, 20, and 21, as well as any and/or all of the other embodiments described herein.

In another preferred embodiment, as well as in any and/or all of the other embodiments described herein, the apparatus 100, the apparatus 200, and/or the apparatus 300, of the present invention can be utilized in order to update any and/or all of the electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs), of or for any user, individual, or patient, any time any one such electronic healthcare record (EHR), electronic medical record or electronic healthcare file (EMR), electronic dental record or file (EDR), electronic pharmacy record or file (EPR), electronic behavioral health record or file (EBHR), or personal health record or file (PHR), of the user, individual, or patient, is updated, changed, alerted, or modified.

In this regard, the apparatus 100, the apparatus 200, and/or the apparatus 300, of the present invention can be utilized in conjunction with, or in connection with, the various and/or numerous electronic healthcare records (EHRs), electronic medical records or electronic healthcare files (EMRs), electronic dental records or files (EDRs), electronic pharmacy records or files (EPRs), electronic behavioral health records or files (EBHRs), and/or personal health records or files (PHRs), which are offered by, or which can be offered by, the various and/or respective providers of the electronic healthcare records (EHRs), electronic medical records or electronic healthcare files (EMRs), electronic dental records or files (EDRs), electronic pharmacy records or files (EPRs), electronic behavioral health records or files (EBHRs), or personal health records or files (PHRs), which currently exist, or which may exist or be offered in the future, in the healthcare, and/or other, marketplace.

In such a preferred embodiment, it is envisioned that the information fields or data fields of each of the respective electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs), can be previously ascertained or identified and can be indexed, mapped, or correlated, with each other in a master records file, and the master records file can be stored in each of the respective databases 10H, 20H, 30H, 40H, and/or 50H.

In a preferred embodiment, each time an information field or data field of one of an individual's or patient's electronic healthcare record (EHR), electronic medical record or electronic healthcare file (EMR), electronic dental record or file (EDR), electronic pharmacy record or file (EPR), electronic behavioral health record or file (EBHR), or personal health record or file (PHR), is updated, changed, altered, or modified, each of the respective central processing computer 10 or the central processing computer component 110A of the central processing computer/distributed ledger/Blockchain technology system 110, or the respective provider communication device(s) 20 or 21, the insurer/payer communication device(s) 30 or 31, and/or the user/patient communication device(s) 40 or 41 can automatically update, change, alter, or modify, the corresponding information field or data field in each of all of the individual's or patient's other electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs). In this regard, any and/or all of the information fields and/or data fields in each of the individual's or patient's other electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs), can be automatically updated, changed, altered, or modified, any time any information field or data field is updated, changed, altered, or modified, in or for any electronic healthcare record (EHR), electronic medical record or electronic healthcare file (EMR), electronic dental record or file (EDR), electronic pharmacy record or file (EPR), electronic behavioral health record or file (EBHR), or personal health record or file (PHR), of or for the individual or patient.

In another preferred embodiment, the healthcare provider can be provided with a generic form, or other form, template, for use in and/or during any remote office visit or the virtual office visit, and/or the remote examination, or the distance examination. Once the respective remote office visit or the virtual office visit, and/or the remote examination, or the distance examination, has ended, the respective central processing computer 10 or the central processing computer component 110A of the central processing computer/distributed ledger/Blockchain technology system 110, or the respective provider communication device(s) 20 or 21, the insurer/payer communication device(s) 30 or 31, and/or the user/patient communication device(s) 40 or 41 can automatically update, change, alter, or modify, the corresponding information field or data field in each of all of the individual's or patient's other electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs), in order to reflect the information or data entered by the healthcare provider into the generic form, or other form, template. In such a preferred embodiment, wherein a generic form, or other form, template is utilized, the information fields or data fields of the same can be can be indexed or correlated with each of the information fields and data fields of each of the individual's or patient's electronic healthcare records (EHRs), electronic medical records or electronic healthcare files (EMRs), electronic dental records or files (EDRs), electronic pharmacy records or files (EPRs), electronic behavioral health records or files (EBHRs), as well as any personal health records or files (PHRs), in the master records file and can be stored in each of the respective databases 10H, 20H, 30H, 40H, and/or 50H.

Figure 22:
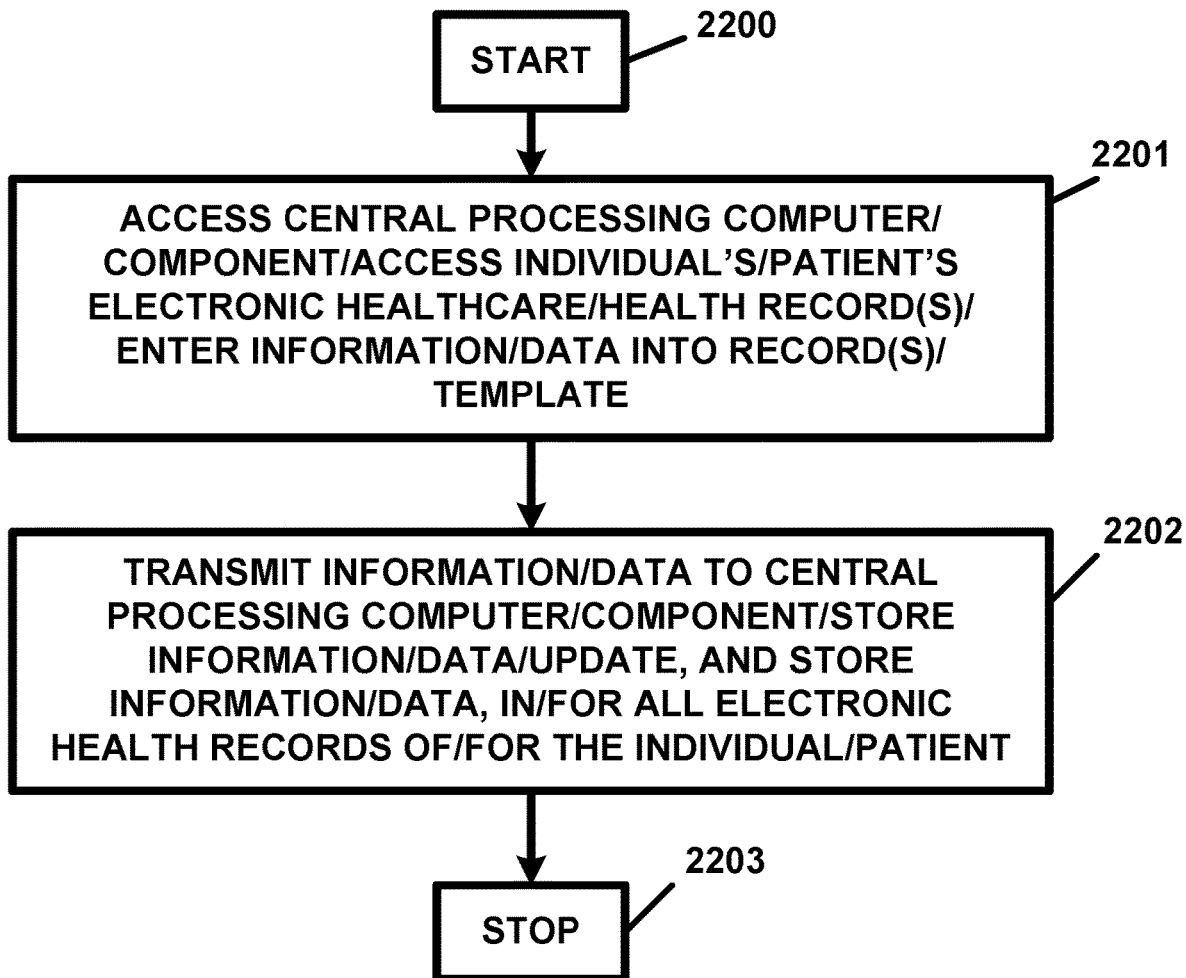
FIG. 22 illustrates yet another preferred embodiment method of utilizing the apparatus of the present invention, in flow diagram form.

FIG. 22 illustrates another preferred embodiment method for utilizing the apparatus 100, the apparatus 200, or the apparatus 300, of the present invention, in flow diagram form. With reference to FIG. 22, the operation of the respective apparatus 100, 200, or 300, can commence at step 2200. At step 2201, the healthcare provider can access the respective central processing computer 10 or the central processing computer component 110A of the central processing computer/distributed ledger/Blockchain technology system 110, via his or her provider communication device 20 or 21. At step 2201, the healthcare provider can access the individual's or patient's electronic healthcare record (EHR) at any time before, during, or after, a remote office visit or a virtual office visit, and/or a remote examination, or a distance examination, of or involving the individual or patient, or any time before, during, or after an in-person office visit or examination of or involving the individual or patient. At any time during step 2201, the healthcare provider can enter information or data into the individual's or patient's electronic healthcare record (EHR). In another preferred embodiment, the healthcare provider, at step 2201, can access, and can enter information or data into, a generic form, or other form, template.

Upon completion of all information or data entry into either the individual's or patient's electronic healthcare record (EHR) or the generic form, or other form, template, the operation of the apparatus 100, 200, or 300, can proceed to step 2202. At step 2202, any and/or all information or data entered by the healthcare provider at step 2201 can be transmitted to, received at, and stored in the database 10H of, the respective central processing computer 10 or the central processing computer component 110A of the central processing computer/distributed ledger/Blockchain technology system 110. At step 2202, the central processing computer 10 or the central processing computer component 110A of the central processing computer/distributed ledger/Blockchain technology system 110 can thereafter utilize the information stored in the master records file and automatically update, change, alter, or modify, the corresponding information field or data field in each of all of the respective information fields and/or data fields of each of all of the individual's or patient's other electronic healthcare records (EHRs), electronic medical records or electronic healthcare files (EMRs), electronic dental records or files (EDRs), electronic pharmacy records or files (EPRs), electronic behavioral health records or files (EBHRs), or personal health records or files (PHRs).

Thereafter, at step 2202, any and/or all updates, changes, alterations, or modifications, to and/or in each of the information fields or data fields of each and/or all of the individual's or patient's electronic healthcare records (EHRs), electronic medical records or electronic healthcare files (EMRs), electronic dental records or files (EDRs), electronic pharmacy records or files (EPRs), electronic behavioral health records or files (EBHRs), or personal health records or files (PHRs), can be stored in the database 10H of the central processing computer 10, or in the database 10H of the central processing computer component 110A of the central processing computer/distributed ledger/Blockchain technology system 110, and/or can be stored in or by the distributed ledger and Blockchain technology system component 110B of the central processing computer/distributed ledger/Blockchain technology system 110. Thereafter, the operation of the respective apparatus 100, 200, or 300, can cease at step 2203.

In another preferred embodiment, the provider communication device 20 or 21 can utilize the information stored in the master records file and any and/or all information or data entered by the healthcare provider at or during step 2201 in order to automatically update, change, alter, or modify, and store in the database 20H, the corresponding information field or data field in each of all of the respective information fields and/or data fields of each of all of the individual's or patient's other electronic healthcare records (EHRs), electronic medical records or electronic healthcare files (EMRs), electronic dental records or files (EDRs), electronic pharmacy records or files (EPRs), electronic behavioral health records or files (EBHRs), or personal health records or files (PHRs).

In this regard, in a preferred embodiment, the apparatus 100, the apparatus 200, and/or the apparatus 300, of the present invention can be utilized in conjunction with, or in connection with, any number and/or types or kinds of the various and/or numerous electronic healthcare records (EHRs), electronic medical records or electronic healthcare files (EMRs), electronic dental records or files (EDRs), electronic pharmacy records or files (EPRs), electronic behavioral health records or files (EBHRs), and/or personal health records or files (PHRs), offered by any of the various providers of same, which exist and/or which are offered in the healthcare marketplace, and/or which may exist or which may be offered in the future.

In another preferred embodiment, the apparatus 100, the apparatus 200, and/or the apparatus 300, of the present invention can be utilized in order to allow an individual or patient, or a caregiver of the individual or patient, to have control over the respective individual's or patient's numerous electronic healthcare records (EHRs), electronic medical records or electronic healthcare files (EMRs), electronic dental records or files (EDRs), electronic pharmacy records or files (EPRs), electronic behavioral health records or files (EBHRs), and/or personal health records or files (PHRs) (hereinafter referred to as "individual's or patient's electronic record(s)"). In such a preferred embodiment, the individual or patient can utilize the apparatus 100, the apparatus 200, and/or the apparatus 300, of the present invention in order to grant permission, to a healthcare provider, a healthcare provider, a healthcare insurer or a healthcare payer, and/or to an intermediary or governmental entity, and/or to any other person or entity, to access or use, and/or to update, change, alter, or modify, and information or data contained in, the individual's or patient's electronic record(s). In such a preferred embodiment, a caregiver of the individual or patient, if so authorized, can also utilize the apparatus 100, the apparatus 200, and/or the apparatus 300, of the present invention in order to grant permission, to a healthcare provider, a healthcare provider, a healthcare insurer or a healthcare payer, and/or to an intermediary or governmental entity, and/or to any other person or entity, to access, and/or to update, change, alter, or modify, any information or data contained in, the individual's or patient's electronic record(s).

In such an embodiment, the apparatus 100, the apparatus 200, and/or the apparatus 300, of the present invention can also record and store, in an electronic record access transaction record or file, of or for the individual or patient, data and/or information regarding, at least, but not limited to, the date and time of the granting of the permission to access, by the individual or patient; the specific or respective electronic healthcare record, electronic medical record or electronic healthcare file, electronic dental record or file, electronic pharmacy record or file, electronic behavioral health record or file, or personal health record or file, to which access has been granted permission; the healthcare provider, healthcare insurer, healthcare payer, intermediary, governmental entity, or other person or entity, who or which has been granted access permission; the date and time of access, by the respective healthcare provider, healthcare insurer, healthcare payer, intermediary, governmental entity, or other person or entity, of the specific or respective electronic healthcare record, electronic medical record or electronic healthcare file, electronic dental record or file, electronic pharmacy record or file, electronic behavioral health record or file, or personal health record or file; the duration of the accessing of, or use of, the specific or respective electronic healthcare record, electronic medical record or electronic healthcare file, electronic dental record or file, electronic pharmacy record or file, electronic behavioral health record or file, or personal health record or file; a video recording or a video clip of the respective healthcare provider, healthcare insurer, healthcare payer, intermediary, governmental entity, or other person or entity, during his or her accessing of, and/or use of, the specific or respective electronic healthcare record, electronic medical record or electronic healthcare file, electronic dental record or file, electronic pharmacy record or file, electronic behavioral health record or file, or personal health record or file; a video recording or video clip of the screen of the respective display device 20E, 30E, or 40E, of the respective communication device 20, 21, 30, 31, 50, or 51, used by the respective healthcare provider, healthcare insurer, healthcare payer, intermediary, governmental entity, or other person or entity, recording all actions taken by the respective healthcare provider, healthcare insurer, healthcare payer, intermediary, governmental entity, or other person or entity during the accessing session; a copy of an access alert message generated and transmitted to a communication device 40 or 41 of the individual or patient, or caregiver; a copy of an electronic record access report, if generated; information regarding a reason for the accessing or use of the specific or respective electronic healthcare record, electronic medical record or electronic healthcare file, electronic dental record or file, electronic pharmacy record or file, electronic behavioral health record or file, or personal health record or file; information regarding a description of any activity performed during the accessing or use of the specific or respective electronic healthcare record, electronic medical record or electronic healthcare file, electronic dental record or file, electronic pharmacy record or file, electronic behavioral health record or file, or personal health record or file; a description of information or data updated, changed, altered, or modified, during the accessing or use of the specific or respective electronic healthcare record, electronic medical record or electronic healthcare file, electronic dental record or file, electronic pharmacy record or file, electronic behavioral health record or file, or personal health record or file; a copy of any insurance claim submitted or claim for payment submitted as a result of the accessing or use of the specific or respective electronic healthcare record, electronic medical record or electronic healthcare file, electronic dental record or file, electronic pharmacy record or file, electronic behavioral health record or file, or personal health record or file, and/or information regarding the status of payment of or for same; any data and/or information, message(s), and/or report(s), described herein as being generated, recorded, or stored, regarding any video call, remote or virtual office visit, remote or distance examination, or in-person office visit or in-person examination described herein or otherwise; and/or any other data and/or information which may be needed, required, or desired, for documenting the accessing and/or the use of the individual's or patient's respective electronic healthcare record, electronic medical record or electronic healthcare file, electronic dental record or file, electronic pharmacy record or file, electronic behavioral health record or file, or personal health record or file.

Figure 23:
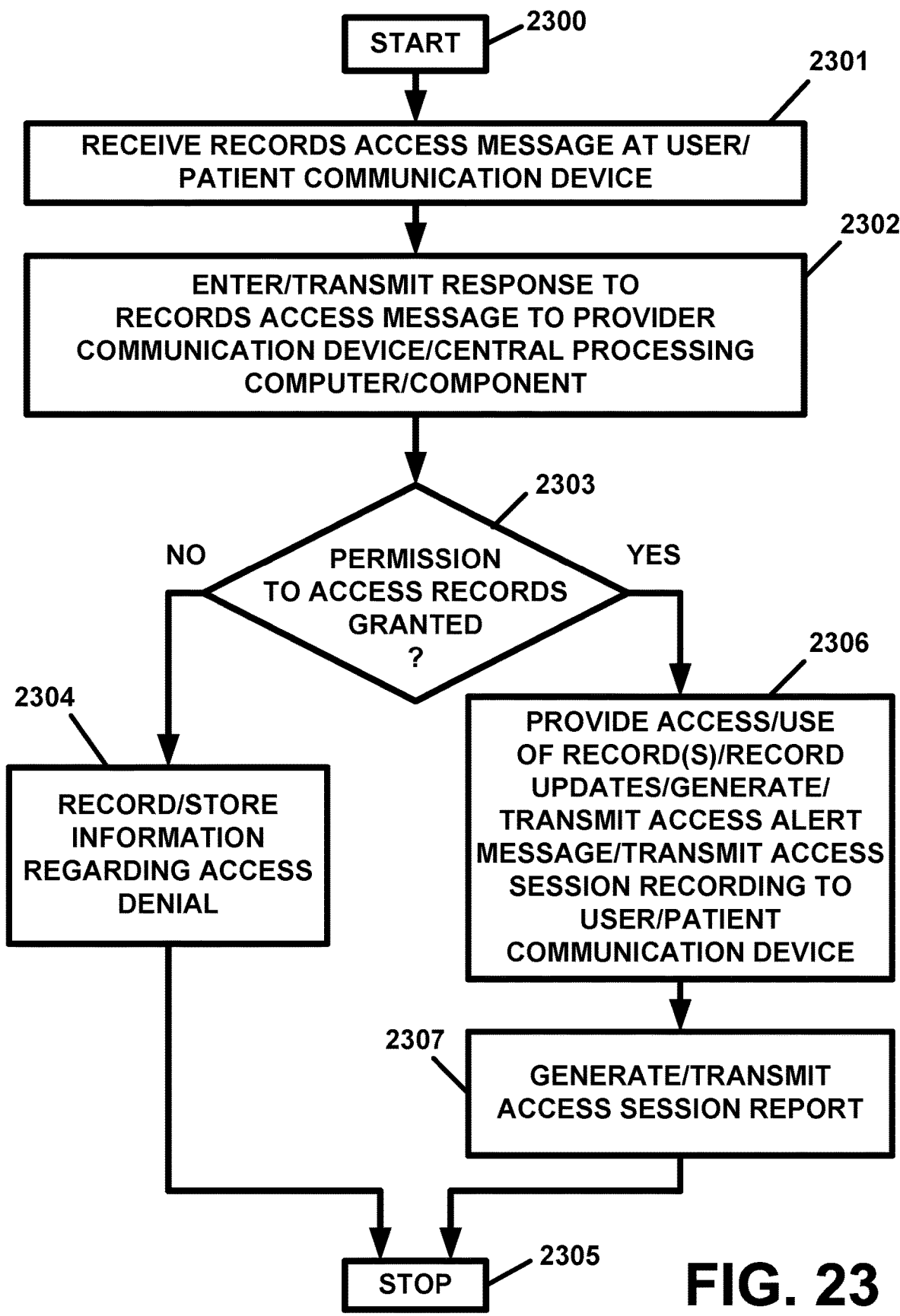
FIG. 23 illustrates still another preferred embodiment method of utilizing the apparatus of the present invention, in flow diagram form.

FIG. 23 illustrates another preferred embodiment method for utilizing the apparatus 300 of the present invention, in flow diagram form. Although described as being utilized in conjunction with, or in connection with, the apparatus 300, it is important to note that the embodiment of FIG. 23 can also be utilized in conjunction with, or in connection with, the apparatus 100 and/or the apparatus 200 in a same, a similar, and/or an analogous, manner as described herein as being utilized with the apparatus 300. With reference to FIG. 23, the operation of the respective apparatus 300 commences at step 2300. At step 2301, the individual or patient can receive a records access request message from a respective healthcare provider, healthcare insurer, healthcare payer, intermediary, governmental entity, or other person or entity, who is seeking permission to access his or her respective electronic healthcare record, electronic medical record or electronic healthcare file, electronic dental record or file, electronic pharmacy record or file, electronic behavioral health record or file, or personal health record or file.

In a preferred embodiment, the records access request message can be transmitted to the user or patient communication device 41 from a provider communication device 21 of or associated with a healthcare provider seeking permission to access the individual's or patient's respective electronic healthcare record, electronic medical record or electronic healthcare file, electronic dental record or file, electronic pharmacy record or file, electronic behavioral health record or file, or personal health record or file, such as prior to, during, or after, conducting a video call, a remote or virtual office visit, a remote or distance examination, or an in-person office visit or an in-person examination, described herein or otherwise, to review the individual's or patient's respective record(s) or file(s) for diagnosis, treatment, treatment planning, wellness, consultation, second opinion, or any other, purpose(s), and/or for any other reason or purpose.

In another preferred embodiment, the records access request message can be transmitted to the user or patient communication device 41 from a insurer/payer communication device 31 of or associated with a healthcare insurer or a healthcare payer seeking permission to access the individual's or patient's respective electronic healthcare record, electronic medical record or electronic healthcare file, electronic dental record or file, electronic pharmacy record or file, electronic behavioral health record or file, or personal health record or file, to process an insurance claim, a claim for payment, or a request for payment, to conduct an audit of the individual's or patient's healthcare, healthcare diagnoses, healthcare treatments, healthcare treatment planning, wellness, wellness planning, and/or for any other purpose(s), to conduct an audit of the individual's or patient's respective healthcare insurance account, healthcare spending account, or healthcare account, to conduct an audit of a healthcare provider of the individual or patient, the healthcare provider's activities in caring for, diagnosing, or treating, the individual or patient and/or for any other purpose(s).

In another preferred embodiment, the records access request message can be transmitted to the user or patient communication device 41 from a governmental entity/intermediary communication device 51 of or associated with any intermediary or governmental entity seeking permission to access the individual's or patient's respective electronic healthcare record, electronic medical record or electronic healthcare file, electronic dental record or file, electronic pharmacy record or file, electronic behavioral health record or file, or personal health record or file, for any reason or purpose.

In a preferred embodiment, at step 2301, the records access request message can be transmitted from the provider communication device 21 directly to the user or patient communication device 41 or can be transmitted from the provider communication device 21 to the central processing computer component 110A of the central processing computer/distributed ledger/Blockchain technology system 110, and then from the central processing computer component 110A of the central processing computer/distributed ledger/Blockchain technology system 110 to the user or patient communication device 41. In instances when the records access request message is transmitted via the central processing computer component 110A of the central processing computer/distributed ledger/Blockchain technology system 110, a record of the same can be stored in the database 10H of the central processing computer component 110A and/or in the respective electronic healthcare record, electronic medical record or electronic healthcare file, electronic dental record or file, electronic pharmacy record or file, electronic behavioral health record or file, or personal health record or file, of the individual or patient. In another preferred embodiment, any records access request message transmitted from any insurer/payer communication device 31 or any governmental entity/intermediary communication device 51 can also be transmitted directly to the user or patient communication device 41 or transmitted, in a similar manner as described above, to the user or patient communication device 41 via the central processing computer component 110A of the central processing computer/distributed ledger/Blockchain technology system 110.

At step 2301, the individual or patient can review the information contained in the records access request message. At step 2302, the individual or patient can elect to grant the requested permission, to access his or her respective electronic healthcare record, electronic medical record or electronic healthcare file, electronic dental record or file, electronic pharmacy record or file, electronic behavioral health record or file, or personal health record or file, or can deny the request for permission to access the respective electronic healthcare record, electronic medical record or electronic healthcare file, electronic dental record or file, electronic pharmacy record or file, electronic behavioral health record or file, or personal health record or file.

At step 2302, the individual or patient can enter information, into the user or patient communication device 41, regarding his of her response or decision to grant or to deny the requested permission, to access his or her respective electronic healthcare record, electronic medical record or electronic healthcare file, electronic dental record or file, electronic pharmacy record or file, electronic behavioral health record or file, or personal health record or file. At step 2302, a records access response message, containing information regarding the individual's or patient's response or decision, to grant or deny permission to access his or her respective electronic healthcare record, electronic medical record or electronic healthcare file, electronic dental record or file, electronic pharmacy record or file, electronic behavioral health record or file, or personal health record or file, can be transmitted either directly to the provider communication device 21 or to the provider communication device 21 via the central processing computer component 110A of the central processing computer/distributed ledger/Blockchain technology system 110. If transmitted to the central processing computer component 110A, a record of the individual's or patient's records access response message can be stored in the database 10H of the central processing computer component 110A and/or in the respective electronic healthcare record, electronic medical record or electronic healthcare file, electronic dental record or file, electronic pharmacy record or file, electronic behavioral health record or file, or personal health record or file, of the individual or patient. In another preferred embodiment, any records access response message can also be transmitted to a respective insurer/payer communication device 31 or any respective governmental entity/intermediary communication device 51, if utilized, either directly or via the central processing computer component 110A of the central processing computer/distributed ledger/Blockchain technology system 110.

At step 2303, the respective provider communication device 21, or the central processing computer component 110A can determine whether or not permission to access the individual's or patient's electronic healthcare record, electronic medical record or electronic healthcare file, electronic dental record or file, electronic pharmacy record or file, electronic behavioral health record or file, or personal health record or file, has been granted. If, at step 2303, it is determined that permission to access the individual's or patient's electronic healthcare record, electronic medical record or electronic healthcare file, electronic dental record or file, electronic pharmacy record or file, electronic behavioral health record or file, or personal health record or file, has not been granted, then the operation of the apparatus 300 will proceed to step 2304.

At step 2304, the apparatus 300 will store and record information regarding the individual's or patient's denial of the healthcare provider's request for permission to access his or her electronic healthcare record, electronic medical record or electronic healthcare file, electronic dental record or file, electronic pharmacy record or file, electronic behavioral health record or file, or personal health record or file. Thereafter, at step 2304, information regarding the denial the healthcare provider's request for permission to access, the individual's or patient's electronic healthcare record, electronic medical record or electronic healthcare file, electronic dental record or file, electronic pharmacy record or file, electronic behavioral health record or file, or personal health record or file, can be stored in the database 10H of the central processing computer component 110A and/or in the respective electronic healthcare record, electronic medical record or electronic healthcare file, electronic dental record or file, electronic pharmacy record or file, electronic behavioral health record or file, or personal health record or file, of the individual or patient. Thereafter, the operation of the apparatus 300 will cease at step 2305. If, at step 2303, it is determined that permission to access the individual's or patient's electronic healthcare record, electronic medical record or electronic healthcare file, electronic dental record or file, electronic pharmacy record or file, electronic behavioral health record or file, or personal health record or file, has been granted, then the operation of the apparatus 300 will proceed to step 2306.

At step 2306, the healthcare provider can be provided with the requested access to the electronic healthcare record, electronic medical record or electronic healthcare file, electronic dental record or file, electronic pharmacy record or file, electronic behavioral health record or file, or personal health record or file, of the individual or patient, via his or her provider communication device 21. At step 2306, the healthcare provider can access any information or data, and/or can update, change, alter, or modify, any information or data, in the individual's or patient's electronic healthcare record, electronic medical record or electronic healthcare file, electronic dental record or file, electronic pharmacy record or file, electronic behavioral health record or file, or personal health record or file, and/or can perform any activity or activities with, using, or involving, the same.

At step 2306, the provider communication device 21 or the central processing computer component 110A of the central processing computer/distributed ledger/Blockchain technology system 110 can generate, and can transmit to the user or patient communication device 41, a records access alert message containing information regarding the accessing of the individual's or patient's respective electronic healthcare record, electronic medical record or electronic healthcare file, electronic dental record or file, electronic pharmacy record or file, electronic behavioral health record or file, or personal health record or file. In a preferred embodiment, a video recording or video clip of the healthcare provider can also be obtained or recorded by video and/or audio recording device(s) 20J of the provider communication device 21 and can be transmitted to the central processing computer component 110A of the central processing computer/distributed ledger/Blockchain technology system 110. In a preferred embodiment, the records access alert message can also contain at least a portion of the video recording or video clip of the healthcare provider so as to allow the individual or patient with authenticate the identity of the healthcare provider.

At step 2306, the records access alert message can be transmitted from the central processing computer component 110A of the central processing computer/distributed ledger/Blockchain technology system 110 or from the provider communication device 21 to the to the user or patient communication device 41. At step 2306, the provider communication device 21 and/or the central processing computer component 110A of the central processing computer/distributed ledger/Blockchain technology system 110 can record, or cause to be recorded, and store, a video recording (hereinafter referred to as the "access session recording") of the healthcare provider's use and/or activities and/or interactions with, or involving, the individual's or patient's respective electronic healthcare record, electronic medical record or electronic healthcare file, electronic dental record or file, electronic pharmacy record or file, electronic behavioral health record or file, or personal health record or file. At step 2306, the access session recording can also be stored in the database 20H of the provider communication device 21, and/or can be stored in the database 10H of the central processing computer component 110A and/or in the respective electronic healthcare record, electronic medical record or electronic healthcare file, electronic dental record or file, electronic pharmacy record or file, electronic behavioral health record or file, or personal health record or file, of the individual or patient.

At step 2306, the access session recording can also be transmitted to the individual's or patient's user or patient communication device 41. Thereafter, at step 2306, the provider communication device 21 and the central processing computer component 110A can store all information regarding the accessing of the respective electronic healthcare record, electronic medical record or electronic healthcare file, electronic dental record or file, electronic pharmacy record or file, electronic behavioral health record or file, or personal health record or file, of the individual or patient. Thereafter, the operation of the apparatus 300 will proceed to step 2307.

At step 2307, the central processing computer component 110A of the central processing computer/distributed ledger/Blockchain technology system 110 and/or the provider communication device 21 can generate and store, in an electronic record access transaction record or file for the individual or patient, and in the database 10H of the central processing computer component 110A, an access session report containing the access session recording and data and/or information regarding, at least, but not limited to, the date and time of the granting of the permission to access by the individual or patient, the specific or respective electronic healthcare record, electronic medical record or electronic healthcare file, electronic dental record or file, electronic pharmacy record or file, electronic behavioral health record or file, or personal health record or file, to which access has been granted permission, the healthcare provider, healthcare insurer, healthcare payer, intermediary, governmental entity, or other person or entity, who or which has been granted access permission. the date and time of access, by the respective healthcare provider, healthcare insurer, healthcare payer, intermediary, governmental entity, or other person or entity, of the specific or respective electronic healthcare record, electronic medical record or electronic healthcare file, electronic dental record or file, electronic pharmacy record or file, electronic behavioral health record or file, or personal health record or file, the duration of the accessing of, or use of, the specific or respective electronic healthcare record, electronic medical record or electronic healthcare file, electronic dental record or file, electronic pharmacy record or file, electronic behavioral health record or file, or personal health record or file, a video recording or a video clip of the respective healthcare provider, healthcare insurer, healthcare payer, intermediary, governmental entity, or other person or entity, during his or her accessing of, and/or use of, the specific or respective electronic healthcare record, electronic medical record or electronic healthcare file, electronic dental record or file, electronic pharmacy record or file, electronic behavioral health record or file, or personal health record or file; a video recording or video clip of the screen of the respective display device 20E, 30E, or 40E, of the respective communication device 20, 21, 30, 31, 50, or 51, used by the respective healthcare provider, healthcare insurer, healthcare payer, intermediary, governmental entity, or other person or entity, recording all actions taken by the respective healthcare provider, healthcare insurer, healthcare payer, intermediary, governmental entity, or other person or entity during the accessing session, a copy of an access alert message generated and transmitted to a communication device 40 or 41 of the individual or patient, or caregiver, a copy of an electronic record access report, if generated, information regarding a reason for the accessing or use of the specific or respective electronic healthcare record, electronic medical record or electronic healthcare file, electronic dental record or file, electronic pharmacy record or file, electronic behavioral health record or file, or personal health record or file, information regarding a description of any activity performed during the accessing or use of the specific or respective electronic healthcare record, electronic medical record or electronic healthcare file, electronic dental record or file, electronic pharmacy record or file, electronic behavioral health record or file, or personal health record or file, a description of information or data updated, changed, altered, or modified, during the accessing or use of the specific or respective electronic healthcare record, electronic medical record or electronic healthcare file, electronic dental record or file, electronic pharmacy record or file, electronic behavioral health record or file, or personal health record or file, a copy of any insurance claim submitted or claim for payment submitted as a result of the accessing or use of the specific or respective electronic healthcare record, electronic medical record or electronic healthcare file, electronic dental record or file, electronic pharmacy record or file, electronic behavioral health record or file, or personal health record or file, and/or information regarding the status of payment of or for same, any data and/or information, message(s), and/or report(s), described herein as being generated, recorded, or stored, regarding any video call, remote or virtual office visit, remote or distance examination, or in-person office visit or in-person examination described herein or otherwise; and/or any other data and/or information which may be needed, required, or desired, for documenting the accessing and/or the use of the individual's or patient's respective electronic healthcare record, electronic medical record or electronic healthcare file, electronic dental record or file, electronic pharmacy record or file, electronic behavioral health record or file, or personal health record or file.

At step 2307, the central processing computer component 110A of the central processing computer/distributed ledger/Blockchain technology system 110 and/or the provider communication device 21 can transmit an access session report message containing the access session report to the user or patient communication device 41. Thereafter, the operation of the apparatus 300 will cease at step 2305.

In another preferred embodiment, the apparatus 300 of FIG. 23 can be used in a same, a similar, and/or an analogous, manner in conjunction with, or in connection with, insurer/payer communication devices 31, in the case of healthcare insurers or healthcare payers seeking access to an individual's or patient's electronic healthcare record, electronic medical record or electronic healthcare file, electronic dental record or file, electronic pharmacy record or file, electronic behavioral health record or file, or personal health record or file, or in conjunction with, or in connection with, governmental entity/intermediary communication device 51, in the case of intermediaries or governmental entities and/or their agents or employees seeking access to an individual's or patient's electronic healthcare record, electronic medical record or electronic healthcare file, electronic dental record or file, electronic pharmacy record or file, electronic behavioral health record or file, or personal health record or file. In another preferred embodiment, the apparatus 300 can also be utilized by a caregiver of the individual or patient in a same, a similar, and/or an analogous, manner as described in connection with the operation of the apparatus 300 in FIG. 23.

In another preferred embodiment of the embodiment of FIG. 23, the individual, patient, or caregiver of the individual or patient, can, at any time, access central processing computer component 110A of the central processing computer/distributed ledger/Blockchain technology system 110 and access the electronic record access transaction record or file of for the individual or patient in order to request, and be provided with, via a respective user or patient communication device 41, and information, data, messages reports, access session report message recordings, session recordings, and/or any other information, which can be stored in the electronic record access transaction record or file of for the individual or patient. In another preferred embodiment, the apparatus 100 or the apparatus 200 can be utilized in a same, a similar, or an analogous, manner as the apparatus 300 in the embodiment of FIG. 23.

In another preferred embodiment of the embodiment of FIG. 23, the apparatus 300 can also, at step 2306 authenticate the healthcare provider, or any other person seeking to access to the individual's or patient's electronic healthcare record, electronic medical record or electronic healthcare file, electronic dental record or file, electronic pharmacy record or file, electronic behavioral health record or file, or personal health record or file, using the location-based authentication described herein and in the embodiment of FIG. 19, prior to allowing him or her access to the individual's or patient's electronic healthcare record, electronic medical record or electronic healthcare file, electronic dental record or file, electronic pharmacy record or file, electronic behavioral health record or file, or personal health record or file.

In another preferred embodiment, the apparatus 100, the apparatus 200, and/or the apparatus 300, of the present invention can be utilized by an individual, a patient, or a caregiver for an individual or patient, to schedule an appointment for an in-office visit, an in-office examination, an in-person visit, an in-person examination, a house-call visit, a house-call examination, a tele-health appointment, a tele-health visit, a remote or a virtual provider visit, or a remote or a distance examination. It is important to note that the terms "tele-health" and "telehealth" are used interchangeable herein.

Figure 24:
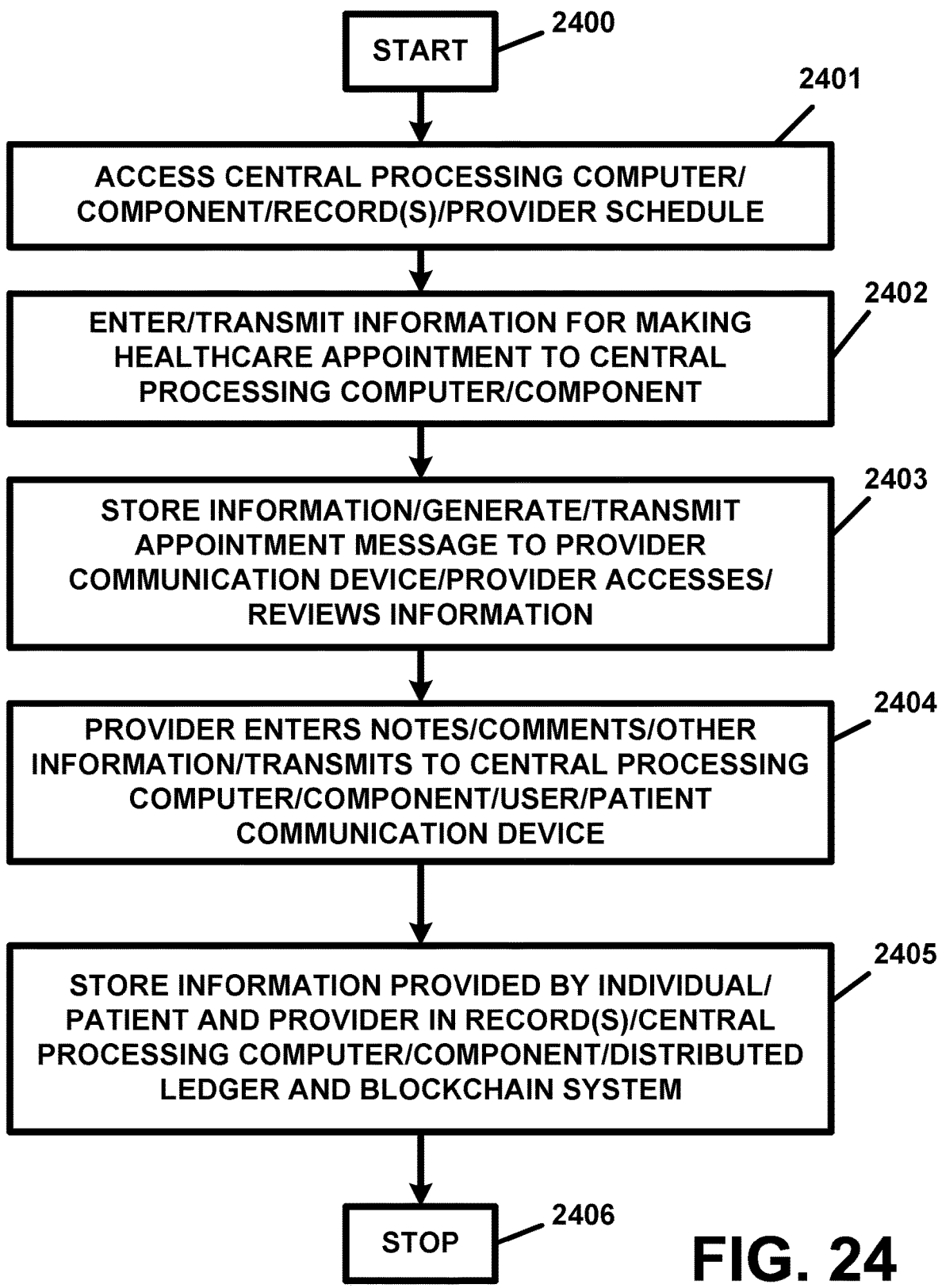
FIG. 24 illustrates another preferred embodiment method of utilizing the apparatus of the present invention, in flow diagram form.

FIG. 24 illustrates another preferred embodiment method for utilizing the apparatus 300 of the present invention, in flow diagram form. Although described as being utilized in conjunction with, or in connection with, the apparatus 300, it is important to note that the method of FIG. 24 can also be utilized in a same, a similar, and/or an analogous manner in conjunction with, or in connection with, the apparatus 100 and/or the apparatus 200. With reference to FIG. 24, the operation of the apparatus 300 commences at step 2400. At step 2401, the individual or patient, or a caregiver of the individual or patient, can access the central processing computer component 110A of the central processing computer/distributed ledger/Blockchain technology system 110 with or using his or her user user or patient communication device 41. At step 2401, the individual or patient, or a caregiver of the individual or patient, can also access the individual's or patient's respective electronic healthcare record, electronic medical record or electronic healthcare file, electronic dental record or file, electronic pharmacy record or file, electronic behavioral health record or file, or personal health record or file (referred to hereinafter as "electronic health record" for purposes of this embodiment of FIG. 24).

At step 2401, the individual or patient, or a caregiver of the individual or patient, can utilize his or her user or patient communication device 41, in communication with the central processing computer component 110A, in order to search for and/or to select, or identify, the healthcare provider with which he or she is seeking to make an appointment. In a preferred embodiment, the appointment can be for any in-office visit, in-office examination, in-person visit, in-person examination, house-call visit, house-call examination, tele-health appointment, tele-health visit, remote or virtual provider visit, or remote or distance examination (referred to hereinafter as "healthcare appointment" for purposes of this embodiment of FIG. 24). At step 2401, the central processing computer component 110A can transmit, to the user or patient communication device 41, information regarding the selected or identified healthcare provider and/or any information regarding his, her, or its, schedule, available appointment days and/or time listings, and/or any other information for allowing the individual or patient, or the caregiver of the individual or patient, to make a healthcare appointment with the selected or identified healthcare provider.

Thereafter, at step 2402, the individual or patient, or the caregiver of the individual or patient, can utilize his or her user or patient communication device 41 in order to enter, and to transmit, to the central processing computer component 110A, any and/or all information needed for making the healthcare appointment with the selected or identified healthcare provider. In a preferred embodiment, at step 2402, the individual or patient, or the caregiver of the individual or patient, can enter into the user or patient communication device 41 and can transmit, to the central processing computer component 110A, information regarding the selected day and time of the healthcare appointment, information for identifying the individual or patient, and/or any notes, comments, or messages, regarding any illness, sickness, condition, or reason for the healthcare appointment. In a preferred embodiment, at step 2402, the individual or patient, or the caregiver of the individual or patient, can also enter into the user or patient communication device 41 and can also transmit, to the central processing computer component 110A, any healthcare insurance information, healthcare account information, healthcare insurance account information, healthcare spending account information, and/or any other information regarding the individual or patient.

In a preferred embodiment, at step 2402, the individual or patient, or the caregiver of the individual or patient, can also enter into the user or patient communication device 41 and can also transmit, to the central processing computer component 110A, any permission needed for allowing the healthcare provider to access the individual's or patient's electronic health record. In a preferred embodiment, at step 2402, the individual or patient, or the caregiver of the individual or patient, can also enter into the user or patient communication device 41 and can also transmit, to the central processing computer component 110A, any picture(s), photograph(s), or video recording or video clip, of or regarding the individual's or patient's condition. In a preferred embodiment, at step 2402, the individual or patient, or the caregiver, can record a video message, in order to provide the healthcare provider with additional or other information, with the user or patient communication device 41, or with any other video recording device, and can transmit the video message which was recorded from the user or patient communication device 41 to the central processing computer component 110A.

In a preferred embodiment, any and all information described herein as being transmitted from the user or patient communication device 41 to the central processing computer component 110A, at and during step 2402, can be, at step 2403, stored in the database 10H of the central processing computer component 110A and/or in the individual's or patient's electronic health record. Thereafter, at step 2403, the central processing computer component 110A can generate a healthcare appointment message and can transmit the healthcare appointment message to the user or patient communication device 41 and/or to the provider communication device 21 of the healthcare provider with whom the healthcare appointment has been made. In another preferred embodiment, at any time ups to the time of the healthcare appointment, the central processing computer component 110A can generate a healthcare appointment reminder message(s) and can transmit the healthcare appointment message(s) to the user or patient communication device 41 and/or to the provider communication device 21.

In a preferred embodiment, at or during step 2403, at any time prior to, before, during, or after, the healthcare appointment, the healthcare provider can access, via his or her provider communication device 21, any information provided by the individual or patient, or the caregiver, at step 2402, including, but not limited to, any of the notes, comments, or messages, regarding any illness, sickness, condition, or reason for the healthcare appointment, any healthcare insurance information, healthcare account information, healthcare insurance account information, healthcare spending account information, and/or any other information regarding the individual or patient, any permission needed for allowing the healthcare provider to access the individual's or patient's electronic health record, any picture(s), photograph(s), or video recording or video clip, of or regarding the individual's or patient's condition, and/or any video message was provided. In a preferred embodiment, at any time prior to, before, during, or after, the healthcare appointment, the healthcare provider can also access and review the individual's or patient's electronic health record.

In another preferred embodiment, the individual or patient, or the caregiver, can, at step 2402, and/or at any time before the healthcare appointment, can access the central processing computer component 110A can enter any additional notes, comments, or messages, regarding any illness, sickness, condition, or reason for the healthcare appointment, any additional or revised healthcare insurance information, healthcare account information, healthcare insurance account information, healthcare spending account information, and/or any other revised information regarding the individual or patient, any revised or updated permission needed for allowing the healthcare provider to access the individual's or patient's electronic health record, any additional or revised picture(s), photograph(s), or video recording(s) or video clip(s), of or regarding the individual's or patient's condition, and/or any additional video message(s), any or all of which can be accessed and reviewed by the healthcare providers at any time prior to, before, during, or after, the healthcare appointment.

At step 2304, the healthcare provider, after reviewing any information provided by the individual or patient, or the caregiver, at step 2402, can also enter into his or her provider communication device 21, and can transmit to the central processing computer component 110A and/or to the user or patient communication device 41 of the individual or patient, or the caregiver, any information, notes, messages, or comments, or any picture(s), photograph(s), or video recording(s) or video clip(s), for including in the individual's or patient's electronic healthcare record regarding the healthcare appointment and/or for providing information to the individual or patient, or the caregiver, in advance of the healthcare appointment.

Thereafter, at step 2405, any and/or all information, described herein as being provided by the individual or patient, or the caregiver, and any and/or all information described herein as being provided by the healthcare provider in the preferred embodiment of FIG. 24, can be stored in the database 10H of the central processing computer component 110A of the central processing computer/distributed ledger/Blockchain technology system 110, and/or in the distributed ledger and Blockchain technology system component 110B of the central processing computer/distributed ledger/Blockchain technology system 110, and/or in the electronic health record of the individual or patient in the database 10H, and/or in the database 20H of the provider communication device 21, and/or in the database 40H of the user or patient communication device 41. Thereafter, the operation of the apparatus 300 will cease at step 2406.

In another preferred embodiment of the embodiment of FIG. 24, the individual or patient, or the caregiver, can utilize his or her user or patient communication device 41 to access, and communicate directly with, the provider communication device 21 of the healthcare provider with whom the healthcare appointment is desired. In this regard, in such a preferred embodiment, the individual or patient, or the caregiver, can dispense with needing to access, and communicating with, the central processing computer component 110A of the central processing computer/distributed ledger/Blockchain technology system 110. In such an embodiment, the individual or patient, or the caregiver, can utilize his or her user or patient communication device 41 to access, and communicate directly with, the provider communication device 21 in order to effectuate the making of the healthcare appointment. In this regard, the preferred embodiment of FIG. 24 can be performed in a same, a similar, and/or an analogous, manner, with all communications and/or interactions taking place solely between the user or patient communication device 41 and the provider communication device 21 of the healthcare provider with whom the healthcare appointment is desired, so as allow the individual or patient, or the caregiver, to make the healthcare appointment directly with the healthcare provider's provider communication device 21.

In another preferred embodiment, the apparatus 100, the apparatus 200, or the apparatus 300, of the present invention can also be utilized in order to allow an individual or patient, or a caregiver of the individual or patient, to identify, and/or to locate, or to allow the apparatus 100, the apparatus 200, or the apparatus 300, to select, identify, or locate, a healthcare provider who is available for conducting an in-office visit, an in-office examination, an in-person visit, an in-person examination, a house-call visit, a house-call examination, a tele-health appointment, a tele-health visit, a remote or a virtual provider visit, or a remote or a distance examination, with the individual or patient, or the caregiver, at any given moment in time, and/or in an emergency situation and/or on an emergency basis.

In such a preferred embodiment, it is envisioned that healthcare providers of any and/or all types or kinds can post, with the central processing computer 10 or with the central processing computer component 110A of the central processing computer/distributed ledger/Blockchain technology system 110, depending upon the apparatus 100, 200, or 300 being used, information regarding themselves, their practices, their qualifications and/or experience, the insurances or payment methods which they accept, and/or any other pertinent information, and/or any information regarding their availability to conduct in-office visits, in-office examinations, in-person visits, in-person examinations, house-call visits, house-call examinations, tele-health appointments, tele-health visits, remote or virtual provider visits, or remote or distance examinations, with the individual or patient, or the caregiver, on an emergency basis and/or at any other given moment in time. In such a preferred embodiment, the respective apparatus 100, 200, or 300, of the present invention can be utilized in to allow an individual or patient, or a caregiver of the individual or patient, to identify, and/or to locate, a healthcare provider, or any number of healthcare providers, who are available in an on-demand basis or otherwise, and to allow the individual or patient, or the caregiver, to schedule an in-office visit, an in-office examination, an in-person visit, an in-person examination, a house-call visit, a house-call examination, a tele-health appointment, a tele-health visit, a remote or a virtual provider visit, or a remote or a distance examination, with the healthcare provider on an on-demand or emergency basis.

Figure 25:
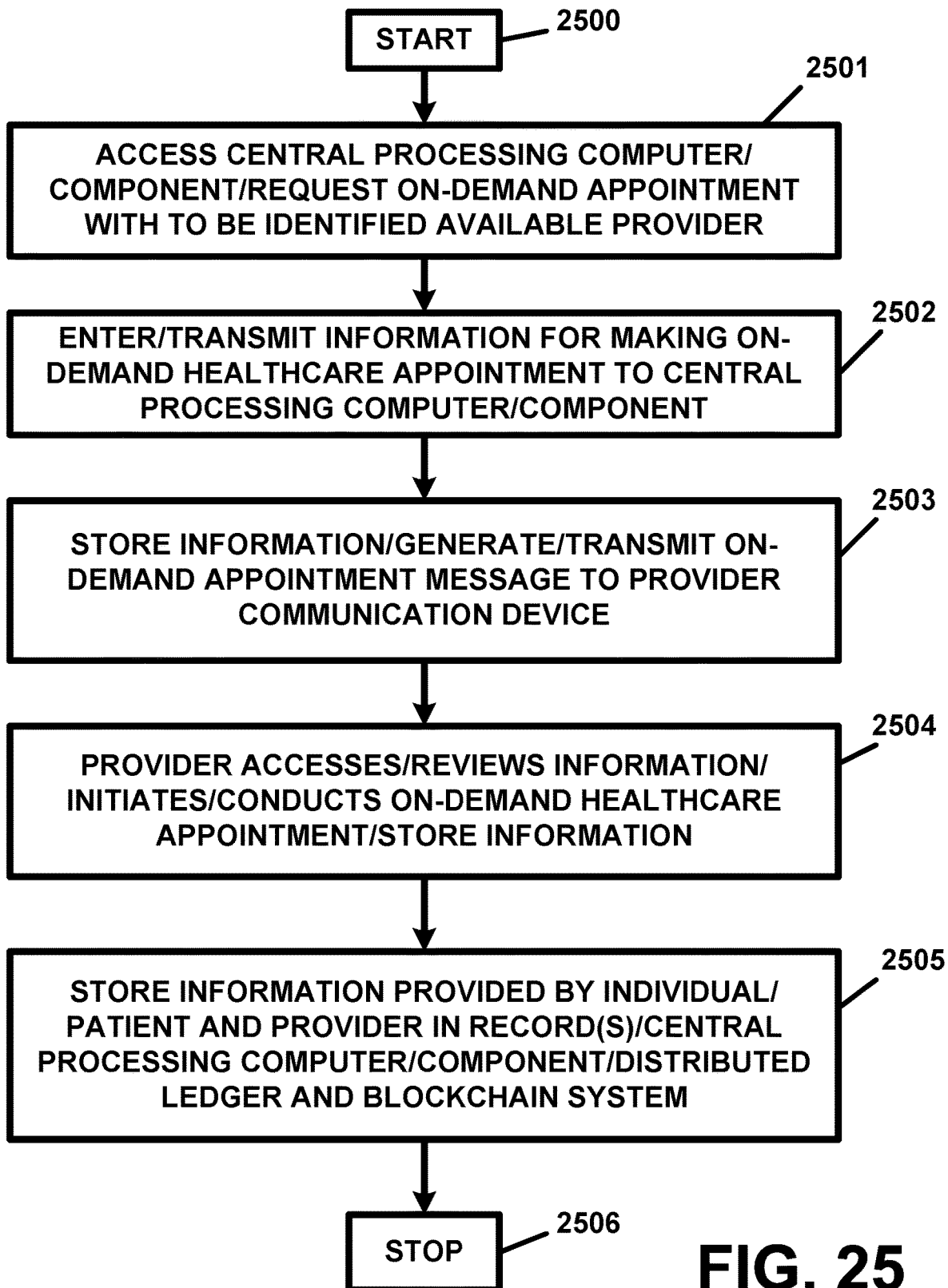
FIG. 25 illustrates yet another preferred embodiment method of utilizing the apparatus of the present invention, in flow diagram form.

FIG. 25 illustrates another preferred embodiment method for utilizing the apparatus 300 of the present invention, in flow diagram form. Although described as being utilized in conjunction with, or in connection with, the apparatus 300, it is important to note that the method of FIG. 25 can also be utilized in a same, a similar, and/or an analogous manner in conjunction with, or in connection with, the apparatus 100 and/or the apparatus 200.

With reference to FIG. 25, the operation of the apparatus 300 commences at step 2500. At step 2501, the individual or patient, or a caregiver of the individual or patient, can access the central processing computer component 110A of the central processing computer/distributed ledger/Blockchain technology system 110 with or using his or her user or patient communication device 41. At step 2501, the individual or patient, or a caregiver of the individual or patient, can also access the individual's or patient's respective electronic healthcare record, electronic medical record or electronic healthcare file, electronic dental record or file, electronic pharmacy record or file, electronic behavioral health record or file, or personal health record or file (referred to hereinafter as "electronic health record" for purposes of this embodiment of FIG. 25).

At step 2501, the individual or patient, or a caregiver of the individual or patient, can utilize his or her user or patient communication device 41, in communication with the central processing computer component 110A, in order to request an appointment with a healthcare provider in an on-demand basis or in an emergency basis. In a preferred embodiment, the appointment can be for any in-office visit, in-office examination, in-person visit, in-person examination, house-call visit, house-call examination, tele-health appointment, tele-health visit, remote or virtual provider visit, or remote or distance examination (referred to hereinafter as "on-demand healthcare appointment" for purposes of this embodiment of FIG. 25). At step 2501, the central processing computer component 110A can transmit, to the user or patient communication device 41, information regarding one or more identified or located healthcare providers, who are available on-demand or on an emergency basis, and/or any information regarding each of one or more identified or located healthcare providers. In a preferred embodiment, the information regarding their area of practice and/or specialization and any other information which might be used for making a selection of a healthcare provider. At step 2501, the individual or patient, or the caregiver, can select the healthcare provider for the on-demand healthcare appointment, and can transmit information regarding the selection from the user or patient communication device 41 to the central processing computer component 110A.

In another preferred embodiment, at step 2501, the healthcare provider can be identified or located as being the only healthcare provider who is available for an on-demand healthcare appointment, or the central processing computer component 110A can select, identify, and/or locate, the healthcare provider for the on-demand healthcare appointment from among a plurality of available healthcare providers and in any appropriate manner, and/or randomly or otherwise.

Thereafter, at step 2502, the individual or patient, or the caregiver, can utilize his or her user or patient communication device 41 in order to enter, and to transmit, to the central processing computer component 110A, any and/or all information needed for making the on-demand healthcare appointment with the identified or located healthcare provider. In a preferred embodiment, at step 2502, the individual or patient, or the caregiver of the individual or patient, can enter into the user or patient communication device 41 and can transmit, to the central processing computer component 110A, information for identifying the individual or patient, and/or any notes, comments, or messages, regarding any illness, sickness, condition, or reason for the on-demand healthcare appointment. In a preferred embodiment, at step 2502, the individual or patient, or the caregiver of the individual or patient, can also enter into the user or patient communication device 41 and can also transmit, to the central processing computer component 110A, any healthcare insurance information, healthcare account information, healthcare insurance account information, healthcare spending account information, and/or any other information regarding the individual or patient.

In a preferred embodiment, at step 2502, the individual or patient, or the caregiver of the individual or patient, can also enter into the user or patient communication device 41 and can also transmit, to the central processing computer component 110A, any permission needed for allowing the healthcare provider to access the individual's or patient's electronic health record. In a preferred embodiment, at step 2502, the individual or patient, or the caregiver of the individual or patient, can also enter into the user or patient communication device 41 and can also transmit, to the central processing computer component 110A, any picture(s), photograph(s), or video recording or video clip, of or regarding the individual's or patient's condition. In a preferred embodiment, at step 2502, the individual or patient, or the caregiver, can record a video message, in order to provide the healthcare provider with additional or other information, with the user or patient communication device 41, or with any other video recording device, and can transmit the video message which was recorded from the user or patient communication device 41 to the central processing computer component 110A.

In a preferred embodiment, any and all information described herein as being transmitted from the user or patient communication device 41 to the central processing computer component 110A, at and during step 2502, can be, at step 2503, stored in the database 10H of the central processing computer component 110A and/or in the individual's or patient's electronic health record. Thereafter, at step 2503, the central processing computer component 110A can generate a healthcare on-demand appointment message and can transmit the healthcare on-demand appointment message to the provider communication device 21 of the healthcare provider with whom the on-demand healthcare appointment is requested.

At step 2504, the healthcare provider can access, via his or her provider communication device 21, any information provided by the individual or patient, or the caregiver, at step 2502, including, but not limited to, any of the notes, comments, or messages, regarding any illness, sickness, condition, or reason for the healthcare appointment, any healthcare insurance information, healthcare account information, healthcare insurance account information, healthcare spending account information, and/or any other information regarding the individual or patient, any permission needed for allowing the healthcare provider to access the individual's or patient's electronic health record, any picture(s), photograph(s), or video recording or video clip, of or regarding the individual's or patient's condition, and/or any video message was provided. In a preferred embodiment, at any time prior to, before, during, or after, the on-demand healthcare appointment, the healthcare provider can also access and review the individual's or patient's electronic health record.

At step 2504, the healthcare provider, after reviewing any information provided by the individual or patient, or the caregiver, at step 2502, can initiate, and can conduct, the on-demand healthcare appointment with the individual or patient. Thereafter, at step 2505, any and/or all information, described herein as being provided by the individual or patient, or the caregiver, and any and/or all information provided by the healthcare provider before or during the on-demand healthcare appointment, can be stored in the database 10H of the central processing computer component 110A of the central processing computer/distributed ledger/ Blockchain technology system 110, and/or in the distributed ledger and Blockchain technology system component 110B of the central processing computer/distributed ledger/Blockchain technology system 110, and/or in the electronic health record of the individual or patient in the database 10H, and/or in the database 20H of the provider communication device 21, and/or in the database 40H of the user or patient communication device 41. Thereafter, the operation of the apparatus 300 will cease at step 2506.

In another preferred embodiment of the embodiment of FIG. 25, the individual or patient, or the caregiver, can utilize his or her user or patient communication device 41 to access, and communicate directly with, the provider communication device 21 of the healthcare provider with whom the on-demand healthcare appointment is desired. In this regard, in such a preferred embodiment, the individual or patient, or the caregiver, can dispense with needing to access, and communicating with, the central processing computer component 110A of the central processing computer/distributed ledger/Blockchain technology system 110. In such an embodiment, the individual or patient, or the caregiver, can utilize his or her user or patient communication device 41 in order to access, and communicate directly with, the provider communication device 21 in order to effectuate the making of the on-demand healthcare appointment. In this regard, the preferred embodiment of FIG. 25 can be performed in a same, a similar, and/or an analogous, manner, with all communications and/or interactions taking place solely between the user or patient communication device 41 and the provider communication device 21 of the healthcare provider with whom the on-demand healthcare appointment is desired, so as allow the individual or patient, or the caregiver, to make the on-demand healthcare appointment directly with the healthcare provider's provider communication device 21.

In view of the foregoing, the apparatus 300 of the embodiment of FIG. 25 can be utilized in order to allow an individual or patient, or a caregiver of the individual or patient, to make an on-demand appointment or an emergency appointment, for any in-office visit, in-office examination, in-person visit, in-person examination, house-call visit, house-call examination, tele-health appointment, tele-health visit, remote or virtual provider visit, or remote or distance examination, with an available healthcare provider at any given time and/or in an on-demand basis or on an emergency basis.

In another preferred embodiment, the apparatus 100, the apparatus 200, and/or the apparatus 300, of the present invention can also be utilized in order to provide healthcare tracking, healthcare monitoring, treatment tracking, treatment plan tracking, and/or wellness tracking, for individuals or patients. In such a preferred embodiment, the user or patient communication device 40 or 41 can be connected to or with, or linked to or with, any of the herein-described healthcare equipment input devices, or healthcare measurement input devices, or healthcare monitoring input devices, or user/patient monitoring systems 94. In a preferred embodiment, the user or patient communication device 40 or 41 can be connected to or with, or linked to or with, any of the herein-described healthcare equipment input devices, or healthcare measurement input devices, or healthcare monitoring input devices, or user/patient monitoring systems 94, via a wired connection, a wireless connection, a Wi-Fi connection, a Bluetooth connection, or any combination of same.

In a preferred embodiment, the user or patient communication device 40 or 41 can be programmed, or can otherwise be designed or configured, to activate, de-activate, and/or control an operation of, any of the healthcare equipment input devices, or healthcare measurement input devices, or healthcare monitoring input devices, or user/patient monitoring systems 94. In a preferred embodiment, the user or patient communication device 40 or 41 can also be programmed. or can otherwise be designed or configured, to obtain measurements or readings from any of the healthcare equipment input devices, or healthcare measurement input devices, or healthcare monitoring input devices, or user/patient monitoring systems 94, at any time desired by the individual or patient, at any pre-defined or pre-determined time intervals, at scheduled times, and/or at any time desired or required by a healthcare provider.

In a preferred embodiment, the user or patient communication device 40 or 41 can obtain a measurement or reading from any healthcare equipment input device, or healthcare measurement input device, or healthcare monitoring input device, or user/patient monitoring system 94, or from a number of healthcare equipment input devices, or healthcare measurement input devices, or healthcare monitoring input devices, or user/patient monitoring systems 94, can store the data and/or information obtained from the respective measurement or reading in the database 40H of the individual's or patient's user or patient communication device 40 or 41 and/or in the individual's or patient's personal health records or files (PHRs) which are stored in the database 40H of the individual's or patient's user or patient communication device 40 or 41. In a preferred embodiment, the user or patient communication device 40 or 41 can also generate a respective healthcare tracking report, healthcare monitoring report, treatment tracking report, treatment plan tracking report, and/or wellness tracking report, and can transmit same to the provider communication device(s) 20 or 21 of each of the individual's or patient's healthcare and/or to central processing computer 10 of the apparatus 100 or to the central processing computer component 110A of the central processing computer/distributed ledger/Blockchain technology system 110 of the apparatus 200 or the apparatus 300. Thereafter, the respective healthcare tracking report, healthcare monitoring report, treatment tracking report, treatment plan tracking report, and/or wellness tracking report, and any data and/or information contained therein can be stored in the respective databases 20H or 10H of the respective devices or computers. Once the respective healthcare tracking report, healthcare monitoring report, treatment tracking report, treatment plan tracking report, and/or wellness tracking report, is received at the provider communication device 20 or 21, the healthcare provider can review the data and/or information contained in the same and take any needed or appropriate action, such as, for example, scheduling an in-office visit, in-office examination, in-person visit, in-person examination, house-call visit, house-call examination, tele-health appointment, tele-health visit, remote or virtual provider visit, or remote or distance examination (referred to hereinafter as "healthcare appointment" for purposes of this embodiment of FIG. 26), with the individual or patient, scheduling a procedure or a surgical procedure, issuing a prescription, or taking any other appropriate course of action.

In a preferred embodiment, and as described herein, the healthcare equipment input devices, or healthcare measurement input devices, or healthcare monitoring input devices, can be, or can be or can include, but are not limited to, any one or more of, and/or any combination of, a thermometer, a digital thermometer, a stethoscope, a heart rate monitor or measurement device, a pulse rate monitor or measurement device, a blood pressure monitor or measurement device, a blood oxygen or percentage oxygen measurement device, a blood pressure measurement device, a blood glucose monitor, a blood oxygen percentage level monitor, an oximeter, a digital finger pulse oximeter, a blood analysis device or machine, a respirator, a respiration monitoring or measurement device, a dialysis machine, a dialysis device, electrocardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laparoscopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedance measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, dental probe, microscopic camera probing device, and/or any other bio-metric or physiological data measuring device(s) and/or data acquisition device data acquisition device. In a preferred embodiment, and as described herein, the healthcare equipment input devices, or healthcare measurement input devices, or healthcare monitoring input devices, can be, or can be a component of, an user input device 40D of the individual's or patient's user or patient communication device 40.

Figure 26:
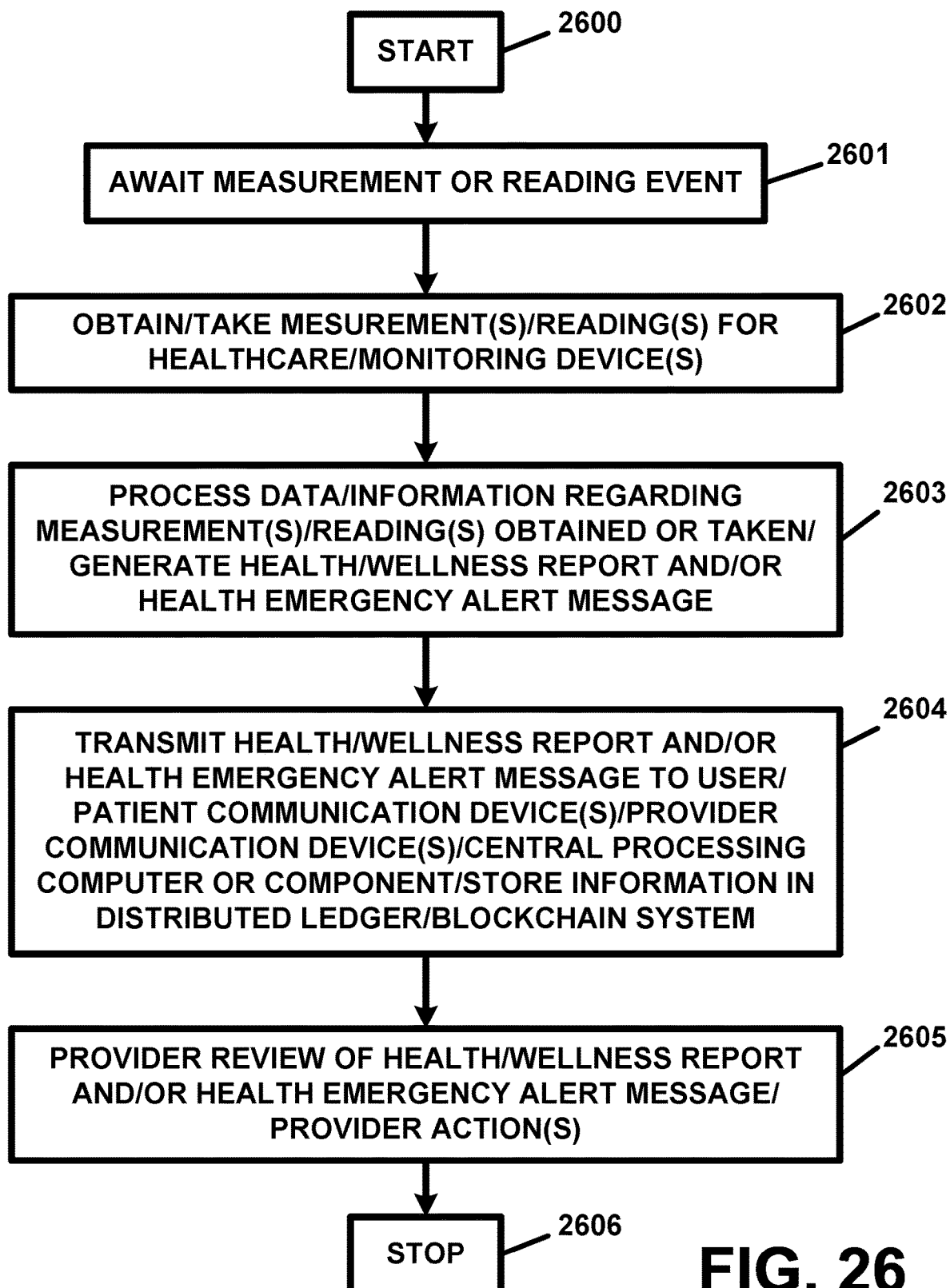
FIG. 26 illustrates yet another preferred embodiment method of utilizing the apparatus of the present invention, in flow diagram form.

FIG. 26 illustrates another preferred embodiment method of utilizing the apparatus 300 of the present invention, in flow diagram form. Although described as being utilized in conjunction with, or in connection with, the apparatus 300, the embodiment of FIG. 26 can also be utilized in a same, a similar, and/or an analogous, manner in conjunction with, or in connection with, the apparatus 100 or the apparatus 200. In the preferred embodiment of FIG. 26, it is envisioned that the individual or patient, or his or her caregiver, can initiate and/or can take or obtain any measurement or reading of, from, or using, any one or more of the healthcare equipment input devices, or healthcare measurement input devices, or healthcare monitoring input devices, or user/patient monitoring systems, at any time or on-demand. It is also envisioned that the individual's or patient's user or patient communication device 41 can be used or can be programmed to initiate and/or to take or obtain any measurement or reading of, from, or using, any one or more of the healthcare equipment input devices, or healthcare measurement input devices, or healthcare monitoring input devices, or user/patient monitoring systems, at one or more scheduled times or at scheduled time intervals. It is also envisioned that the individual's or patient's user or patient communication device 41 can be programmed to initiate and/or to take or obtain any measurement or reading of, from, or using, any one or more of the healthcare equipment input devices, or healthcare measurement input devices, or healthcare monitoring input devices, or user/patient monitoring systems, at one or more scheduled times or at scheduled time intervals, such as by being programmed by the individual or patient, his or her caregiver, or his or her healthcare provider, or by a healthcare provider via his or her provider communication device 21, or via the central processing computer component 110A of the central processing computer and distributed ledger and Blockchain technology system 110. It is also envisioned that the individual's or patient's healthcare provider, remotely and/or by using his or her provider communication device 21, and/or that the central processing computer component 110A of the central processing computer and distributed ledger and Blockchain technology system 110, can initiate and/or can take or obtain any measurement or reading of, from, or using, any one or more of the healthcare equipment input devices, or healthcare measurement input devices, or healthcare monitoring input devices, or user/patient monitoring systems, at any time, on-demand, at one or more scheduled times or at scheduled time intervals. In the above-described manner, any of the herein-described healthcare, and/or healthcare-related, and/or wellness-related, measurements or readings regarding the individual or patient can be obtained and reported by using the healthcare equipment input devices, or healthcare measurement input devices, or healthcare monitoring input devices, or user/patient monitoring systems 94.

With reference to FIG. 26, the operation of the apparatus 300 commences at step 2600. At step 2601, the individual's or patient's user or patient communication device 41 can await a healthcare, and/or healthcare-related, and/or wellness-related, measurement or reading event (hereinafter "the measurement or reading event"). In a preferred embodiment, the measurement or reading event can include or can entail the obtaining or the taking of a measurement or reading from any one or more of the herein-described healthcare equipment input devices, or healthcare measurement input devices, or healthcare monitoring input devices, or user/patient monitoring systems 94. As and for an example, in an exemplary embodiment of FIG. 26, the measurement or reading event can include the obtaining or the taking of measures of readings for each of blood pressure, pulse rate, heart rate, blood-glucose level or blood-sugar level, blood oxygen percentage level, and body temperature by using each respective item of healthcare equipment input devices, healthcare measurement input devices, healthcare monitoring input devices, or user/patient monitoring systems 94. It is important to note, however, that any measurement or reading can be taken by or with any one or more of the herein-described healthcare equipment input devices, healthcare measurement input devices, healthcare monitoring input devices, or user/patient monitoring systems 94, or by or with any combination of same.

At step 2602, upon the detection of, or the occurrence of, the measurement or reading event, the individual's or patient's user or patient communication device 41 can take or obtain any and/or all measurements or readings with or using the healthcare equipment input device(s), healthcare measurement input device(s), healthcare monitoring input device(s), or user/patient monitoring system(s) 94. In a preferred embodiment, the user or patient communication device 41, and/or the CPU 40A of same, can activate, control the operation of, and/or de-activate, the respective healthcare equipment input device(s), healthcare measurement input device(s), healthcare monitoring input device(s), or user/patient monitoring systems 94, as needed in order to obtain any measurement or reading for any and/or all measurements or readings.

At step 2603, the user or patient communication device 41 can process any and/or all data and/or information regarding any one or more and/or any and/or all of the measurements or readings obtained or taken with or from, each of the respective healthcare equipment input device(s), healthcare measurement input device(s), healthcare monitoring input device(s), or user/patient monitoring system(s) 94, during step 2602. At step 2603, the user or patient communication device 41 can determine whether or not any measurement or reading obtained or taken, using each respective healthcare equipment input device(s), healthcare measurement input device(s), healthcare monitoring input device(s), or user/patient monitoring system(s) 94, is higher or lower than normal or expected for the individual or patient, within range of that which is normal or expected for the individual or patient, or represents a healthcare emergency situation for or regarding the individual or patient.

At step 2603, the user or patient communication device 41 can generate a healthcare tracking report, a healthcare monitoring report, a treatment tracking report, a treatment plan tracking report, and/or a wellness tracking report (hereinafter referred to as "health/wellness report") which an contain information regarding the identify of the individual or patient, information regarding all of the measurements or readings obtained or taken during the measurement or reading event, the identify of the respective healthcare equipment input device(s), healthcare measurement input device(s), healthcare monitoring input device(s), or user/patient monitoring system(s) 94, used on obtaining or taking each measurement or recording, the date and time of the measurement or reading event, an identification of the user or patient communication device 41 that generated the health/wellness report, the IP address of the user or patient communication device 41, for, or in the case of, a stationary user or patient communication device 41, or information regarding the position or location of the user or patient communication device 41, as determined by the global positioning device 40K of the user or patient communication device 41, for, or in the case of, a mobile user or patient communication device 41, at the time of the generation of the health/wellness report, and/or any other data and/or information which can be deemed to be of interest regarding the measurement or reading event. In a preferred embodiment, if, at step 2603, the user or patient communication device 41 determines that any single measurement or reading, or any number of measurements or readings, is higher or lower than normal or expected for the individual or patient, or represents a healthcare emergency situation for or regarding the individual or patient, then the user or patient communication device 41 can, at step 2603, generate a health emergency alert message which, in a preferred embodiment, can contain information regarding, or for highlighting, the measurement(s) or reading(s), detected as being higher or lower than normal or expected for the individual or patient or as representing the healthcare emergency situation, and the health/wellness report and/or any information described herein as being contained in the health/wellness report.

At step 2604, the user or patient communication device 41 can transmit the health/wellness report and/or the health emergency alert message, if applicable, to each user or patient communication device 41 of or associated with the individual or patient, to each user or patient communication device 41 of or associated with the caregiver of the individual or patient, and to each provider communication device 41 associated with healthcare provider of the individual or patient, and/or to each provider communication device 41 associated with each healthcare provider of the individual or patient. At step 2604, the user or patient communication device 41 can transmit the health/wellness report and/or the health emergency alert message, if applicable, to central processing computer component 110A of the central processing computer and distributed ledger and Blockchain technology system 110 for storage in the database 10H of same and/or in the individual's or patient's electronic healthcare records or files, and/or for storage in the distributed ledger and Blockchain technology system component 110B of the central processing computer/distributed ledger/Blockchain technology system 110.

At step 2605, the healthcare provider can review the health/wellness report and/or the health emergency alert message, if applicable, and take appropriate action regarding same. For example, at step 2605, the healthcare provider can contact the individual or patient, or his or her caregiver, can schedule an in-office visit, in-office examination, in-person visit, in-person examination, house-call visit, house-call examination, tele-health appointment, tele-health visit, remote or virtual provider visit, or remote or distance examination, immediately and/or in the near future, schedule a procedure, remotely program or reprogram the individual's or patient's user or patient communication device 41 to reschedule another measurement or reading event or other measurements or readings, and/or perform any other activity deemed appropriate. At step 2605, the healthcare provider can also utilize the position or location information, of the user or patient communication device 41, in order to authenticate the individual or patient, as described herein, and/or as well as to be able to direct any assistance or emergency services to the individual or patient at the determined position or location information, of the user or patient communication device 41. Thereafter, at step 2605, the provider communication device 21 can store information regarding the healthcare provider's actions. Thereafter, the operation of the apparatus will cease at step 2606.

In any and/or all of the embodiments described herein, the apparatus 100, the apparatus 200, and/or the apparatus 300, can perform any and/or all of the functionalities described in U.S. Patent Application Publication No. 2017/0011190, which corresponds to U.S. patent application Ser. No. 15/275,537. Applicant hereby incorporates by reference herein the subject matter and teachings of U.S. patent application Ser. No. 15/275,537, which published as U.S. Patent Application Publication No. 2017/0011190, entitled "Apparatus And Method For Processing And/Or For Providing Healthcare Information And/Or Healthcare-Related Information", the subject matter and teachings of which are hereby incorporated by reference herein in their entirety. As and for an example, Applicant hereby incorporates by reference herein at least the subject matter and teachings of U.S. Patent Application Publication No. 2017/0011190 which are disclosed at paragraphs 0168 through 0226 and at paragraphs 0264 through 0619 and at FIGS. 7A through 29 (corresponding to Sheets 7 through 40 of the Drawings) as well as the entirety of the subject matter and teachings of U.S. Patent Application Publication No. 2017/0011190.

Applicant also hereby incorporates by reference herein the subject matter and teachings of U.S. patent application Ser. No. 15/230,400, which published as U.S. Patent Application Publication No. 2016/0342744, entitled "Apparatus And Method For Processing And/Or Providing Healthcare Information And/Or Healthcare-Related Information With Or Using An Electronic Healthcare Record Or Electronic Healthcare Records", the subject matter and teachings of which are hereby incorporated by reference herein in their entirety. As and for an example, Applicant hereby incorporates by reference herein at least the subject matter and teachings of U.S. Patent Application Publication No. 2016/0342744 which are disclosed at paragraphs 0192 through 0278 and at paragraphs 0341 through 0947 and at FIGS. 11 through 38 (corresponding to Sheets 11 through 50 of the Drawings) as well as the entirety of the subject matter and teachings of U.S. Patent Application Publication No. 2016/0342744.

Applicant also hereby incorporates by reference herein the subject matter and teachings of U.S. Pat. No. 6,662,194, entitled "Apparatus And Method For Providing Recruitment Information", the subject matter and teachings of which are hereby incorporated by reference herein in their entirety. At the very least, Applicant incorporates by reference herein the subject matter and teachings of U.S. Pat. No. 6,662,194 which disclose and teach various searching functionalities and scheduling and appointment functionalities as well as the entirety of the subject matter and teachings of U.S. Pat. No. 6,662,194.

In any and/or all of the embodiments described herein, any of the data and/or information, of any type or kind, and including, but not limited to, any and/or all of the data, information, messages, reports, video recordings or video clips, audio recordings, pictures, photographs, and/or other information, described herein as being transmitted to, received by processed by, generated by, transmitted from, or stored by or in, the central processing computer component 110A of the central processing computer/distributed ledger/Blockchain technology system 110 of the apparatus 300 or the apparatus 200, can also be stored by and in the distributed ledger and Blockchain technology system component 110B of the central processing computer/distributed ledger/Blockchain technology system 110. In any and/or all of the embodiments described herein, any of the data and/or information, of any type or kind, and including, but not limited to, any and/or all of the data, information, messages, reports, video recordings or video clips, audio recordings, pictures, photographs, and/or other information, described herein as being transmitted to, received by processed by, generated by, transmitted from, or stored by or in, the central processing computer 10 of the apparatus 100, can also be stored by and in a distributed ledger and Blockchain technology system. In this regard, the apparatus of the present invention and/or the apparatus 100, the apparatus 200, and/or the apparatus 300, can be utilized to safeguard and/or to secure any and/or all of the herein-described data and/or information, described herein in any and/or all of the embodiments described herein, utilizing a distributed ledger and Blockchain technology system.

The apparatus 100, the apparatus 200, the apparatus 300, and/or the method, of the present invention can also be utilized to facilitate and/or to conduct remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary. The apparatus 100, the apparatus 200, the apparatus 300, and/or the method, of the present invention can also be utilized to schedule remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

Any provider of an individual or patient, any insurer or payer of an individual or patient, any caregiver of an individual or patient, or any other authorized third party, intermediary, person, or entity, can also enter and store any note(s), comment(s), or message(s) in the individual's or patient's electronic healthcare record.

Any insurance claim form or the payment request form can be date stamped and/or time stamped. In this manner, claim or payment request processing can be tracked or monitored so as to facilitate audits of the insurer or payer in order to ascertain if the insurer or payer is properly and/or efficiently handling a claim or payment request for the individual or patient, and/or if the insurer or payer is in compliance with any laws, rules, or regulations, governing claims or payment processing and/or handling. Information regarding the date stamped and/or time stamped claims, including the insurer's or the payer's processing or handling of same, and the response or reply to same, can also be stored by the present invention and can be accessed and/or obtained by any authorized user or entity.

The apparatus 100, the apparatus 200, the apparatus 300, and/or the method, of the present invention can also generate a co-payment message or a deductible message containing information regarding a co-payment due by the individual or patient to the provider under the individual's or patient's insurance policy or payment program or a deductible which has to be met by the individual or patient under the individual's or patient's insurance policy or payment program.

The apparatus 100, the apparatus 200, the apparatus 300, and/or the method, of the present invention can also be utilized in connection with or in conjunction with a personal healthcare record which an individual or patient can maintain for himself, herself, and/or for any children, parents, relatives, friends, or any other individuals whom the individual or patient may be providing care for as a caregiver or a person assisting a caregiver for another. In a preferred embodiment, the personal healthcare record can be stored on one or more user or patient communication devices 40 or 41 which can include, but which are not limited to a personal computer, a laptop computer, a tablet, a cellular telephone, a wireless telephone, a television, a digital television, a personal digital assistant (PDA), a smart phone, a Smartphone, a watch, or any other of the herein-described devices, or other devices, which can be used as a user or patient communication device. The personal healthcare record can be stored in any number of user communication devices 40 or 41.

An individual or patient can utilize the apparatus 100, the apparatus 200, or the apparatus 300, of the present invention to enter notes, comments, messages, and/or video recording(s) and/or recorded video clip(s) of himself or herself, and/or any information regarding how they are feeling, information regarding a sickness, an illness, a symptom, information regarding types of medications they must take and time intervals for taking same, information regarding their diet, foods eaten, drinks ingested, exercise activity, provider information, allergies, and/or any other healthcare information, healthcare-related information, wellness information, fitness information, diet information, exercise of fitness information, nutritional information, and/or any other information which can find application in a healthcare or healthcare-related setting or scenario or any other information pertinent to the individual or patient as well as any individual(s) for whom the individual or patient is serving as a caregiver.

An individual or patient can utilize the apparatus 100, the apparatus 200, or the apparatus 300, of the present invention, at any time and with any suitable user or patient communication device 40 or 41 to enter or input, and/or to store, in a personal healthcare record, any relevant healthcare information, healthcare-related information, wellness information, fitness information, diet information, exercise of fitness information, nutritional information, and/or any other information, and/or any video recording(s) and/or recorded video clip(s) of himself or herself, which can find application in a healthcare or healthcare-related setting or scenario. The user of patient communication device 40 or 41 can also be programmed to provide timed alerts or messages to remind the individual or patient to take medication, eat certain foods, intake certain liquids, schedule an appointment with a provider, check the status of an insurance claim or a payment claim, to exercise, provide diet or exercise reminders, or to perform any other action or activity for himself or herself or to perform any of the above for a person whom he or she is a caregiver.

The individual or patient can, at any time and from any location, access the apparatus 100, the apparatus 200, or the apparatus 300, of the present invention and upload or transmit to the central processing computer 10 and/or the central processing computer component 110A of the central processing computer/distributed ledger/Blockchain technology system 110 any and/or all information in his or her personal healthcare record into relevant portions of his or her electronic healthcare record and/or into a portion of same dedicated to receiving and storing the personal healthcare record information. The individual or patient can also download or receive from the central processing computer 10 and/or from the central processing computer component 110A of the central processing computer/distributed ledger/Blockchain technology system 110, any data and/or information that is stored in the individual's or patient's electronic healthcare record(s).

The user or patient communication device 40 or 41 can also automatically receive, store or record in the personal healthcare record, and transmit to the central processing computer 10 and/or central processing computer component 110A of the central processing computer/distributed ledger/Blockchain technology system 110, any data and/or information which can be obtained with or from a wearable sensor or implantable sensor or device such as a wearable or implantable heart rate monitor, blood pressure monitor, blood sugar monitor, blood glucose monitor, blood oxygen percentage level monitor, oximeter, digital finger pulse oximeter, or any other device or monitor which can monitor a physiological parameter(s) or a biometric parameter(s). The user or patient communication device 40 or 41 can also automatically receive, store or record in the personal healthcare record, and transmit to the central processing computer 10 and/or central processing computer component 110A of the central processing computer/distributed ledger/Blockchain technology system 110, any data and/or information which can be obtained with or from a wearable sensor or implantable sensor or device, such as any user/patient monitoring system(s) 94, which can be or can include, a gyroscope, an accelerometer, a decelerometer, a magnetometer, an RFID tag(s), a thermometer for measuring temperature of the environment, a device for measuring body temperature, a device for measuring speed of movement, a device for measuring distance traveled, or any other device or devices which can measure and record information regarding three-dimensional movements of the individual or patient, such as for measuring an individual's or patient's activities and/or for measuring, monitoring, or tracking, the individual's or patients activities and/or performance of various activities. In a preferred embodiment, and depending upon the application, the user/patient monitoring system(s) 94 can also be, or include, any devices or equipments which are needed, required, or desired, for measuring, monitoring, and/or tracking individual or patient activity or performance using any type or kind of optical-based camera (OBC) tracking systems, local positioning system (LPS) tracking systems, and/or global positioning system/global navigation satellite system (GPS/GNSS) tracking systems, and/or any other tracking system, which are or can be utilized to track players or athletes during sporting or athletic competitions or training.

The user or patient communication device 40 or 41 can be linked via a wireless or Bluetooth or other suitable communication link with one or more of these wearable or implantable sensors and/or or tracking systems. Data and/or information obtained from the wearable or implantable sensors can be transmitted to the central processing computer 10, and/or central processing computer component 110A of the central processing computer/distributed ledger/Blockchain technology system 110, and stored in the individual's or patient's electronic healthcare record(s).

The user or patient communication device 40 or 41 and/or the personal health record utilized in connection with same, can be equipped with hardware and/or software for translating any data and/or information from one language into any other language, for translating audio information into text information for storing in the user or patient communication device, for storing audio information, for translating text information into audio information, for providing reminders to schedule appointments with providers, for providing reminders for scheduled appointments with providers, and/or for providing any other functions which are described herein as being performed in connection with the user or patient communication device 40 or 41. The apparatus 100, the apparatus 200, or the apparatus 300, of the present invention can also be utilized to receive information from an individual or patient regarding a personal healthcare record, to store and update an electronic healthcare record with the personal healthcare record information, and thereafter, to generate a new personal healthcare record using any new or updated information from the electronic healthcare record(s). The apparatus 100, the apparatus 200, or the apparatus 300, of the present invention can provide and maintain up-to-date electronic healthcare records and personal healthcare records for individuals or patients.

The respective user or patient communication device 40 or 41 of the apparatus 100, of the apparatus 200, or of the apparatus 300, of the present invention can also be utilized to be a personal healthcare monitoring and/or planning tool or device for monitoring and/or planning healthcare and/or healthcare-related activities, events, occurrences, and/or happenings, for the individual or patient, the individual's or patient's children, parents, relatives, or those for whom the individual or patient serves or acts as a caregiver. The user or patient communication device 40 or 41 can also be utilized to be a personal wellness, fitness, and/or nutritional monitoring and/or planning tool or device for monitoring and/or planning wellness or wellness-related, fitness or fitness-related, and/or nutritional or nutritional-related, activities, events, occurrences, and/or happenings, for the individual or patient, the individual's or patient's children, parents, relatives, or those for whom the individual or patient serves or acts as a caregiver. The user or patient communication device 40 or 41 can also be equipped with any needed or desired software or software application or any number of software applications needed, required, or desired for enabling the user or patient communication device 40 or 41 to provide the herein-described features, functions, and/or functionality. The apparatus 100, the apparatus 200, the apparatus 300, of the present invention can also be utilized to provide information regarding individual and/or family healthcare planning, and/or monitoring, individual and/or family wellness planning and/or monitoring, individual and/or family fitness planning and/or monitoring, and/or individual and/or family nutritional planning and/or monitoring.

The apparatus 100, the apparatus 200, the apparatus 300, of the present invention can also be utilized to schedule appointments, and/or remote or virtual office visits or examinations, with providers and to provide automatically generated appointment reminders.

In another preferred embodiment, the apparatus 100 of the present invention can also be utilized to create, manage, and/or maintain, a comprehensive and/or a centralized electronic healthcare record system. It is understood that different providers and insurers or payers might utilize or employ any number, or types or kinds, of electronic healthcare records, electronic medical records, electronic dental records, electronic pharmacy records, and/or electronic behavioral healthcare records, each of which may be located in or on different computers or located at different physical locations, and that any individual, patient, or user, may have a healthcare or healthcare-related record, a healthcare or healthcare-related file, or a healthcare or healthcare-related history, on any one or more of these separate electronic healthcare records, electronic medical records, electronic dental records, electronic pharmacy records, and/or electronic behavioral healthcare records. It is also understood that each individual or patient may also have a personal health record stored or located on his or her user or patient communication device 40.

In a preferred embodiment, any one or more of the healthcare records computers 60 can be associated with a different electronic healthcare record, electronic medical record, electronic dental record, electronic pharmacy record, and/or electronic behavioral healthcare record, or any number or combination of electronic healthcare records, electronic medical records, electronic dental records, electronic pharmacy records, and/or electronic behavioral healthcare records, and/or can be utilized by, or associated with, any provider(s) of the same.

In a preferred embodiment, the database 10H can, for each individual or patient who utilizes the apparatus 100, 200, and/or 300, and method of the present invention, contain any number of electronic healthcare records, electronic medical records, electronic dental records, electronic pharmacy records, and/or electronic behavioral healthcare records, containing data and/or information regarding the individual or patient, and/or the database 10H can contain any number of links or hyperlinks to any number of electronic healthcare records, electronic medical records, electronic dental records, electronic pharmacy records, and/or electronic behavioral healthcare records, which are located on healthcare records computers 60, or on any other computers, or computer systems, which are separate and apart from the central processing computer 10, the central processing computer/distributed ledger/Blockchain technology system 110, the central processing computer component 110A of the central processing computer/distributed ledger/Blockchain technology system 110, and/or the distributed ledger and Blockchain technology system component 110B of the central processing computer/distributed ledger/Blockchain technology system 110, and which respective record or records can also contain data and/or information for or regarding the individual or patient.

In a preferred embodiment, and in instances where an individual's or patient's healthcare-related records, healthcare or healthcare-related files, or healthcare or healthcare-related histories, are stored and/or located in different or separate electronic healthcare records, electronic medical records, electronic dental records, electronic pharmacy records, and/or electronic behavioral healthcare records, or stored or located on different or separate computers or computer systems, including, but not limited to, the central processing computer 10, the central processing computer/distributed ledger/Blockchain technology system 110, the central processing computer component 110A of the central processing computer/distributed ledger/Blockchain technology system 110, and/or the distributed ledger and Blockchain technology system component 110B of the central processing computer/distributed ledger/Blockchain technology system 110, the healthcare records computers 60, or any other computers or computer systems, the apparatus 100, the apparatus 200, the apparatus 300, and in particular, the database 10H or the central processing computer 10 or of the central processing computer component 110A of the central processing computer/distributed ledger/Blockchain technology system 110, can also contain a master individual or patient index containing, for each individual or patient, the individual's or patient's name, address, social security number or other uniquely assigned identification number or identifying data or information, mother's maiden name, name of spouse or partner, name(s) of child, children or others for who the individual or patient is responsible for providing care legally or otherwise, each electronic healthcare records, electronic medical records, electronic dental records, electronic pharmacy records, and/or electronic behavioral healthcare records, containing data and/or information regarding the individual or patient, or in or on which the individual or patient has a record, file, history, or entry, and/or a link(s) or hyperlink(s) to each electronic healthcare records, electronic medical records, electronic dental records, electronic pharmacy records, and/or electronic behavioral healthcare records, containing data and/or information regarding the individual or patient, or in or on which the individual or patient has a record, file, history, or entry.

In a preferred embodiment, the apparatus 100, the apparatus 200, the apparatus 300, and/or the method of the present invention can be utilized to provide for a comprehensive electronic healthcare record, file, or history, for each individual or patient as well as to facilitate access to comprehensive healthcare or healthcare-related data and/or information for or regarding an individual or patient via the central processing computer 10, the central processing computer 10, the central processing computer/distributed ledger/Blockchain technology system 110, the central processing computer component 110A of the central processing computer/distributed ledger/Blockchain technology system 110, and/or the distributed ledger and Blockchain technology system component 110B of the central processing computer/distributed ledger/Blockchain technology system 110.

In a preferred embodiment, an individual's or patient's electronic healthcare record, file or history, can be contained in any number of electronic healthcare records, electronic medical records, electronic dental records, electronic pharmacy records, and/or electronic behavioral healthcare records, regardless of where each respective record is or may be stored.

Figure 27:
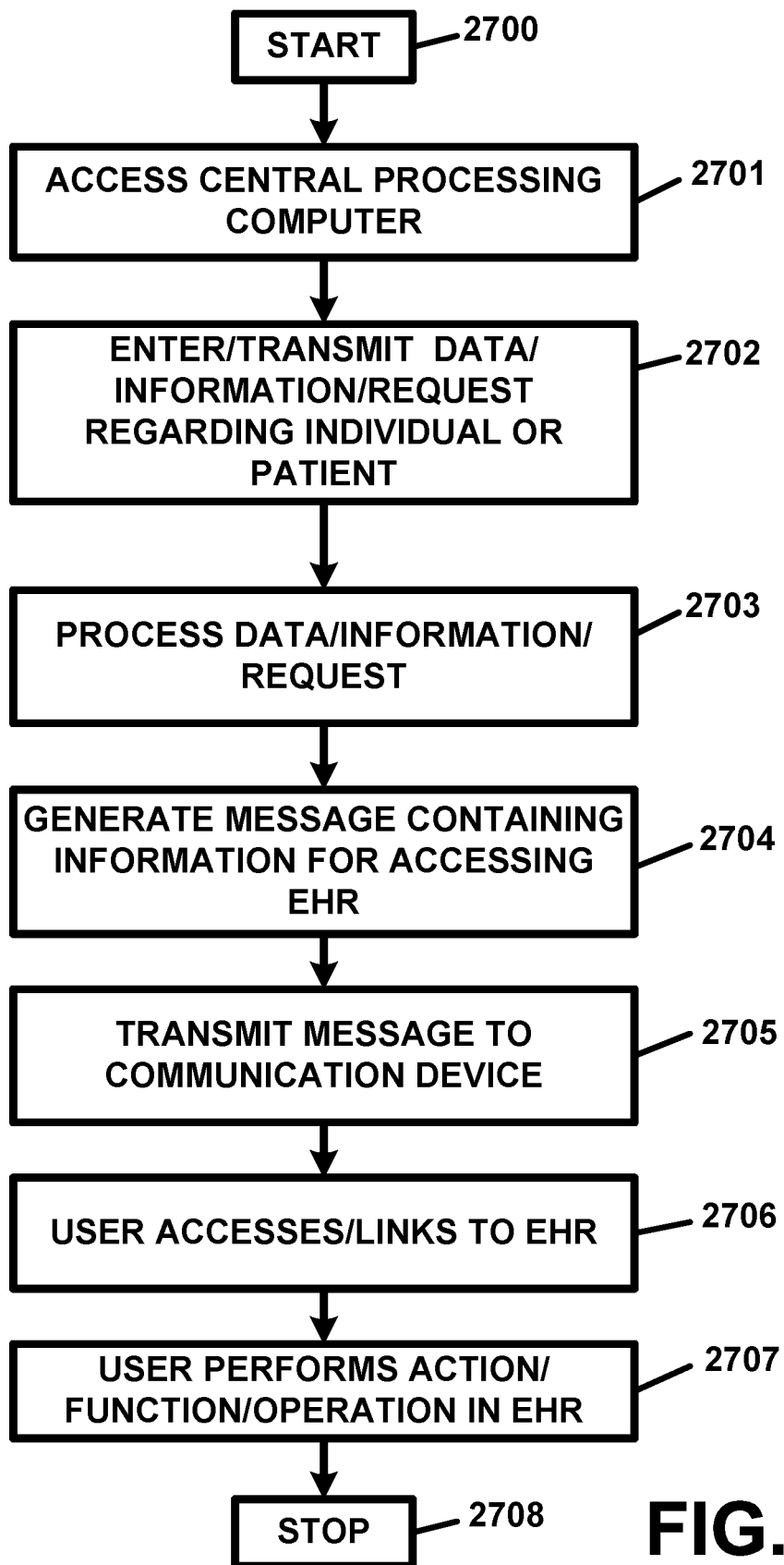
FIG. 27 illustrates another preferred embodiment method of utilizing the apparatus of the present invention, in flow diagram form.

FIG. 27 illustrates a preferred embodiment method for utilizing the apparatus 100, the apparatus 200, and/or the apparatus 300, and/or the method of the present invention, in flow diagram form. In a preferred embodiment, any authorized user, individual, patient, provider, insurer, payer, or any authorized third party or authorized intermediary, or any governmental entity, and/or any other authorized person or entity, can utilize the apparatus 100, the apparatus 200, and/or the apparatus 300, and/or the method of the present invention to access, view, change, alter, modify, or update, or make an entry or entries to, an individual's or patient's electronic healthcare record, file or history, regardless of where each component electronic healthcare record, electronic medical record, electronic dental record, electronic pharmacy record, and/or electronic behavioral healthcare record, is stored. For the sake of simplicity in describing this preferred embodiment of FIG. 27, the term "user" will be used to refer to any authorized user, individual, patient, caregiver, provider, insurer, payer, or any authorized third party or authorized intermediary, or any governmental entity, who or which uses the embodiment of FIG. 27. Although described as being utilized in conjunction with, or in connection with, the apparatus 300, the embodiment of FIG. 27 can also be utilized in a same, a similar, and/or an analogous, manner with the apparatus 100 and/or the apparatus 200.

With reference to FIG. 27, the operation of the apparatus 300 commences at step 2700. At step 2701, the user can access the central processing computer component 110A of the central processing computer/distributed ledger/Blockchain technology system 110 using the user's respective communication device or computer 21, 31, 41, or 51. At step 2702, the user, who is seeking to access an individual's or patient's healthcare record, file, or history, will enter, into his or her respective communication device or computer 21, 31, 41, or 51, and transmit to the central processing computer component 110A of the central processing computer/distributed ledger/Blockchain technology system 110 any data or information regarding the individual or patient and/or a request to access the healthcare, record, or history, of the individual or patient. At step 2703, the central processing computer component 110A of the central processing computer/distributed ledger/Blockchain technology system 110 will receive and/or process the data or information, or the request.

At step 2704, the central processing computer component 110A of the central processing computer/distributed ledger/Blockchain technology system 110 will generate a message containing information for accessing the individual's or patient's healthcare record, file, or history. In a preferred embodiment, the message can contain any number of links or hyperlinks to any and/or all of the electronic healthcare records, electronic medical records, electronic dental records, electronic pharmacy records, and/or electronic behavioral healthcare records, which contain data and/or information regarding the individual or patient, and/or any number of links or hyperlinks to any of the respective healthcare records computers 60 or other computers of computer systems on which any of the above-referenced electronic healthcare records, electronic medical records, electronic dental records, electronic pharmacy records, and/or electronic behavioral healthcare records, are stored.

At step 2705, the central processing computer component 110A of the central processing computer/distributed ledger/Blockchain technology system 110 will transmit the message to the respective communication device or computer 21, 31, 41, or 51 being used by the user. Thereafter, the user, at step 2706, can access or link to the individual's or patient's healthcare record, file, or history, or can access or link to the pertinent or desired electronic healthcare records, electronic medical records, electronic dental records, electronic pharmacy records, and/or electronic behavioral healthcare records, or portion(s) of same containing data or information for or regarding individual or patient.

At step 2707, the user can perform any needed or desired action, function, or operation on or regarding, the individual's or patient's data and/or information which is stored or contained in any one or more the individual's or patient's healthcare records, electronic medical records, electronic dental records, electronic pharmacy records, and/or electronic behavioral healthcare records, or portion(s) of same containing data or information for or regarding individual or patient. At step 2707, the central processing computer component 110A of the central processing computer/distributed ledger/Blockchain technology system 110 can record and store, in the database 10H, information regarding any and/or all of the actions of the user, and/or information regarding the individual's or patient's healthcare record(s), electronic medical record(s), electronic dental record(s), electronic pharmacy record(s), and/or electronic behavioral healthcare record(s), or portion(s) of same, accessed and/or utilized by the user, and/or any other information regarding the user's actions or activities.

At step 2707, the central processing computer component 110A of the central processing computer/distributed ledger/Blockchain technology system 110 can generate, store, and transmit, to the user or patient communication device 41 of the individual or patient whose record or records have been accessed, and/or to the respective provider communication device 21 for each healthcare provider of the individual or patient, a record(s) access report containing information regarding the identity of the user and information regarding the user's actions or activities regarding or involving the individual's or patient's healthcare record(s), electronic medical record(s), electronic dental record(s), electronic pharmacy record(s), and/or electronic behavioral healthcare record(s), or portion(s) of same.

At step 2707, any and/or all information regarding the user's access of, and/or actions or activities regarding, the individual's or patient's healthcare record(s), electronic medical record(s), electronic dental record(s), electronic pharmacy record(s), and/or electronic behavioral healthcare record(s), or portion(s) of same, and/or the record(s) access report, can be stored in the database 10H of the central processing computer component 110A of the central processing computer and distributed ledger and Blockchain technology system 110 and/or in the distributed ledger and Blockchain technology system component 110B of the central processing computer/distributed ledger/Blockchain technology system 110. Thereafter, the operation of the apparatus 100 will cease at step 2708.

In a preferred embodiment, the user can access any one or more, or any and/or all of, the electronic healthcare records, electronic medical records, electronic dental records, electronic pharmacy records, and/or electronic behavioral healthcare records, or portion(s) of same which contain data or information for or regarding individual or patient. In this regard, the apparatus 300 and method of the present invention can be utilized to provide a comprehensive healthcare record, file, or history, for an individual or patient by providing any and/or all healthcare or healthcare-related data and/or information, for or regarding an individual or patient, and/or any and/or all link(s) or hyperlink(s) to any and/or all of the electronic healthcare records, electronic medical records, electronic dental records, electronic pharmacy records, and/or electronic behavioral healthcare records, which contain any and/or all healthcare or healthcare-related data or information for or regarding individual or patient.

In another preferred embodiment, any individual, patient, user, provider, insurer or payer, or third party or intermediary, or any governmental entity, can create any link or hyperlink to any electronic healthcare record(s), electronic medical record(s), electronic dental record(s), electronic pharmacy record(s), and/or electronic behavioral healthcare record(s), which contain or which are to contain healthcare or healthcare-related data or information for or regarding any individual or patient.

In another preferred embodiment, the apparatus 100, the apparatus 200, and/or the apparatus 300, and/or method of the present invention can be utilized in order to allow an individual or a patient, or one responsible for the care of an individual or patient, to enter notes, comments, or messages, regarding or relating to the individual or patient into one or more of any of the individual's or patient's electronic healthcare record(s), electronic medical record(s), electronic dental record(s), electronic pharmacy record(s), and/or electronic behavioral healthcare record(s). Any respective note, comment, or message can be in text form, audio form, or video form, and/or any combination of same, and can contain information regarding a symptom, an illness, an experience, a treatment, a diagnosis, a treatment plan, an activity, a problem, a concern, a thought or an idea, a question, a question for a healthcare provider, or any other information which the individual or patient, or one caring for the individual or patient, may deem important to be recorded or noted in the respective electronic healthcare record(s), electronic medical record(s), electronic dental record(s), electronic pharmacy record(s), and/or electronic behavioral healthcare record(s), or which can be communicated to, or otherwise made available to, a provider or to an insurer or payer.

In a preferred embodiment, a healthcare provider can access, obtain, and/or use, the information provided or contained in the note, comment, or message, or provided or contained in multiple notes, comments, or messages, for any suitable purpose, such as, but not limited to, for preparing for or for use during an examination, an office visit, a telehealth visit, or any herein-described video call, for use during an examination with the individual or patient or for use during a procedure and an administration of a treatment, for use during a conversation or telephone discussion, or video call, with the individual or patient, for use during a consultation or discussion, or video call, with the individual, patient, a family member or caregiver of the individual or patient, or another provider, or a payer or insurer any third party or intermediary, for use during reviewing, updating, modifying, or performing any other activity in connection with, an individual's or patient's healthcare records, files, or histories, for use while making a diagnosis, for use while formulating a treatment or a treatment plan, for use in reviewing or evaluating an individual's or patient's diagnosis or treatment, for use in treatment planning and/or the evaluating of same, for use in care management, for use in monitoring or evaluating a recovery, for use in providing continuing or on-going care or treatment, for use in connection with the providing of a remote healthcare services or tele-health services, and/or for any other suitable use or purpose.

In a preferred embodiment, these notes, comments or messages, can be provided by the individual or patient, or by any person caring for the individual or patient while making an appointment, in advance of an office visit or an examination or procedure, in advance of a tele-health visit or video call, in connection with any tele-health related activity, or for the purpose of making and entering a note, comment, or message, into the individual's or patient's respective electronic healthcare record(s), electronic medical record(s), electronic dental record(s), electronic pharmacy record(s), and/or electronic behavioral healthcare record(s). In this regard, the apparatus 100 and method of the present invention allows an individual or patient, or one responsible for caring for the individual or patient, to make and enter any notes, comments, or messages, into the individual's or patient's respective electronic healthcare record(s), electronic medical record(s), electronic dental record(s), electronic pharmacy record(s), and/or electronic behavioral healthcare record(s) so as to facilitate accurate and complete healthcare information record keeping.

In a preferred embodiment, any provider of an individual or patient, any insurer or payer of an individual or patient, any caregiver of an individual or patient, or any other authorized third party, intermediary, person, or entity, can also enter and store any note(s), comment(s), or message(s) in the individual's, patient's, or caregiver's, electronic healthcare record, as well as access and/or be provided with any note(s), comment(s), or message(s), provided by the individual, the patient, caregiver, or other person.

Figure 28A:
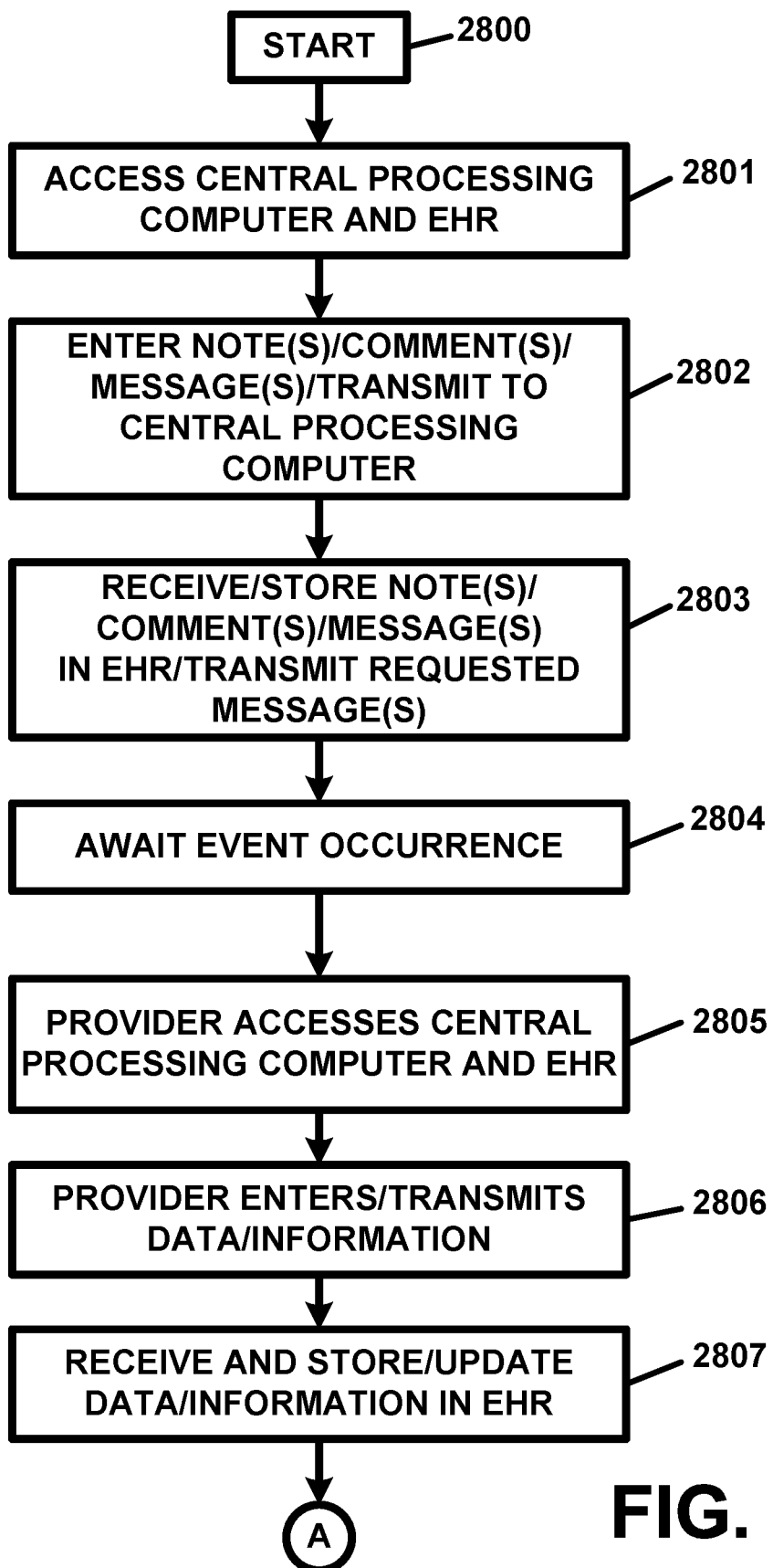
FIGS. 28A and 28B illustrate still another preferred embodiment method of utilizing the apparatus of the present invention, in flow diagram form.
Figure 28B:
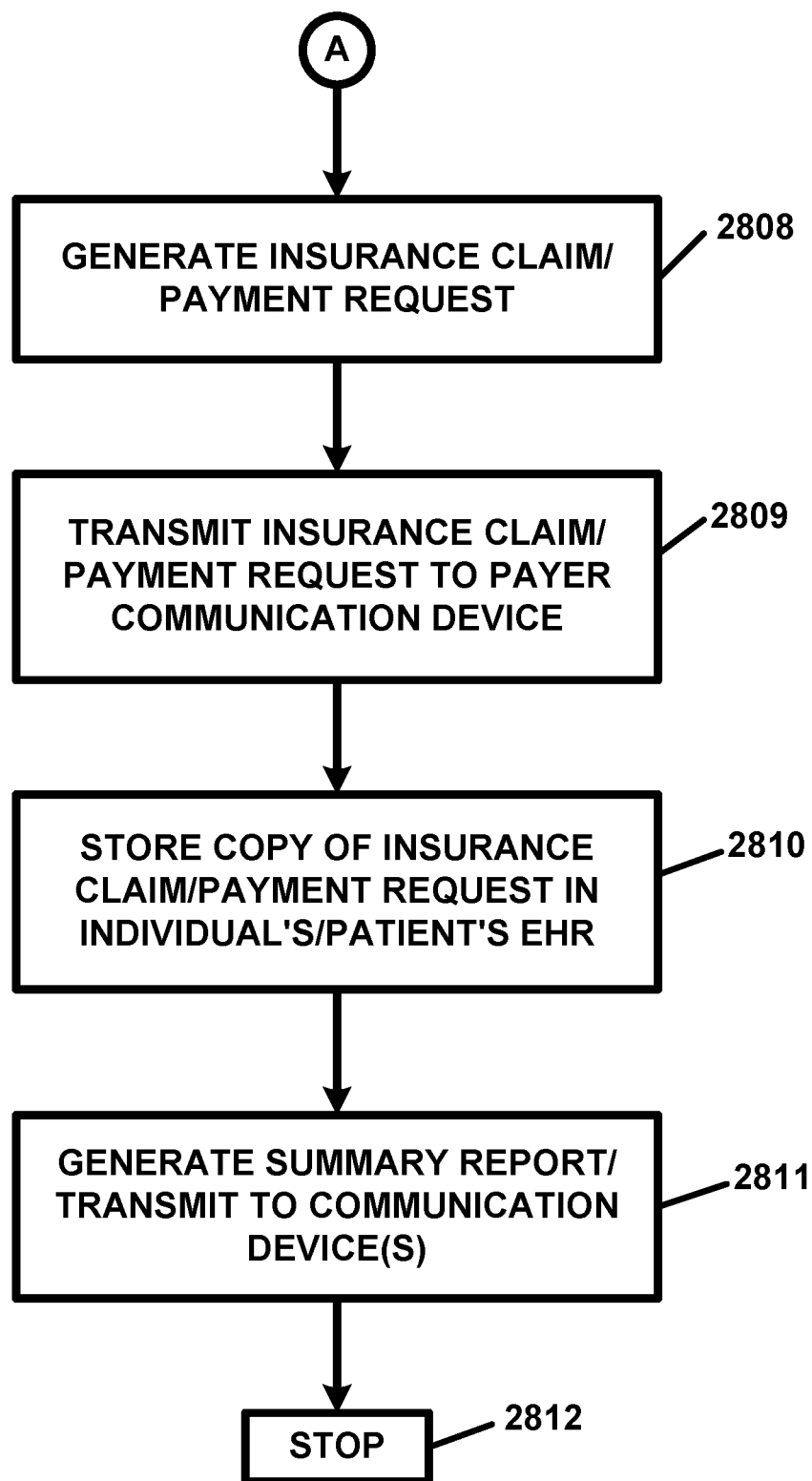

FIGS. 28A and 28B illustrate another preferred embodiment method for utilizing the apparatus 100, the apparatus 200, or the apparatus 300, and/or method of the present invention, in flow diagram form. As an example, the embodiment of FIGS. 28A and 28B will be described as being used by an individual or patient, to enter a note, comments, or a message, into his or her electronic healthcare record and that such note, comments, or message, can be used by a healthcare provider in rendering or providing a healthcare service to or for the individual or patient. It is, however, important to note that the embodiment of FIGS. 28A and 28B can be used by any individual, patient, or by any individual or user who is a spouse, family member, relative, friend, or any other person or entity or caregiver, who is responsible for caring for, or who for providing care for the individual or patient. Further, it is also important to note that the embodiment of FIGS. 28A and 28B can be utilized by any other individual, user, caregiver or care provider, healthcare provider, provider, payer, insurer, third party, intermediary, or any other person or entity who or which provides care for or who provides any kind of service or services for the individual or patient. Although described as being utilized in conjunction with, or in connection with, the apparatus 300, the embodiment of FIGS. 27A and 28B can also be utilized in a same, a similar, and/or an analogous, manner with the apparatus 100 and/or the apparatus 200.

With reference to FIGS. 28A and 28B, the operation of the apparatus 300 commences at step 2800. At step 2801, the individual or patient can access the central processing computer component 110A of the central processing computer/ distributed ledger/Blockchain technology system 110 using the his or her user communication device 41.

At step 2802, the individual or patient can enter, and transmit to the central processing computer component 110A of the central processing computer/distributed ledger/ Blockchain technology system 110, any note(s), comment(s), or message(s) into his or her electronic healthcare record.

The note(s), comment(s), or message(s) can contain any information regarding the individual's or patient's state of health or well-being, an illness, a symptom, a sickness, a feeling of discomfort, notes, concerns, or questions for his or her provider, notes, concerns, or questions for or reasons for an upcoming provider appointment, examination, or procedure, notes regarding diet or food intake, notes regarding activities, or any other notes, comments, messages, or information which the individual or patient might desire to place into his or her electronic healthcare record. In a preferred embodiment, the note(s), comment(s), or message(s), can be entered as a text entry. In another preferred embodiment, the individual or patient, at step 2802, can also, or in addition to entering a text note, comment, or message, utilize any one or more of the microphone or audio recording device and/or the camera or video recording device associated with the user or patient communication device 40 in order to enter an audio message or a video or audio and video message.

At step 2802, the individual or patient can record an audio message or a video message, or provide a picture or a video clip, in addition to or instead of providing a text note, comment or message in any instances or for any reason. For example, the individual or patient may feel a need to provide a more in-depth explanation, provide a picture or video clip of a physical condition, provide an explanation while providing a picture or video clip to explain a condition, or for any reason whatsoever. At step 2802, the individual or patient can also request or instruct that his or her provider or providers, insurer(s) or payer(s), or caregiver(s), be notified of and/or be provided with the note(s), the comment(s), or the message(s). At step 2802, the respective note(s), comment(s), or message(s) along with any other information, requests, or instructions, can be transmitted to the central processing computer component 110A of the central processing computer/distributed ledger/Blockchain technology system 110.

At step 2803, the central processing computer component 110A of the central processing computer/distributed ledger/ Blockchain technology system 110 can receive and/or store the note(s), comment(s), or message(s), in the individual's or patient's electronic healthcare record. At step 2803, the central processing computer component 110A of the central processing computer/distributed ledger/Blockchain technology system 110 can also determine if the individual or patient requested or instructed that his or her provider or providers, insurer(s) or payer(s), or caregiver(s), be notified of and/or be provided with the note(s), the comment(s), or the message(s). If the central processing computer component 110A of the central processing computer/distributed ledger/Blockchain technology system 110 determines that the individual or patient requested or instructed that his or her provider or providers, insurer(s) or payer(s), or caregiver(s), be notified of and/or be provided with the note(s), the comment(s), or the message(s), the central processing computer component 110A of the central processing computer/distributed ledger/Blockchain technology system 110 will generate any and/or all notification or alert messages and transmit same to the respective provider communication device(s) 21, insurer or payer communication device(s) 31, or user or patient communication device(s) 41 used or associated with the caregiver(s).

A record or note of any such notification or alert message(s) being sent can also be recorded in the individual's or patient's electronic healthcare record and a confirmation message can be generated and sent to the individual's or patient's user communication device 41 in order to provide notification to the individual or patient that such notification or alert message(s) has/have indeed been sent as requested or instructed. Any and/or all of the notification or alert messages can be sent as any one or more of, or any combination of, an e-mail message, a text message, an SMS message, a telephone message, a facsimile message, or any other electronic transmission or message.

At step 2804, the apparatus 300 will await an occurrence of an event upon which the provider may access, or act on or regarding, the note(s), comment(s), or message(s) or any number of notes, comments, or messages. The event can be an office visit or a tele-health visit by the individual or patient, a conversation between the provider and the individual or patient or a caregiver, an examination of the individual or patient, an administration of a treatment to the individual or patient, a procedure being performed on or regarding the individual or patient, a review of information contained in the individual's or patient's electronic healthcare record, a diagnosis of the individual or patient, a determination of a treatment for the individual or patient, a determination of a treatment plan for the individual or patient, an evaluation of or regarding the individual or patient, or for any other event, occurrence, or happening wherein such note(s), comment(s), or message(s) might be deemed pertinent or useful.

Upon the occurrence of the event at step 2804, the operation of the apparatus 300 will proceed to step 2805. At step 2805, the provider can access the central processing computer component 110A of the central processing computer/distributed ledger/Blockchain technology system 110, the individual's or patient's electronic healthcare record, and/or the note(s), comment(s), or message(s) and can review same. The provider can for example, access the individual's or patient's electronic healthcare record, and/or the note(s), comment(s), or message(s), prior to an office visit, a house call, or a remote or tele-health appointment, with or an examination of, the individual or patient so as to prepare for same, during an examination or a procedure, during an office visit, a house call, or a remote or tele-health appointment, with or an examination of, the individual or patient, in making a diagnosis or prescribing a treatment or a treatment plan, or for any other purpose.

At step 2806, the provider can then enter, and transmit to the central processing computer component 110A of the central processing computer/distributed ledger/Blockchain technology system 110, via or using the provider communication device 21, any data and/or information regarding any examination finding(s), the individual's or patient's symptom(s), any observation(s), a diagnosis or diagnoses of possible diagnosis or possible diagnoses, a prescribed treatment(s), a treatment plan(s), or any other data or information regarding the individual or patient, information regarding or obtained during the examination, the procedure, or any other interaction with the patient, into the individual's or patient's electronic healthcare record. At step 2807, the central processing computer component 110A of the central processing computer/distributed ledger/Blockchain technology system 110 can receive and store the data and/or information entered during step 2806 into any one or more of the individual's or patient's electronic healthcare record or electronic healthcare records and update the individual's or patient's electronic healthcare record or electronic healthcare records.

At step 2808, the central processing computer component 110A of the central processing computer/distributed ledger/Blockchain technology system 110 will generate an insurance claim form or a payment request form which can meet and/or satisfy the formal claim submission requirements of the individual's or the patient's insurer, insurance company, or payer and which is suitable for submission to the respective insurer, insurance company or payer of the individual or patient. In a preferred embodiment, the insurance claim form or the payment request form is automatically generated by the central processing computer 10 in response to the storing of the data and/or information at step 2807.

At step 2809, the insurance claim form or the payment request form can be transmitted by or submitted by the central processing computer component 110A of the central processing computer/distributed ledger/Blockchain technology system 110 to the respective payer communication device 31 of the individual or the patient. At step 2809, the insurance claim form or the payment request form or a copy of same can also be transmitted by the central processing computer component 110A of the central processing computer/distributed ledger/Blockchain technology system 110 to the provider communication device(s) 21 of the provider. At step 2809, the insurance claim form or the payment request form or a copy of same can also be transmitted by the central processing computer component 110A of the central processing computer/distributed ledger/Blockchain technology system 110 to the provider communication device(s) 21 of any of the individual's or patient's other providers, to the user communication device 41 of the individual or patient, or to a user communication device 41 of a caregiver of the individual or patient, or to a governmental entity/intermediary communication device 51 of any governmental entity or intermediary.

At step 2810, the insurance claim form or the payment request form or a copy of same can also be stored in the individual's or patient's electronic healthcare record or electronic healthcare records. In a preferred embodiment, the insurance claim form or the payment request form or the copy of same can be transmitted directly to a respective payer communication device 31, provider communication device 22, user communication device 41, or governmental entity/intermediary communication device 51, either directly, such as via any suitable electronic or other transmission, or indirectly, such as via an e-mail server in the case when the copy of the insurance claim form or the payment request form is included in, or is attached to, an e-mail message. The copy of the insurance claim form or the payment request form can also be stored by or in the respective provider communication device 21, the respective user communication device 41, or the respective governmental entity/intermediary communication device 51.

At step 2811, the central processing computer component 110A of the central processing computer/distributed ledger/Blockchain technology system 110 can also generate a respective summary report regarding the office visit, the examination, the interaction with the provider, or the provider's action(s). The summary report can contain a summary or a clinical summary which can contain information regarding the office visit, the examination, the tele-health visit, or the interaction with the provider, as well as instructions for the individual or patient. A copy of the respective summary report can also be transmitted, at step 2811, by the central processing computer component 110A of the central processing computer/distributed ledger/Blockchain technology system 110, to the user communication device 41 of the individual or patient, or of a caregiver of the individual or patient, to the provider communication device 21 of the provider as well as the respective provider communication device 21 of any other healthcare provider or healthcare providers of the individual or patient, to the payer communication device 31, and/or to a governmental entity/intermediary communication device 51.

The respective summary report can also contain individual-specific or patient-specific educational information or individual-specific or patient-specific instructional information, or a link(s) or hyperlink(s) to same, regarding a diagnosis, a treatment, a treatment plan, an office visit summary, a procedure summary, a treatment summary, or any other information relating thereto, so as to provide this educational information or instructional information to the individual or patient.

The individual or patient can thereafter access or obtain the educational information or instructional information via the apparatus 300 and method of the present invention. In this manner, the apparatus 300 and method of the present invention can provide individual-specific or patient-specific educational information or individual-specific or patient-specific instructional information regarding the diagnosis, treatment, treatment plan, or a summary of the office visit, the examination, the interaction with the provider, or the provider's action(s).

In a preferred embodiment, the apparatus 300 or the central processing computer component 110A of the central processing computer/distributed ledger/Blockchain technology system 110 can be programmed to identify the individual-specific or patient-specific educational information or individual-specific or patient-specific instructional information regarding the diagnosis, the treatment, the treatment plan, the office visit, the examination, the tele-health visit, or the interaction with the provider, or the provider's action(s), and/or any information, link(s), or hyperlink(s) relating thereto or pertaining thereto. The respective summary report can also contain a link(s) or hyperlink(s) to a social network website, a social network support group(s), a social networking activity, meeting, forum, chat room discussion, support group meeting or discussion, other individual member of a social network with whom the individual or patient can make contact with, or any other social networking or social networking-related information.

The respective summary report, in a preferred embodiment, can also be stored in the individual's or patient's electronic healthcare record. At step 2811, any information regarding the note(s), comment(s), or message(s) entered into the individual's or patient's electronic healthcare record by the individual, patient, or caregiver, and/or the provider, any information regarding any action taken by the provider, the insurance claim form or the payment request form, and/or the summary report can be stored in the individual's or patient's electronic healthcare record, the database 10H of the central processing computer component 110A of the central processing computer and distributed ledger and Blockchain technology system 110 and/or in the distributed ledger and Blockchain technology system component 110B of the central processing computer/distributed ledger/Blockchain technology system 110. Thereafter, the operation of the apparatus 100 will cease at step 2812.

In another preferred embodiment, as well as in any and/or all of the embodiments described herein, a caregiver can also enter a note(s), comment(s), or message(s), or any other information, into the individual's or the patient's electronic healthcare record. In a preferred embodiment, a caregiver can utilize a user communication device 41 in order to enter a note(s), comment(s), or message(s), or any other information, into the individual's or the patient's electronic healthcare record.

In another preferred embodiment, the insurance claim form or the payment request form, which is transmitted to the insurer or payer communication device 31 at step 2809 can be date stamped and/or time stamped. In this manner, any processing of any claim or payment request can be tracked or monitored so as to facilitate audits of the insurer or payer in order to ascertain if the insurer or payer is properly and/or efficiently handling a claim or payment request for the individual or patient, and/or if the insurer or payer is in compliance with any laws, rules, or regulations, governing claims or payment processing and/or handling. Information regarding the date stamped and/or time stamped claims or requests for payment, including the insurer's or the payer's processing or handling of same, and the response or reply to same, can also be stored in the database 10H of the central processing computer component 110A of the central processing computer and distributed ledger and Blockchain technology system 110 and/or in the distributed ledger and Blockchain technology system component 110B of the central processing computer/distributed ledger/Blockchain technology system 110, and can be accessed and/or obtained by any authorized user or entity. In this manner, the apparatus 30 of the present invention can also be utilized in order to ascertain information regarding the processing and/or the handling of claims or payment requests by a respective insurer or payer for any individual or patient or for any group or groups of individuals or patients.

In another preferred embodiment, the central processing computer component 110A of the central processing computer and distributed ledger and Blockchain technology system 110 can also generate a co-payment message or a deductible message containing information regarding a co-payment due by the individual or patient to the provider under the individual's or patient's insurance policy or payment program or a deductible which has to be met by the individual or patient under the individual's or patient's insurance policy or payment program. In another preferred embodiment, the co-payment message or the deductible message can be transmitted to the provider's communication device 21 during step 2809 or at any other time. The co-payment message or the deductible message can also be transmitted to the payer's communication device 31, to the user communication device 41 of the individual or patient or a caregiver, and/or to a governmental entity/intermediary communication device 51.

In another preferred embodiment, the apparatus 300 and method of the present invention can be utilized in connection with or in conjunction with a personal healthcare record which an individual or patient can maintain for himself, herself, and/or for any children, parents, relatives, friends, or any other individuals whom the individual or patient may be providing care for as a caregiver or a person assisting a caregiver for another. In a preferred embodiment, the personal healthcare record can be stored on one or more user communication devices 41 which can include, but which are not limited to a personal computer, a laptop computer, a tablet, a cellular telephone, a wireless telephone, a television, a digital television, a personal digital assistant (PDA), a smartphone, a smart watch, or any other of the herein-described devices, or other devices, which can be used as a user communication device 41. The personal healthcare record can be stored in any number of user communication devices 41.

In a preferred embodiment, the individual or patient can enter notes, comments, messages, information regarding how they are feeling, information regarding a sickness, an illness, a symptom, information regarding types of medications they must take and time intervals for taking same, information regarding their diet, foods eaten, drinks ingested, exercise activity, provider information, allergies, and/or any other healthcare information, healthcare-related information, wellness information, fitness information, diet information, exercise of fitness information, nutritional information, and/or any other information which can find application in a healthcare or healthcare-related setting or scenario or any other information pertinent to the individual or patient as well as any individual(s) for whom the individual or patient is serving as a caregiver. In this manner, an individual or patient can, at any time and with any suitable user communication device 41, enter or input, and store in a personal healthcare record, any relevant healthcare information, healthcare-related information, wellness information, fitness information, diet information, exercise of fitness information, nutritional information, and/or any other information which can find application in a healthcare or healthcare-related setting or scenario. In a preferred embodiment, the user communication device 41 can be programmed to provide timed alerts or messages to remind the individual or patient to take medication, to eat certain foods, to intake certain liquids, to schedule an appointment with a provider, to check the status of an insurance claim or a payment claim, to exercise, to provide diet or exercise reminders, or to perform any other action or activity for himself or herself or to perform any of the above for a person whom he or she is a caregiver.

The individual or patient can, at any time and from any location, access the central processing computer component 110A of the central processing computer/distributed ledger/Blockchain technology system 110 via the user communication device 41 and upload or transmit to the central processing computer component 110A of the central processing computer/distributed ledger/Blockchain technology system 110 any and/or all information in his or her personal healthcare record into relevant portions of his or her electronic healthcare record and/or into a portion of same dedicated to receiving and storing the personal healthcare record information. In a preferred embodiment, the individual or patient can also download or receive, from the central processing computer component 110A of the central processing computer/distributed ledger/Blockchain technology system 110, any data and/or information that is stored in the individual's or patient's electronic healthcare record(s).

In another preferred embodiment, the user communication device 41 can automatically receive, store or record, in the personal healthcare record, and transmit to the central processing computer component 110A of the central processing computer/distributed ledger/Blockchain technology system 110, any data and/or information which can be obtained by or with, or from, a wearable sensor or implantable sensor or device such as a wearable or implantable heart rate monitor, blood pressure monitor, oximeter, digital finger pulse oximeter, blood sugar monitor, or any other device or monitor which can monitor a physiological parameter(s) or a biometric parameter(s). In a preferred embodiment, the user communication device 41 can be linked via a wireless or Bluetooth, or other, suitable communication link with one or more of these wearable or implantable sensors. In a preferred embodiment, the data and/or information obtained from the wearable or implantable sensor(s) can be transmitted to the central processing computer component 110A of the central processing computer/distributed ledger/Blockchain technology system 110 and stored in the individual's or patient's electronic healthcare record(s) and in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110, and can be accessed and/or obtained by any authorized user or entity.

In another preferred embodiment, the user communication device 41 and/or the personal health record utilized in connection with same, can be equipped with hardware and/or software for translating any data and/or information from one language into any other language, for translating audio information into text information for storing in the user communication device 41, for storing audio information, for translating text information into audio information, for providing reminders to schedule appointments with providers, for providing reminders for scheduled appointments with providers, and/or for providing any other functions which are described herein as being performed in connection with the user communication device 41.

In another preferred embodiment, the apparatus 100, the apparatus 200, and/or the apparatus 300, and/or method of the present invention can be utilized by a healthcare provider or other authorized person or entity in order to perform a diagnosis of, and/or to prescribe a treatment or a treatment plan for, a sickness, illness and/or any other condition.

Figure 29A:
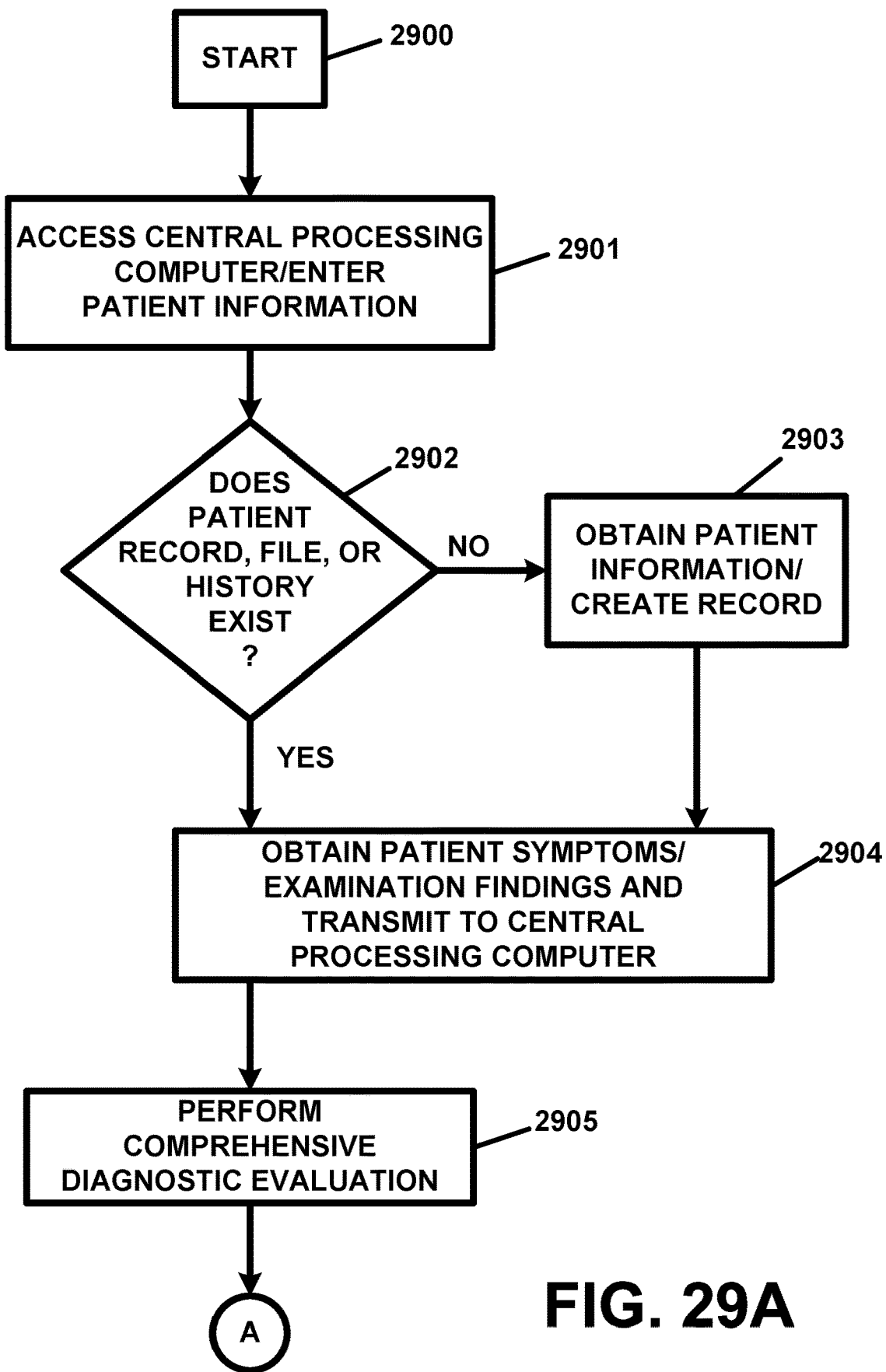

FIGS. 29A and 29B illustrate another preferred embodiment method for utilizing the apparatus 300 and method of the present invention, in flow diagram form. While the method of FIGS. 29A and 29B is described in the context of a medical doctor or other healthcare professional performing a diagnosis of, and/or prescribing a treatment or a treatment plan for, a medical condition, the apparatus 300 and method of FIGS. 29A and 29B can be used in a same, a similar, and/or an analogous, manner, by any type or kind of healthcare provider described herein, including, but not limited to, medical doctors, surgeons, physicians, dentists, orthodontists, periodontists, endodontists, oral surgeons, osteopaths, psychologists, optometrists, podiatrists, osteopaths, chiropractors, pharmacists, therapists, physical therapists, respiratory therapists, nurses, healthcare aids, nurse practitioners, physician's assistant, nutritionists, and/or any other person, individual, and/or professional, who can provide healthcare, healthcare-related, and/or wellness and/or wellness-related, services and/or products, insurance companies, healthcare insurance companies, disability insurance companies, property or casualty insurance companies, health maintenance organizations, healthcare providers, healthcare payers, and/or any other payer and/or provider of healthcare services and/or products, healthcare claims processing entities, organizations, companies, or centers, healthcare insurance brokers and/or agents, and/or any other third party and/or intermediary, and/or any governmental entity, who or which acts on behalf of another and/or assists in the providing of healthcare and/or related services, and/or any other healthcare provider or healthcare professional described herein (hereinafter referred to in this preferred embodiment as a "provider" or "user").

The preferred embodiment method of FIGS. 29A and 29B may also be utilized by any user, individual, patient, caregiver, provider, insurer, payer, and/or intermediary or governmental entity, in order to ascertain a diagnosis or a treatment and/or in order to check on, to verify, and/or to ascertain, the correctness of a diagnosis of another and/or to formulate, plan, check on, verify, and/or ascertain, the correctness of a diagnosis, a treatment, or a treatment plan.

Although described as being utilized in conjunction with, or in connection with, the apparatus 300, the embodiment of FIGS. 29A and 29B can also be utilized in a same, a similar, and/or an analogous, manner with the apparatus 100 and/or the apparatus 200.

With reference to FIGS. 29A and 29B, the operation of the apparatus 300 commences at step 2900. At step 2901, the provider or user can access the central processing computer component 110A of the central processing computer and distributed ledger and Blockchain technology system 110 using his or her respective provider communication device 21 or user or patient communication device 41, and can enter data and/or information regarding the individual or the patient and can transmit the same to the central processing computer and distributed ledger and Blockchain technology system 110.

At step 2902, the central processing computer component 110A of the central processing computer and distributed ledger and Blockchain technology system 110 will determine if an electronic healthcare record, file, or history, exists for the individual or the patient. If, at step 2902, it is determined that an electronic healthcare record, file, or history, does not exist for the individual or the patient, the central processing computer component 110A of the central processing computer and distributed ledger and Blockchain technology system 110, at step 2903, can request that an electronic healthcare record, file, or history, be created for the individual or the patient and/or can process information for creating and/or create an electronic healthcare record, file, or history, for the individual or the patient family. In a preferred embodiment, at step 2903, the provider or the user can enter and transmit any data and/or information, from his or her respective provider communication device 21 or user or patient communication device 41, to the central processing computer component 110A of the central processing computer and distributed ledger and Blockchain technology system 110, and the central processing computer component 110A of the central processing computer and distributed ledger and Blockchain technology system 110 can process information for creating, and will create, the electronic healthcare record, file, or history, for the individual or patient.

In another preferred embodiment, the provider or user may, at step 2902 or 2903, decide for any appropriate reason to create an electronic healthcare record for the individual or the patient. In this regard, the apparatus 300 and method of the present invention can be utilized to create an electronic healthcare record for an individual or a patient. In a preferred embodiment, any information regarding the date and time of the creation of the electronic healthcare record, the person, individual, patient, caregiver, provider, payer, or other individual or entity, who or which created the electronic healthcare record, the reason for the creation of the same, and/or any other pertinent or relevant information regarding the creation of the electronic healthcare record, can be stored in the electronic healthcare record of the individual or patient as well as in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

Any electronic healthcare record created at step 2903 can include any relevant and/or pertinent information for or regarding the individual or patient, such as, for example, but not limited to, his or her name, address, social security number, caregiver information, information identifying other individuals for whom the individual or patient is a caregiver, healthcare insurance or payer information, provider information, and/or any other data and/or information described herein as being stored in the database 10H and/or in any electronic healthcare record described herein, including personal and/or family healthcare history and/or any other information related thereto for the individual or the patient. The information can be provided by the provider, by the individual or the patient, by a caregiver, by another individual accompanying, assisting, or acting for or on behalf of, the individual or the patient, or can be obtained with or from, or provided by or from, a healthcare device, healthcare monitoring equipment, or any device, system, apparatus, or equipment, which can be used in measuring, monitoring, obtaining, and/or monitoring, healthcare data or information of or regarding the individual or the patient.

Upon any creation of any electronic healthcare record, file, or history, of or for the individual or patient, an alert message can also be generated by the central processing computer component 110A, of the central processing computer and distributed ledger and Blockchain technology system 110, and can be transmitted to a respective user or patient communication device 41 of the individual, patient, or caregiver for the individual or the patient, to a provider communication device 21 of any other identified provider of the individual or the patient, to the insurer or payer communication device 31 of the insurer or payer of the individual or patient, or to any governmental entity/intermediary communication device 51 of any governmental entity or authorized intermediary. In this regard, the apparatus 300 of the present invention can provide an alert message or a notification message to the individual, the patient, or the caregiver for same, regarding any creation of an electronic healthcare record for the individual or patient. It can be readily appreciated that any such alert message or notification message can also serve as a deterrent to, or for, acts of, or attempts of, healthcare identity theft and/or any fraudulent activity relating to same.

Any alert message or notification message can also contain any information regarding the date and time of the creation of the electronic healthcare record, the person, individual, patient, caregiver, provider, payer, or other individual or entity, who or which created the electronic healthcare record, the reason for the creation of same, and/or any other pertinent or relevant information regarding the creation of the electronic healthcare record and can be stored in the electronic healthcare record as well as in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

Any alert message or notification message can be, or can be included in, or be attached to, an e-mail message, an instant messaging message, an electronic transmission, or an electronic data transmission or electronic data interchange, or can be transmitted via any other data or information transmission, and/or can be transmitted via or using any appropriate or necessary computer(s) or device(s). The alert message or the notification message can also be transmitted in a recorded telephone call or in a facsimile (fax) transmission.

At step 2903, the information provided by the provider, or by the individual, the patient, or the caregiver or other individual, or obtained with or from the respective healthcare device, healthcare monitoring equipment, or device, system, apparatus, or equipment, can be entered via the provider communication device 21, can be transmitted to the central processing computer component 110A of the central processing computer and distributed ledger and Blockchain technology system 110, and can be stored in the individual's or the patient's newly created electronic healthcare record as well as in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110. Thereafter, the operation of the apparatus 300 will proceed to step 2904.

If, at step 2902, it is determined that the individual's or the patient's electronic healthcare record, file, or history, does, in fact, already exist, then the operation of the apparatus 300 will proceed to step 2904. At step 2904, the provider can enter, and can transmit from his or her provider communication device 21, any data or information regarding the individual or the patient. At step 2904, data and/or information regarding the individual's or the patient's symptoms, if any, and/or examination findings, procedure findings, data and/or information previously stored in the electronic healthcare record, file, or history by the individual, patient, or caregiver, including any notes or comments previously stored in the electronic healthcare record, file, or history prior to a provider visit or appointment, or any herein-described video call or tele-health, or remote, examination visit or appointment, or any procedure visit or appointment, or any data and/or information obtained from the individual, the patient, a caregiver or other individual, or any information obtained from any tests, procedures, examination, or any data and/or information obtained with or from any healthcare device, healthcare monitoring equipment, or device, system, apparatus, or equipment, can be entered via the provider communication device 21 or via the user or patient communication device 41, and can be transmitted to, and can be stored at, the central processing computer component 110A of the central processing computer and distributed ledger and Blockchain technology system 110 and/or in the individual's or the patient's electronic healthcare record, file, or history, and/or can be stored in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

At step 2904, data and/or information, which can be obtained via any of the herein-described healthcare equipment input devices 20D or 40D, healthcare measurement input devices 20D or 40D, or healthcare monitoring input devices 20D or 40D, can also be transmitted to the central processing computer component 110A of the central processing computer and distributed ledger and Blockchain technology system 110. The data and/or information obtained via any of the described healthcare equipment input devices 20D or 40D, healthcare measurement input devices 20D or 40D, or healthcare monitoring input devices 20D or 40D, can be transmitted, from the respective provider communication device 21 or user or patient communication device 41, to the central processing computer component 110A of the central processing computer and distributed ledger and Blockchain technology system 110.

In this manner, the data and/or information which is transmitted to the central processing computer component 110A of the central processing computer and distributed ledger and Blockchain technology system 110, at step 2904, can include provider or user entered data and/or information, which can be entered via the user input device 20D or 40D, such as, for example, a keyboard, a mouse, a cardreader, or other input device which can be utilized in conjunction with a computer or a communication device, and/or can include data and/or information which can be obtained and/or acquired by any of the herein-described healthcare equipment input devices 20D or 40D, healthcare measurement input devices 20D or 40D, or healthcare monitoring input devices 20D or 40D. In the case of a dental examination or oral examination, data and/or information can also be obtained by or with, and transmitted from, any dental probe described herein.

In a preferred embodiment, both provider or user entered data and/or information, obtained and/or acquired by any of the herein-described healthcare equipment input devices 20D or 40D, healthcare measurement input devices 20D or 40D, or healthcare monitoring input devices 20D or 40D, can be utilized in performing a patient diagnosis. In another preferred embodiment, only data and/or information obtained and/or acquired by any of the herein-described healthcare equipment input devices 20D or 40D, healthcare measurement input devices 20D or 40D, or healthcare monitoring input devices 20D or 40D, can be utilized in performing an individual diagnosis or a patient diagnosis. In another preferred embodiment, only provider or user entered data and/or information can be utilized in performing an individual diagnosis or a patient diagnosis.

The central processing computer component 110A of the central processing computer and distributed ledger and Blockchain technology system 110 will, at step 2905, receive and/or process the data and/or information transmitted from the respective provider communication device 21 or from the user or patient communication device 41 at step 2904, which data and/or information can include any of the above-described data and/or information regarding the individual or the patient, the individual's or the patient symptoms, if any, examination findings, and/or any other data and/or information, in conjunction with the individual's of the patient's health, healthcare, medical, dental, or other healthcare-related information, history and/or other information, medical or healthcare theories, principles, criteria and/or other medical or healthcare information needed to make a diagnosis.

In a preferred embodiment, the central processing computer component 110A of the central processing computer and distributed ledger and Blockchain technology system 110 can utilize any one or more of various and/or suitable artificial intelligence (AI) programs, algorithms, and/or software applications, any one or more of various and/or suitable machine learning (ML) programs, algorithms, and/or software applications, and/or any one or more of various and/or suitable analytics programs, algorithms, and/or software applications, in processing any data and/or information for making a diagnosis for or regarding the individual or the patient and/or for assisting the provider in making, or arriving at, a diagnosis for or regarding the individual or the patient. At step 2905, the central processing computer component 110A of the central processing computer and distributed ledger and Blockchain technology system 110 will perform a comprehensive diagnostic evaluation of the individual's or the patient's symptoms, illness, condition, if any, and/or the examination findings or procedure findings. In a preferred embodiment, the central processing computer component 110A of the central processing computer and distributed ledger and Blockchain technology system 110 can also utilize any one or more of various and/or suitable artificial intelligence (AI) programs, algorithms, and/or software applications, any one or more of various and/or suitable machine learning (ML) programs, algorithms, and/or software applications, and/or any one or more of various and/or suitable analytics programs, algorithms, and/or software applications, in processing any data and/or information for performing a comprehensive diagnostic evaluation for or regarding the individual or patient.

The comprehensive diagnostic evaluation or diagnosis can be based upon provider or user entered data and/or information, any data and/or information stored in or entered into the individual's or the patient's electronic healthcare record, file, or history, any of the data and/or information described herein as being obtained by, entered into, and/or transmitted to, the central processing computer component 110A of the central processing computer and distributed ledger and Blockchain technology system 110, at step 2904, or any data and/or information obtained or acquired by any of the herein-described healthcare equipment input devices 20D or 40D, healthcare measurement input devices 20D or 40D, or healthcare monitoring input devices 20D or 40D, or the comprehensive diagnostic evaluation can be based upon only data and/or information obtained and/or acquired by any of the herein-described healthcare equipment input devices 20D or 40D, healthcare measurement input devices 20D or 40D, or healthcare monitoring input devices 20D or 40D, or the comprehensive diagnostic evaluation can be based upon only provider or user entered data and/or information. In another preferred embodiment, the comprehensive diagnostic evaluation or diagnosis can also be based on, or arrived at by using, artificial intelligence information and/or processing routines, machine learning information and/or processing routines, and/or analytics information and/or processing routines.

For example, a provider can enter patient symptom information along with patient data and/or information obtained from any of the herein-described healthcare equipment input devices 20D or 40D, healthcare measurement input devices 20D or 40D, or healthcare monitoring input devices 20D or 40D. A diagnosis or a comprehensive diagnostic evaluation can, thereafter, be processed by utilizing data and/or information obtained from both the provider and/or the individual or patient, and/or from any of the herein-described healthcare equipment input devices 20D or 40D, healthcare measurement input devices 20D or 40D, or healthcare monitoring input devices 20D or 40D, and/or by utilizing any other information described herein or otherwise, and/or by using any suitable diagnostic information and/or processing routines, any suitable artificial intelligence information and/or processing routines, any suitable machine learning information and/or processing routines, and/or any suitable analytics information and/or processing routines.

Individual data or patient data can also be obtained solely from any of the herein-described healthcare equipment input devices 20D or 40D, healthcare measurement input devices 20D or 40D, or healthcare monitoring input devices 20D or 40D, with such individual data or patient data being utilized in order to arrive at a diagnosis or a comprehensive diagnostic evaluation. Individual data or information or patient data or information, in another preferred embodiment, can also be obtained solely from a provider or from the individual or the patient himself or herself, or from a caregiver. An individual or patient can also utilize the apparatus 300, in this preferred embodiment, in connection with or in conjunction with any suitable home healthcare equipment input devices, home healthcare measurement input devices, and/or home healthcare monitoring input devices.

In another preferred embodiment, the individual or the patient, or his or her caregiver, or any other person assisting the individual or patient, can access the central processing computer component 110A of the central processing computer and distributed ledger and Blockchain technology system 110, via his or her user or patient communication device 41 and, at step 2904 or at any other appropriate time, can enter or input information regarding a condition, symptom, a blood pressure reading, a heart rate or pulse rate, a blood sugar level or blood glucose level, a blood oxygen level, a blood oxygen percentage level, an oximeter reading, a digital finger pulse oximeter reading, or any other data or information pertaining to the individual or the patient.

The data or information entered by the individual, patient, caregiver, or other person, can also be obtained via any of the herein-described healthcare equipment input devices, healthcare measurement input devices, or healthcare monitoring input devices, which can be located at the individual's or the patient's home, at a hospital, in or at a vehicle of any kind or type, at an individual's or patient's bedside, or at any other appropriate or suitable location, and can also be transmitted to the central processing computer component 110A of the central processing computer and distributed ledger and Blockchain technology system 110, via the respective healthcare equipment input device(s), healthcare measurement input device(s), or healthcare monitoring input device(s), or, in a case where the respective healthcare equipment input device(s), healthcare measurement input device(s), or healthcare monitoring input device(s), is or can be connected with or linked with the user or patient communication device 41, via the user or patient communication device 41. In this preferred embodiment, the individual, patient, or the caregiver or other person, can enter or input information, such as, but not limited to, his or her, or the individual's or patient's, condition, notes, symptoms, blood pressure readings, heart rate or pulse rate readings, blood sugar level or blood glucose level, blood oxygen level, blood oxygen percentage level, or any other data or information which can be entered by, or obtained by, the individual, the patient, or the caregiver or other person.

The data and/or information entered by the individual, the patient, or the caregiver or other person, can be transmitted to, and received by, the central processing computer component 110A of the central processing computer and distributed ledger and Blockchain technology system 110 and/or the provider communication device 21, and can be stored in the individual's or patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110, and/or in the database 20H of the provider communication device 21. In a preferred embodiment, any data and/or information described herein as being obtained, transmitted, and/or stored, at or during step 2904 and/or 2905, can be accessed by and reviewed by the provider, or by any other authorized provider, individual, caregiver, user, insurer, payer, or other authorized individual or entity, at any time.

As and for and illustrative example, an individual or patient being treated for high blood pressure can be instructed by the provider to take his or her own blood pressure reading, or to have it taken by a caregiver or other person assisting the individual or patient, each day for an instructed or pre-determined time period, and to transmit the reading(s) to the central processing computer component 110A of the central processing computer and distributed ledger and Blockchain technology system 110, for storage in his or her electronic healthcare record, file, or history, and/or to transmit the reading(s) to the provider communication device 21.

The reading(s) can be transmitted to the central processing computer component 110A of the central processing computer and distributed ledger and Blockchain technology system 110, and/or to the provider communication device 21, via the respective device or via the user's or patient's communication device 41. The provider, or any other authorized provider, individual, caregiver, user, insurer, payer, or other authorized individual or entity, can, at any time, access the individual's or the patient's electronic healthcare record, file, or history, and review the blood pressure reading(s) taken by, or entered by, the individual or the patient, or the caregiver or other person assisting the individual or the patient. The provider can also utilize the data and/or information entered or provided by the individual, patient, or caregiver or other person, in making an examination finding, in noting a symptom, in making a diagnosis, or in prescribing a course of treatment.

In another preferred embodiment, the central processing computer component 110A of the central processing computer and distributed ledger and Blockchain technology system 110, and/or the provider communication device 21, can be programmed to process and/or to analyze the data or information entered by the individual, the patient, or the caregiver, based on pre-defined criteria or otherwise, based on artificial intelligence information or processing routines, based on machine learning information or processing routines, and/or based on analytics information or processing routines, and can automatically generate a message and transmit and/or provide the message to the provider via the provider communication device 21 or to or via a second provider communication device 21 in order to provide the provider with a notification of a individual's or the patient's condition. For example, if the provider wants to be notified if the individual's or the patient's blood pressure is or was a certain reading, is or was above or below a certain reading, has changed, or has not changed, the provider can program the apparatus 300 or the central processing computer component 110A of the central processing computer and distributed ledger and Blockchain technology system 110, or the provider communication device 21, to analyze any entered or provided individual or patient blood pressure data or information, and if the blood pressure reading is determined to, or to have been, be a certain reading, to be, or to have been, above or below a certain reading, has changed, or has not changed, the central processing computer component 110A of the central processing computer and distributed ledger and Blockchain technology system 110 can generate a message containing information regarding the individual's or the patient's blood pressure condition and can transmit the message to the provider communication device 21, or to a second provider communication device 20, of the provider. Thereafter, the provider can receive, review, and/or act in response to, the information contained in the message.

Although a blood pressure condition has been described as a monitored condition in the above example, it is important to note that the apparatus 300 and method of the present invention can be utilized in a same, a similar, and/or an analogous, manner in order to monitor any condition capable of being monitored by any of the healthcare devices or equipment or healthcare measurement devices or equipment described herein, so that any data or information capable of being obtained by any of herein-described healthcare devices or equipment or healthcare measurement devices or equipment can be automatically monitored, analyzed, and/or reported, to the provider. In this regard, heart rate or pulse rate reading, a blood sugar or blood glucose level or reading, a blood oxygen level or reading, a body temperature reading, a pulse oximeter level or reading, and or any other data and/or information, or condition, can be automatically monitored and/or reported to the provider of an individual or patient.

In another preferred embodiment, the provider, as well as any individual, patient, caregiver, user, insurer or payer, or any authorized governmental entity or intermediary, via his or her respective provider communication device 21, user or patient communication device 41, insurer or payer communication device 31, or governmental entity/intermediary communication device 51, and using the Internet and/or the World Wide Web, a telephone line, a cellular or wireless communication network, or any other communication network or system, can access, control, or monitor, or can obtain readings, measurements, data, or information, from or via any o the herein-described or other healthcare device(s), healthcare monitoring device(s), or healthcare measurement device(s) or equipment, which can be, or which can include, but which is not limited to, any of the devices or equipment described herein which can be used to obtain any type or kind of healthcare data or information or healthcare-related data or information from, for, or regarding, an individual or patient.

In this regard, in another preferred embodiment, the provider, or any authorized provider, or any individual, patient, caregiver, user, insurer or payer, or any authorized governmental entity or intermediary, can, from a remote location, monitor the individual or patient, and/or control and/or monitor a healthcare device(s) or equipment being used to monitor the individual or the patient. The provider, or any authorized provider, or any individual, patient, caregiver, user, insurer or payer, or any authorized governmental entity or intermediary, can also utilize the apparatus 300 and method of the present invention in order to remotely monitor the individual or the patient in a hospital, in a healthcare facility, in or on a vehicle of any type or kind, or in the individual's or the patient's own home.

The provider, or any authorized provider, or any individual, patient, caregiver, user, insurer or payer, or any authorized governmental entity or intermediary, can also be automatically notified, via or by means of a message being transmitted from the respective device or equipment to the respective provider communication device 21, to the user or patient communication device 41, to the insurer or payer communication device 31, or to the governmental entity/intermediary communication device 51, or via or by means of a message being transmitted from the central processing computer component 110A of the central processing computer and distributed ledger and Blockchain technology system 110 to the respective provider communication device 21, to the user or patient communication device 41, to the insurer or payer communication device 31, or to the governmental entity/intermediary communication device 51, of or regarding a detected, or a detection of, or an alert regarding, an emergency situation, a healthcare emergency situation, or any other occurrence which warrants notifying a provider.

Any data or information obtained by the provider can also be transmitted to the central processing computer and distributed ledger and Blockchain technology system 110 for inclusion in the individual's or the patient's electronic healthcare record, file, or history, and/or can be processed and/or stored in the manner described herein with regard to steps 2904 and 2905 described herein, and/or in any other appropriate manner consistent with the teachings and use of the apparatus 300 and method of the present invention.

In the above described manner, the apparatus 300 and method of the present invention can be utilized in order to allow a provider, or any authorized provider, or any individual, patient, caregiver, user, insurer or payer, or any authorized governmental entity or intermediary, to monitor an individual or patient, or any number of individuals or patients, from a remote location and/or via any of the respective provider communication devices 21, user or patient communication devices 41, insurer or payer communication devices 31, or governmental entity/intermediary communication devices 51, described herein.

At step 2906, the central processing computer and distributed ledger and Blockchain technology system 110 will generate a diagnostic report which can include a diagnosis of the individual's or the patient's condition. The diagnostic report, which is generated at step 2906, can include a single diagnosis and/or a list of possible diagnoses, along with their respective probabilities of occurrence and/or statistical information corresponding thereto, which may pertain to the individual's or the patient's condition.

At step 2907, the central processing computer and distributed ledger and Blockchain technology system 110 will then generate a treatment report which will outline and/or prescribe treatment for the single diagnosis and/or for the list of possible diagnoses. The central processing computer and distributed ledger and Blockchain technology system 110, when generating the treatment report, can process data and/or information for or regarding the same in conjunction with information regarding possible drug interactions and/or treatment interactions. The central processing computer and distributed ledger and Blockchain technology system 110, when processing data and/or information for generating the treatment report, can also utilize artificial intelligence information or processing routines, machine learning information or processing routines, and/or analytics information or processing routines. In another preferred embodiment, the diagnostic report and/or the treatment report can also contain information regarding any of the notes, comments, or messages, which were, or which may have been, previously entered by the individual or patient, or by a caregiver of the individual or patient, into the individual's or patient's electronic healthcare record, file, or history.

At step 2908, the central processing computer and distributed ledger and Blockchain technology system 110 will transmit the diagnostic report and/or treatment report to the provider's communication device 21 at which point the provider can obtain information regarding the diagnosis or possible diagnoses, if any, and information regarding the corresponding treatment plan(s).

At step 2908, the central processing computer and distributed ledger and Blockchain technology system 110 can also transmit the diagnostic report and/or treatment report to the provider communication device 21 of any other authorized provider of the individual or patient, or to a user or patient communication device 41 of the individual or patient, or caregiver of same, or to the insurer or payer communication device 31 of the individual's or patient's insurer or payer, or insurers or payers, or to a governmental entity/intermediary communication device 51 of or associated with an authorized governmental entity or intermediary, at which point the respective provider, individual, patient, caregiver, insurer or payer, or governmental entity or intermediary, can review and obtain any information contained in the respective diagnostic report and/or treatment report or any other information regarding any diagnosis or possible diagnoses and/or any information regarding any prescribed treatment, treatments, or treatment plans contained therein. It can also be readily appreciated that any such diagnostic report or treatment report being sent to any one or more of the herein-described providers, insurers or payers, the individual, patient, or caregiver for the individual or the patient can, or to an authorized governmental entity or intermediary, can also be used as a deterrent to or for healthcare identity theft and/or any fraudulent activity relating to same.

Upon any generation and/or transmission of the diagnostic report or the treatment report, each respective report or reports can be stored in the electronic healthcare record, file, or history, of the individual or patient, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

Any of the herein-described diagnostic reports and/or treatment reports can also be stored in the electronic healthcare record, file, or history, of the individual or patient, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110. At any time after receiving the diagnostic report or the treatment report, any provider, the individual, patient, or caregiver, the insurer or payer, or any governmental entity or intermediary can report a mistake or any fraudulent or suspected fraudulent activity regarding the same by transmitting, from his, her, or its, respective communication device 21, 31, 41, or 51, to the central processing computer component 110A of the central processing computer and distributed ledger and Blockchain technology system 110, a message reporting any such detected or suspected mistake or any such detected or suspected fraudulent activity regarding or involving the individual or the patient, his or her healthcare record, file, or history, or a mistaken diagnosis, treatment, insurance claim or claim for payment, or a fraudulent diagnosis, treatment, or insurance claim or claim for payment. Any such message can also be stored in the individual's or the patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

Any of the herein-described diagnostic reports, treatment reports, or messages, can be, or can be included in, or can be attached to, an e-mail message, an instant messaging message, an electronic transmission, or an electronic data transmission or electronic data interchange, and/or can be transmitted via any other data or information transmission, and/or can be transmitted via or using any appropriate or necessary computer(s) or device(s). The message can also be transmitted in a recorded telephone call or in a fax transmission.

With reference once again to FIGS. 29A and 29B, the provider can then, at step 2909, review the diagnostic report and/or the treatment report and can choose the final diagnosis and/or the treatment plan for same to administer to the individual or the patient. At step 2910, the provider can transmit information regarding the final diagnosis and the treatment plan, including the prescribed treatment and/or treatment plan, if any, to the central processing computer component 110A of the central processing computer and distributed ledger and Blockchain technology system 110.

The prescribed treatment and/or treatment plan can also include a prescribed treatment, treatment regimen, information or instructions regarding further or additional examination and/or tests or testing, information regarding one or more prescriptions for further examination or testing, one or more provider or treatment referrals, one or more prescriptions for further testing, blood work, x-rays, MRIs, CAT scans, PET scans, or other information gathering or testing, one or more prescriptions for prescribed drugs, medication, therapy, physical therapy, and/or other therapy. At step 2910, any prescription for any drug, medication, or therapy, can also be transmitted to a respective provider communication device 21 of or associated with any other providers such as a respective pharmacy, a therapist, or a treatment facility. Similarly, at step 2910, any prescription for further examination or for follow-up testing of any kind, or any provider or treatment referral, can also be transmitted to a provider communication device 21 of or associated with a respective provider. At step 2910, any prescription for any drug, medication, or therapy, can also be transmitted to a respective payer communication device 31 of or associated with an insurer or payer of the individual or patient, and any prescription for further examination or for follow-up testing of any kind, or any provider or treatment referral, can also be transmitted to a respective payer communication device 31 of or associated with an insurer or payer of the individual or patient.

In another preferred embodiment, at step 2910, the provider can also generate and/or transmit a prescription or an electronic prescription for a medication, a medicine, or a drug, or for a procedure, a test, an analysis, an analysis work-up, blood work, a treatment, or a therapy, or can generate and/or transmit a referral to another provider, for submission or transmission to the respective pharmacy or other provider, and for storage in the individual's or the patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

At step 2910, any data and/or information regarding any/or all of the herein-described final diagnoses and treatment plans, prescribed treatments and/or treatment plans, treatment regimens, or any of the information or instructions regarding further or additional examination and/or tests or testing, information regarding one or more prescriptions for further examination or testing, one or more provider or treatment facility referrals, one or more prescriptions for further testing, blood work, x-rays, MRIs, CAT scans, PET scans, or other information gathering or testing, prescriptions for prescribed drugs, medication, therapy, physical therapy, and/or other therapy, further examination or follow-up testing of any kind, referrals, or electronic prescriptions, can also be stored in the individual's or the patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110, and can also be transmitted to the respective user or patient communication device 41 of the individual, patient, or caregiver for the individual or the patient, to the provider communication device 21 of any other identified provider of the individual or the patient, to the insurer or payer communication device 31 of the insurer or payer of the individual or patient, or to any governmental entity/intermediary communication device 51 of any authorized governmental entity or intermediary.

In another preferred embodiment, the final diagnosis and treatment plan, including the prescribed treatment and/or treatment plan, can also be transmitted by the central processing computer component 110A of the central processing computer and distributed ledger and Blockchain technology system 110, at step 2910, back to the provider for his or her records, to another provider of the individual or patient, to a payer or insurer of the individual or patient, to the individual or patient, or to a governmental entity, third party, or intermediary, by transmitting the final diagnosis and/or treatment plan, to a respective provider communication device 21, to a respective payer communication device 31, to a respective user or patient communication device 41, or to a respective governmental entity/intermediary communication device 51, either directly, such as via any suitable electronic or other transmission, or indirectly, such as via an e-mail server in an instance or situation where the final diagnosis and/or treatment plan is included in, or is attached to, an e-mail message.

In a preferred embodiment, a copy of the final diagnosis and treatment plan can also be stored by or in the respective provider communication device 21, the respective payer communication device 31, the respective user or patient communication device 41, or the respective governmental entity/intermediary communication device 51.

In another preferred embodiment, the final diagnosis and treatment plan can contain individual-specific or patient-specific educational information or individual-specific or patient-specific instructional information, or a link(s) or hyperlink(s) to same, regarding the diagnosis, treatment, or treatment plan, or information relating thereto, so as to provide this educational information or instructional information to the individual or patient, or to a caregiver. The individual or patient can thereafter access or obtain the educational information or instructional information via the apparatus 300 and method of the present invention. In this manner, the apparatus 300 and method of the present invention can provide individual-specific or patient-specific educational information or individual-specific or patient-specific instructional information regarding the diagnosis, treatment, or treatment plan.

In another preferred embodiment, the apparatus 300 or the central processing computer component 110A of the central processing computer and distributed ledger and Blockchain technology system 110 can be programmed to identify the individual-specific or patient-specific educational information or the individual-specific or patient-specific instructional information regarding the diagnosis, treatment, or treatment plan, and/or any information, link(s), or hyperlink(s), relating thereto or pertaining thereto.

In another preferred embodiment, the central processing computer component 110A of the central processing computer and distributed ledger and Blockchain technology system 110 can also be programmed to identify, and to include, in a diagnostic report or in a treatment report, information regarding an insurance policy, product, or service, and/or an insurance exchange computer(s) 70 from which same may be purchased or subscribed to, which may be of interest to, or which could be helpful or beneficial to the individual or the patient based on a diagnosis, a possible diagnosis, a prescribed treatment, a prescribed treatment, and/or suggested or required drug or medication, therapy, or procedure, identified in a respective diagnostic report or treatment report, and can include information or a link or links, or a hyperlink or hyperlinks, to the insurance exchange computer(s) 70.

In another preferred embodiment, the central processing computer component 110A of the central processing computer and distributed ledger and Blockchain technology system 110 can also be programmed to identify, and to include, in a diagnostic report or a treatment report, information regarding a social network computer(s) 80 containing information or links to social networking support groups or social networking-based groups or information sources which may be of interest to, or which could be helpful or beneficial to the individual or the patient based on a diagnosis, a possible diagnosis, a prescribed treatment, a prescribed treatment, and/or a suggested or required drug or medication, therapy, or procedure, identified in a respective diagnostic report or treatment report, and can include information or a link or links, or a hyperlink or hyperlinks, to the social network, a social network computer(s) 80, a social networking web site or support group, a social networking blog or chat room or discussion group, or any other social networking information.

In another preferred embodiment, the central processing computer component 110A of the central processing computer and distributed ledger and Blockchain technology system 110 can be programmed to identify, and to include, in a diagnostic report or a treatment report, information regarding a media computer 90 or a media source which can provide information which may be of interest to, or which could be helpful or beneficial to the individual or the patient based on a diagnosis, a possible diagnosis, a prescribed treatment, a prescribed treatment, and/or a suggested or required drug or medication, therapy, or procedure, identified in a respective diagnostic report or treatment report, and can include information or a link or links, or a hyperlink or hyperlinks, to the media computer(s) 90.

In another preferred embodiment, the central processing computer component 110A of the central processing computer and distributed ledger and Blockchain technology system 110, in addition to generating any of the herein-described diagnostic reports, treatment reports, or treatment plans, can also generate a wellness report, an exercise report, fitness report, a nutritional report, a diet report, a rehabilitation report, a therapy report, and/or any other report containing wellness information, exercise information, fitness information, suggested exercises and/or suggested fitness routines, nutritional information, diets, rehabilitation exercises or activities, and/or therapy information. The respective wellness report, exercise report, fitness report, nutritional report, diet report, rehabilitation report, therapy report, and/or any other report, can be generated using any data and/or information contained in the individual's, patient's, or caregiver's electronic healthcare record or electronic healthcare file, and/or by using any information regarding any examination findings, procedure findings, symptoms, diagnoses, possible diagnoses, treatments, treatment plans, or any other information used in generating any of the herein-described diagnostic reports, treatment reports, or treatment plans. The respective wellness report, exercise report, fitness report, nutritional report, diet report, rehabilitation report, therapy report, and/or any other report, can be generated using data and/or information provided by any individual, patient, caregiver, by any provider, by any insurer or payer, and/or or by any governmental entity, intermediary, or third party.

The respective wellness report, exercise report, fitness report, nutritional report, diet report, rehabilitation report, therapy report, and/or any other report, can also be generated in connection with the generation of any diagnostic report, treatment report, or treatment plan. In a preferred embodiment, any of the herein-described diagnostic reports, treatment reports, or treatment plans, can also include or contain the respective wellness report, exercise report, fitness report, nutritional report, diet report, rehabilitation report, therapy report, and/or any other report, or can include or contain a link(s) or a hyperlink(s) to the respective wellness report, exercise report, fitness report, nutritional report, diet report, rehabilitation report, therapy report, and/or any other report. Any and/or all of the respective wellness reports, exercise reports, fitness reports, nutritional reports, diet reports, rehabilitation reports, therapy reports, and/or any other reports, can be stored in the individual's, the patient's, or the caregiver's, electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

Any of the herein-described diagnostic reports, treatment reports, or treatment plans, wellness reports, exercise reports, fitness reports, nutritional reports, diet reports, rehabilitation reports, therapy reports, and/or any other reports, can contain or include a link(s) or hyperlink(s) to a respective individual's, patient's, or caregiver's, electronic healthcare record, file, or history, and/or to any number of the electronic healthcare records, files, or histories, of the respective individual, patient, or caregiver.

In another preferred embodiment, any individual, patient, or caregiver, provider, or insurer or payer, or any governmental entity, intermediary, or third party, can access the central processing computer component 110A of the central processing computer and distributed ledger and Blockchain technology system 110 with or by using a respective communication device 41, 21, 31, or 51, and can request that a respective wellness report, exercise report, fitness report, nutritional report, diet report, rehabilitation report, therapy report, and/or any other report, be generated for the individual or patient. Thereafter, the central processing computer component 110A of the central processing computer and distributed ledger and Blockchain technology system 110 can generate the respective wellness report, exercise report, fitness report, nutritional report, diet report, rehabilitation report, therapy report, and/or any other report, can transmit the same to the respective communication device 41, 21, 31, or 51 of the requesting individual, patient, or caregiver, provider, or insurer or payer, or any governmental entity, intermediary, or third party, and/or can store the same in the electronic healthcare record, file, or history, of the individual, patient, or caregiver, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

In another preferred embodiment, any of the herein-described diagnostic reports, treatment reports, treatment plans, wellness reports, exercise reports, fitness reports, nutritional reports, diet reports, rehabilitation reports, therapy reports, and/or any other reports, can include or can contain data and/or information regarding suggested or recommended providers, healthcare facilities, treatment facilities or centers, suggested appointments with providers, lifestyle suggestions, wellness or fitness suggestions, diet suggestions, and/or a link(s) or hyperlink(s) to any of the above data and/or information.

At step 2911, the central processing computer component 110A of the central processing computer and distributed ledger and Blockchain technology system 110 will store any data and/or information to update, or for updating, and will update, the individual's or the patient's electronic healthcare record, file, or history, in the database 10H so as to include all of the data and information herein-described as being processed and/or generated by the central processing computer component 110A of the central processing computer and distributed ledger and Blockchain technology system 110, including, but not limited to, the individual or the patient's symptoms, if any, the examination findings, the information contained in the diagnostic report and/or the treatment report, the final diagnosis and/or the prescribed treatment, as well as any other reports, messages, or other data or information, described as being generated, transmitted, or exchanged, by and/or between any of the computers or communication devices 110A, 21, 31, 41, 51, 70, 80, an/or 90, in the embodiment if FIGS. 29A and 29B, as well as any and/or all of the other embodiments described herein.

At step 2911, the central processing computer component 110A of the central processing computer and distributed ledger and Blockchain technology system 110 can also update any healthcare records, files, or histories, of the individual or the patient which are stored in any healthcare records computer(s) 60 or in any respective database(s) 60H of same.

At step 2911, the central processing computer component 110A of the central processing computer and distributed ledger and Blockchain technology system 110 can also generate a message containing information regarding the individual's or the patient's condition(s) or symptoms, if any, the examination findings, the procedure findings, or any of the information contained in the diagnostic report and/or the treatment report, the final diagnosis and/or the prescribed treatment. At step 2911, the central processing computer component 110A of the central processing computer and distributed ledger and Blockchain technology system 110 can also transmit the message as an e-mail message, as a text message, as an instant messaging message, or as any other type of message, in electronic form or otherwise, to the individual or patient such as by transmitting the same to the user or patient communication device 41 of or associated with the individual or patient, and/or to any one or more of a provider communication device 21 of or associated with the provider or another provider, a payer communication device 31 of or associated with the individual's or patient's payer or insurer, or, if authorized or allowed, to a governmental entity/intermediary communication device 51 of or associated with a governmental entity or intermediary authorized or allowed to receive the same.

The message or messages, or any other communication(s) or transmission(s) described herein as being provided to the individual or patient, to the provider or another provider, to the payer or insurer, or to the governmental entity or intermediary, can also contain information such as advertisement(s) or marketing materials for a healthcare product(s) or service(s), an advertisement(s) or marketing materials for a health, wellness, or exercise, product(s) or service(s), or a news report or other information, pertinent to the individual or patient, or pertinent to or relating to the individual's or patient's condition or symptoms, if any, any examination finding(s), any information contained in the diagnostic report and/or the treatment report, or any final diagnosis and/or prescribed treatment.

At step 2911, the central processing computer component 110A of the central processing computer and distributed ledger and Blockchain technology system 110, in response to a request by the provider, can also process information in order to request or to create a subscription for the individual or patient so that the individual or patient can receive future information, by mail, by e-mail message, by text message, or otherwise, regarding a news report or other data or information which would be of interest to the individual or patient or pertinent to the individual's or patient's condition.

In the manner described above, the individual or patient can be provided with information regarding his or her provider's actions taken on his or her behalf, or the provider's diagnosis or treatment planning, pursuant to a diagnosis or a condition. In the manner described above, news or other information regarding an individual's or patient's health condition, symptoms, diagnosis, or treatment, can also be disseminated to the individual or patient on a regular and/or on an on-going basis. In this regard, news or information, which may be pertinent, relevant, or otherwise helpful, for allowing an individual or patient to understand a diagnosis, a treatment plan or regimen, a condition, or an illness, or which can help the individual or patient to take corrective or preventive action or measures regarding a condition or an illness, can be provided to the individual or patient, or can be transmitted to the individual's or patient's user or patient communication device 41, at the provider's direction or discretion, on a one-time basis, on a regular on on-going basis, or when the news or information becomes available, and/or at any other time and/or at or in response to an occurrence of any event.

In another preferred embodiment, information regarding a providing of news or information to the individual or patient, as with the individual's or patient's other healthcare information, can be ordered, prescribed, or otherwise disseminated or provided, to the individual or patient pursuant to, and/or in accordance with, any and/or all healthcare privacy laws, rules, or regulations, in effect at the time in given jurisdiction or political subdivision.

The news or information described herein can also be disseminated or provided to an individual or patient based on, or in response to, a diagnosis, a prescribed treatment, a treatment plan, a drug or medication which can be recommended or prescribed for the individual or patient, a recommended or prescribed procedure or operation, a recommended or prescribed physical therapy, drug or medication therapy, alternate therapy, herbal therapy, acupuncture therapy, or any other therapy, which may be recommended or prescribed by any of the providers or types of providers described herein, or in response to any other action taken by any provider in response to a condition, symptom, family healthcare history, diagnosis, or any other information obtained, regarding the individual or patient.

In a preferred embodiment, any of the data and/or information described herein as being obtained, processed, generated, transmitted, and/or stored, by the apparatus 300 of the embodiment of FIGS. 29A and 29B, can be stored in the individual's or the patient's electronic healthcare records, files, or histories, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110. At step 2911, the central processing computer component 110A of the central processing computer and distributed ledger and Blockchain technology system 110 will process any/or all information updating, and will update, the individual's or the patient's electronic healthcare records, files, or histories, so that the updated healthcare records, files, or histories, will be available for the individual's or the patient's next treatment, diagnosis, or other healthcare intervention. Thereafter, operation of the apparatus 300 will cease at step 2912.

In another preferred embodiment, any and/or all of the data or information which is input, transmitted to, or provided by, the apparatus 300, when used as described in the embodiment of FIGS. 29A and 29B, can be dated stamped and/or time stamped.

In yet another preferred embodiment, any and/or all of the data or information which is input, transmitted to, or provided by, the apparatus 300, when used as described in the embodiment of FIGS. 29A and 29B, can be dated stamped and/or time stamped and can stored for each individual, patient, caregiver, provider, insurer or payer, intermediary, healthcare records computer 60 owner, operator or company, insurance exchange computer 70 or insurance exchange owner, operator, or company, social networking computer 80 owner, operator or company, social networking company, support group, information source, discussion group, or chat room, or media computer 90 or media source or company. The above-described information can be stored, and/or can be sorted, and/or accessed, for efficient record keeping purposes, auditing purposes, evaluation purposes, and/or for any other purpose(s).

In another preferred embodiment, the diagnostic report and/or the treatment report can be accompanied by medical information, dental information, textbook materials, laboratory materials, reference materials, video clips of any pertinent information, audio clips of any pertinent information, hyperlinks to informational sources, information regarding providers and/or facilities for obtaining treatment and/or therapy, provider and/or facility contact information, and/or any other pertinent and/or relevant information.

In another preferred embodiment, the central processing computer component 110A of the central processing computer and distributed ledger and Blockchain technology system 110, upon generating the respective diagnostic report or treatment report or treatment plan, can also processing information regarding any of the herein-described providers and can identify a provider or providers who or which may be able to provide services to the individual or patient in helping to make or arrive at a diagnosis, to select a diagnosis from a list of possible diagnoses, to provide a treatment, to perform a needed treatment, procedure, surgery, or other service for the individual or patient, or to devise or design a treatment plan for the individual or patient. In a preferred embodiment, the diagnostic report or the treatment report or treatment plan can contain information regarding the identified provider or providers including their respective contact information.

In another preferred embodiment, the central processing computer component 110A of the central processing computer and distributed ledger and Blockchain technology system 110 can generate and transmit a notification message to the respective provider communication devices 21 of any of the identified provider or providers so as to inform them that they have been identified as being able to provide a service to the individual or patient in the respective diagnostic report, treatment report, or treatment plan. In another preferred embodiment, the notification message can also contain the diagnostic report, the treatment report, or the treatment plan, or a link or hyperlink to same, provided that the inclusion of such information has been permitted by the individual, patient, or caregiver, and/or the provision of such information is not made in violation of any applicable healthcare privacy laws, rules, or regulations.

In another preferred embodiment, the central processing computer component 110A of the central processing computer and distributed ledger and Blockchain technology system 110, upon generating the respective diagnostic report or treatment report or treatment plan, can also process information regarding any of the herein-described providers of any good(s), product(s), service(s), therapy(ies), medications, blood, organs, healthcare devices or equipment, or any other goods, products, or services, which may be identified as being essential to, or helpful in, making or arriving at a diagnosis, selecting a diagnosis from a list of possible diagnoses, providing a treatment, performing a needed treatment, procedure, surgery, or other service for the individual or patient, or designing, implementing, and/or effectuating, a treatment plan for the individual or patient. In a preferred embodiment, the diagnostic report to the treatment report or treatment plan can also contain information regarding the identified provider or providers of such good(s), product(s), service(s), therapy(ies), medications, blood, organs, healthcare devices or equipment, or any other goods, products, or services, including their respective contact information.

In another preferred embodiment, the central processing computer component 110A of the central processing computer and distributed ledger and Blockchain technology system 110 can generate and transmit a notification message to any identified provider or providers of any goods, products, services, therapy(ies), medications, blood, organs, healthcare devices or equipment, or any other goods, products, or services, informing them that they have been identified as being able to provide a respective good, products, services, therapy, medication, blood, organ, healthcare device or equipment, or any other good(s), product(s), or service(s), to the individual or patient in the respective diagnostic report, treatment report, or treatment plan. In another preferred embodiment, the notification message can also contain the diagnostic report, the treatment report, or the treatment plan, or a link or hyperlink to same, provided that the inclusion of such information has been permitted by the individual, patient, or caregiver, and/or the provision of such information is not made in violation of any applicable healthcare privacy laws, rules, or regulations.

In another preferred embodiment, the diagnostic report and/or treatment report can be accompanied by health and/or wellness information which can include suggestions for health and/or wellness foods, goods, products, and/or services. The diagnostic report and/or treatment report can also be accompanied by health and/or fitness information, diets, nutritional information, and/or any other information which may be of assistance to the individual or the patient and/or provider. The diagnostic report and/or treatment report can also contain warnings regarding misdiagnoses, warnings about treatments, and/or information about experimental treatments. The diagnostic report and/or treatment report can also contain information, statistical, analytical, and/or otherwise, regarding diagnoses, misdiagnoses, treatment successes, and/or treatment failures. The diagnostic report and/or treatment report can also contain information regarding alternate medicine such as treatments regarding herbal remedies and/or treatments, meditation, self-healing, faith healing, yoga, tai chi, exercise therapy, and/or other therapies and/or therapy types.

As noted above, the method of utilizing the present invention, as described in FIGS. 29A and 29B, is equally applicable to, and can be utilized in a same, a similar, and/or an analogous, manner, by any and/or all of the respective healthcare providers, professionals, and/or related providers, described herein or otherwise. The apparatus of FIGS. 29A and 29B can also be utilized in a same, a similar, and/or an analogous, manner, by any of the herein-described users, individuals, patients, caregivers, healthcare providers, or healthcare insurers, healthcare payers, governmental entities, or intermediaries. In another preferred embodiment, the apparatus 300 can also be utilized so as to ensure that all privacy laws, rules, and regulations, and patient confidentiality laws, rules, and regulations, are followed and/or abided by, and/or so as to ensure that complete confidentiality is maintained, so as to allow any of the herein-described users, individuals, patients, caregivers, healthcare providers, or healthcare insurers, healthcare payers, governmental entities, or intermediaries, to access and use the apparatus 300 in any appropriate manner.

The apparatus 300 of FIGS. 29A and 29B can also utilize electronic signatures and/or can process electronic signatures and/or electronic signature information which can correspond to any of the herein-described individuals or entities who or which utilize the apparatus 300.

In another preferred embodiment, the apparatus 300 and method of the present invention can be utilized so as to ensure that a proper treatment and/or procedure is performed on the individual or the patient. Referring once again to FIGS. 29A and 29B and the above description of same, the apparatus 300 of the present invention can also be utilized so as to ensure that a subsequent treatment and/or treatments are performed as prescribed. As noted above and, in particular, information regarding a final diagnosis and a prescribed treatment can be stored in the individual's or the patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

When the individual or the patient seeks treatment from a subsequent provider, medical doctor, surgeon, dentist, or other healthcare professional, the respective provider, medical doctor, surgeon, dentist, or other healthcare professional, can access the central processing computer component 110A of the central processing computer and distributed ledger and Blockchain technology system 110 at the time of treatment, can access the individual's or the patient's electronic healthcare record, file, or history, and can access the prescribed treatment plan stored therein in order to ensure or confirm that the treatment to be provided is called for in the prescribed treatment or is otherwise appropriate. In this manner, the apparatus 300 of the present invention can be utilized in order to prevent healthcare, medical, and/or surgical, mistakes, mishaps, and/or other instances when an improper treatment could occur or could result.

It is also envisioned that the subsequent care provider, medical doctor, surgeon, dentist, or other healthcare professional, could also re-evaluate the individual's or the patient's condition and/or electronic healthcare record, file, or history, and seek additional assistance and/or perform a separate and independent assessment and/or diagnosis of the individual or the patient. In any event, the apparatus 300 of the present invention can provide the subsequent care provider, medical doctor, surgeon, dentist, or other healthcare professional, with the individual's or the patient's complete healthcare record, file, or history, as well as any other information, including, but not limited to, information regarding any past diagnoses and/or any past treatments and/or drug or other prescriptions. In this manner, a subsequent care provider can be provided with up to date healthcare information regarding an individual or patient at a time of an administration of a treatment.

For example, the apparatus 300 of the present invention can be utilized in the following manner. A patient who is scheduled for surgery on a certain body part (e.g. his or her left ankle) can enter a hospital. Due to a hospital clerical error, the right ankle is noted to be operated on. Prior to the surgery, the surgeon, using a provider communication device 21, located in the operating room or in another location in the hospital, can access the central processing computer component 110A of the central processing computer and distributed ledger and Blockchain technology system 110 in order to verify the procedure to be performed on the patient. In response to providing information regarding the patient, the central processing computer component 110A of the central processing computer and distributed ledger and Blockchain technology system 110, can transmit a message to the provider communication device 21 containing information indication that the patient's left ankle is to be the subject of the operation. Thereafter, the surgeon can perform the correct and prescribed surgery and the patient's electronic healthcare record, file, or history, can be updated accordingly.

Although described in connection with a surgical procedure, the apparatus 300 can be used in a same, a similar, and/or an analogous, manner in connection with any treatment, test, procedure, or other action, which can be performed by any provider or healthcare professional described herein. In this manner, the apparatus 300 of the present invention can be utilized to pre-screen subsequent and/or follow-up treatments and/or procedures so as to prevent healthcare mistakes and/or mishaps.

In another preferred embodiment, the provider or healthcare professional can access the central processing computer component 110A of the central processing computer and distributed ledger and Blockchain technology system 110 with or via the provider communication device 21, access the individual's or the patient's electronic healthcare record, file, or history, and enter or input information concerning a treatment and/or a procedure which is to be performed. Thereafter, the central processing computer component 110A of the central processing computer and distributed ledger and Blockchain technology system 110 can process the information and transmit a message to the provider communication device 21 informing the provider or healthcare professional that the treatment and/or procedure is either the prescribed or correct treatment or procedure or that it is not the prescribed or the incorrect treatment or procedure. The message provided by the central processing computer component 110A of the central processing computer and distributed ledger and Blockchain technology system 110, to the treating provider or healthcare professional, can also include information regarding the treatment or the procedure, such as instructions, steps, and/or any other accompanying or related information regarding same.

In another preferred embodiment, the apparatus 300 of FIGS. 29A and 29B can be utilized to perform diagnoses by utilizing entered data and/or information and/or data and/or information which can be obtained by, acquired by, and/or measured by, any of the herein-described user input devices 20D or 40D and/or any of the herein-described healthcare devices or healthcare equipment.

In any and/or all of the embodiments described herein, the central processing computer component 110A of the central processing computer and distributed ledger and Blockchain technology system 110, in performing any processing of any of the patient information, diagnosis information, and/or treatment information, described herein, can perform such processing in conjunction with drug and/or other treatment interaction information, so as to provide an added safeguard in the diagnosis and treatment planning processes. Any and/or all processing described herein as being performed by the central processing computer component 110A of the central processing computer and distributed ledger and Blockchain technology system 110 can also be performed in conjunction with each individual's or patient's electronic healthcare record, file, or history and any and/or all data and/or information contained or stored therein, which can, at the very least include, healthcare or medical history information, family history information, allergic conditions information, and/or with any other information deemed important and/or essential in the diagnosis and/or treatment of the individual or patient.

In another preferred embodiment, any of the diagnostic reports or treatment reports can also contain an advertisement or advertisements for any goods, products, or services, including, but not limited to, any healthcare, healthcare-related, fitness, wellness, nutritional, and/or any other, goods, products, or services.

In another preferred embodiment, the apparatus 300 of the embodiment of FIGS. 29A and 29B can also be utilized in a same, a similar, and/or in an analogous, manner, by any of the herein-described users, individuals, patients, caregivers providers, insurers, payers, and/or governmental entities or intermediaries, in order to ascertain a diagnosis or a treatment and/or in order to check on, to verify, and/or to ascertain the correctness of a diagnosis of an individual or patient, and/or to formulate, to plan, to check on, to verify, and/or to ascertain the correctness of a diagnosis, a treatment, or a treatment plan.

In another preferred embodiment, the apparatus 300 of the embodiment of FIGS. 29A and 29B can also be programmed and/or utilized in order to automatically identify and locate a provider for the individual or patient upon the generation of the diagnostic report at step 2906, or upon the generation of the treatment report or the treatment plan at step 2906, can automatically schedule an appointment for the individual or patient with the identified or located provider, and can automatically include the appointment information in the respective diagnostic report, treatment report, or treatment plan.

In another preferred embodiment, in a situation where a healthcare device or healthcare equipment, or a plurality of healthcare devices(s) or a plurality of pieces of healthcare equipment, is or are to be utilized in connection with the apparatus 100, 200, or 300, of the present invention, in order to allow a provider, an insurer or payer, or any intermediary or third party, or another individual or user, to remotely monitor an individual or patient, or to remotely control or monitor a healthcare device or healthcare equipment for an individual or patient, information, a link, or a hyperlink, corresponding to, or associated with, each healthcare device or each piece of healthcare equipment, assigned to or used for an individual or a patient, can be stored in the database 10H of the central processing computer 10 or in the database 10H of the central processing computer component 110A of the central processing computer and distributed ledger and Blockchain technology system 110, in the electronic healthcare record, file, or history, of the individual or patient, or the caregiver, and/or in the individual's or patient's electronic healthcare record, file, or history, which is stored in database 60H of the healthcare records computer 60.

FIG. 30 illustrates another preferred embodiment method for utilizing the apparatus 300 and method of the present invention, in flow diagram form. FIG. 30 illustrates another preferred embodiment method for utilizing the apparatus 300 and method of the present invention in order to allow, or to facilitate, a remote monitoring and/or treatment, of an individual or patient by a provider, a caregiver, an insurer, a payer, or any governmental entity, intermediary, or third party, and/or to allow or to facilitate a remote control and/or a remote monitoring of a healthcare device or a piece of healthcare equipment used to monitor, to diagnose, to evaluate, to treat, or to care for, the individual or the patient, by a provider, a caregiver, an insurer, a payer, or any governmental entity, intermediary, or third party.

With reference to FIG. 30, the operation of the apparatus 300 commences at step 3000. At step 3001, the respective provider, insurer, payer, caregiver, or any governmental entity, intermediary, or third party, or any other individual or user, can utilize a respective provider communication device 21, an insurer or payer communication device 32, a user or patient communication device 42, a governmental entity/intermediary communication device 51, or any other computer or communication device, in order to access the central processing computer component 110A of the central processing computer and distributed ledger and Blockchain technology system 110. At step 3002, the respective provider, insurer, payer, caregiver, or any governmental entity, intermediary, or third party, or any other individual or user, can enter, and can transmit, to the central processing computer component 110A of the central processing computer and distributed ledger and Blockchain technology system 110, and central processing computer component 110A of the central processing computer and distributed ledger and Blockchain technology system 110 can receive, store, or process, any appropriate identification information, authorization information, an access code, a password, or any other data or information, which can be used to ensure that the respective provider, insurer, payer, caregiver, or any governmental entity, intermediary, or third party, or any other individual or user, is authorized to access the central processing computer component 110A of the central processing computer and distributed ledger and Blockchain technology system 110, is authorized to perform a remote control or monitoring operation regarding the individual or patient, or is authorized to access the electronic healthcare record, file, or history, of the individual or patient.

At step 3003, the central processing computer component 110A of the central processing computer and distributed ledger and Blockchain technology system 110 will determine whether or not the respective provider, insurer, payer, caregiver, or any governmental entity, intermediary, or third party, or any other individual or user, is authorized to access the central processing computer component 110A of the central processing computer and distributed ledger and Blockchain technology system 110, is authorized to perform a remote control or monitoring operation regarding the individual or patient, or is authorized to access the electronic healthcare record, file, or history of the individual or patient. If, at step 3003, the central processing computer component 110A of the central processing computer and distributed ledger and Blockchain technology system 110, determines that the respective provider, insurer, payer, caregiver, or any governmental entity, intermediary, or third party, or any other individual or user, is not authorized to access the central processing computer component 110A of the central processing computer and distributed ledger and Blockchain technology system 110, or is not authorized to perform a remote control or monitoring operation regarding the individual or patient, or is not authorized to access the electronic healthcare record, file, or history, of the individual or patient, the operation of the apparatus 300 will cease at step 3007.

If, at step 3003, the central processing computer component 110A of the central processing computer and distributed ledger and Blockchain technology system 110 determines that the respective provider, insurer, payer, caregiver, or any governmental entity, intermediary, or third party, or any other individual or user, is authorized to access the central processing computer component 110A of the central processing computer and distributed ledger and Blockchain technology system 110, and is authorized to perform a remote control or monitoring operation regarding the individual or patient, and is authorized to access the electronic healthcare record, file, or history, of the individual or patient, then the operation of the apparatus 300 will proceed to step 3004.

At step 3004, the respective provider, insurer, payer, caregiver, or any governmental entity, intermediary, or third party, or any other individual or user, can then access the individual's or the patient's electronic healthcare record, file, or history, and can select the respective healthcare device or healthcare devices, or the respective healthcare equipment or pieces of healthcare equipment which he or she desires to access, control, or monitor. The respective provider, insurer, payer, caregiver, or any governmental entity, intermediary, or third party, or any other individual or user, can then access the healthcare device or each of the healthcare devices, or the healthcare equipment or each piece of healthcare equipment, one by one, by using data or information obtained from, or via a link or hyperlink to each healthcare device or each piece of healthcare equipment in, the individual's or the patient's electronic healthcare record, file, or history. The respective provider, insurer, payer, caregiver, or any governmental entity, intermediary, or third party, or any other individual or user, can also access the healthcare device or each healthcare devices or the healthcare equipment or each of the pieces of healthcare equipment via an appropriate link or hyperlink to each of same which can be stored in, accessed via, or otherwise obtained from, the individual's or the patient's electronic healthcare record, file, or history, the database 10H of the central processing computer component 110A of the central processing computer and distributed ledger and Blockchain technology system 110, and/or via the database 60H of the healthcare records computer 60.

At step 3005, the respective provider, insurer, payer, caregiver, or any governmental entity, intermediary, or third party, or any other individual or user, can then access the healthcare device, each healthcare device, the healthcare equipment, and/or each piece of healthcare equipment, and control the operation or same, monitor the operation of same, confirm that the same is operating properly, obtain data and/or information from same, and/or obtain a measurement or reading from same. As and for an illustrative example, and for the sake of simplicity, in a situation where an individual or patient is under a provider's care for high blood pressure, his or her provider, in seeking to monitor the individual's or a patient's blood pressure on regular basis, can access the individual's or patient's blood pressure measurement device, which is the healthcare device in this example, and can obtain, and record, a blood pressure measurement or reading for the individual or patient, at any time. In a preferred embodiment, where this blood pressure reading can be performed live, such as by appointment, the provider can take the individual's or patient's blood pressure live or in real-time. Any other healthcare device(s) or healthcare equipment can be accessed, controlled, monitored, and/or used, in a same, a similar, and/or an analogous, manner.

In another preferred embodiment, the individual or patient can take his or her own blood pressure measurement or reading, or can take it with the help or assistance of another individual, and the measurement or reading can be stored in the blood pressure measurement device. Any other healthcare device(s) or healthcare equipment can be accessed, controlled, monitored, and/or used, in a same, a similar, and/or an analogous, manner.

At step 3005, the respective provider, insurer, payer, caregiver, or any governmental entity, intermediary, or third party, or any other individual or user, can also control an operation of the respective healthcare device or healthcare equipment, can monitor an operation of the respective healthcare device or healthcare equipment, or can view or observe data, information, video, audio, or other information, provided by the respective healthcare device or healthcare equipment, or by any camera, microphone, or video-conferencing device or equipment. In another preferred embodiment, the herein-described dental probe can be utilized as a respective healthcare device or healthcare equipment in order to allow the performance of a remote dental examination. In a preferred embodiment, any picture, photograph, or video information, obtained via a respective healthcare device or healthcare equipment can be transmitted to the provider communication device 21 and can be viewed via a separate viewing screen or viewing window on or via the display device 20E.

At step 3005, respective provider, insurer, payer, caregiver, or any governmental entity, intermediary, or third party, or any other individual or user, can also view any results obtained by, recorded by, or transmitted from, the respective healthcare device or healthcare equipment, retrieve previously stored or recorded information or results obtained via or with the respective healthcare device or healthcare equipment, or can perform any desired operation, function, or task, with or using the respective healthcare device or healthcare equipment. At step 3005, the respective provider, insurer, payer, caregiver, or any governmental entity, intermediary, or third party, or any other individual or user, can also activate a video camera, a microphone or audio recording device, video conferencing equipment, a telephone, or an intercom, so as to communicate with the individual or patient or any other person.

Upon obtaining the information or results from the respective healthcare device or healthcare equipment, the respective provider, insurer, payer, caregiver, or any governmental entity, intermediary, or third party, or any other individual or user, can then, at step 3006, view and store, or record, the obtained data, information, or results in the individual's or patient's electronic healthcare record, file, or history. In instances when multiple healthcare devices or multiple pieces of healthcare equipment are to be accessed, steps 3005 and 3006 can be repeated, as described herein, for each healthcare device or for each piece of healthcare equipment. In another preferred embodiment, data and/or information regarding any actions taken or performed by the respective provider, insurer, payer, caregiver, or any governmental entity, intermediary, or third party, or any other individual or user, the time, date, and/or duration of same, any healthcare devices or healthcare equipment involved or utilized, any respective data and/or information obtained from the same, and any observations, notes, comments or messages, made by the respective provider, insurer, payer, caregiver, or any governmental entity, intermediary, or third party, or any other individual or user, and/or any other data or information, can be stored in the individual's or patient's healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110. Any of the above-described data and/or information can also be stored in the individual's or patient's electronic healthcare record, file, or history, stored in the database 60H of the healthcare records computer 60.

At step 3006, the central processing computer component 110A of the central processing computer and distributed ledger and Blockchain technology system 110 can automatically generate an insurance claim form or a request for payment and can transmit the same to the payer communication device 31 of the insurer or payer of the individual or patient. In a preferred embodiment, the insurance claim form or a request for payment can also be stored in the individual's or patient's healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110. Upon the completion of the operation at step 3006, the operation of the apparatus 300 will cease at step 3007.

Although described as being utilized in conjunction with the apparatus 300, the embodiment of FIG. 30 can also be utilized in a same, a similar, and/or an analogous, manner in conjunction with the apparatus 100 and/or the apparatus 200.

In another preferred embodiment, the respective provider, insurer, payer, caregiver, or any governmental entity, intermediary, or third party, or any other individual or user, at step 3005 can perform a respective monitoring, or data or information gathering, activity, can perform an examination, can engage in making a diagnosis, can effectuate a treatment, can perform a procedure, can observe and/or interact with the individual or the patient, or can engage in any other activity. Any data and/or information regarding, or obtained, along with any notes, comments, or messages, made or recorded, can be stored in the individual's or patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

In another preferred embodiment, an individual or patient, a caregiver, or a person assisting the individual or patient, can also use the apparatus 300 to obtain information or results regarding the individual or patient from a healthcare device or healthcare equipment, and can store or record the obtained information or results in the respective healthcare device or healthcare equipment, or in a personal computer or any other computer. In this embodiment, the respective provider can thereafter access the respective healthcare device, healthcare equipment, personal computer, or other computer, remotely, in person, or otherwise, and can retrieve, obtain, or upload, the information or results. The provider can then review and store or record the obtained information or results in the individual's or patient's electronic healthcare record, file, or history.

In another preferred embodiment, the embodiment of FIG. 30 can also be utilized by a provider or healthcare professional in order to perform a procedure, a surgery, or a surgical procedure, on an individual or patient, or to administer a treatment to an individual or patient, remotely, and/or via data, information, link(s), or a hyperlink(s), contained in the individual's or patient's electronic healthcare record, file, or history by allowing the provider or healthcare professional to access, control, manipulate, and/or monitor, a respective healthcare device or healthcare equipment, an instrument(s), a surgical instrument(s), and/or any other device(s) or equipment which can be used in performing any procedure, surgery, or surgical procedure, on an individual or patient, and/or in administering a treatment to an individual or patient. In this regard, in a preferred embodiment, the apparatus 300 can be utilized in order to allow a provider or healthcare professional to perform procedures, surgeries, or surgical procedures, or to administer treatments remotely and via data, information, link(s), or a hyperlink(s), contained in the individual's or patient's electronic healthcare record, file, or history. Any data and/or information regarding these procedures, surgeries, or surgical procedures, or administration of treatments can be recorded with or by any of the herein-described microphones, audio recording devices, cameras, and/or video recording devices, and any data and/or information obtained with, by, or from, any healthcare device(s) or healthcare equipment reading(s) utilized in or during the respective procedures, surgery, or surgical procedure, and/or administration of a treatment, can be stored in the individual's electronic healthcare record, file, or history, and in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

In this regard, procedures, surgeries, or surgical procedures, and/or administrations of treatments, can be performed using the apparatus 300, and any data and/or information regarding the same, including audio information, video information, and/or any data and/or information obtained with, by, or from, any healthcare device(s) or healthcare equipment reading(s) utilized in or during the respective procedure, surgery, or surgical procedure, and/or administration of a treatment, can be stored in any manner described herein.

In another preferred embodiment, a respective provider, insurer, payer, caregiver, or any governmental entity, intermediary, or third party, or any other individual or user, can access, control, monitor, perform a diagnostic check on or regarding, repair, reset, calibrate, perform maintenance on, or re-program, artificial limbs, artificial organs, implanted or implantable devices, pacemakers, defibrillators, and/or any other prosthetic and/or other devices, via a link(s) or hyperlink(s) to same which can be stored in an individual's, patient's, or caregiver's, electronic healthcare record, file, or history. Data and/or information regarding any such accessing, controlling, monitoring, performing of a diagnostic check on or regarding, repairing, or re-programming, of any of the herein-described artificial limbs, artificial organs, implanted or implantable devices, pacemakers, defibrillators, and/or any other prosthetic and/or other devices, by the respective person, including, but not limited to, the date and/or time of same and/or any and/or all actions taken or services performed by the respective person, and can also be stored in the individual's, patient's, or caregiver's, electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110.

The central processing computer component 110A of the central processing computer and distributed ledger and Blockchain technology system 110 can, thereafter, generate and/or transmit a respective insurance claim or request for payment to the payer communication device 31 of the respective insurer or payer of the individual or patient so as to ensure the provider is compensated for his or her services.

In another preferred embodiment, an individual or patient, a caregiver, or a person assisting the individual or patient, can use a healthcare device or healthcare equipment in order to obtain information or results regarding the individual or patient and to store or record the obtained information or results in the healthcare device or healthcare equipment or in a user or patient communication device 41. Thereafter, the individual or patient, the caregiver, or the person assisting the individual or patient, can access the central processing computer component 110A of the central processing computer and distributed ledger and Blockchain technology system 110 via or using the user or patient communication device 41, can access the individual's or patient's electronic healthcare record, file, or history, and can transmit the information or results to the central processing computer component 110A of the central processing computer and distributed ledger and Blockchain technology system 110, and the information or results can then be stored in the individual's or patient's electronic healthcare record, file, or history, in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110. Thereafter, a respective provider, insurer, payer, or any governmental entity, intermediary, or third party, can access the central processing computer component 110A of the central processing computer and distributed ledger and Blockchain technology system 110, can access the individual's or patient's electronic healthcare record, file, or history, and can obtain or review the information or results.

In another preferred embodiment, the embodiment of FIG. 30 can be used by a respective provider, insurer, payer, caregiver, or any governmental entity, intermediary, or third party, or any other individual or user, in order to monitor an individual or patient at home, at work, in a hospital, at a healthcare facility, during an operation or a procedure, during a test, during an office visit with another provider, during an MM, a Cat Scan, a PET scan, or any other procedure, during an exercise session, while asleep, while on vacation, while in surgery, during a stress test, and/or or at any other time or place.

In another preferred embodiment, the embodiment of FIG. 30 can be used by a respective provider, insurer, payer, caregiver, or any governmental entity, intermediary, or third party, or any other individual or user, in order to monitor an individual or patient while they are located at any type or kind of premises, including, but not limited to, a residential premises, a commercial premises, or a healthcare facility or premises, or while they are located in, or traveling in, any type of land, sea, air, or space vehicle. The embodiment of FIG. 30 can also be used by a respective provider, insurer, payer, caregiver, or any governmental entity, intermediary, or third party, or any other individual or user, in order to monitor an individual or patient while they are located at, or while they are located in, or traveling in, a motor vehicle, an automobile, a mass transportation vehicle, a truck, a tractor trailer, a bus, a school bus, a commercial vehicle, commercial equipment, industrial equipment, a military vehicle, a snowmobile, a jetski, a scooter, a recreational vehicle, a motorcycle, a minibike, a go-cart, a moped, an unmanned vehicle, a train, a subway train, an aircraft, an airplane, a jet, a helicopter, a glider, a spacecraft, a space shuttle, a satellite, an unmanned aircraft, a commercial aircraft, a military aircraft, a boat, a marine vessel, a marine vehicle, a motor boat, a sailboat, a ship, a cruise ship, a commercial boat, a military boat, an unmanned boat, or a submarine.

In the above-described embodiment, any necessary or appropriate information, or any link(s) or hyperlink(s), for facilitating access to the respective premises, vehicle, healthcare device, or healthcare equipment, or for facilitating an accessing, a controlling, or a monitoring, of any healthcare device, healthcare equipment, video device, audio device, videoconferencing device, or communication device, can be provided or stored, or otherwise made available, in the individual's or patient's electronic healthcare record, file, or history, and/or in the database 10H of the central processing computer component 110A of the central processing computer and distributed ledger and Blockchain technology system 110, and/or in the distributed ledger and Blockchain technology system component 110B of the central processing computer/distributed ledger/Blockchain technology system 110, and/or in the database 60H of the healthcare records computer 60.

In any and/or all of the embodiments described herein, any of the data and/or information, and/or any of the reports or messages, described herein as being received by, stored by, processed by, generated by, transmitted by, and/or otherwise provided by, the apparatus 100, the apparatus 200, and/or the apparatus 300, and/or by any of the respective computers or communication devices 10, 20, 21, 30, 31, 40, 41, 50, 51, 60, 70, 80, 90, 110, 110A, and/or 110B, of the same, can be translated from one language into another language by any of the herein-described and respective central processing computer(s) 10, provider communications devices 20 or 21, payer communication devices 30 or 31, user or patient communication devices 40 or 41, governmental entity/intermediary communication devices 50 or 51, healthcare records computers 60, insurance exchange computers 70, social networking computers 80, media computers 90, central processing computer component(s) 110A of the central processing computer and distributed ledger and Blockchain technology system 110, distributed ledger and Blockchain technology system component 110B of the central processing computer/distributed ledger/Blockchain technology system 110, and/or the central processing computer/distributed ledger/Blockchain technology system 110.

In a preferred embodiment, the central processing computer 10 and/or the central processing computer component 110A of the central processing computer and distributed ledger and Blockchain technology system 110 can receive a request to translate any desired or selected data, information, report, message, note, or comment, into another language, from a respective communication device 20, 21, 30, 31, 40, 41, 50, 51, 60, 70, 80, 90, can translate the respective data, information, report, message, note, or comment, into the requested or specified language, and can transmit the translated data, information, report, message, note, or comment, to the respective communication device 20, 21, 30, 31, 40, 41, 50, 51, 60, 70, 80, 90, of the requesting user or entity.

In another preferred embodiment, any data, information, report, message, note, or comment, or any function, described-herein as being capable of being provided by, or performed by, the apparatus 100, the apparatus 200, or the apparatus 300, can, if needed, be translated or converted, by the respective apparatus 100, apparatus 200, or apparatus 300, or by the central processing computer 10, the central processing computer component(s) 110A of the central processing computer and distributed ledger and Blockchain technology system 110, or by any of the computers or communication devices 20, 21, 30, 31, 40, 41, 50, 51, 60, 70, 80, and/or 90, of same, into a foreign language or a foreign language counterpart, or can be translated or converted into a corresponding foreign language code or other information. In an preferred embodiment, any translation or conversion can be performed automatically in response to a respective individual, patient, caregiver, provider, healthcare professional, insurer or payer, governmental entity or intermediary, or third party, registering or requesting a language preference or a translation or conversion request or order with the respective apparatus 100, apparatus 200, or apparatus 300, at any time, or in response to a request or a selection to provide, display, of store, the data, information, report, message, note, or comment, or code, or to convert the data, information, report, message, note, or comment, or code, into a foreign language at any time.

In a preferred embodiment, any individual, patient, caregiver, provider, healthcare professional, insurer or payer, governmental entity or intermediary, or third party, can view any information or information screens provided by the respective apparatus 100, apparatus 200, or apparatus 300, in any selected foreign language, can request and can be provided with a translation or a conversion of any data, information, report, message, note, or comment, described herein, into any selected foreign language, or can generate or transmit any claim forms, claims, requests, messages, reports, of other information, in any selected foreign or other language.

In a preferred embodiment, any translation or conversion from one language to another can be performed using a pre-stored look-up table or translation software, which can be stored or provided in the database 10H of the central processing computer 10 or the central processing computer component(s) 110A of the central processing computer and distributed ledger and Blockchain technology system 110, or stored or provided in any of the databases 20H, 30H, 40H, 50H, 60H, 70H, 80H, and/or 90H, of any of the respective communication devices or computers 20, 21, 30, 31, 40, 41, 50, 51, 60, 70, 80, and/or 90, described herein, each of which communication devices or computers can also contain, can be equipped with, or can have, foreign language translations or foreign language counterparts of any data, information, report, message, note, or comment, or code(s), which can be used, stored, processed, or generated, in connection with the use of any of the embodiments or functionality of the respective apparatus 100, apparatus 200, or apparatus 300, of the present invention described herein. In a preferred embodiment, any translation or conversion can also be performed using a language translation or code translation software of processing routines. In a preferred embodiment, the apparatus 100, the apparatus 200, or the apparatus 300, of the present invention can translate or convert any of the data, information, report, message, note, or comment, or any code(s), or any other report(s), form(s). request(s), or message(s), described herein, into any number of foreign languages. In a preferred embodiment, information in any look-up tables or software can be entered and stored manually so as to ensure accurate, correct, and up-to-date, translations. In another preferred embodiment, the apparatus 100, apparatus 200, or apparatus 300, or the central processing computer 10 and/or the central processing computer component(s) 110A of the central processing computer and distributed ledger and Blockchain technology system 110, or any of the herein-described respective communication devices or computers 20, 21, 30, 31, 40, 41, 50, 51, 60, 70, 80, and/or 90, can also perform any translations or conversions using language translation software or processing routines.

The apparatus 100, the apparatus 200, the apparatus 300, of the present invention can also be utilized to provide social networking functionality and capability via an electronic healthcare record(s) or any. Any of the herein-described individuals, patients, caregivers, providers, insurers, payers, third parties, or other entities, can access a social network via any of the electronic healthcare records described herein. Each and every type or kind of electronic healthcare record utilized in or in connection with the present invention can have information, link(s), or hyperlink(s), to any social networking web sites, web pages, support groups, on-line forums, on-link information services, as well as social networking web sites or social networking web pages to or for social networking members, support groups, information providers, healthcare providers, as well as any of the providers, insurers, payers, individuals, patient, third parties, intermediaries, or any other persons or entities described herein who are or who may be members of any social network.

The apparatus 100, the apparatus 200, the apparatus 300, of the present invention can also be utilized to provide an individual or patient with information, or a link(s) or a hyperlink(s) to information, regarding a social networking website or a social networking company, any information provided thereby or thereat, or information regarding any social networking support groups or social networking support group members, on-line seminars, forums, chat room discussions, or others, with which or whom the individual or patient may engage upon the individual or patient being diagnosed with an illness, a sickness, or a condition, or upon the individual or patient about to undergo or undergoing a treatment, a procedure, or an operation, or about to embark upon or already involved in a treatment plan.

The providing of the social networking information to the individual or patient can also serve to allow the individual or patient to learn more about a diagnosis, a treatment, or a treatment plan, to interact with others who have been diagnosed with the same or a similar illness, a sickness, or a condition, or others who may be undergoing the same or a similar treatment or who may be following a same or a similar treatment plan. The apparatus 100, the apparatus 200, the apparatus 300, of the present invention can also be utilized so as to identify and provide the individual or patient with information or link(s) or hyperlink(s) to a social networking website, a social networking company, a support group or support groups, a member of the social network members of the social network, social networking lectures, classes, or seminars, social networking sponsored lectures, classes, or seminars, social networking discussions, question and answer sessions, or informational or other forums, or any other social networking or social networking sponsored activities or events, for any number of social networks.

The apparatus 100, the apparatus 200, the apparatus 300, of the present invention can also be utilized in a same, similar, or analogous manner, in order to process and/or to provide veterinary healthcare information and/or veterinary healthcare-related information for and regarding any kind or type of animal or animals or any type or kind of pet or pets.

The present invention can also be utilized as a clearinghouse for facilitating the offering, selling, buying, trading, and/or other commerce and/or transactions, involving healthcare and/or healthcare-related services, products and/or goods.

The apparatus 100, the apparatus 200, the apparatus 300, of the present invention can also provide for cloud-based healthcare or healthcare-related data and/or information processing and/or storage, cloud-based electronic healthcare records, cloud-based electronic healthcare records storage and/or retrieval, a cloud-based electronic healthcare records system or platform, and/or cloud based processing and/or storage of any and/or all of the data and/or information described herein as being processed by the apparatus 100, the apparatus 200, the apparatus 300, and/or the methods, of the present invention.

In any and/or all of the embodiments described herein, any of the herein-described data and/or information, any recorded video calls or video call recordings, and/or any data and/or information regarding, obtained, entered, or recorded, via any video call(s) and/or remote office visit(s), and/or any video call reports and/or the remote or virtual office visit reports or any remote or distance examination reports, and/or any photograph of the individual, the patient, or the caregiver, and/or any picture or photograph of the healthcare provider, can be accessed by any authorized user by accessing same via the central processing computer 10 or the via the central processing computer component 110A of the central processing computer/distributed ledger/Blockchain technology system 110.

In any and/or all of the embodiments described herein, data and/or information regarding any of the herein-described insurance claims, claims for payment, and/or any other request for a payment, for, regarding, or relating to, any video call, video chat session, or videoconference, can contain, or can contain as an attachment, a copy of a recording of the video call, the video chat session, or the videoconference.

In any and/or all of the embodiments described herein, data and/or information regarding any of the herein-described insurance claims, claims for payment, and/or any other request for a payment, for, regarding, or relating to, any video call, video chat session, or videoconference, can be stored in the electronic healthcare record of or for the individual or the patient using the distributed ledger and/or blockchain technology system.

While the present invention has been described and illustrated in various preferred and alternate embodiments, such descriptions are merely illustrative of the present invention and are not to be construed to be limitations thereof. In this regard, the present invention encompasses all modifications, variations and/or alternate embodiments, with the scope of the present invention being limited only by the claims which follow.

What is claimed is:

1. An apparatus, comprising:
a central processing computer, wherein the central processing computer is specially programmed for facilitating a tele-health visit involving a video call and a first electronic healthcare record for or associated with an individual or a patient, wherein the first electronic healthcare record is provided by a first records provider, and further wherein the central processing computer is specially programmed to update a second electronic healthcare record, an electronic medical record, an electronic dental record, an electronic pharmacy record, an electronic behavioral health record, or a personal healthcare record, for or associated with the individual or the patient, wherein the second electronic healthcare record, the electronic medical record, the electronic dental record, the electronic pharmacy record, the electronic behavioral health record, or the personal healthcare record, for or associated with the individual or the patient, is provided by a second records provider, and further wherein the central processing computer further comprises:
a database, wherein the database stores the first electronic healthcare record for or associated with the individual or the patient, and further wherein the database stores a master records file, wherein information fields or data fields of the first electronic healthcare record, provided by the first records provider, and information fields or data fields of the second electronic healthcare record, the electronic medical record, the electronic dental record, the electronic pharmacy record, the electronic behavioral health record, or the personal healthcare record, for or associated with the individual or the patient, provided by the second records provider, are indexed, mapped, or correlated, with each other and are stored in the master records file,
wherein the apparatus facilitates a video call between a user communication device associated with the individual or the patient and a provider communication device associated with a healthcare provider, wherein video information regarding the individual or the patient is displayed along with a portion of the first electronic healthcare record for or associated with the individual or the patient on a display device of the provider communication device, and further wherein the provider communication device processes information for updating the first electronic healthcare record for or associated with the individual or the patient, and further wherein the central processing computer stores the information for updating, and stores an update to, the first electronic healthcare record for or associated with the individual or the patient in the database, and further wherein the central processing computer utilizes information stored in the master records file and automatically updates the second electronic healthcare record for or associated with the individual or the patient, or the central processing computer utilizes information stored in the master records file and automatically updates the electronic medical record, the electronic dental record, the electronic pharmacy record, the electronic behavioral health record, or the personal healthcare record, for or associated with the individual or the patient.

2. The apparatus of claim 1, wherein the apparatus or the central processing computer generates an insurance claim form or a request for payment form, and further wherein the apparatus or the central processing computer transmits the insurance claim form or the request for payment form to an insurer communication device.

3. The apparatus of claim 1, wherein the central processing computer transmits a first profile photograph to the provider communication device, wherein the first profile photograph is a file photograph of the individual or the patient, and wherein the central processing computer transmits a second profile photograph to the user communication device, wherein the second profile photograph is a file photograph of the healthcare provider.

4. The apparatus of claim 1, wherein the central processing computer authenticates the individual or the patient for the video call by processing information regarding an IP address assigned to, or associated with, the user communication device, or wherein the central processing computer authenticates the healthcare provider for the video call by processing information regarding an IP address assigned to, or associated with, the provider communication device.

5. The apparatus of claim 1, wherein the central processing computer authenticates the individual or the patient for the video call by processing position or location information for the user communication device, wherein the position or location information is obtained by a global positioning device located at the user communication device, and further wherein the position or location information is transmitted from the user communication device to the central processing computer, or wherein the central processing computer authenticates the healthcare provider for the video call by processing position or location information for the provider communication device, wherein the position or location information is obtained by a global positioning device located at the user communication device, and further wherein the position or location information is transmitted from the user communication device to the central processing computer.

6. The apparatus of claim 1, further comprising:
an RFID tag, wherein the RFID tag is assigned to the individual or the patient; and
an RFID reader, wherein the RFID reader is assigned to the healthcare provider, wherein the RFID reader reads or scans information from or associated with the RFID tag,
wherein the central processing computer processes the information from or associated with the RFID tag and verifies an identity of the individual or the patient, and further wherein the central processing computer generates an identity verification message and transmits the identity verification message to the provider communication device, wherein the identity verification message contains a link or a hyperlink to the first electronic healthcare record for or associated with the individual or the patient.

7. The apparatus of claim 1, further comprising:
an RFID tag, wherein the RFID tag is assigned to a second individual; and
an RFID reader, wherein the RFID reader is assigned to a public building, structure, venue, or vehicle, wherein the RFID reader reads or scans information from the RFID tag,
wherein the central processing computer processes information from the RFID tag, identifies the second individual, and determines that the second individual has a sickness, an illness, a bacterial infection, a viral infection, a contagious infection, or a need for an immunization.

8. The apparatus of claim 1, wherein the central processing computer transmits an appointment message to the user communication device or to a second user communication device, and further wherein the appointment message contains a link or a hyperlink, wherein the video call is initiated via the link or the hyperlink.

9. The apparatus of claim 1, wherein the central processing computer generates a healthcare threat alert message, and further wherein the central processing computer transmits the healthcare threat alert message to the user communication device.

10. The apparatus of claim 1, wherein the central processing computer generates a healthcare threat alert message, and further wherein the central processing computer transmits the healthcare threat alert message to a second user communication device, wherein the second user communication device is associated with a second individual or a second patient.

11. The apparatus of claim 1, wherein the central processing computer generates a healthcare threat alert message, and further wherein the central processing computer transmits the healthcare threat alert message to the provider communication device.

12. The apparatus of claim 1, wherein the central processing computer transmits a reminder message to the user communication device or to a second user communication device, wherein the reminder message contains a link or a hyperlink, wherein the video call is initiated via the link or the hyperlink.

13. The apparatus of claim 1, wherein the healthcare provider is a dental healthcare provider.

14. The apparatus of claim 13, wherein the apparatus identifies the dental healthcare provider as being available for the video call.

15. The apparatus of claim 13, wherein the video information is transmitted from a dental probe, and further wherein the video information is received by the provider communication device.

16. The apparatus of claim 13, wherein the central processing computer receives information regarding a note, a message, or a comment, transmitted from the user communication device.

17. The apparatus of claim 1, wherein the user communication device transmits data obtained from a healthcare device or healthcare equipment, or biometric data or performance tracking data, to the provider communication device before, during, or after, the video call.

18. The apparatus of claim 1, wherein the apparatus identifies the healthcare provider as being available for the video call.

19. The apparatus of claim 1, wherein the video call is an on-demand healthcare appointment.

20. The apparatus of claim 1, wherein the provider communication device generates a video call alert message, and further wherein the provider communication device transmits the video call alert message to the user communication device.

21. The apparatus of claim 1, wherein the first electronic healthcare record is associated with the healthcare provider, and further wherein the second electronic healthcare record, the electronic medical record, the electronic dental record, the electronic pharmacy record, or the electronic behavioral health record, is associated with a second healthcare provider.

22. The apparatus of claim 1, wherein the apparatus processes information for scheduling the video call, and further wherein the apparatus processes information for allowing the individual or the patient to grant the healthcare provider access to the first electronic healthcare record prior to the video call.

23. A computer-implemented method, comprising:
storing, in a database of a central processing computer, a first electronic healthcare record for or associated with an individual or a patient;
storing, in the database of the central processing computer, a master records file, wherein information fields or data fields of the first electronic healthcare record, provided by a first records provider, and information fields or data fields of a second electronic healthcare record, an electronic medical record, an electronic dental record, an electronic pharmacy record, an electronic behavioral health record, or a personal healthcare record, for or associated with the individual or the patient, provided by a second records provider, are indexed, mapped, or correlated, with each other and are stored in the master records file;
providing or facilitating, with or using the central processing computer, a tele-health visit involving a video call between a user communication device associated with the individual or the patient and a provider communication device associated with a healthcare provider, wherein the central processing computer is specially programmed for facilitating the tele-health visit involving the video call and the first electronic healthcare record for or associated with the individual or the patient, wherein the first electronic healthcare record is provided by the first records provider, and further wherein the central processing computer is specially programmed to update the second electronic healthcare record, the electronic medical record, the electronic dental record, the electronic pharmacy record, the electronic behavioral health record, or the personal healthcare record, for or associated with the individual or the patient, wherein the second electronic healthcare record, the electronic medical record, the electronic dental record, the electronic pharmacy record, the electronic behavioral health record, or the personal healthcare record, for or associated with the individual or the patient, is provided by the second records provider;
displaying, via a display device of the provider communication device, video information regarding the individual or the patient along with a portion of the first electronic healthcare record for or associated with the individual or the patient;
processing, with or using the provider communication device, information for updating the first electronic healthcare record for or associated with the individual or the patient;

storing, with or using the central processing computer, information for updating the first electronic healthcare record for or associated with the individual or the patient in the database;

updating, with or using the central processing computer, the first electronic healthcare record for or associated with the individual or the patient; and automatically updating, with or using the central processing computer and utilizing information stored in the master records file, the second electronic healthcare record for or associated with the individual or the patient, or automatically updating, with or using the central processing computer and utilizing information stored in the master records file, the electronic medical record, the electronic dental record, the electronic pharmacy record, the electronic behavioral health record, or the personal healthcare record, for or associated with the individual or the patient.

24. The computer-implemented method of claim 23, further comprising:

generating an insurance claim form or a request for payment form;

transmitting the insurance claim form or the request for payment form to an insurer communication device.

25. The computer-implemented method of claim 23, further comprising:

transmitting a first profile photograph to the provider communication device, wherein the first profile photograph is a file photograph of the individual or the patient; and transmitting a second profile photograph to the user communication device, wherein the second profile photograph is a file photograph of the healthcare provider.

26. The computer-implemented method of claim 23, further comprising:

authenticating the individual or the patient for the video call using information regarding an IP address assigned to, or associated with, the user communication device, or authenticating the healthcare provider for the video call using information regarding an IP address assigned to, or associated with, the provider communication device.

27. The computer-implemented method of claim 23, further comprising:

assigning an RFID tag to the individual or the patient;
assigning an RFID reader to the healthcare provider;
reading or scanning, with the RFID reader, information from or associated with the RFID tag;

processing the information from or associated with the RFID tag;

verifying an identity of the individual or the patient;

generating an identity verification message;

transmitting the identity verification message to the provider communication device, wherein the identity verification message contains a link or a hyperlink to the first electronic healthcare record for or associated with the individual or the patient.

28. The computer-implemented method of claim 23, further comprising:

assigning an RFID tag to a second individual;

assigning an RFID reader to a public building, structure, venue, or vehicle;

reading or scanning, with the RFID reader, information from the RFID tag;

processing information from the RFID tag;

identifying the second individual; and determining that the second individual has a sickness, an illness, a bacterial infection, a viral infection, a contagious infection, or a need for an immunization.

29. The computer-implemented method of claim 28, further comprising:

generating a healthcare threat alert message; and transmitting the healthcare threat alert message to the user communication device, or transmitting the healthcare threat alert message to a second user communication device, wherein the second user communication device is associated with a second individual or a second patient.

30. The computer-implemented method of claim 28, further comprising:

generating a healthcare threat alert message; and transmitting the healthcare threat alert message to the provider communication device, or transmitting the healthcare treat alert message to a second provider communication device.

31. The computer-implemented method of claim 28, further comprising:

receiving, with the provider communication device, information regarding a note, a message, or a comment, transmitted from the user communication device, or receiving, with the provider communication device, data obtained from a healthcare device or healthcare equipment, or biometric data or performance tracking data, before, during, or after, the video call.

* * * * *